United States Patent
Jang et al.

(10) Patent No.: US 10,654,944 B2
(45) Date of Patent: *May 19, 2020

(54) CELL ENGAGING BINDING MOLECULES

(71) Applicant: Y-BIOLOGICS INC., Daejeon (KR)

(72) Inventors: Seil Jang, Sejong (KR); Bum-Chan Park, Daejeon (KR); Young Woo Park, Daejeon (KR)

(73) Assignee: Y-BIOLOGICS INC. (KR)

( * ) Notice: Subject to any disclaimer, the term of this patent is extended or adjusted under 35 U.S.C. 154(b) by 0 days.

This patent is subject to a terminal disclaimer.

(21) Appl. No.: 16/372,196

(22) Filed: Apr. 1, 2019

(65) Prior Publication Data
US 2019/0309094 A1 Oct. 10, 2019

Related U.S. Application Data

(60) Provisional application No. 62/719,484, filed on Aug. 17, 2018, provisional application No. 62/655,762, filed on Apr. 10, 2018.

(51) Int. Cl.
| | | |
|---|---|---|
| *C07K 16/00* | (2006.01) | |
| *C07K 16/46* | (2006.01) | |
| *C07K 16/24* | (2006.01) | |
| *C07K 16/28* | (2006.01) | |
| *C07K 16/32* | (2006.01) | |
| *A61P 35/00* | (2006.01) | |
| *A61K 39/00* | (2006.01) | |

(52) U.S. Cl.
CPC ............ *C07K 16/468* (2013.01); *A61P 35/00* (2018.01); *C07K 16/241* (2013.01); *C07K 16/2803* (2013.01); *C07K 16/2809* (2013.01); *C07K 16/2818* (2013.01); *C07K 16/2827* (2013.01); *C07K 16/2863* (2013.01); *C07K 16/2887* (2013.01); *C07K 16/2896* (2013.01); *C07K 16/32* (2013.01); *A61K 2039/505* (2013.01); *C07K 2317/14* (2013.01); *C07K 2317/24* (2013.01); *C07K 2317/31* (2013.01); *C07K 2317/522* (2013.01); *C07K 2317/53* (2013.01); *C07K 2317/55* (2013.01); *C07K 2317/56* (2013.01); *C07K 2317/565* (2013.01); *C07K 2317/64* (2013.01); *C07K 2317/732* (2013.01); *C07K 2317/734* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 4,526,938 A | 7/1985 | Churchill et al. | |
| 4,816,567 A | 3/1989 | Cabilly et al. | |
| 4,880,078 A | 11/1989 | Inoue et al. | |
| 4,946,778 A | 8/1990 | Ladner et al. | |
| 4,980,286 A | 12/1990 | Morgan et al. | |
| 5,122,464 A | 6/1992 | Wilson et al. | |
| 5,128,326 A | 7/1992 | Balazs et al. | |
| 5,260,203 A | 11/1993 | Ladner et al. | |
| 5,290,540 A | 3/1994 | Prince et al. | |
| 5,476,786 A | 12/1995 | Huston | |
| 5,482,858 A | 1/1996 | Huston et al. | |
| 5,679,377 A | 10/1997 | Bernstein et al. | |
| 5,807,715 A | 9/1998 | Morrison et al. | |
| 5,837,242 A | 11/1998 | Holliger et al. | |
| 5,855,913 A | 1/1999 | Hanes et al. | |
| 5,874,064 A | 2/1999 | Edwards et al. | |
| 5,912,015 A | 6/1999 | Bernstein et al. | |
| 5,916,597 A | 6/1999 | Lee et al. | |
| 5,934,272 A | 8/1999 | Lloyd et al. | |
| 5,959,083 A | 9/1999 | Bosslet et al. | |
| 5,985,309 A | 11/1999 | Edwards et al. | |
| 5,985,320 A | 11/1999 | Edwards et al. | |
| 5,989,463 A | 11/1999 | Tracy et al. | |
| 6,019,968 A | 2/2000 | Platz et al. | |
| 6,054,297 A | 4/2000 | Carter et al. | |
| 6,075,181 A | 6/2000 | Kucherlapati et al. | |
| 6,150,584 A | 11/2000 | Kucherlapati et al. | |
| 6,407,213 B1 | 6/2002 | Carter et al. | |
| 6,492,123 B1 | 12/2002 | Holliger et al. | |
| 6,639,055 B1 | 10/2003 | Carter et al. | |
| 6,719,971 B1 | 4/2004 | Carter et al. | |
| 6,800,738 B1 | 10/2004 | Carter et al. | |

(Continued)

FOREIGN PATENT DOCUMENTS

| | | |
|---|---|---|
| EP | 1752471 B1 | 11/2008 |
| EP | 1772465 B1 | 2/2009 |

(Continued)

OTHER PUBLICATIONS

Almagro & Fransson, Frontiers in Bioscience 2008 13:1619-33 (Year: 2008).*
De Genst et al., Dev Comp Immunol 2006; 30:187-98 (Year: 2006).*
Yoshinaga et al., J. Biochem 2008; 143:593-601 (Year: 2008).*
Arnett et al., 2004, "Crystal structure of a human CD3-epsilon/delta dimer in complex with a UCHT1 single-chain antibody fragment," Proc Natl Acad Sci USA, 101(46):16268-16273.
Brinkmann et al., 2017, "The making of bispecific antibodies," MAbs, 9(2):182-212.
Chang et al., 2017, "Combination Therapy with Bispecific Antibodies and PD-1 Blockade Enhances the Antitumor Potency of T Cells," Cancer Res., 77(19):5384-5394, Author Manuscript Published OnlineFirst on Aug. 17, 2017 (40 pages).

(Continued)

*Primary Examiner* — Meera Natarajan
(74) *Attorney, Agent, or Firm* — Jones Day

(57) ABSTRACT

The present disclosure is broadly concerned with the field of cancer immunotherapy. For example, the present disclosure generally related to a binding molecule comprising antibody variable light (VL) regions, variable heavy (VH) regions, constant heavy 1 (CH1) regions, and light chain constant (CL) regions that are configured to form two antigen binding Fab regions and an antigen binding Fv region so that the binding molecule binds to two different antigens.

14 Claims, 59 Drawing Sheets

Specification includes a Sequence Listing.

(56) References Cited

U.S. PATENT DOCUMENTS

| | | | |
|---|---|---|---|
| 7,612,181 | B2 | 11/2009 | Wu et al. |
| 8,476,409 | B2 | 7/2013 | Baum et al. |
| 8,859,738 | B2 | 10/2014 | Himmler et al. |
| 8,921,279 | B2 | 12/2014 | Himmler et al. |
| 9,045,528 | B2 | 6/2015 | Ruker et al. |
| 9,133,274 | B2 | 9/2015 | Himmler et al. |
| 9,651,559 | B2 | 5/2017 | Himmler et al. |
| 9,856,311 | B2 | 1/2018 | Ruker et al. |
| 2009/0298195 | A1 | 12/2009 | Ruker et al. |
| 2010/0048877 | A1 | 2/2010 | Ruker et al. |
| 2010/0256340 | A1 | 10/2010 | Brinkmann et al. |
| 2011/0054151 | A1 | 3/2011 | Lazar et al. |
| 2011/0251375 | A1 | 10/2011 | Ruker et al. |
| 2012/0094874 | A1 | 4/2012 | Ruker et al. |
| 2012/0276104 | A1 | 11/2012 | Woisetschlager |
| 2013/0245233 | A1 | 9/2013 | Lei et al. |
| 2013/0266568 | A1 | 10/2013 | Brinkmann et al. |
| 2013/0267686 | A1 | 10/2013 | Brinkmann et al. |
| 2015/0376603 | A1 | 12/2015 | Himmler et al. |
| 2016/0108118 | A1 | 4/2016 | Kang et al. |
| 2016/0355600 | A1 | 12/2016 | Moore et al. |
| 2017/0204164 | A1 | 7/2017 | Himmler et al. |
| 2017/0247432 | A1 | 8/2017 | Himmler et al. |
| 2017/0369868 | A1 | 12/2017 | Himmler et al. |
| 2018/0051095 | A1 | 2/2018 | Ruker et al. |
| 2019/0248900 | A1 | 8/2019 | Park et al. |
| 2019/0309093 | A1 | 10/2019 | Jang et al. |
| 2019/0338029 | A1 | 11/2019 | Jang et al. |

FOREIGN PATENT DOCUMENTS

| | | |
|---|---|---|
| EP | 1699826 B1 | 3/2009 |
| EP | 2046831 B1 | 1/2012 |
| EP | 2028193 B1 | 3/2012 |
| EP | 2546268 A1 | 1/2013 |
| EP | 2463302 B1 | 4/2015 |
| EP | 2158220 B1 | 4/2017 |
| EP | 2044117 B1 | 9/2017 |
| WO | WO 1986005807 A1 | 10/1986 |
| WO | WO 1989001036 A1 | 2/1989 |
| WO | WO 1991005548 A1 | 5/1991 |
| WO | WO 1992019244 A2 | 11/1992 |
| WO | WO 1993011161 A1 | 6/1993 |
| WO | WO 1996020698 A2 | 7/1996 |
| WO | WO 1996027011 A1 | 9/1996 |
| WO | WO 1997032572 A2 | 9/1997 |
| WO | WO 1997044013 A1 | 11/1997 |
| WO | WO 1998031346 A1 | 7/1998 |
| WO | WO 1999015154 A1 | 4/1999 |
| WO | WO 1999020253 A1 | 4/1999 |
| WO | WO 1999066903 A2 | 12/1999 |
| WO | WO 2014144357 A1 | 9/2014 |
| WO | WO 2018015448 A1 | 1/2018 |
| WO | WO 2018026248 A1 | 2/2018 |
| WO | WO 2018127610 A1 | 7/2018 |
| WO | WO 2018178047 A1 | 10/2018 |
| WO | WO 2018178101 A1 | 10/2018 |

OTHER PUBLICATIONS

Coloma et al., 1997, "Design and production of novel tetravalent bispecific antibodies," Nat Biotechnol., 15(2):159-163.
Dall'Acqua et al., 2006, "Modulation of the effector functions of a human IgG1 through engineering of its hinge region," J Immunol., 177(2):1129-1138.
Esensten et al., 2016, "CD28 Costimulation: From Mechanism to Therapy," Immunity, 44(5):973-988.
Feige et al., 2009, "An unfolded CH1 domain controls the assembly and secretion of IgG antibodies," Mol Cell, 34(5):569-579.
Feige et al., 2010, "How antibodies fold," Trends Biochem Sci., 35(4):189-198.
Godar et a., 2018, "Therapeutic bispecific antibody formats: a patent applications review (1994-2017)," Expert Opin Ther Pat., 28(3):251-276.
Hadrup et al., 2013, "Effector CD4 and CD8 T cells and their role in the tumor microenvironment," Cancer Microenviron, 6(2):123-133.
Hasenhindl et al., 2013, "Stability assessment on a library scale: a rapid method for the evaluation of the commutability and insertion of residues in C-terminal loops of the CH3 domains of IgG1-Fc," Protein Eng Des Sel., 26(10):675-682.
Hasenhindl et al., 2014, "Creating stable stem regions for loop elongation in Fcabs—insights from combining yeast surface display, in silico loop reconstruction and molecular dynamics simulations," Biochim Biophys Acta., 1844(9):1530-1540.
Horn et al., 2017, "CD3xPDL1 bi-specific T cell engager (BiTE) simultaneously activates T cells and NKT cells, kills PDL1+ tumor cells, and extends the survival of tumor-bearing humanized mice," Oncotarget., 8(35):57964-57980.
Iwahori et al., 2015, "Engager T cells: a new class of antigen-specific T cells that redirect bystander T cells," Mol Ther., 23(1):171-178.
Jez et al., 2012, "Significant impact of single N-glycan residues on the biological activity of Fc-based antibody-like fragments," J Biol Chem., 287(29):24313-24319.
Kainer et al., 2012, "Correlation between CD16a binding and immuno effector functionality of an antigen specific immunoglobulin Fc fragment (Fcab)," Arch Biochem Biophys., 526(2):154-158.
Leung et al., 2015, "A HER2-specific Modified Fc Fragment (Fcab) Induces Antitumor Effects Through Degradation of HER2 and Apoptosis," Mol Ther., 23(11):1722-1733 and Erratum, Mol Ther., 23(11):1794.
Liu et al., 2017, "Fc Engineering for Developing Therapeutic Bispecific Antibodies and Novel Scaffolds," Front Immunol., 8:38 (15 pages).
Lobner et al., 2016, "Engineered IgG1-Fc—one fragment to bind them all," Immunol Rev., 270(1):113-131.
Lobner et al., 2017, "Fcab-HER2 Interaction: a Ménage à Trois. Lessons from X-Ray and Solution Studies," Structure, 25(6):878-889.e1-e5.
Lobner et al., 2017, "Two-faced Fcab prevents polymerization with VEGF and reveals thermodynamics and the 2.15 Å crystal structure of the complex," MAbs, 9(7):1088-1104.
Lu et al., 2016, "Tetravalent anti-CD20/CD3 bispecific antibody for the treatment of B cell lymphoma," Biochem Biophys Res Commun., 473(4):808-813.
Lutterbuese et al., 2010, "T cell-engaging BiTE antibodies specific for EGFR potently eliminate KRAS- and BRAF-mutated colorectal cancer cells," Proc Natl Acad Sci USA, 107(28):12605-12610.
Metz et al., 2012, "Bispecific antibody derivatives with restricted binding functionalities that are activated by proteolytic processing," Protein Eng Des Sel., 25(10):571-580.
Miguet et al., 2007, "Full activation of the T cell receptor requires both clustering and conformational changes at CD3," Immunity, 26(1):43-54.
Moore et al., 2011, "Application of dual affinity retargeting molecules to achieve optimal redirected T-cell killing of B-cell lymphoma," Blood, 117(17):4542-4551.
Renders et al., 2003, "Engineered CD3 antibodies for immunosuppression," Clin Exp Immunol., 133(3):307-309.
Spiess et al. 2015, "Alternative molecular formats and therapeutic applications for bispecific antibodies," Mol Immunol., 67(2 Pt A):95-106.
Traxlmayr et al., 2014, "Construction of pH-sensitive Her2-binding IgG1-Fc by directed evolution," Biotechnol J., 9(8):1013-1022.
Tsai et al., 2016, "CD19xCD3 DART protein mediates human B-cell depletion in vivo inhumanized BLT mice," Mol Ther Oncolytics, 3:15024.
Vossen et al., 1995, "Fc receptor binding of anti-CD3 monoclonal antibodies is not essential for immunosuppression, but triggers cytokine-related side effects," Eur J Immunol., 25(6):1492-1496.
Wang et al. 2013, "Retargeting T cells for HER2-positive tumor killing by a bispecific Fv-Fc antibody," PLoS One, 8(9):e75589.

(56) References Cited

OTHER PUBLICATIONS

Woisetschlager et al., 2014, "In vivo and in vitro activity of an immunoglobulin Fc fragment (Fcab) with engineered Her-2/neu binding sites," Biotechnol J., 9(6):844-851.
Zhou et al., 2012, "Impact of intrinsic affinity on functional binding and biological activity of EGFR antibodies," Mol Cancer Ther., 11(7):1467-1476.
Zou et al., 2015, "Immunotherapy based on bispecific T-cell engager with hIgG1 Fc sequence as a new therapeutic strategy in multiple myeloma," Cancer Sci., 106(5):512-521.
U.S. Appl. No. 16/372,172, filed Apr. 1, 2019, Y-Biologics, Inc.
U.S. Appl. No. 16/372,190, filed Apr. 1, 2019, Y-Biologics, Inc.
Adams et al., 2016, "Extending the half-life of a fab fragment through generation of a humanized anti-human serum albumin Fv domain: An investigation into the correlation between affinity and serum half-life," Mabs, 8(7):1336-1346.
Bitter et al., 1987, "Expression and secretion vectors for yeast," Methods Enzymol., 153:516-544.
Bloch-Gallego et al., 1993, "Antennapedia homeobox peptide enhances growth and branching of embryonic chicken motoneurons in vitro," J Cell Biol., 120(2):485-492.
Boerner et al., 1991, "Production of antigen-specific human monoclonal antibodies from in vitro-primed human splenocytes," J Immunol., 147(1):86-95.
Bruggemann et al., 1997, "Production of human antibody repertoires in transgenic mice," Curr Opin Biotechnol., 8(4):455-458.
During et al., 1989, "Controlled release of dopamine from a polymeric brain implant: in vivo characterization," Ann Neurol., 25(4):351-356.
Foecking et al., 1986, "Powerful and versatile enhancer-promoter unit for mammalian expression vectors", Gene, 45(1):101-105.
Holliger et al., 1993, ""Diabodies": small bivalent and bispecific antibody fragments," Proc Natl Acad Sci USA, 90(14):6444-6448.
Honegger et al., 2001, "Yet another numbering scheme for immunoglobulin variable domains: an automatic modeling and analysis tool," J Mol Biol., 309(3):657-670.
Hoogenboom et al., 1992, "By-passing immunisation Human antibodies from synthetic repertoires of germline VH gene segments rearranged in vitro," J Mol Biol., 227(2):381-388.
Howard eta l., 1989, "Intracerebral drug delivery in rats with lesion-induced memory deficits," J Neurosurg., 71(1):105-112.
Hudson et al., 2003, "Engineered antibodies," Nat Med., 9(1):129-134.
Huehls et al., 2015, "Bispecific T-cell engagers for cancer immunotherapy," Immunol Cell Biol., 93(3):290-296.
Huston et al., 1993, "Antigen recognition and targeted delivery by the single-chain Fv," Cell Biophys., 22(1-3):189-224.
Inouye et al., 1985, "Up-promoter mutations in the lpp gene of *Escherichia coli*," Nucleic Acids Res., 13(9):3101-3110.
Jakobovits, 1995, "Production of fully human antibodies by transgenic mice," Curr Opin Biotechnol., 6(5):561-566.
Jones et al., 1986, "Replacing the complementarity-determining regions in a human antibody with those from a mouse," Nature, 321(6069):522-525.
Klein et al., 2009, "Examination of the contributions of size and avidity to the neutralization mechanisms of the anti-HIV antibodies b12 and 4E10," Proc Natl Acad Sci USA, 106(18):7385-7390.
Klein et al., 2014, "Design and characterization of structured protein linkers with differing flexibilities," Protein Eng Des Sel., 27(10):325-330.
Kohler et al., 1975, "Continuous cultures of fused cells secreting antibody of predefined specificity," Nature, 256(5517):495-497.
Kontermann, 2006, "Immunoliposomes for cancer therapy," Curr Opin Mol Ther., 8(1):39-45.
Kufer et al., 2004, "A revival of bispecific antibodies," Trends Biotechnol, 22(5):238-244.
Lam et al., 1997, "Microencapsulation of Recombinant Humanized Monoclonal Antibody for Local Delivery," Proc. Int'l. Symp. Control Rel. Bioact. Mater., 24:759-760.

Langer et al., 1983, "Chemical and Physical Structure of Polymers as Carriers for Controlled Release of Bioactive Agents: A Review," Journal of Macromolecular Science, Part C, 23(1):61-126.
Langer, 1990, "New methods of drug delivery," Science, 249(4976):1527-1533.
Lee et al., 1999, "BiP and immunoglobulin light chain cooperate to control the folding of heavy chain and ensure the fidelity of immunoglobulin assembly," Mol Biol Cell, 10(7):2209-2219.
Lefranc et al., 2003, "IMGT unique numbering for immunoglobulin and T cell receptor variable domains and Ig superfamily V-like domains," Dev Comp Immunol., 27(1):55-77.
Levy et al., 1985, "Inhibition of calcification of bioprosthetic heart valves by local controlled-release diphosphonate," Science, 228(4696):190-192.
Li et al., 2006, "Human antibodies for immunotherapy development generated via a human B cell hybridoma technology," Proc Natl Acad Sci USA, 103(10):3557-3562.
Logan et al., 1984, "Adenovirus tripartite leader sequence enhances translation of mRNAs late after infection," Proc Natl Acad Sci USA, 81(12):3655-3659.
Lowy et al., 1980, "Isolation of transforming DNA: cloning the hamster aprt gene," Cell, 22(3):817-823.
Lu et al., 2005, "A fully human recombinant IgG-like bispecific antibody to both the epidermal growth factor receptor and the insulin-like growth factor receptor for enhanced antitumor activity," J Biol Chem., 280(20):19665-19672.
Maclean et al., 1997, "Immunoliposomes as targeted delivery vehicles for cancer therapeutics (Review)," Int J Oncol., 11(2):325-332.
Malik et al., 2007, "Recent advances in protein and peptide drug delivery systems," Curr Drug Deliv., 4(2):141-151.
Marks et al., 1991, "By-passing immunization Human antibodies from V-gene libraries displayed on phage," J Mol Biol., 222(3):581-597.
Merchant et al., 1998, "An efficient route to human bispecific IgG," Nat Biotechnol., 16(7):677-681.
Moore et al., 2018, "Development of MGD007, a gpA33 × CD3-Bispecific DART Protein for T-Cell Immunotherapy of Metastatic Colorectal Cancer," Mol Cancer Ther., 17(8):1761-1772.
Morgan et al., 1993, "Human gene therapy," Annu Rev Biochem., 62:191-217.
Morrison et al., 1984, "Chimeric human antibody molecules: mouse antigen-binding domains with human constant region domains," Proc Natl Acad Sci USA. 81(21):6851-6855.
Mulligan et al., 1981, "Selection for animal cells that express the *Escherichia coli* gene coding for xanthine-guanine phosphoribosyltransferase," Proc Natl Acad Sci USA, 78(4):2072-2076.
Mulligan, 1993, "The basic science of gene therapy," Science, 260(5110):926-932.
Ning et al., 1996, "Intratumoral radioimmunotherapy of a human colon cancer xenograft using a sustained-release gel," Radiother Oncol., 39(2):179-189.
O'Hare et al., 1981, "Transformation of mouse fibroblasts to methotrexate resistance by a recombinant plasmid expressing a prokaryotic dihydrofolate reductase," Proc Natl Acad Sci USA, 78(3):1527-1531.
Park et al., 2005, "Biodegradable polymers for microencapsulation of drugs," Molecules, 10(1):146-161.
Pluckthun et al., 1989, "Expression of functional antibody Fv and Fab fragments in *Escherichia coli*," Methods Enzymol, 178:497-515.
Presta, 1992, "Antibody engineering," Curr Opin in Structural Biology, 2:593-596.
Putney et al., 1998, "Improving protein therapeutics with sustained-release formulations," Nat Biotechnol., 16(2):153-157.
Ridgway et al., 1996, "'Knobs-into-holes' engineering of antibody CH3 domains for heavy chain heterodimerization," Protein Eng., 9(7):617-621.
Riechmann et al., 1988, "Reshaping human antibodies for therapy," Nature, 332(6162):323-327.
Ruther et al., 1983, "Easy identification of cDNA clones," EMBO J., 2(10):1791-1794.

(56) References Cited

OTHER PUBLICATIONS

Santerre et al., 1984, "Expression of prokaryotic genes for hygromycin B and G418 resistance as dominant-selection markers in mouse L cells," Gene, 30(1-3):147-156.
Saudek et al. 1989, "A preliminary trial of the programmable implantable medication system for insulin delivery," N Engl J Med., 321(9):574-579.
Sefton, 1987, "Implantable pumps," Crit Rev Biomed Eng., 14(3):201-240.
Sikora, 1993, "Gene therapy for cancer," Trends in Biotechnology, 11(5):197-201.
Song et al., 1996, "Antibody mediated lung targeting of long-circulating emulsions," PDA J Pharm Sci Technol., 50(6):372-377.
Streltsov et al., 2004, "Structural evidence for evolution of shark Ig new antigen receptor variable domain antibodies from a cell-surface receptor," Proc Natl Acad Sci USA, 101(34):12444-12449.
Szybalska et al., 1962, "Genetics of human cell line. IV. DNA-mediated heritable transformation of a biochemical trait," Proc Natl Acad Sci USA, 48:2026-2034.
Buchwald et al., 1980, "Long-term, continuous intravenous heparin administration by an implantable infusion pump in ambulatory patients with recurrent venous thrombosis," Surgery, 88(4):507-516.
Campagne et al., 2018, "Integrated Pharmacokinetic/Pharmacodynamic Model of a Bispecific CD3xCD123 DART Molecule in Nonhuman Primates: Evaluation of Activity and Impact of Immunogenicity," Clin Cancer Res., 24(11):2631-2641.
Carter et al., 1992, "Humanization of an anti-p185HER2 antibody for human cancer therapy," Proc Natl Acad Sci USA, 89(10):4285-4289.
Chao et al., 2006, "Isolating and engineering human antibodies using yeast surface display," Nat Protoc., 1(2):755-768.
Chen et al., 1999, "Selection and analysis of an optimized anti-VEGF antibody: crystal structure of an affinity-matured Fab in complex with antigen," J Mol Biol., 293(4):865-881.
Chothia et al., 1987, "Canonical structures for the hypervariable regions of immunoglobulins," J Mol Biol., 196(4):901-917.
Clackson et al., 1991, "Making antibody fragments using phage display libraries," Nature, 352(6336):624-628.
Cleek et al., 1997, "Biodegradable Polymeric Carriers for a bFGF Antibody for Cardiovascular Application," Pro. Int'l. Symp. Control. Rel. Bioact. Mater, 24:853-854.
Cockett et al., 1990, "High level expression of tissue inhibitor of metalloproteinases in Chinese hamster ovary cells using glutamine synthetase gene amplification," Biotechnology (N Y), 8(7):662-667.
Colbere-Garapin et al., 1981, "A new dominant hybrid selective marker for higher eukaryotic cells," J Mol Biol., 150(1):1-14.
Crouse et al., 1983, "Expression and amplification of engineered mouse dihydrofolate reductase mimgenes," Mol Cell Biol., 3(2):257-266.

Dennis et al., 2002, "Albumin binding as a general strategy for improving the pharmacokinetics of proteins," J Biol Chem., 277(38):35035-35043.
Digiammarino et al., 2011, "Ligand association rates to the inner-variable-domain of a dual-variable-domain immunoglobulin are significantly impacted by linker design," Mabs, 3(5):487-494.
Taylor et al., 1992, "A transgenic mouse that expresses a diversity of human sequence heavy and light chain immunoglobulins," Nucleic Acids Res., 20(23):6287-6295.
Tolstoshev, 1993, "Gene therapy, concepts, current trials and future directions," Annu Rev Pharmacol Toxicol., 33:573-596.
Van Dijk et al., 2001, "Human antibodies as next generation therapeutics," Curr Opin Chem Biol., 5(4):368-374.
Van Heeke et al., 1989, "Expression of human asparagine synthetase in *Escherichia coli*," J Biol Chem., 264(10):5503-5509.
Wigler et al., 1977, "Transfer of purified herpes virus thymidine kinase gene to cultured mouse cells," Cell, 11(1):223-232.
Wigler et al., 1980, "Transformation of mammalian cells with an amplifiable dominant-acting gene," Proc Natl Acad Sci USA, 77(6):3567-3570.
Wolf et al., 2005, "Bites: bispecific antibody constructs with unique anti-tumor activity," Drug Discov Today, 10(18):1237-1244.
Woolven et al., 1999, "The structure of the llama heavy chain constant genes reveals a mechanism for heavy-chain antibody formation," Immunogenetics, 50(1-2):98-101.
Wu et al., 1987, "Receptor-mediated in vitro gene transformation by a soluble DNA carrier system," J Biol Chem., 262(10):4429-4432.
Wu et al., 1991, "Delivery systems for gene therapy," Biotherapy, 3(1):87-95.
Yuraszeck et al., 2017, "Translation and Clinical Development of Bispecific T-cell Engaging Antibodies for Cancer Treatment," Clin Pharmacol Ther., 101(5):634-645.
Zhang et al., 2015, "3D Structural Fluctuation of IgG1 Antibody Revealed by Individual Particle Electron Tomography," Sci Rep., 5:9803 and Corrigendum, 2016, Sci Rep., 6:17919.
Digiandomenico et al., 2014, "A multifunctional bispecific antibody protects against Pseudomonas aeruginosa," Sci Transl Med., 6(262):262ra155 (13 pages).
International Search Report and Written Opinion dated Aug. 12, 2019 of International Patent Application No. PCT/IB2019/052896 (published as WO 2019197979) (12 pages).
Kontermann et al., 2015, "Bispecific antibodies," Drug Discov Today, 20(7):838-847.
Schoonjans et al., 2000, "Fab chains as an efficient heterodimerization scaffold for the production of recombinant bispecific and trispecific antibody derivatives," J Immunol., 165(12):7050-7057.
Weidle et al., 2013, "The intriguing options of multispecific antibody formats for treatment of cancer," Cancer Genomics Proteomics, 10(1):1-18.
Yang et al., 2017, "Bispecific Antibodies as a Development Platform for New Concepts and Treatment Strategies," Int. J. Mol. Sci., 18(1):48 (21 pages).

\* cited by examiner

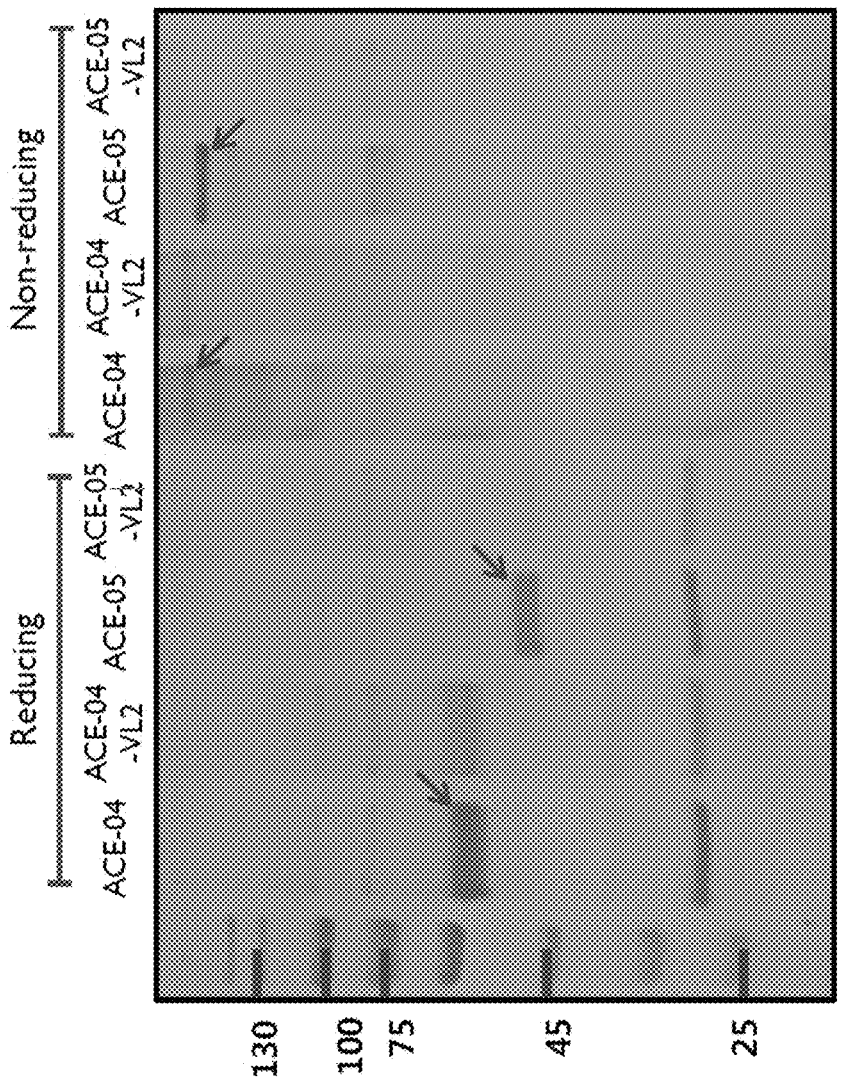
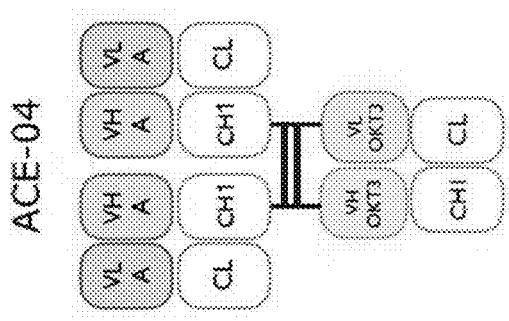
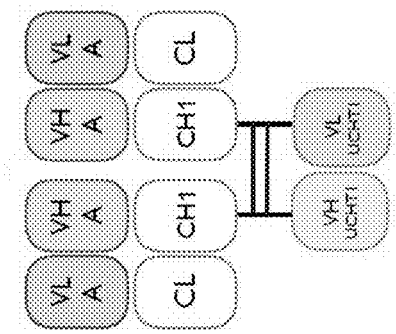
FIG. 4C
FIG. 4A
FIG. 4B

| Samples | PD-L1 interaction | | | | CD3 interaction | | | |
| --- | --- | --- | --- | --- | --- | --- | --- | --- |
| | $K_D$ | $K_{on}$ | $K_{dis}$ | $R^2$ | $K_D$ | $K_{on}$ | $K_{dis}$ | $R^2$ |
| ACE-05 | $1.09 \times 10^{-11}$ | $9.23 \times 10^5$ | $1.00 \times 10^{-5}$ | 0.9967 | $6.82 \times 10^{-9}$ | $2.55 \times 10^4$ | $1.74 \times 10^{-4}$ | 0.9989 |
| BiTE-05 | $3.44 \times 10^{-10}$ | $2.94 \times 10^5$ | $1.01 \times 10^{-4}$ | 0.9975 | $1.16 \times 10^{-9}$ | $1.83 \times 10^5$ | $2.11 \times 10^{-4}$ | 0.9961 |
| YBL-007 anti-PD-L1 | $1.32 \times 10^{-11}$ | $1.02 \times 10^6$ | $1.34 \times 10^{-5}$ | 0.9965 | - | - | - | - |
| UCHT1 anti-CD3 | - | - | - | - | $8.35 \times 10^{-10}$ | $2.41 \times 10^5$ | $2.01 \times 10^{-4}$ | 0.9907 |

FIG. 12C

Simultaneous binding of ACE-05

SEQUENCE LISTING

<160> NUMBER OF SEQ ID NOS: 135

<210> SEQ ID NO 1
<211> LENGTH: 369
<212> TYPE: PRT
<213> ORGANISM: Artificial Sequence
<220> FEATURE:
<223> OTHER INFORMATION: ACE-05-VH amino acid sequence

<400> SEQUENCE: 1

Gln Met Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Lys Pro Arg Asp Gly Tyr Asn Leu Val Ala Phe Asp Ile Trp Gly
            100                 105                 110

Gln Gly Thr Met Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Lys Val Glu Pro Lys Ser Cys
            210                 215                 220

Asp Lys Thr His Thr Cys Pro Pro Cys Pro Ala Pro Glu Leu Leu Gly
225                 230                 235                 240

Gly Pro Gly Gly Gly Gly Ser Glu Val Gln Leu Gln Gln Ser Gly Pro
            245                 250                 255

Glu Leu Val Lys Pro Gly Pro Ser Met Lys Ile Ser Cys Lys Ala Ser
            260                 265                 270

Gly Tyr Ser Phe Thr Gly Tyr Thr Met Asn Trp Val Lys Gln Ser His
            275                 280                 285

Gly Lys Asn Leu Glu Trp Met Gly Leu Ile Asn Pro Tyr Lys Gly Val
            290                 295                 300

Ser Thr Tyr Asn Gln Lys Phe Lys Asp Lys Ala Thr Leu Thr Val Asp
305                 310                 315                 320

Lys Ser Ser Ser Thr Ala Tyr Met Glu Leu Leu Ser Leu Thr Ser Glu
                325                 330                 335

Asp Ser Ala Val Tyr Tyr Cys Ala Arg Ser Gly Tyr Tyr Gly Asp Ser
            340                 345                 350

Asp Trp Tyr Phe Asp Val Trp Gly Gln Gly Thr Leu Thr Val Phe
            355                 360                 365

Ser

<210> SEQ ID NO 2
<211> LENGTH: 355
<212> TYPE: PRT
<213> ORGANISM: Artificial Sequence
<220> FEATURE:
<223> OTHER INFORMATION: ACE-05-VL amino acid sequence

<400> SEQUENCE: 2

Gln Met Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
            35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Lys Pro Arg Asp Gly Tyr Asn Leu Val Ala Phe Asp Ile Trp Gly
            100                 105                 110

Gln Gly Thr Met Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala

```
            130                 135                 140
Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
                195                 200                 205

Lys Pro Ser Asn Thr Lys Val Asp Lys Lys Val Glu Pro Lys Ser Cys
                210                 215                 220

Asp Lys Thr His Thr Cys Pro Pro Cys Pro Ala Pro Glu Leu Leu Gly
225                 230                 235                 240

Gly Pro Gly Gly Gly Ser Asp Ile Gln Met Thr Gln Thr Thr Ser
                245                 250                 255

Ser Leu Ser Ala Ser Leu Gly Asp Arg Val Thr Ile Ser Cys Arg Ala
                260                 265                 270

Ser Gln Asp Ile Arg Asn Tyr Leu Asn Trp Tyr Gln Gln Lys Pro Asp
                275                 280                 285

Gly Thr Val Lys Leu Leu Ile Tyr Tyr Thr Ser Arg Leu His Ser Gly
                290                 295                 300

Val Pro Ser Lys Phe Ser Gly Ser Gly Ser Gly Thr Asp Tyr Ser Leu
305                 310                 315                 320

Thr Ile Ser Asn Leu Glu Gln Glu Asp Ile Ala Thr Tyr Phe Cys Gln
                325                 330                 335

Gln Gly Asn Thr Leu Pro Trp Thr Phe Ala Gly Gly Thr Lys Leu Glu
                340                 345                 350

Ile Lys Arg
        355

<210> SEQ ID NO 3
<211> LENGTH: 218
<212> TYPE: PRT
<213> ORGANISM: Artificial Sequence
<220> FEATURE:
<223> OTHER INFORMATION: ACE-05-LC amino acid sequence

<400> SEQUENCE: 3

Gln Leu Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
                20                  25                  30

Tyr Asp Val His Trp Tyr Gln Gln Leu Pro Gly Ala Ala Pro Lys Leu
            35                  40                  45

Leu Ile Tyr Gly Asp Ile Asn Arg Pro Ser Gly Val Pro Asp Arg Phe
    50                  55                  60

Ser Gly Ser Lys Ser Gly Ile Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Gly Val Phe Gly Gly Gly Thr Lys Leu Thr Val Leu Arg
                100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
```

```
                130                 135                 140
Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
            165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 4
<211> LENGTH: 121
<212> TYPE: PRT
<213> ORGANISM: Artificial Sequence
<220> FEATURE:
<223> OTHER INFORMATION: Fab region (PD-L1) in VH of ACE-04, ACE-05, ACE-09, and ACE-12

<400> SEQUENCE: 4

```
Gln Met Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Lys Pro Arg Asp Gly Tyr Asn Leu Val Ala Phe Asp Ile Trp Gly
            100                 105                 110

Gln Gly Thr Met Val Thr Val Ser Ser
        115                 120
```

<210> SEQ ID NO 5
<211> LENGTH: 8
<212> TYPE: PRT
<213> ORGANISM: Artificial Sequence
<220> FEATURE:
<223> OTHER INFORMATION: Fab region (PD-L1) in CDR H1 of ACE-04, ACE-05, ACE-09, and ACE-12

<400> SEQUENCE: 5

```
Gly Gly Thr Phe Ser Ser Tyr Ala
1               5
```

<210> SEQ ID NO 6
<211> LENGTH: 8
<212> TYPE: PRT
<213> ORGANISM: Artificial Sequence
<220> FEATURE:
<223> OTHER INFORMATION: Fab region (PD-L1) in CDR H2 of ACE-04, ACE-05, ACE-09, and ACE-12

<400> SEQUENCE: 6

```
Ile Ile Pro Ile Leu Gly Ile Ala
1               5
```

<210> SEQ ID NO 7
<211> LENGTH: 14
<212> TYPE: PRT
<213> ORGANISM: Artificial Sequence
<220> FEATURE:
<223> OTHER INFORMATION: Fab region (PD-L1) CDR H3 of ACE-04, ACE-05, ACE-09, and ACE-12

<400> SEQUENCE: 7

Ala Lys Pro Arg Asp Gly Tyr Asn Leu Val Ala Phe Asp Ile
1               5                   10

<210> SEQ ID NO 8
<211> LENGTH: 112
<212> TYPE: PRT
<213> ORGANISM: Artificial Sequence
<220> FEATURE:
<223> OTHER INFORMATION: Fab region (PD-L1) in VL of ACE-04, ACE-05, ACE-09, and ACE-12

<400> SEQUENCE: 8

Gln Leu Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Ala Ala Pro Lys Leu
        35                  40                  45

Leu Ile Tyr Gly Asp Ile Asn Arg Pro Ser Gly Val Pro Asp Arg Phe
    50                  55                  60

Ser Gly Ser Lys Ser Gly Ile Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Gly Val Phe Gly Gly Gly Thr Lys Leu Thr Val Leu Arg
            100                 105                 110

<210> SEQ ID NO 9
<211> LENGTH: 9
<212> TYPE: PRT
<213> ORGANISM: Artificial Sequence
<220> FEATURE:
<223> OTHER INFORMATION: Fab region (PD-L1) in CDR L1 of ACE-04, ACE-05, ACE-09, and ACE-12

<400> SEQUENCE: 9

Ser Ser Asn Ile Gly Ala Gly Tyr Asp
1               5

<210> SEQ ID NO 10
<211> LENGTH: 3
<212> TYPE: PRT
<213> ORGANISM: Artificial Sequence
<220> FEATURE:
<223> OTHER INFORMATION: Fab region (PD-L1) in CDR L2 of ACE-04, ACE-05, ACE-09, and ACE-12

<400> SEQUENCE: 10

Gly Asp Ile
1

<210> SEQ ID NO 11
<211> LENGTH: 11
<212> TYPE: PRT

```
<213> ORGANISM: Artificial Sequence
<220> FEATURE:
<223> OTHER INFORMATION: Fab region (PD-L1) in CDR L3 of ACE-04, ACE-05,
      ACE-09, and ACE-12

<400> SEQUENCE: 11

Gln Ser Tyr Asp Ser Ser Leu Ser Gly Gly Val
1               5                   10

<210> SEQ ID NO 12
<211> LENGTH: 122
<212> TYPE: PRT
<213> ORGANISM: Artificial Sequence
<220> FEATURE:
<223> OTHER INFORMATION: Fv region (CD3) in VH of ACE-05, ACE-09,
      ACE-10, ACE-11, and ACE-12

<400> SEQUENCE: 12

Glu Val Gln Leu Gln Gln Ser Gly Pro Glu Leu Val Lys Pro Gly Pro
1               5                   10                  15

Ser Met Lys Ile Ser Cys Lys Ala Ser Gly Tyr Ser Phe Thr Gly Tyr
            20                  25                  30

Thr Met Asn Trp Val Lys Gln Ser His Gly Lys Asn Leu Glu Trp Met
        35                  40                  45

Gly Leu Ile Asn Pro Tyr Lys Gly Val Ser Thr Tyr Asn Gln Lys Phe
    50                  55                  60

Lys Asp Lys Ala Thr Leu Thr Val Asp Lys Ser Ser Ser Thr Ala Tyr
65                  70                  75                  80

Met Glu Leu Leu Ser Leu Thr Ser Glu Asp Ser Ala Val Tyr Tyr Cys
                85                  90                  95

Ala Arg Ser Gly Tyr Tyr Gly Asp Ser Asp Trp Tyr Phe Asp Val Trp
            100                 105                 110

Gly Gln Gly Thr Thr Leu Thr Val Phe Ser
        115                 120

<210> SEQ ID NO 13
<211> LENGTH: 10
<212> TYPE: PRT
<213> ORGANISM: Artificial Sequence
<220> FEATURE:
<223> OTHER INFORMATION: Fv region (CD3) in CDR H1 of ACE-05, ACE-09,
      ACE-10, ACE-11, and ACE-12

<400> SEQUENCE: 13

Gly Tyr Ser Phe Thr Gly Tyr Thr Met Asn
1               5                   10

<210> SEQ ID NO 14
<211> LENGTH: 10
<212> TYPE: PRT
<213> ORGANISM: Artificial Sequence
<220> FEATURE:
<223> OTHER INFORMATION: Fv region (CD3) in CDR H2 of ACE-05, ACE-09,
      ACE-10, ACE-11, and ACE-12

<400> SEQUENCE: 14

Leu Ile Asn Pro Tyr Lys Gly Val Ser Thr
1               5                   10

<210> SEQ ID NO 15
<211> LENGTH: 13
<212> TYPE: PRT
<213> ORGANISM: Artificial Sequence
<220> FEATURE:
```

<223> OTHER INFORMATION: Fv region (CD3) in CDR H3 of ACE-05, ACE-09,
      ACE-10, ACE-11, and ACE-12

<400> SEQUENCE: 15

Ser Gly Tyr Tyr Gly Asp Ser Asp Trp Tyr Phe Asp Val
1               5                   10

<210> SEQ ID NO 16
<211> LENGTH: 108
<212> TYPE: PRT
<213> ORGANISM: Artificial Sequence
<220> FEATURE:
<223> OTHER INFORMATION: Fv region (CD3) in VL of ACE-05, ACE-09,
      ACE-10, ACE-11, and ACE-12

<400> SEQUENCE: 16

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Arg Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Lys Phe Ser Gly
50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Trp
                85                  90                  95

Thr Phe Ala Gly Gly Thr Lys Leu Glu Ile Lys Arg
            100                 105

<210> SEQ ID NO 17
<211> LENGTH: 11
<212> TYPE: PRT
<213> ORGANISM: Artificial Sequence
<220> FEATURE:
<223> OTHER INFORMATION: Fv region (CD3) in CDR L1 of ACE-05, ACE-09,
      ACE-10, ACE-11, and ACE-12

<400> SEQUENCE: 17

Arg Ala Ser Gln Asp Ile Arg Asn Tyr Leu Asn
1               5                   10

<210> SEQ ID NO 18
<211> LENGTH: 7
<212> TYPE: PRT
<213> ORGANISM: Artificial Sequence
<220> FEATURE:
<223> OTHER INFORMATION: Fv region (CD3) in CDR L2 of ACE-05, ACE-09,
      ACE-10, ACE-11, and ACE-12

<400> SEQUENCE: 18

Tyr Thr Ser Arg Leu His Ser
1               5

<210> SEQ ID NO 19
<211> LENGTH: 9
<212> TYPE: PRT
<213> ORGANISM: Artificial Sequence
<220> FEATURE:
<223> OTHER INFORMATION: Fv region (CD3) in CDR L3 of ACE-05, ACE-09,
      ACE-10, ACE-11, and ACE-12

<400> SEQUENCE: 19

Gln Gln Gly Asn Thr Leu Pro Trp Thr
1               5

<210> SEQ ID NO 20
<211> LENGTH: 1110
<212> TYPE: DNA
<213> ORGANISM: Artificial Sequence
<220> FEATURE:
<223> OTHER INFORMATION: ACE-05-VH nucleotide sequence

<400> SEQUENCE: 20

| | | |
|---|---|---|
| cagatgcagc tggtgcagtc tggggctgag gtgaagaagc ctgggtcctc ggtgaaggtc | 60 |
| tcctgcaagg cttctggagg caccttcagc agctatgcta tcagctgggt gcgacaggcc | 120 |
| cctggacaag gcttgagtg gatgggaagg atcatccta tccttggtat agcaaactac | 180 |
| gcacagaagt tccagggcag agtcacgatt accgcggaca atccacgag cacagcctac | 240 |
| atggagctga gcagcctgag atctgaggac acggccgtgt attactgtgc gaaaccgaga | 300 |
| gatggctaca atttggttgc ttttgatatc tggggccaag gacgatggt caccgtctcc | 360 |
| tcagctagca ccaagggccc atcggtcttc cccctggcac cctcctccaa gagcacctct | 420 |
| gggggcacag cggccctggg ctgcctggtc aaggactact tccccgaacc ggtgacggtg | 480 |
| tcgtggaact caggcgccct gaccagcggc gtgcacacct tcccggctgt cctacagtcc | 540 |
| tcaggactct actccctcag cagcgtggtg accgtgccct ccagcagcct gggcacccag | 600 |
| acctacatct gcaacgtgaa tcacaagccc agcaacacca aggtggacaa gaaagttgag | 660 |
| cccaaatctt gtgacaaaac tcacacatgc ccaccgtgcc cagcacctga actcctgggg | 720 |
| ggaccgggcg gaggtgggag tgaggtgcag ctccagcagt ctggacctga gctggtgaag | 780 |
| cctggacctt caatgaagat atcctgcaag gcttctggtt actcattcac tggctacacc | 840 |
| atgaactggg tgaagcagag tcatggaaag aaccttgagt ggatgggact tattaatcct | 900 |
| tacaaaggtg ttagtaccta caaccagaag ttcaaggaca aggccacact gactgtagac | 960 |
| aagtcatcca gcacagccta catggaactc ctcagtctga catctgagga ctctgcagtc | 1020 |
| tattactgtg caagatcggg gtactacggt gatagtgact ggtacttcga tgtctgggc | 1080 |
| caggggacca cgctgaccgt cttctcataa | 1110 |

<210> SEQ ID NO 21
<211> LENGTH: 1068
<212> TYPE: DNA
<213> ORGANISM: Artificial Sequence
<220> FEATURE:
<223> OTHER INFORMATION: ACE-05-VL nucleotide sequence

<400> SEQUENCE: 21

| | | |
|---|---|---|
| cagatgcagc tggtgcagtc tggggctgag gtgaagaagc ctgggtcctc ggtgaaggtc | 60 |
| tcctgcaagg cttctggagg caccttcagc agctatgcta tcagctgggt gcgacaggcc | 120 |
| cctggacaag gcttgagtg gatgggaagg atcatccta tccttggtat agcaaactac | 180 |
| gcacagaagt tccagggcag agtcacgatt accgcggaca atccacgag cacagcctac | 240 |
| atggagctga gcagcctgag atctgaggac acggccgtgt attactgtgc gaaaccgaga | 300 |
| gatggctaca atttggttgc ttttgatatc tggggccaag gacgatggt caccgtctcc | 360 |
| tcagctagca ccaagggccc atcggtcttc cccctggcac cctcctccaa gagcacctct | 420 |
| gggggcacag cggccctggg ctgcctggtc aaggactact tccccgaacc ggtgacggtg | 480 |
| tcgtggaact caggcgccct gaccagcggc gtgcacacct tcccggctgt cctacagtcc | 540 |

```
tcaggactct actccctcag cagcgtggtg accgtgccct ccagcagcct gggcacccag      600
acctacatct gcaacgtgaa tcacaagccc agcaacacca aggtggacaa gaaagttgag      660
cccaaatctt gtgacaaaac tcacacatgc ccaccgtgcc cagcacctga actcctgggg      720
ggaccgggcg aggtgggag tgacatccag atgacccaga ccacctcctc cctgtctgcc       780
tccctgggcg acagagtcac catcagttgc agggcaagtc aggacattag aaattattta      840
aactggtatc aacagaaacc agatggaact gttaaactcc tgatctacta cacatcaaga      900
ttacactcag gagtcccatc aaagttcagt ggcagtgggt ctggaacaga ttattctctc      960
accattagca acctggagca agaggatatt gccacttact tttgccaaca gggtaatacg     1020
cttccgtgga cgttcgctgg aggcaccaag ctggaaatca aacggtaa                 1068

<210> SEQ ID NO 22
<211> LENGTH: 657
<212> TYPE: DNA
<213> ORGANISM: Artificial Sequence
<220> FEATURE:
<223> OTHER INFORMATION: ACE-05-LC nucleotide sequence

<400> SEQUENCE: 22
cagctcgtgc tgactcagcc gccctcagtg tctggggccc cagggcagag ggtcaccatc       60
tcctgcactg ggagcagctc caacatcggg gcaggttatg atgtacactg gtatcagcaa      120
cttccaggag cagcccccaa actcctcatc tatggcgaca tcaatcggcc ctcaggggtc      180
cctgaccgat tctctggctc caagtctggc atctcagcct ccctggctat cactgggctc      240
caggctgagg acgaggctga ttattactgc cagtcctatg acagcagcct gagtgggggg      300
gtgttcggcg agggaccaa gctgaccgtc ctaagaaccg tggctgcacc atctgtcttc       360
atcttcccgc catctgatga gcagttgaaa tctggaactg cctctgttgt gtgcctgctg      420
aataacttct atcccagaga ggccaaagta cagtggaagg tggataacgc cctccaatcg      480
ggtaactccc aggagagtgt cacagagcag gacagcaagg acagcaccta cagcctcagc      540
agcaccctga cgctgagcaa agcagactac gagaaacaca agtctacgc ctgcgaagtc       600 acccatcagg gcctgagctc gcccgtcaca aagagcttca caggggaga gtgttaa         657

<210> SEQ ID NO 23
<211> LENGTH: 369
<212> TYPE: PRT
<213> ORGANISM: Artificial Sequence
<220> FEATURE:
<223> OTHER INFORMATION: ACE-10-VH amino acid sequence

<400> SEQUENCE: 23

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
```

```
            100                 105                 110
Ala Gly Thr Thr Val Thr Val Ser Ala Ala Ser Thr Lys Gly Pro Ser
            115                 120                 125

Val Phe Pro Leu Ala Pro Ser Ser Lys Ser Thr Ser Gly Gly Thr Ala
            130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Val Glu Pro Lys Ser Cys
            210                 215                 220

Asp Lys Thr His Thr Cys Pro Pro Cys Pro Ala Pro Glu Leu Leu Gly
225                 230                 235                 240

Gly Pro Gly Gly Gly Gly Ser Glu Val Gln Leu Gln Gln Ser Gly Pro
            245                 250                 255

Glu Leu Val Lys Pro Gly Pro Ser Met Lys Ile Ser Cys Lys Ala Ser
            260                 265                 270

Gly Tyr Ser Phe Thr Gly Tyr Thr Met Asn Trp Val Lys Gln Ser His
            275                 280                 285

Gly Lys Asn Leu Glu Trp Met Gly Leu Ile Asn Pro Tyr Lys Gly Val
            290                 295                 300

Ser Thr Tyr Asn Gln Lys Phe Lys Asp Lys Ala Thr Leu Thr Val Asp
305                 310                 315                 320

Lys Ser Ser Ser Thr Ala Tyr Met Glu Leu Leu Ser Leu Thr Ser Glu
            325                 330                 335

Asp Ser Ala Val Tyr Tyr Cys Ala Arg Ser Gly Tyr Tyr Gly Asp Ser
            340                 345                 350

Asp Trp Tyr Phe Asp Val Trp Gly Gln Gly Thr Thr Leu Thr Val Phe
            355                 360                 365

Ser

<210> SEQ ID NO 24
<211> LENGTH: 355
<212> TYPE: PRT
<213> ORGANISM: Artificial Sequence
<220> FEATURE:
<223> OTHER INFORMATION: ACE-10-VL amino acid sequence

<400> SEQUENCE: 24

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
            35                  40                  45

Gly Ala Ile Tyr Pro Gly Asn Gly Asp Thr Ser Tyr Asn Gln Lys Phe
        50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
            85                  90                  95
```

-continued

Ala Arg Ser Thr Tyr Tyr Gly Gly Asp Trp Tyr Phe Asn Val Trp Gly
                100                 105                 110

Ala Gly Thr Thr Val Thr Val Ser Ala Ala Ser Thr Lys Gly Pro Ser
                115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
                195                 200                 205

Lys Pro Ser Asn Thr Lys Val Asp Lys Val Glu Pro Lys Ser Cys
                210                 215                 220

Asp Lys Thr His Thr Cys Pro Pro Cys Pro Ala Pro Glu Leu Leu Gly
225                 230                 235                 240

Gly Pro Gly Gly Gly Ser Asp Ile Gln Met Thr Gln Thr Thr Ser
                245                 250                 255

Ser Leu Ser Ala Ser Leu Gly Asp Arg Val Thr Ile Ser Cys Arg Ala
                260                 265                 270

Ser Gln Asp Ile Arg Asn Tyr Leu Asn Trp Tyr Gln Gln Lys Pro Asp
                275                 280                 285

Gly Thr Val Lys Leu Leu Ile Tyr Tyr Thr Ser Arg Leu His Ser Gly
                290                 295                 300

Val Pro Ser Lys Phe Ser Gly Ser Gly Ser Gly Thr Asp Tyr Ser Leu
305                 310                 315                 320

Thr Ile Ser Asn Leu Glu Gln Glu Asp Ile Ala Thr Tyr Phe Cys Gln
                325                 330                 335

Gln Gly Asn Thr Leu Pro Trp Thr Phe Ala Gly Gly Thr Lys Leu Glu
                340                 345                 350

Ile Lys Arg
       355

<210> SEQ ID NO 25
<211> LENGTH: 213
<212> TYPE: PRT
<213> ORGANISM: Artificial Sequence
<220> FEATURE:
<223> OTHER INFORMATION: ACE-10-LC amino acid sequence

<400> SEQUENCE: 25

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
                20                  25                  30

His Trp Phe Gln Gln Lys Pro Gly Ser Ser Pro Lys Pro Trp Ile Tyr
                35                  40                  45

Ala Thr Ser Asn Leu Ala Ser Gly Val Pro Val Arg Phe Ser Gly Ser
                50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

-continued

```
Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 26
<211> LENGTH: 121
<212> TYPE: PRT
<213> ORGANISM: Artificial Sequence
<220> FEATURE:
<223> OTHER INFORMATION: Fab region (CD20) in VH of ACE-10

<400> SEQUENCE: 26

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala
        115                 120

<210> SEQ ID NO 27
<211> LENGTH: 8
<212> TYPE: PRT
<213> ORGANISM: Artificial Sequence
<220> FEATURE:
<223> OTHER INFORMATION: Fab region (CD20) in CDR H1 of ACE-10

<400> SEQUENCE: 27

Gly Tyr Thr Phe Thr Ser Tyr Asn
1               5

<210> SEQ ID NO 28
<211> LENGTH: 8
<212> TYPE: PRT
<213> ORGANISM: Artificial Sequence
<220> FEATURE:
<223> OTHER INFORMATION: Fab region (CD20) in CDR H2 of ACE-10
```

<400> SEQUENCE: 28

Ile Tyr Pro Gly Asn Gly Asp Thr
1               5

<210> SEQ ID NO 29
<211> LENGTH: 14
<212> TYPE: PRT
<213> ORGANISM: Artificial Sequence
<220> FEATURE:
<223> OTHER INFORMATION: Fab region (CD20) in CDR H3 of ACE-10

<400> SEQUENCE: 29

Ala Arg Ser Thr Tyr Tyr Gly Gly Asp Trp Tyr Phe Asn Val
1               5                   10

<210> SEQ ID NO 30
<211> LENGTH: 107
<212> TYPE: PRT
<213> ORGANISM: Artificial Sequence
<220> FEATURE:
<223> OTHER INFORMATION: Fab region (CD20) in VL of ACE-10

<400> SEQUENCE: 30

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
            20                  25                  30

His Trp Phe Gln Gln Lys Pro Gly Ser Ser Pro Lys Pro Trp Ile Tyr
        35                  40                  45

Ala Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys Arg
            100                 105

<210> SEQ ID NO 31
<211> LENGTH: 5
<212> TYPE: PRT
<213> ORGANISM: Artificial Sequence
<220> FEATURE:
<223> OTHER INFORMATION: Fab region (CD20) in CDR L1 of ACE-10

<400> SEQUENCE: 31

Ser Ser Val Ser Tyr
1               5

<210> SEQ ID NO 32
<211> LENGTH: 3
<212> TYPE: PRT
<213> ORGANISM: Artificial Sequence
<220> FEATURE:
<223> OTHER INFORMATION: Fab region (CD20) in CDR L2 of ACE-10

<400> SEQUENCE: 32

Ala Thr Ser
1

<210> SEQ ID NO 33
<211> LENGTH: 9

<212> TYPE: PRT
<213> ORGANISM: Artificial Sequence
<220> FEATURE:
<223> OTHER INFORMATION: Fab region (CD20) in CDR L3 of ACE-10

<400> SEQUENCE: 33

Gln Gln Trp Thr Ser Asn Pro Pro Thr
1               5

<210> SEQ ID NO 34
<211> LENGTH: 1110
<212> TYPE: DNA
<213> ORGANISM: Artificial Sequence
<220> FEATURE:
<223> OTHER INFORMATION: ACE-10-VH nucleotide sequence

<400> SEQUENCE: 34

| | | | | |
|---|---|---|---|---|
| caggtgcagc | tgcagcagcc | tggagccgag | ctggtgaagc | ccggcgccag cgtgaagatg | 60 |
| agctgcaagg | ccagcggcta | caccttcacc | agctacaaca | tgcactgggt gaagcagacc | 120 |
| cctggaagag | gactggagtg | gatcggcgcc | atctaccccg | gcaacggcga caccagctac | 180 |
| aaccagaagt | tcaagggcaa | ggccacactg | accgccgaca | agagcagcag caccgcctac | 240 |
| atgcagctga | gcagcctgac | cagcgaggac | agcgccgtgt | actactgcgc ccgcagcacc | 300 |
| tactacggcg | gcgactggta | cttcaacgtg | tggggagctg | gaaccaccgt gaccgtgagc | 360 |
| gccgctagca | ccaagggccc | atcggtcttc | cccctggcac | cctcctccaa gagcacctct | 420 |
| ggggggcacag | cggccctggg | ctgcctggtc | aaggactact | tccccgaacc ggtgacggtg | 480 |
| tcgtggaact | caggcgccct | gaccagcggc | gtgcacacct | tcccggctgt cctacagtcc | 540 |
| tcaggactct | actccctcag | cagcgtggtg | accgtgccct | ccagcagcct gggcacccag | 600 |
| acctacatct | gcaacgtgaa | tcacaagccc | agcaacacca | aggtggacaa gaaggttgag | 660 |
| cccaaatctt | gtgacaaaac | tcacacatgc | ccaccgtgcc | cagcacctga actcctgggg | 720 |
| ggaccgggcg | gaggtgggag | tgaggtgcag | ctccagcagt | ctggacctga gctggtgaag | 780 |
| cctggacctt | caatgaagat | atcctgcaag | gcttctggtt | actcattcac tggctacacc | 840 |
| atgaactggg | tgaagcagag | tcatggaaag | aaccttgagt | ggatgggact tattaatcct | 900 |
| tacaaaggtg | ttagtaccta | caaccagaag | ttcaaggaca | aggccacact gactgtagac | 960 |
| aagtcatcca | gcacagccta | catggaactc | ctcagtctga | catctgagga ctctgcagtc | 1020 |
| tattactgtg | caagatcggg | gtactacggt | gatagtgact | ggtacttcga tgtctggggc | 1080 |
| caggggacca | cgctgaccgt | cttctcataa | | | 1110 |

<210> SEQ ID NO 35
<211> LENGTH: 1068
<212> TYPE: DNA
<213> ORGANISM: Artificial Sequence
<220> FEATURE:
<223> OTHER INFORMATION: ACE-10-VL nucleotide sequence

<400> SEQUENCE: 35

| | | | | |
|---|---|---|---|---|
| caggtgcagc | tgcagcagcc | tggagccgag | ctggtgaagc | ccggcgccag cgtgaagatg | 60 |
| agctgcaagg | ccagcggcta | caccttcacc | agctacaaca | tgcactgggt gaagcagacc | 120 |
| cctggaagag | gactggagtg | gatcggcgcc | atctaccccg | gcaacggcga caccagctac | 180 |
| aaccagaagt | tcaagggcaa | ggccacactg | accgccgaca | agagcagcag caccgcctac | 240 |
| atgcagctga | gcagcctgac | cagcgaggac | agcgccgtgt | actactgcgc ccgcagcacc | 300 |
| tactacggcg | gcgactggta | cttcaacgtg | tggggagctg | gaaccaccgt gaccgtgagc | 360 |

```
gccgctagca ccaagggccc atcggtcttc ccctggcac cctcctccaa gagcacctct    420
gggggcacag cggccctggg ctgcctggtc aaggactact ccccgaacc ggtgacggtg    480 tcgtggaact caggcgccct gaccagcggc gtgcacacct tcccggctgt cctacagtcc    540
tcaggactct actccctcag cagcgtggtg accgtgccct ccagcagcct gggcacccag    600
acctacatct gcaacgtgaa tcacaagccc agcaacacca aggtggacaa gaaggttgag    660
cccaaatctt gtgacaaaac tcacacatgc ccaccgtgcc cagcacctga actcctgggg    720
ggaccgggcg gaggtgggag tgacatccag atgacccaga ccacctcctc cctgtctgcc    780
tccctgggcg acagagtcac catcagttgc agggcaagtc aggacattag aaattattta    840
aactggtatc aacagaaacc agatggaact gttaaactcc tgatctacta cacatcaaga    900
ttacactcag gagtcccatc aaagttcagt ggcagtgggt ctggaacaga ttattctctc    960
accattagca acctggagca agaggatatt gccacttact tttgccaaca gggtaatacg   1020
cttccgtgga cgttcgctgg aggcaccaag ctggaaatca acggtaa              1068

<210> SEQ ID NO 36
<211> LENGTH: 642
<212> TYPE: DNA
<213> ORGANISM: Artificial Sequence
<220> FEATURE:
<223> OTHER INFORMATION: ACE-10-LC nucleotide sequence

<400> SEQUENCE: 36
cagatcgtgc tgagccagag ccctgctatc ctgagcgcca gccctggcga gaaggtgacc     60
atgacctgcc gcgccagcag cagcgtgagc tacatccact ggttccagca gaagcccggc    120
agcagcccca gccctggat ctacgccacc agcaacctgg ccagcggagt gcctgtgcgc    180
ttcagcggca gcggcagcgg caccagctac agcctgacca tcagcagagt ggaggctgag    240
gacgccgcta cctactactg ccagcagtgg accagcaacc cccccacctt cggcggcggc    300
accaagctgg agatcaagag aaccgtggct gcaccatctg tcttcatctt cccgccatct    360
gatgagcagt tgaaatctgg aactgcctct gttgtgtgcc tgctgaataa cttctatccc    420
agagaggcca aagtacagtg gaaggtggat aacgccctcc aatcgggtaa ctcccaggag    480
agtgtcacag agcaggacag caaggacagc acctacagcc tcagcagcac cctgacgctg    540
agcaaagcag actacgagaa acacaaagtc tacgcctgcg aagtcaccca tcagggcctg    600
agctcgcccg tcacaaagag cttcaacagg ggagagtgtt ag                      642

<210> SEQ ID NO 37
<211> LENGTH: 367
<212> TYPE: PRT
<213> ORGANISM: Artificial Sequence
<220> FEATURE:
<223> OTHER INFORMATION: ACE-11-VH amino acid sequence

<400> SEQUENCE: 37

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60
```

-continued

```
Ser Arg Leu Ser Ile Asn Lys Asp Asn Ser Lys Ser Gln Val Phe Phe
 65                  70                  75                  80

Lys Met Asn Ser Leu Gln Ser Asn Asp Thr Ala Ile Tyr Tyr Cys Ala
                 85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Gly Gly Gly Gly Ser Glu Val Gln Leu Gln Gln Ser Gly Pro Glu Leu
                245                 250                 255

Val Lys Pro Gly Pro Ser Met Lys Ile Ser Cys Lys Ala Ser Gly Tyr
            260                 265                 270

Ser Phe Thr Gly Tyr Thr Met Asn Trp Val Lys Gln Ser His Gly Lys
        275                 280                 285

Asn Leu Glu Trp Met Gly Leu Ile Asn Pro Tyr Lys Gly Val Ser Thr
290                 295                 300

Tyr Asn Gln Lys Phe Lys Asp Lys Ala Thr Leu Thr Val Asp Lys Ser
305                 310                 315                 320

Ser Ser Thr Ala Tyr Met Glu Leu Leu Ser Leu Thr Ser Glu Asp Ser
                325                 330                 335

Ala Val Tyr Tyr Cys Ala Arg Ser Gly Tyr Tyr Gly Asp Ser Asp Trp
            340                 345                 350

Tyr Phe Asp Val Trp Gly Gln Gly Thr Thr Leu Thr Val Phe Ser
        355                 360                 365
```

<210> SEQ ID NO 38
<211> LENGTH: 353
<212> TYPE: PRT
<213> ORGANISM: Artificial Sequence
<220> FEATURE:
<223> OTHER INFORMATION: ACE-11-VL amino acid sequence

<400> SEQUENCE: 38

```
Gln Val Gln Leu Lys Gln Ser Gly Pro Gly Leu Val Gln Pro Ser Gln
  1               5                  10                  15

Ser Leu Ser Ile Thr Cys Thr Val Ser Gly Phe Ser Leu Thr Asn Tyr
                 20                  25                  30

Gly Val His Trp Val Arg Gln Ser Pro Gly Lys Gly Leu Glu Trp Leu
             35                  40                  45

Gly Val Ile Trp Ser Gly Gly Asn Thr Asp Tyr Asn Thr Pro Phe Thr
         50                  55                  60
```

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
            85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
            115                 120                 125

Pro Leu Ala Pro Ser Ser Lys Ser Thr Ser Gly Gly Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Gly Gly Gly Gly Ser Asp Ile Gln Met Thr Gln Thr Thr Ser Ser Leu
            245                 250                 255

Ser Ala Ser Leu Gly Asp Arg Val Thr Ile Ser Cys Arg Ala Ser Gln
            260                 265                 270

Asp Ile Arg Asn Tyr Leu Asn Trp Tyr Gln Gln Lys Pro Asp Gly Thr
            275                 280                 285

Val Lys Leu Leu Ile Tyr Tyr Thr Ser Arg Leu His Ser Gly Val Pro
            290                 295                 300

Ser Lys Phe Ser Gly Ser Gly Ser Gly Thr Asp Tyr Ser Leu Thr Ile
305                 310                 315                 320

Ser Asn Leu Glu Gln Glu Asp Ile Ala Thr Tyr Phe Cys Gln Gln Gly
            325                 330                 335

Asn Thr Leu Pro Trp Thr Phe Ala Gly Gly Thr Lys Leu Glu Ile Lys
            340                 345                 350

Arg

<210> SEQ ID NO 39
<211> LENGTH: 214
<212> TYPE: PRT
<213> ORGANISM: Artificial Sequence
<220> FEATURE:
<223> OTHER INFORMATION: ACE-11-LC amino acid sequence

<400> SEQUENCE: 39

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
            35                  40                  45

Lys Tyr Ala Ser Glu Ser Ile Ser Gly Ile Pro Ser Arg Phe Ser Gly
        50                  55                  60

Ser Gly Ser Gly Thr Asp Phe Thr Leu Ser Ile Asn Ser Val Glu Ser

Glu Asp Ile Ala Asp Tyr Tyr Cys Gln Gln Asn Asn Asn Trp Pro Thr
            85                  90                  95

Thr Phe Gly Ala Gly Thr Lys Leu Glu Leu Lys Arg Thr Val Ala Ala
        100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 40
<211> LENGTH: 119
<212> TYPE: PRT
<213> ORGANISM: Artificial Sequence
<220> FEATURE:
<223> OTHER INFORMATION: Fab region (CD20) in VH of ACE-11

<400> SEQUENCE: 40

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala
        115

<210> SEQ ID NO 41
<211> LENGTH: 8
<212> TYPE: PRT
<213> ORGANISM: Artificial Sequence
<220> FEATURE:
<223> OTHER INFORMATION: Fab region (CD20) in CDR H1 of ACE-11

<400> SEQUENCE: 41

Gly Phe Ser Leu Thr Asn Tyr Gly
1               5

<210> SEQ ID NO 42
<211> LENGTH: 7

```
<212> TYPE: PRT
<213> ORGANISM: Artificial Sequence
<220> FEATURE:
<223> OTHER INFORMATION: Fab region (CD20) in CDR H2 of ACE-11

<400> SEQUENCE: 42

Ile Trp Ser Gly Gly Asn Thr
1               5

<210> SEQ ID NO 43
<211> LENGTH: 13
<212> TYPE: PRT
<213> ORGANISM: Artificial Sequence
<220> FEATURE:
<223> OTHER INFORMATION: Fab region (CD20) in CDR H3 of ACE-11

<400> SEQUENCE: 43

Ala Arg Ala Leu Thr Tyr Tyr Asp Tyr Glu Phe Ala Tyr
1               5                   10

<210> SEQ ID NO 44
<211> LENGTH: 108
<212> TYPE: PRT
<213> ORGANISM: Artificial Sequence
<220> FEATURE:
<223> OTHER INFORMATION: Fab region (CD20) in VL of ACE-11

<400> SEQUENCE: 44

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys Arg
            100                 105

<210> SEQ ID NO 45
<211> LENGTH: 6
<212> TYPE: PRT
<213> ORGANISM: Artificial Sequence
<220> FEATURE:
<223> OTHER INFORMATION: Fab region (CD20) in CDR L1 of ACE-11

<400> SEQUENCE: 45

Gln Ser Ile Gly Thr Asn
1               5

<210> SEQ ID NO 46
<211> LENGTH: 3
<212> TYPE: PRT
<213> ORGANISM: Artificial Sequence
<220> FEATURE:
<223> OTHER INFORMATION: Fab region (CD20) in CDR L2 of ACE-11

<400> SEQUENCE: 46

Tyr Ala Ser
1
```

<210> SEQ ID NO 47
<211> LENGTH: 9
<212> TYPE: PRT
<213> ORGANISM: Artificial Sequence
<220> FEATURE:
<223> OTHER INFORMATION: Fab region (CD20) in CDR L3 of ACE-11

<400> SEQUENCE: 47

Gln Gln Asn Asn Asn Trp Pro Thr Thr
1               5

<210> SEQ ID NO 48
<211> LENGTH: 1104
<212> TYPE: DNA
<213> ORGANISM: Artificial Sequence
<220> FEATURE:
<223> OTHER INFORMATION: ACE-11-VH nucleotide sequence

<400> SEQUENCE: 48

```
caagtccaac tgaaacaatc gggtccgggt ctggtccaac cgtcccaatc actgagcatc      60
acctgtaccg tgtcgggctt ctcgctgacc aattatggtg tgcattgggt tcgtcagagt     120
ccgggcaaag gtctggaatg gctgggcgtt atttggtccg gcggtaatac cgattacaac     180
accccgttta cgagtcgcct gtccatcaat aaagacaact cgaaaagcca ggtgttttc      240
aaaatgaatt cactgcaatc gaacgatacc gcgatttatt actgcgcacg tgctctgacg     300
tattacgact atgaatttgc ctactggggc cagggtaccc tggtgacggt tagcgcggct     360
agcaccaagg gcccatcggt cttccccctg gcaccctcct ccaagagcac ctctgggggc     420
acagcggccc tgggctgcct ggtcaaggac tacttccccg aaccggtgac ggtgtcgtgg     480
aactcaggcg ccctgaccag cggcgtgcac accttcccgg ctgtcctaca gtcctcagga     540
ctctactccc tcagcagcgt ggtgaccgtg ccctccagca gcctgggcac ccagacctac     600
atctgcaacg tgaatcacaa gcccagcaac accaaggtgg acaagaaggt tgagcccaaa     660
tcttgtgaca aaactcacac atgcccaccg tgcccagcac ctgaactcct ggggggaccg     720
ggcggaggtg ggagtgaggt gcagctccag cagtctggac ctgagctggt gaagcctgga     780
ccttcaatga agatatcctg caaggcttct ggttactcat tcactggcta ccatatgaac     840
tgggtgaagc agagtcatgg aaagaacctt gagtggatgg gacttattaa tccttacaaa     900
ggtgttagta cctacaacca gaagttcaag gacaaggcca cactgactgt agacaagtca     960
tccagcacag cctacatgga actcctcagt ctgacatctg aggactctgc agtctattac    1020
tgtgcaagat cggggtacta cggtgatagt gactggtact cgatgtctg gggccagggg    1080
accacgctga ccgtcttctc ataa                                            1104
```

<210> SEQ ID NO 49
<211> LENGTH: 1062
<212> TYPE: DNA
<213> ORGANISM: Artificial Sequence
<220> FEATURE:
<223> OTHER INFORMATION: ACE-11-VL nucleotide sequence

<400> SEQUENCE: 49

```
caagtccaac tgaaacaatc gggtccgggt ctggtccaac cgtcccaatc actgagcatc      60
acctgtaccg tgtcgggctt ctcgctgacc aattatggtg tgcattgggt tcgtcagagt     120
ccgggcaaag gtctggaatg gctgggcgtt atttggtccg gcggtaatac cgattacaac     180
accccgttta cgagtcgcct gtccatcaat aaagacaact cgaaaagcca ggtgttttc      240
```

```
aaaatgaatt cactgcaatc gaacgatacc gcgatttatt actgcgcacg tgctctgacg    300
tattacgact atgaatttgc ctactggggc cagggtaccc tggtgacggt tagcgcggct    360
agcaccaagg gcccatcggt cttccccctg gcaccctcct ccaagagcac ctctgggggc    420
acagcggccc tgggctgcct ggtcaaggac tacttccccg aaccggtgac ggtgtcgtgg    480
aactcaggcg ccctgaccag cggcgtgcac accttcccgg ctgtcctaca gtcctcagga    540
ctctactccc tcagcagcgt ggtgaccgtg ccctccagca gctgggcac ccagacctac     600 atctgcaacg tgaatcacaa gcccagcaac accaaggtgg acaagaaggt tgagcccaaa    660
tcttgtgaca aaactcacac atgcccaccg tgcccagcac ctgaactcct ggggggaccg    720
ggcggaggtg ggagtgacat ccagatgacc cagaccacct cctccctgtc tgcctccctg    780
ggcgacagag tcaccatcag ttgcagggca agtcaggaca ttagaaatta tttaaactgg    840
tatcaacaga accagatgg aactgttaaa ctcctgatct actacacatc aagattacac      900
tcaggagtcc catcaaagtt cagtggcagt gggtctggaa cagattattc tctcaccatt    960
agcaacctgg agcaagagga tattgccact tacttttgcc aacagggtaa tacgcttccg   1020
tggacgttcg ctggaggcac caagctggaa atcaaacggt aa                      1062

<210> SEQ ID NO 50
<211> LENGTH: 645
<212> TYPE: DNA
<213> ORGANISM: Artificial Sequence
<220> FEATURE:
<223> OTHER INFORMATION: ACE-11-LC nucleotide sequence

<400> SEQUENCE: 50
gatattctgc tgacccagag cccggtgatc ctgagtgttt cccgggcga acgtgtgtca      60 ttttcgtgtc gcgcgagcca gtctattggt accaatatcc actggtatca gcaacgtacg    120
aacggctctc cgcgcctgct gattaaatac gccagtgaat ccatttcagg catcccgagc    180
cgcttttcgg gcagcggttc tggcaccgat ttcacgctga gtattaactc cgtggaatca    240
gaagatatcg cagactatta ctgccagcaa acaataact ggccgaccac gtttggtgct     300
ggcaccaaac tggaactgaa agaaccgtg gctgcaccat ctgtcttcat cttcccgcca     360
tctgatgagc agttgaaatc tggaactgcc tctgttgtgt gcctgctgaa taacttctat    420
cccagagagg ccaaagtaca gtggaaggtg dataacgccc tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gttaa                    645

<210> SEQ ID NO 51
<211> LENGTH: 120
<212> TYPE: PRT
<213> ORGANISM: Artificial Sequence
<220> FEATURE:
<223> OTHER INFORMATION: Fab region (Her2) in VH of ACE-00

<400> SEQUENCE: 51

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45
```

```
Ala Arg Ile Tyr Pro Thr Asn Gly Tyr Thr Arg Tyr Ala Asp Ser Val
        50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
            115                 120

<210> SEQ ID NO 52
<211> LENGTH: 108
<212> TYPE: PRT
<213> ORGANISM: Artificial Sequence
<220> FEATURE:
<223> OTHER INFORMATION: Fab region (Her2) in VL of ACE-00

<400> SEQUENCE: 52

Asp Ile Gln Met Thr Gln Ser Pro Ser Ser Leu Ser Ala Ser Val Gly
 1                   5                  10                  15

Asp Arg Val Thr Ile Thr Cys Arg Ala Ser Gln Asp Val Asn Thr Ala
                20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
 50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg
            100                 105

<210> SEQ ID NO 53
<211> LENGTH: 121
<212> TYPE: PRT
<213> ORGANISM: Artificial Sequence
<220> FEATURE:
<223> OTHER INFORMATION: Fv region (TNF alpha) in VH of ACE-00

<400> SEQUENCE: 53

Glu Val Gln Leu Val Glu Ser Gly Gly Gly Leu Val Gln Pro Gly Arg
 1                   5                  10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
            35                  40                  45

Ser Ala Ile Thr Trp Asn Ser Gly His Ile Asp Tyr Ala Asp Ser Val
 50                  55                  60

Glu Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser
```

```
<210> SEQ ID NO 54
<211> LENGTH: 108
<212> TYPE: PRT
<213> ORGANISM: Artificial Sequence
<220> FEATURE:
<223> OTHER INFORMATION: Fv region (TNF alpha) in VL of ACE-00

<400> SEQUENCE: 54

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys Arg
            100                 105

<210> SEQ ID NO 55
<211> LENGTH: 15
<212> TYPE: PRT
<213> ORGANISM: Artificial Sequence
<220> FEATURE:
<223> OTHER INFORMATION: Core hinge region sequence of IgG1

<400> SEQUENCE: 55

Glu Pro Lys Ser Cys Asp Lys Thr His Thr Cys Pro Pro Cys Pro
1               5                   10                  15

<210> SEQ ID NO 56
<211> LENGTH: 12
<212> TYPE: PRT
<213> ORGANISM: Artificial Sequence
<220> FEATURE:
<223> OTHER INFORMATION: Core hinge region sequence of IgG2

<400> SEQUENCE: 56

Glu Arg Lys Cys Cys Val Glu Cys Pro Pro Cys Pro
1               5                   10

<210> SEQ ID NO 57
<211> LENGTH: 61
<212> TYPE: PRT
<213> ORGANISM: Artificial Sequence
<220> FEATURE:
<223> OTHER INFORMATION: Core hinge region sequence of IgG3

<400> SEQUENCE: 57

Glu Leu Lys Thr Pro Leu Asp Thr Thr His Thr Cys Pro Arg Cys Pro
1               5                   10                  15

Glu Pro Lys Ser Cys Asp Thr Pro Pro Cys Pro Arg Cys Pro Glu
            20                  25                  30

Pro Lys Ser Cys Asp Thr Pro Pro Cys Pro Arg Cys Pro Glu Pro
        35                  40                  45

Lys Ser Cys Asp Thr Pro Pro Cys Pro Arg Cys Pro
```

<210> SEQ ID NO 58
<211> LENGTH: 12
<212> TYPE: PRT
<213> ORGANISM: Artificial Sequence
<220> FEATURE:
<223> OTHER INFORMATION: Core hinge region sequence of IgG4

<400> SEQUENCE: 58

```
Glu Ser Lys Tyr Gly Pro Pro Cys Pro Ser Cys Pro
1               5                   10
```

<210> SEQ ID NO 59
<211> LENGTH: 106
<212> TYPE: PRT
<213> ORGANISM: Artificial Sequence
<220> FEATURE:
<223> OTHER INFORMATION: A representative CL region of the Fab region

<400> SEQUENCE: 59

```
Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105
```

<210> SEQ ID NO 60
<211> LENGTH: 98
<212> TYPE: PRT
<213> ORGANISM: Artificial Sequence
<220> FEATURE:
<223> OTHER INFORMATION: A representative CH1 region of the Fab region

<400> SEQUENCE: 60

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val
```

<210> SEQ ID NO 61
<211> LENGTH: 124

```
<212> TYPE: PRT
<213> ORGANISM: Artificial Sequence
<220> FEATURE:
<223> OTHER INFORMATION: Fab region (CD19) in VH of ACE-02, and ACE-03

<400> SEQUENCE: 61

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Trp Pro Gly Asp Gly Asp Thr Asn Tyr Asn Gly Lys Phe
    50                  55                  60

Lys Gly Lys Ala Thr Leu Thr Ala Asp Glu Ser Ser Ser Thr Ala Tyr
65                  70                  75                  80

Met Gln Leu Ser Ser Leu Ala Ser Glu Asp Ser Ala Val Tyr Phe Cys
                85                  90                  95

Ala Arg Arg Glu Thr Thr Thr Val Gly Arg Tyr Tyr Tyr Ala Met Asp
            100                 105                 110

Tyr Trp Gly Gln Gly Thr Thr Val Thr Val Ser Ser
        115                 120

<210> SEQ ID NO 62
<211> LENGTH: 5
<212> TYPE: PRT
<213> ORGANISM: Artificial Sequence
<220> FEATURE:
<223> OTHER INFORMATION: Fab region (CD19) in CDR H1 of ACE-02, and
      ACE-03

<400> SEQUENCE: 62

Ser Tyr Trp Met Asn
1               5

<210> SEQ ID NO 63
<211> LENGTH: 17
<212> TYPE: PRT
<213> ORGANISM: Artificial Sequence
<220> FEATURE:
<223> OTHER INFORMATION: Fab region (CD19) in CDR H2 of ACE-02, and
      ACE-03

<400> SEQUENCE: 63

Gln Ile Trp Pro Gly Asp Gly Asp Thr Asn Tyr Asn Gly Lys Phe Lys
1               5                   10                  15

Gly

<210> SEQ ID NO 64
<211> LENGTH: 15
<212> TYPE: PRT
<213> ORGANISM: Artificial Sequence
<220> FEATURE:
<223> OTHER INFORMATION: Fab region (CD19) in CDR H3 of ACE-02, and
      ACE-03

<400> SEQUENCE: 64

Arg Glu Thr Thr Thr Val Gly Arg Tyr Tyr Tyr Ala Met Asp Tyr
1               5                   10                  15

<210> SEQ ID NO 65
<211> LENGTH: 111
<212> TYPE: PRT
```

<213> ORGANISM: Artificial Sequence
<220> FEATURE:
<223> OTHER INFORMATION: Fab region (CD19) in VL of ACE-02, and ACE-03

<400> SEQUENCE: 65

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys
            100                 105                 110

<210> SEQ ID NO 66
<211> LENGTH: 10
<212> TYPE: PRT
<213> ORGANISM: Artificial Sequence
<220> FEATURE:
<223> OTHER INFORMATION: Fab region (CD19) in CDR L1 of ACE-02, and
      ACE-03

<400> SEQUENCE: 66

Gln Ser Val Asp Tyr Asp Gly Asp Ser Tyr
1               5                   10

<210> SEQ ID NO 67
<211> LENGTH: 3
<212> TYPE: PRT
<213> ORGANISM: Artificial Sequence
<220> FEATURE:
<223> OTHER INFORMATION: Fab region (CD19) in CDR L2 of ACE-02, and
      ACE-03

<400> SEQUENCE: 67

Asp Ala Ser
1

<210> SEQ ID NO 68
<211> LENGTH: 9
<212> TYPE: PRT
<213> ORGANISM: Artificial Sequence
<220> FEATURE:
<223> OTHER INFORMATION: Fab region (CD19) in CDR L3 of ACE-02, and
      ACE-03

<400> SEQUENCE: 68

Gln Gln Ser Thr Glu Asp Pro Trp Thr
1               5

<210> SEQ ID NO 69
<211> LENGTH: 119
<212> TYPE: PRT
<213> ORGANISM: Artificial Sequence
<220> FEATURE:
<223> OTHER INFORMATION: Fv region (CD3) in VH of ACE-02

<400> SEQUENCE: 69

```
Gln Val Gln Leu Val Gln Ser Gly Gly Val Val Gln Pro Gly Arg
1               5                   10                  15

Ser Leu Arg Leu Ser Cys Lys Ala Ser Gly Tyr Thr Phe Thr Ser Tyr
            20                  25                  30

Thr Met His Trp Val Arg Gln Ala Pro Gly Lys Gly Leu Glu Trp Ile
        35                  40                  45

Gly Tyr Ile Asn Pro Ser Ser Gly Tyr Thr Tyr Asn Gln Lys Phe
    50                  55                  60

Lys Asp Arg Phe Thr Ile Ser Ala Asp Lys Ser Lys Ser Thr Ala Phe
65                  70                  75                  80

Leu Gln Met Asp Ser Leu Arg Pro Glu Asp Thr Gly Val Tyr Phe Cys
                85                  90                  95

Ala Arg Trp Gln Asp Tyr Asp Val Tyr Phe Asp Tyr Trp Gly Gln Gly
                100                 105                 110

Thr Pro Val Thr Val Ser Ser
            115
```

```
<210> SEQ ID NO 70
<211> LENGTH: 8
<212> TYPE: PRT
<213> ORGANISM: Artificial Sequence
<220> FEATURE:
<223> OTHER INFORMATION: Fv region (CD3) in CDR H1 of ACE-02

<400> SEQUENCE: 70

Gly Tyr Thr Phe Thr Ser Tyr Thr
1               5
```

```
<210> SEQ ID NO 71
<211> LENGTH: 8
<212> TYPE: PRT
<213> ORGANISM: Artificial Sequence
<220> FEATURE:
<223> OTHER INFORMATION: Fv region (CD3) in CDR H2 of ACE-02

<400> SEQUENCE: 71

Ile Asn Pro Ser Ser Gly Tyr Thr
1               5
```

```
<210> SEQ ID NO 72
<211> LENGTH: 12
<212> TYPE: PRT
<213> ORGANISM: Artificial Sequence
<220> FEATURE:
<223> OTHER INFORMATION: Fv region (CD3) in CDR H3 of ACE-02

<400> SEQUENCE: 72

Ala Arg Trp Gln Asp Tyr Asp Val Tyr Phe Asp Tyr
1               5                   10
```

```
<210> SEQ ID NO 73
<211> LENGTH: 107
<212> TYPE: PRT
<213> ORGANISM: Artificial Sequence
<220> FEATURE:
<223> OTHER INFORMATION: Fv region (CD3) in VL of ACE-02

<400> SEQUENCE: 73

Asp Ile Gln Met Thr Gln Ser Pro Ser Ser Leu Ser Ala Ser Val Gly
1               5                   10                  15

Asp Arg Val Thr Met Thr Cys Arg Ala Ser Ser Ser Val Ser Tyr Met
            20                  25                  30
```

```
His Trp Tyr Gln Gln Thr Pro Gly Lys Ala Pro Lys Pro Trp Ile Tyr
        35                  40                  45

Ala Thr Ser Asn Leu Ala Ser Gly Val Pro Ser Arg Phe Ser Gly Ser
 50                  55                  60

Gly Ser Gly Thr Asp Tyr Thr Leu Thr Ile Ser Ser Leu Gln Pro Glu
65                   70                  75                  80

Asp Ile Ala Thr Tyr Tyr Cys Gln Gln Trp Ser Ser Asn Pro Pro Thr
                 85                  90                  95

Phe Gly Gln Gly Thr Lys Leu Gln Ile Thr Arg
            100                 105

<210> SEQ ID NO 74
<211> LENGTH: 6
<212> TYPE: PRT
<213> ORGANISM: Artificial Sequence
<220> FEATURE:
<223> OTHER INFORMATION: Fv region (CD3) in CDR L1 of ACE-02

<400> SEQUENCE: 74

Ser Ser Ser Val Ser Tyr
1               5

<210> SEQ ID NO 75
<211> LENGTH: 3
<212> TYPE: PRT
<213> ORGANISM: Artificial Sequence
<220> FEATURE:
<223> OTHER INFORMATION: Fv region (CD3) in CDR L2 of ACE-02

<400> SEQUENCE: 75

Ala Thr Ser
1

<210> SEQ ID NO 76
<211> LENGTH: 9
<212> TYPE: PRT
<213> ORGANISM: Artificial Sequence
<220> FEATURE:
<223> OTHER INFORMATION: Fv region (CD3) in CDR L3 of ACE-02

<400> SEQUENCE: 76

Gln Gln Trp Ser Ser Asn Pro Pro Thr
1               5

<210> SEQ ID NO 77
<211> LENGTH: 118
<212> TYPE: PRT
<213> ORGANISM: Artificial Sequence
<220> FEATURE:
<223> OTHER INFORMATION: Fv region (CD3) in VH of ACE-03

<400> SEQUENCE: 77

Val Gln Leu Val Gln Ser Gly Gly Gly Val Val Gln Pro Gly Arg Ser
1               5                   10                  15

Leu Arg Leu Ser Cys Lys Ala Ser Gly Tyr Thr Phe Thr Arg Tyr Thr
            20                  25                  30

Met His Trp Val Arg Gln Ala Pro Gly Lys Gly Leu Glu Trp Ile Gly
        35                  40                  45

Tyr Ile Asn Pro Ser Arg Gly Tyr Thr Asn Tyr Asn Gln Lys Val Lys
    50                  55                  60

Asp Arg Phe Thr Ile Ser Thr Asp Lys Ser Lys Ser Thr Ala Phe Leu
65                  70                  75                  80
```

```
Gln Met Asp Ser Leu Arg Pro Glu Asp Thr Ala Val Tyr Tyr Cys Ala
                85                  90                  95

Arg Tyr Tyr Asp Asp His Tyr Cys Leu Asp Tyr Trp Gly Gln Gly Thr
            100                 105                 110

Pro Val Thr Val Ser Ser
        115

<210> SEQ ID NO 78
<211> LENGTH: 8
<212> TYPE: PRT
<213> ORGANISM: Artificial Sequence
<220> FEATURE:
<223> OTHER INFORMATION: Fv region (CD3) in CDR H1 of ACE-03, and ACE-04

<400> SEQUENCE: 78

Gly Tyr Thr Phe Thr Arg Tyr Thr
1               5

<210> SEQ ID NO 79
<211> LENGTH: 8
<212> TYPE: PRT
<213> ORGANISM: Artificial Sequence
<220> FEATURE:
<223> OTHER INFORMATION: Fv region (CD3) in CDR H2 of ACE-03, and ACE-04

<400> SEQUENCE: 79

Ile Asn Pro Ser Arg Gly Tyr Thr
1               5

<210> SEQ ID NO 80
<211> LENGTH: 12
<212> TYPE: PRT
<213> ORGANISM: Artificial Sequence
<220> FEATURE:
<223> OTHER INFORMATION: Fv region (CD3) in CDR H3 of ACE-03, and ACE-04

<400> SEQUENCE: 80

Ala Arg Tyr Tyr Asp Asp His Tyr Cys Leu Asp Tyr
1               5                   10

<210> SEQ ID NO 81
<211> LENGTH: 107
<212> TYPE: PRT
<213> ORGANISM: Artificial Sequence
<220> FEATURE:
<223> OTHER INFORMATION: Fv region (CD3) in VL of ACE-03

<400> SEQUENCE: 81

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Val Ser Tyr Met
            20                  25                  30

Asn Trp Tyr Gln Gln Thr Pro Gly Lys Ala Pro Lys Arg Trp Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Tyr Thr Phe Thr Ile Ser Ser Leu Gln Pro Glu
65                  70                  75                  80

Asp Ile Ala Thr Tyr Tyr Cys Gln Gln Trp Ser Ser Asn Pro Phe Thr
                85                  90                  95

Phe Gly Gln Gly Thr Lys Leu Gln Ile Thr Arg
            100                 105
```

<210> SEQ ID NO 82
<211> LENGTH: 5
<212> TYPE: PRT
<213> ORGANISM: Artificial Sequence
<220> FEATURE:
<223> OTHER INFORMATION: Fv region (CD3) in CDR L1 of ACE-03, and ACE-04

<400> SEQUENCE: 82

Ser Ser Val Ser Tyr
1               5

<210> SEQ ID NO 83
<211> LENGTH: 3
<212> TYPE: PRT
<213> ORGANISM: Artificial Sequence
<220> FEATURE:
<223> OTHER INFORMATION: Fv region (CD3) in CDR L2 of ACE-03, and ACE-04

<400> SEQUENCE: 83

Asp Thr Ser
1

<210> SEQ ID NO 84
<211> LENGTH: 9
<212> TYPE: PRT
<213> ORGANISM: Artificial Sequence
<220> FEATURE:
<223> OTHER INFORMATION: Fv region (CD3) in CDR L3 of ACE-03

<400> SEQUENCE: 84

Gln Gln Trp Ser Ser Asn Pro Phe Thr
1               5

<210> SEQ ID NO 85
<211> LENGTH: 119
<212> TYPE: PRT
<213> ORGANISM: Artificial Sequence
<220> FEATURE:
<223> OTHER INFORMATION: Fv region (CD3) in VH of ACE-04

<400> SEQUENCE: 85

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
                20                  25                  30

Thr Met His Trp Val Lys Gln Arg Pro Gly Gln Gly Leu Glu Trp Ile
            35                  40                  45

Gly Tyr Ile Asn Pro Ser Arg Gly Tyr Thr Asn Tyr Asn Gln Lys Phe
        50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
                100                 105                 110

Thr Thr Val Thr Val Ser Ala
        115

<210> SEQ ID NO 86
<211> LENGTH: 107
<212> TYPE: PRT
<213> ORGANISM: Artificial Sequence
<220> FEATURE:

<223> OTHER INFORMATION: Fv region (CD3) in VL of ACE-04

<400> SEQUENCE: 86

```
Gln Ile Val Leu Thr Gln Ser Pro Ala Ile Met Ser Ala Ser Pro Gly
1               5                   10                  15

Glu Lys Val Thr Met Thr Cys Ser Ala Ser Ser Val Ser Tyr Met
            20                  25                  30

Asn Trp Tyr Gln Gln Lys Ser Gly Thr Ser Pro Lys Arg Trp Ile Tyr
        35                  40                  45

Asp Thr Ser Lys Leu Ala Ser Gly Val Pro Ala His Phe Arg Gly Ser
    50                  55                  60

Gly Ser Gly Thr Ser Tyr Ser Leu Thr Ile Ser Gly Met Glu Ala Glu
65                  70                  75                  80

Asp Ala Ala Thr Tyr Tyr Cys Gln Gln Trp Ser Ser Asn Pro Phe Thr
                85                  90                  95

Phe Gly Ser Gly Thr Lys Leu Glu Ile Asn Arg
            100                 105
```

<210> SEQ ID NO 87
<211> LENGTH: 8
<212> TYPE: PRT
<213> ORGANISM: Artificial Sequence
<220> FEATURE:
<223> OTHER INFORMATION: Fv region (CD3) in CDR L3 of ACE-04

<400> SEQUENCE: 87

```
Gln Gln Trp Ser Ser Asn Pro Phe
1               5
```

<210> SEQ ID NO 88
<211> LENGTH: 364
<212> TYPE: PRT
<213> ORGANISM: Artificial Sequence
<220> FEATURE:
<223> OTHER INFORMATION: ACE-02-VH amino acid sequence

<400> SEQUENCE: 88

```
Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Trp Pro Gly Asp Gly Asp Thr Asn Tyr Asn Gly Lys Phe
    50                  55                  60

Lys Gly Lys Ala Thr Leu Thr Ala Asp Glu Ser Ser Ser Thr Ala Tyr
65                  70                  75                  80

Met Gln Leu Ser Ser Leu Ala Ser Glu Asp Ser Ala Val Tyr Phe Cys
                85                  90                  95

Ala Arg Arg Glu Thr Thr Thr Val Gly Arg Tyr Tyr Ala Met Asp
                100                 105                 110

Tyr Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
```

```
                    165                 170                 175
Phe Pro Ala Val Leu Gln Ser Ser Gly Leu Tyr Ser Leu Ser Ser Val
                180                 185                 190

Val Thr Val Pro Ser Ser Ser Leu Gly Thr Gln Thr Tyr Ile Cys Asn
            195                 200                 205

Val Asn His Lys Pro Ser Asn Thr Lys Val Asp Lys Arg Val Glu Pro
        210                 215                 220

Lys Ser Cys Asp Lys Thr His Thr Cys Pro Pro Cys Pro Ala Pro Glu
225                 230                 235                 240

Leu Leu Gly Gly Pro Gln Val Gln Leu Val Gln Ser Gly Gly Gly Val
                245                 250                 255

Val Gln Pro Gly Arg Ser Leu Arg Leu Ser Cys Lys Ala Ser Gly Tyr
            260                 265                 270

Thr Phe Thr Ser Tyr Thr Met His Trp Val Arg Gln Ala Pro Gly Lys
        275                 280                 285

Gly Leu Glu Trp Ile Gly Tyr Ile Asn Pro Ser Ser Gly Tyr Thr Lys
    290                 295                 300

Tyr Asn Gln Lys Phe Lys Asp Arg Phe Thr Ile Ser Ala Asp Lys Ser
305                 310                 315                 320

Lys Ser Thr Ala Phe Leu Gln Met Asp Ser Leu Arg Pro Glu Asp Thr
                325                 330                 335

Gly Val Tyr Phe Cys Ala Arg Trp Gln Asp Tyr Asp Val Tyr Phe Asp
            340                 345                 350

Tyr Trp Gly Gln Gly Thr Pro Val Thr Val Ser Ser
        355                 360
```

<210> SEQ ID NO 89
<211> LENGTH: 352
<212> TYPE: PRT
<213> ORGANISM: Artificial Sequence
<220> FEATURE:
<223> OTHER INFORMATION: ACE-02-VL amino acid sequence

<400> SEQUENCE: 89

```
Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Trp Pro Gly Asp Gly Asp Thr Asn Tyr Asn Gly Lys Phe
    50                  55                  60

Lys Gly Lys Ala Thr Leu Thr Ala Asp Glu Ser Ser Ser Thr Ala Tyr
65                  70                  75                  80

Met Gln Leu Ser Ser Leu Ala Ser Glu Asp Ser Ala Val Tyr Phe Cys
                85                  90                  95

Ala Arg Arg Glu Thr Thr Thr Val Gly Arg Tyr Tyr Ala Met Asp
            100                 105                 110

Tyr Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
```

```
                165                 170                 175
Phe Pro Ala Val Leu Gln Ser Ser Gly Leu Tyr Ser Leu Ser Ser Val
            180                 185                 190

Val Thr Val Pro Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Asp Ile Gln Met Thr Gln Ser Pro Ser Ser Leu
                245                 250                 255

Ser Ala Ser Val Gly Asp Arg Val Thr Met Thr Cys Arg Ala Ser Ser
            260                 265                 270

Ser Val Ser Tyr Met His Trp Tyr Gln Gln Thr Pro Gly Lys Ala Pro
        275                 280                 285

Lys Pro Trp Ile Tyr Ala Thr Ser Asn Leu Ala Ser Gly Val Pro Ser
    290                 295                 300

Arg Phe Ser Gly Ser Gly Ser Gly Thr Asp Tyr Thr Leu Thr Ile Ser
305                 310                 315                 320

Ser Leu Gln Pro Glu Asp Ile Ala Thr Tyr Tyr Cys Gln Gln Trp Ser
                325                 330                 335

Ser Asn Pro Pro Thr Phe Gly Gln Gly Thr Lys Leu Gln Ile Thr Arg
            340                 345                 350

<210> SEQ ID NO 90
<211> LENGTH: 218
<212> TYPE: PRT
<213> ORGANISM: Artificial Sequence
<220> FEATURE:
<223> OTHER INFORMATION: ACE-02-LC, ACE-03-LC (anti-CD19 antibody light
      chain)

<400> SEQUENCE: 90

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175
```

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys
            210                 215

<210> SEQ ID NO 91
<211> LENGTH: 363
<212> TYPE: PRT
<213> ORGANISM: Artificial Sequence
<220> FEATURE:
<223> OTHER INFORMATION: ACE-03-VH amino acid sequence

<400> SEQUENCE: 91

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Trp Pro Gly Asp Gly Asp Thr Asn Tyr Asn Gly Lys Phe
    50                  55                  60

Lys Gly Lys Ala Thr Leu Thr Ala Asp Glu Ser Ser Ser Thr Ala Tyr
65                  70                  75                  80

Met Gln Leu Ser Ser Leu Ala Ser Glu Asp Ser Ala Val Tyr Phe Cys
                85                  90                  95

Ala Arg Arg Glu Thr Thr Val Gly Arg Tyr Tyr Ala Met Asp
            100                 105                 110

Tyr Trp Gly Gln Gly Thr Thr Val Thr Val Ser Ser Ala Ser Thr Lys
            115                 120                 125

Gly Pro Ser Val Phe Pro Leu Ala Pro Ser Ser Lys Ser Thr Ser Gly
        130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
            165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
            195                 200                 205

Val Asn His Lys Pro Ser Asn Thr Lys Val Asp Lys Arg Val Glu Pro
        210                 215                 220

Lys Ser Cys Asp Lys Thr His Thr Cys Pro Pro Cys Pro Ala Pro Glu
225                 230                 235                 240

Leu Leu Gly Gly Pro Val Gln Leu Val Gln Ser Gly Gly Val Val
            245                 250                 255

Gln Pro Gly Arg Ser Leu Arg Leu Ser Cys Lys Ala Ser Gly Tyr Thr
            260                 265                 270

Phe Thr Arg Tyr Thr Met His Trp Val Arg Gln Ala Pro Gly Lys Gly
        275                 280                 285

Leu Glu Trp Ile Gly Tyr Ile Asn Pro Ser Arg Gly Tyr Thr Asn Tyr
        290                 295                 300

Asn Gln Lys Val Lys Asp Arg Phe Thr Ile Ser Thr Asp Lys Ser Lys
305                 310                 315                 320

Ser Thr Ala Phe Leu Gln Met Asp Ser Leu Arg Pro Glu Asp Thr Ala
            325                 330                 335

Val Tyr Tyr Cys Ala Arg Tyr Tyr Asp Asp His Tyr Cys Leu Asp Tyr
        340                 345                 350

Trp Gly Gln Gly Thr Pro Val Thr Val Ser Ser
        355                 360

<210> SEQ ID NO 92
<211> LENGTH: 352
<212> TYPE: PRT
<213> ORGANISM: Artificial Sequence
<220> FEATURE:
<223> OTHER INFORMATION: ACE-03-VL amino acid sequence

<400> SEQUENCE: 92

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Trp Pro Gly Asp Gly Asp Thr Asn Tyr Asn Gly Lys Phe
    50                  55                  60

Lys Gly Lys Ala Thr Leu Thr Ala Asp Glu Ser Ser Ser Thr Ala Tyr
65                  70                  75                  80

Met Gln Leu Ser Ser Leu Ala Ser Glu Asp Ser Ala Val Tyr Phe Cys
                85                  90                  95

Ala Arg Arg Glu Thr Thr Thr Val Gly Arg Tyr Tyr Ala Met Asp
            100                 105                 110

Tyr Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Asp Ile Gln Met Thr Gln Ser Pro Ser Ser Leu
                245                 250                 255

Ser Ala Ser Val Gly Asp Arg Val Thr Ile Thr Cys Ser Ala Ser Ser
            260                 265                 270

Ser Val Ser Tyr Met Asn Trp Tyr Gln Gln Thr Pro Gly Lys Ala Pro
        275                 280                 285

Lys Arg Trp Ile Tyr Asp Thr Ser Lys Leu Ala Ser Gly Val Pro Ser
    290                 295                 300

Arg Phe Ser Gly Ser Gly Ser Gly Thr Asp Tyr Thr Phe Thr Ile Ser
305                 310                 315                 320

Ser Leu Gln Pro Glu Asp Ile Ala Thr Tyr Tyr Cys Gln Gln Trp Ser
            325                 330                 335

Ser Asn Pro Phe Thr Phe Gly Gln Gly Thr Lys Leu Gln Ile Thr Arg
            340                 345                 350

<210> SEQ ID NO 93
<211> LENGTH: 469
<212> TYPE: PRT
<213> ORGANISM: Artificial Sequence
<220> FEATURE:
<223> OTHER INFORMATION: ACE-04-VH amino acid seqeunce

<400> SEQUENCE: 93

Gln Met Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Lys Pro Arg Asp Gly Tyr Asn Leu Val Ala Phe Asp Ile Trp Gly
            100                 105                 110

Gln Gly Thr Met Val Thr Val Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Gly Gly Gly Gly Ser Gln Val Gln Leu Gln Gln Ser Gly Ala
                245                 250                 255

Glu Leu Ala Arg Pro Gly Ala Ser Val Lys Met Ser Cys Lys Ala Ser
            260                 265                 270

Gly Tyr Thr Phe Thr Arg Tyr Thr Met His Trp Val Lys Gln Arg Pro
        275                 280                 285

Gly Gln Gly Leu Glu Trp Ile Gly Tyr Ile Asn Pro Ser Arg Gly Tyr
    290                 295                 300

Thr Asn Tyr Asn Gln Lys Phe Lys Asp Lys Ala Thr Leu Thr Thr Asp
305                 310                 315                 320

Lys Ser Ser Ser Thr Ala Tyr Met Gln Leu Ser Ser Leu Thr Ser Glu
                325                 330                 335

```
Asp Ser Ala Val Tyr Tyr Cys Ala Arg Tyr Tyr Asp Asp His Tyr Cys
                340                 345                 350

Leu Asp Tyr Trp Gly Gln Gly Thr Thr Val Thr Val Ser Ala Ala Ser
            355                 360                 365

Thr Lys Gly Pro Ser Val Phe Pro Leu Ala Pro Ser Ser Lys Ser Thr
370                 375                 380

Ser Gly Gly Thr Ala Ala Leu Gly Cys Leu Val Lys Asp Tyr Phe Pro
385                 390                 395                 400

Glu Pro Val Thr Val Ser Trp Asn Ser Gly Ala Leu Thr Ser Gly Val
                405                 410                 415

His Thr Phe Pro Ala Val Leu Gln Ser Ser Gly Leu Tyr Ser Leu Ser
            420                 425                 430

Ser Val Val Thr Val Pro Ser Ser Ser Leu Gly Thr Gln Thr Tyr Ile
        435                 440                 445

Cys Asn Val Asn His Lys Pro Ser Asn Thr Lys Val Asp Lys Arg Val
450                 455                 460

Glu Pro Lys Ser Cys
465

<210> SEQ ID NO 94
<211> LENGTH: 460
<212> TYPE: PRT
<213> ORGANISM: Artificial Sequence
<220> FEATURE:
<223> OTHER INFORMATION: ACE-04-VL amino acid sequence

<400> SEQUENCE: 94

Gln Met Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Arg Ile Ile Pro Ile Leu Gly Ile Ala Asn Tyr Ala Gln Lys Phe
        50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Lys Pro Arg Asp Gly Tyr Asn Leu Val Ala Phe Asp Ile Trp Gly
            100                 105                 110

Gln Gly Thr Met Val Thr Val Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220
```

```
Asp Lys Thr His Thr Cys Pro Pro Cys Pro Ala Glu Leu Leu Gly
225                 230                 235                 240

Gly Pro Gly Gly Gly Ser Gln Ile Val Leu Thr Gln Ser Pro Ala
            245                 250                 255

Ile Met Ser Ala Ser Pro Gly Glu Lys Val Thr Met Thr Cys Ser Ala
        260                 265                 270

Ser Ser Ser Val Ser Tyr Met Asn Trp Tyr Gln Gln Lys Ser Gly Thr
    275                 280                 285

Ser Pro Lys Arg Trp Ile Tyr Asp Thr Ser Lys Leu Ala Ser Gly Val
    290                 295                 300

Pro Ala His Phe Arg Gly Ser Gly Ser Gly Thr Ser Tyr Ser Leu Thr
305                 310                 315                 320

Ile Ser Gly Met Glu Ala Glu Asp Ala Ala Thr Tyr Tyr Cys Gln Gln
            325                 330                 335

Trp Ser Ser Asn Pro Phe Thr Phe Gly Ser Gly Thr Lys Leu Glu Ile
        340                 345                 350

Asn Arg Thr Val Ala Ala Pro Ser Val Phe Ile Phe Pro Pro Ser Asp
    355                 360                 365

Glu Gln Leu Lys Ser Gly Thr Ala Ser Val Val Cys Leu Leu Asn Asn
370                 375                 380

Phe Tyr Pro Arg Glu Ala Lys Val Gln Trp Lys Val Asp Asn Ala Leu
385                 390                 395                 400

Gln Ser Gly Asn Ser Gln Glu Ser Val Thr Glu Gln Asp Ser Lys Asp
            405                 410                 415

Ser Thr Tyr Ser Leu Ser Ser Thr Leu Thr Leu Ser Lys Ala Asp Tyr
        420                 425                 430

Glu Lys His Lys Val Tyr Ala Cys Glu Val Thr His Gln Gly Leu Ser
    435                 440                 445

Ser Pro Val Thr Lys Ser Phe Asn Arg Gly Glu Cys
    450                 455                 460

<210> SEQ ID NO 95
<211> LENGTH: 218
<212> TYPE: PRT
<213> ORGANISM: Artificial Sequence
<220> FEATURE:
<223> OTHER INFORMATION: ACE-04-LC, ACE-09-LC, and ACE-12-LC (anti-PD-L1
      antibody light chain)

<400> SEQUENCE: 95

Gln Leu Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Ala Ala Pro Lys Leu
        35                  40                  45

Leu Ile Tyr Gly Asp Ile Asn Arg Pro Ser Gly Val Pro Asp Arg Phe
    50                  55                  60

Ser Gly Ser Lys Ser Gly Ile Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Gly Val Phe Gly Gly Gly Thr Lys Leu Thr Val Leu Arg
            100                 105                 110

Ser Val Ala Ala Pro Ser Val Phe Ile Phe Pro Pro Ser Asp Glu Gln
        115                 120                 125
```

Leu Lys Ser Gly Thr Ala Ser Val Val Cys Leu Leu Asn Asn Phe Tyr
            130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
                180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys
            210                 215

<210> SEQ ID NO 96
<211> LENGTH: 364
<212> TYPE: PRT
<213> ORGANISM: Artificial Sequence
<220> FEATURE:
<223> OTHER INFORMATION: ACE-09-VH amino acid sequence (without G4S
      linker)

<400> SEQUENCE: 96

Gln Met Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Lys Pro Arg Asp Gly Tyr Asn Leu Val Ala Phe Asp Ile Trp Gly
            100                 105                 110

Gln Gly Thr Met Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
            130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
            210                 215                 220

Asp Lys Thr His Thr Cys Pro Pro Cys Pro Ala Pro Glu Leu Leu Gly
225                 230                 235                 240

Gly Pro Glu Val Gln Leu Gln Gln Ser Gly Pro Glu Leu Val Lys Pro
                245                 250                 255

Gly Pro Ser Met Lys Ile Ser Cys Lys Ala Ser Gly Tyr Ser Phe Thr

```
                260                265                270
Gly Tyr Thr Met Asn Trp Val Lys Gln Ser His Gly Lys Asn Leu Glu
            275                280                285
Trp Met Gly Leu Ile Asn Pro Tyr Lys Gly Val Ser Thr Tyr Asn Gln
            290                295                300
Lys Phe Lys Asp Lys Ala Thr Leu Thr Val Asp Lys Ser Ser Ser Thr
305                310                315                320
Ala Tyr Met Glu Leu Leu Ser Leu Thr Ser Glu Asp Ser Ala Val Tyr
                325                330                335
Tyr Cys Ala Arg Ser Gly Tyr Tyr Gly Asp Ser Asp Trp Tyr Phe Asp
                340                345                350
Val Trp Gly Gln Gly Thr Thr Leu Thr Val Phe Ser
            355                360

<210> SEQ ID NO 97
<211> LENGTH: 350
<212> TYPE: PRT
<213> ORGANISM: Artificial Sequence
<220> FEATURE:
<223> OTHER INFORMATION: ACE-09-VL amino acid sequence (without G4S
      linker)

<400> SEQUENCE: 97

Gln Met Gln Leu Val Gln Ser Gly Ala Glu Val Lys Lys Pro Gly Ser
1               5                   10                  15
Ser Val Lys Val Ser Cys Lys Ala Ser Gly Gly Thr Phe Ser Ser Tyr
            20                  25                  30
Ala Ile Ser Trp Val Arg Gln Ala Pro Gly Gln Gly Leu Glu Trp Met
        35                  40                  45
Gly Arg Ile Ile Pro Ile Leu Gly Ile Ala Asn Tyr Ala Gln Lys Phe
    50                  55                  60
Gln Gly Arg Val Thr Ile Thr Ala Asp Lys Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Lys Pro Arg Asp Gly Tyr Asn Leu Val Ala Phe Asp Ile Trp Gly
            100                 105                 110
Gln Gly Thr Met Val Thr Val Ser Ser Ala Ser Thr Lys Gly Pro Ser
        115                 120                 125
Val Phe Pro Leu Ala Pro Ser Ser Lys Ser Thr Ser Gly Gly Thr Ala
    130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Ser Leu Gly Thr Gln Thr Tyr Ile Cys Asn Val Asn His
        195                 200                 205
Lys Pro Ser Asn Thr Lys Val Asp Lys Val Glu Pro Lys Ser Cys
    210                 215                 220
Asp Lys Thr His Thr Cys Pro Pro Cys Pro Ala Pro Glu Leu Leu Gly
225                 230                 235                 240
Gly Pro Asp Ile Gln Met Thr Gln Thr Thr Ser Ser Leu Ser Ala Ser
                245                 250                 255
```

Leu Gly Asp Arg Val Thr Ile Ser Cys Arg Ala Ser Gln Asp Ile Arg
                260                 265                 270

Asn Tyr Leu Asn Trp Tyr Gln Gln Lys Pro Asp Gly Thr Val Lys Leu
            275                 280                 285

Leu Ile Tyr Tyr Thr Ser Arg Leu His Ser Gly Val Pro Ser Lys Phe
        290                 295                 300

Ser Gly Ser Gly Ser Gly Thr Asp Tyr Ser Leu Thr Ile Ser Asn Leu
305                 310                 315                 320

Glu Gln Glu Asp Ile Ala Thr Tyr Phe Cys Gln Gln Gly Asn Thr Leu
                325                 330                 335

Pro Trp Thr Phe Ala Gly Gly Thr Lys Leu Glu Ile Lys Arg
            340                 345                 350

<210> SEQ ID NO 98
<211> LENGTH: 374
<212> TYPE: PRT
<213> ORGANISM: Artificial Sequence
<220> FEATURE:
<223> OTHER INFORMATION: ACE-12-VH amino acid sequence (with 10
      residues)

<400> SEQUENCE: 98

Gln Met Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Lys Pro Arg Asp Gly Tyr Asn Leu Val Ala Phe Asp Ile Trp Gly
            100                 105                 110

Gln Gly Thr Met Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Gly Gly Gly Gly Ser Gly Gly Gly Gly Ser Glu Val Gln Leu
                245                 250                 255

Gln Gln Ser Gly Pro Glu Leu Val Lys Pro Gly Pro Ser Met Lys Ile
            260                 265                 270

```
Ser Cys Lys Ala Ser Gly Tyr Ser Phe Thr Gly Tyr Thr Met Asn Trp
        275                 280                 285

Val Lys Gln Ser His Gly Lys Asn Leu Glu Trp Met Gly Leu Ile Asn
    290                 295                 300

Pro Tyr Lys Gly Val Ser Thr Tyr Asn Gln Lys Phe Lys Asp Lys Ala
305                 310                 315                 320

Thr Leu Thr Val Asp Lys Ser Ser Thr Ala Tyr Met Glu Leu Leu
                325                 330                 335

Ser Leu Thr Ser Glu Asp Ser Ala Val Tyr Tyr Cys Ala Arg Ser Gly
        340                 345                 350

Tyr Tyr Gly Asp Ser Asp Trp Tyr Phe Asp Val Trp Gly Gln Gly Thr
        355                 360                 365

Thr Leu Thr Val Phe Ser
    370

<210> SEQ ID NO 99
<211> LENGTH: 359
<212> TYPE: PRT
<213> ORGANISM: Artificial Sequence
<220> FEATURE:
<223> OTHER INFORMATION: ACE-12-VL amino acid sequence (with 9 residues)

<400> SEQUENCE: 99

Gln Met Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Lys Pro Arg Asp Gly Tyr Asn Leu Val Ala Phe Asp Ile Trp Gly
            100                 105                 110

Gln Gly Thr Met Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Gly Gly Ser Gly Gly Gly Gly Ser Gly Asp Ile Gln Met Thr
                245                 250                 255
```

Gln Thr Thr Ser Ser Leu Ser Ala Ser Leu Gly Asp Arg Val Thr Ile
            260                 265                 270

Ser Cys Arg Ala Ser Gln Asp Ile Arg Asn Tyr Leu Asn Trp Tyr Gln
        275                 280                 285

Gln Lys Pro Asp Gly Thr Val Lys Leu Leu Ile Tyr Tyr Thr Ser Arg
    290                 295                 300

Leu His Ser Gly Val Pro Ser Lys Phe Ser Gly Ser Gly Ser Gly Thr
305                 310                 315                 320

Asp Tyr Ser Leu Thr Ile Ser Asn Leu Glu Gln Glu Asp Ile Ala Thr
                325                 330                 335

Tyr Phe Cys Gln Gln Gly Asn Thr Leu Pro Trp Thr Phe Ala Gly Gly
            340                 345                 350

Thr Lys Leu Glu Ile Lys Arg
        355

<210> SEQ ID NO 100
<211> LENGTH: 1095
<212> TYPE: DNA
<213> ORGANISM: Artificial Sequence
<220> FEATURE:
<223> OTHER INFORMATION: ACE-02-VH nucleotide sequence

<400> SEQUENCE: 100
caggttcaat tgcagcaaag cggggctgag ttggtacggc ctgggtccag cgtgaagata     60
tcatgtaagg cttctggata tgccttctcc tcttactgga tgaactgggt caagcaacgg    120
ccaggacaag gcctggagtg gattgggcaa atatggcccg ggacggaga tactaattat     180
aatggcaagt ttaaggggaa agctacactg accgcagacg aaagctcctc tacggcctat    240
atgcagctct catctcttgc gtccgaagat agtgcagtat attttttgtgc cgccgcgag   300
accaccacgg ttgggaggta ctattacgcg atggattact ggggccaggg gactacagtt    360
acggtttcat cagctagcac caaggggccca tcggtcttcc ccctggcacc ctcctccaag    420
agcacctctg ggggcacagc ggccctgggc tgcctggtca aggactactt ccccgaaccg    480
gtgacggtgt cgtggaactc aggcgccctg accagcggcg tgcacacctt cccggctgtc    540
ctacagtcct caggactcta ctccctcagc agcgtggtga ccgtgccctc cagcagcctg    600
ggcacccaga cctacatctg caacgtgaat cacaagccca gcaacaccaa ggtggacaag    660
agagttgagc ccaaatcttg tgacaaaact cacacatgcc caccgtgccc agcacctgaa    720
ctcctggggg gaccgcaggt gcagctggtg cagagcggcg cgggcgtggt gcagcccggc    780
cgcagcctgc gcctgagctg caaggccagc ggctacacct tcaccagcta ccatgcac    840
tgggtgcgcc aggcccccgg caagggcctg gagtggatcg gctacatcaa ccccagcagc    900
ggctacacca gtacaaacca gaagttcaag gaccgcttca ccatcagcgc cgacaagagc    960
aagagcaccg ccttcctgca gatggacagc ctgcgccccg aggacaccgg cgtgtacttc   1020
tgcgccgct gcaggacta cgacgtgtac ttcgactact ggggccaggg caccccgtg    1080
accgtgagca gctaa                                                    1095

<210> SEQ ID NO 101
<211> LENGTH: 1059
<212> TYPE: DNA
<213> ORGANISM: Artificial Sequence
<220> FEATURE:
<223> OTHER INFORMATION: ACE-02-VL nucleotide sequence

<400> SEQUENCE: 101

```
caggttcaat tgcagcaaag cggggctgag ttggtacggc ctgggtccag cgtgaagata    60
tcatgtaagg cttctggata tgccttctcc tcttactgga tgaactgggt caagcaacgg   120
ccaggacaag gcctggagtg gattgggcaa atatggcccg ggacggaga tactaattat    180 aatggcaagt ttaaggggaa agctacactg accgcagacg aaagctcctc tacggcctat   240
atgcagctct catctcttgc gtccgaagat agtgcagtat attttttgtgc gcgccgcgag   300 accaccacgt tgggaggta ctattacgcg atggattact ggggccaggg gactacagtt    360
acggtttcat cagctagcac caagggccca tcggtcttcc ccctggcacc ctcctccaag   420
agcacctctg gggcacagc ggccctgggc tgcctggtca aggactactt ccccgaaccg    480
gtgacggtgt cgtggaactc aggcgccctg accagcggcg tgcacacctt cccggctgtc   540
ctacagtcct caggactcta ctccctcagc agcgtggtga ccgtgccctc cagcagcctg   600
ggcacccaga cctacatctg caacgtgaat cacaagccca gcaacaccaa ggtggacaag   660
agagttgagc ccaaatcttg tgacaaaact cacacatgcc caccgtgccc agcacctgaa   720
ctcctggggg gaccggacat ccagatgacc cagagcccca gcagcctgag cgccagcgtg   780
ggcgaccgcg tgaccatgac ctgccgcgcc agcagcagcg tgagctacat gcactggtac   840
cagcagaccc ccggcaaggc ccccaagccc tggatctacg ccaccagcaa cctggccagc   900
ggcgtgccca ccgcttcag cggcagcggc agcggcaccg actacaccct gaccatcagc   960
agcctgcagc ccgaggacat cgccacctac tactgccagc agtggagcag caacccccc    1020 accttcggcc agggcaccaa gctgcagatc acccgctaa                          1059

<210> SEQ ID NO 102
<211> LENGTH: 657
<212> TYPE: DNA
<213> ORGANISM: Artificial Sequence
<220> FEATURE:
<223> OTHER INFORMATION: ACE-02-LC, and ACE-03-LC (anti-CD19 antibody
      light chain nucleotide sequence)

<400> SEQUENCE: 102
gatattcaac tcacgcaatc tccagcaagt ctcgcagtta gtttggggca gcgagctaca    60
ataagttgca aggcgagcca atccgtggat tatgatggag acagctatct taactggtat   120
cagcaaattc caggccagcc acccaagttg ctgatctacg acgcgtcaaa cctggtctca   180
gggatccctc caagatttag cggctcaggt tcaggtacgg attttacgct caatatccat   240
cctgtagaga aggttgatgc agctacatac cactgtcaac agagtaccga ggatccttgg   300
accttcggag gcggtacaaa gctggagatc aagagaaccg tggctgcacc atctgtcttc   360
atcttcccgc catctgatga gcagttgaaa tctggaactg cctctgttgt gtgcctgctg   420
aataacttct atcccagaga ggccaaagta cagtggaagg tggataacgc cctccaatcg   480
ggtaactccc aggagagtgt cacagagcag gacagcaagg acagcaccta cagcctcagc   540
agcaccctga cgctgagcaa agcagactac gagaaacaca agtctacgc ctgcgaagtc    600 acccatcagg gcctgagctc gcccgtcaca aagagcttca caggggaga gtgttaa       657

<210> SEQ ID NO 103
<211> LENGTH: 1092
<212> TYPE: DNA
<213> ORGANISM: Artificial Sequence
<220> FEATURE:
<223> OTHER INFORMATION: ACE-03-VH nucleotide sequence

<400> SEQUENCE: 103
```

```
caggttcaat tgcagcaaag cggggctgag ttggtacggc ctgggtccag cgtgaagata      60
tcatgtaagg cttctggata tgccttctcc tcttactgga tgaactgggt caagcaacgg     120
ccaggacaag gcctggagtg gattgggcaa atatggcccg gggacggaga tactaattat     180
aatggcaagt ttaaggggaa agctacactg accgcagacg aaagctcctc tacggcctat     240
atgcagctct catctcttgc gtccgaagat agtgcagtat attttgtgc gcgccgcgag      300 accaccacgt tgggaggta ctattacgcg atggattact ggggccaggg gactacagtt      360
acggtttcat cagctagcac caagggccca tcggtcttcc ccctggcacc ctcctccaag     420
agcacctctg ggggcacagc ggccctgggc tgcctggtca aggactactt ccccgaaccg     480
gtgacggtgt cgtggaactc aggcgccctg accagcggcg tgcacacctt cccggctgtc     540
ctacagtcct caggactcta ctccctcagc agcgtggtga ccgtgccctc cagcagcctg     600
ggcacccaga cctacatctg caacgtgaat cacaagccca gcaacaccaa ggtggacaag     660
agagttgagc ccaaatcttg tgacaaaact cacacatgcc caccgtgccc agcacctgaa     720
ctcctggggg gaccggtgca gctggtgcag agcggcggcg gcgtggtgca gcccggccgc     780
agcctgcgcc tgagctgcaa ggccagcggc tacaccttca cccgctacac catgcactgg     840
gtgcgccagg ccccggcaa gggcctggag tggatcggct acatcaaccc cagccgcggc     900
tacaccaact acaaccagaa ggtgaaggac cgcttcacca tcagcaccga caagagcaag     960
agcaccgcct tcctgcagat ggacagcctg cgccccgagg acaccgccgt gtactactgc    1020
gcccgctact acgacgacca ctactgcctg gactactggg gccagggcac ccccgtgacc    1080
gtgagcagct aa                                                        1092
```

<210> SEQ ID NO 104
<211> LENGTH: 1059
<212> TYPE: DNA
<213> ORGANISM: Artificial Sequence
<220> FEATURE:
<223> OTHER INFORMATION: ACE-03-VL nucleotide sequence

<400> SEQUENCE: 104

```
caggttcaat tgcagcaaag cggggctgag ttggtacggc ctgggtccag cgtgaagata      60
tcatgtaagg cttctggata tgccttctcc tcttactgga tgaactgggt caagcaacgg     120
ccaggacaag gcctggagtg gattgggcaa atatggcccg gggacggaga tactaattat     180
aatggcaagt ttaaggggaa agctacactg accgcagacg aaagctcctc tacggcctat     240
atgcagctct catctcttgc gtccgaagat agtgcagtat attttgtgc gcgccgcgag      300 accaccacgg ttgggaggta ctattacgcg atggattact ggggccaggg gactacagtt     360
acggtttcat cagctagcac caagggccca tcggtcttcc ccctggcacc ctcctccaag     420
agcacctctg ggggcacagc ggccctgggc tgcctggtca aggactactt ccccgaaccg     480
gtgacggtgt cgtggaactc aggcgccctg accagcggcg tgcacacctt cccggctgtc     540
ctacagtcct caggactcta ctccctcagc agcgtggtga ccgtgccctc cagcagcctg     600
ggcacccaga cctacatctg caacgtgaat cacaagccca gcaacaccaa ggtggacaag     660
agagttgagc ccaaatcttg tgacaaaact cacacatgcc caccgtgccc agcacctgaa     720
ctcctggggg gaccggacat ccagatgacc cagagcccca gcagcctgag cgccagcgtg     780
ggcgaccgcg tgaccatcac ctgcagcgcc agcagcagcg tgagctacat gaactggtac    840
cagcagaccc ccggcaaggc ccccaagcgc tggatctacg acaccagcaa gctggccagc    900
```

| | |
|---|---|
| ggcgtgccca gccgcttcag cggcagcggc agcggcaccg actacacctt caccatcagc | 960 |
| agcctgcagc ccgaggacat cgccacctac tactgccagc agtggagcag caacccttc | 1020 |
| accttcggcc agggcaccaa gctgcagatc accgctaa | 1059 |

<210> SEQ ID NO 105
<211> LENGTH: 1410
<212> TYPE: DNA
<213> ORGANISM: Artificial Sequence
<220> FEATURE:
<223> OTHER INFORMATION: ACE-04-VH nucleotide seqeunce

<400> SEQUENCE: 105

| | |
|---|---|
| cagatgcagc tggtgcagtc tggggctgag gtgaagaagc ctgggtcctc ggtgaaggtc | 60 |
| tcctgcaagg cttctggagg caccttcagc agctatgcta tcagctgggt gcgacaggcc | 120 |
| cctggacaag gcttgagtg gatgggaagg atcatcccta tccttggtat agcaaactac | 180 |
| gcacagaagt tccagggcag agtcacgatt accgcggaca aatccacgag cacagcctac | 240 |
| atggagctga gcagcctgag atctgaggac acggccgtgt attactgtgc gaaaccgaga | 300 |
| gatggctaca atttggttgc ttttgatatc tggggccaag gacgatggt caccgtctcc | 360 |
| tcagctagca ccaagggccc atcggtcttc cccctggcac cctcctccaa gagcacctct | 420 |
| gggggcacag cggccctggg ctgcctggtc aaggactact tccccgaacc ggtgacggtg | 480 |
| tcgtggaact caggcgccct gaccagcggc gtgcacacct tcccggctgt cctacagtcc | 540 |
| tcaggactct actccctcag cagcgtggtg accgtgccct ccagcagcct gggcacccag | 600 |
| acctacatct gcaacgtgaa tcacaagccc agcaacacca aggtggacaa gaaagttgag | 660 |
| cccaaatctt gtgacaaaac tcacacatgc ccaccgtgcc cagcacctga actcctgggg | 720 |
| ggaccgggcg aggtgggag tcaggtccag ttgcaacagt ctggagccga gctcgccagg | 780 |
| ccaggagcct ccgtcaaaat gtcatgcaag gcctcagggt acacatttac cgatatacc | 840 |
| atgcactggg tgaaacaaag accaggtcag ggacttgaat ggatcggtta cattaacccc | 900 |
| tctagaggct atacgaatta caaccagaaa ttcaaagaca agcaacact tacgactgac | 960 |
| aaatccagta gtacggctta catgcagctc tcatctttga cttcagaaga ctctgctgta | 1020 |
| tattattgtg cccgctatta cgatgaccat tactgccttg attactgggg ccagggcact | 1080 |
| actgttaccg taagtgcggc tagcaccaag ggcccatcgg tcttccccct ggcaccctcc | 1140 |
| tccaagagca cctctggggg cacagcggcc ctgggctgcc tggtcaagga ctacttcccc | 1200 |
| gaaccggtga cggtgtcgtg gaactcaggc gccctgacca gcggcgtgca caccttcccg | 1260 |
| gctgtcctac agtcctcagg actctactcc ctcagcagcg tggtgaccgt gccctccagc | 1320 |
| agcctgggca cccagaccta catctgcaac gtgaatcaca gcccagcaa caccaaggtg | 1380 |
| gacaagagag ttgagcccaa atcttgttga | 1410 |

<210> SEQ ID NO 106
<211> LENGTH: 1383
<212> TYPE: DNA
<213> ORGANISM: Artificial Sequence
<220> FEATURE:
<223> OTHER INFORMATION: ACE-04-VL nucleotide sequence

<400> SEQUENCE: 106

| | |
|---|---|
| cagatgcagc tggtgcagtc tggggctgag gtgaagaagc ctgggtcctc ggtgaaggtc | 60 |
| tcctgcaagg cttctggagg caccttcagc agctatgcta tcagctgggt gcgacaggcc | 120 |
| cctggacaag gcttgagtg gatgggaagg atcatcccta tccttggtat agcaaactac | 180 |

```
gcacagaagt tccagggcag agtcacgatt accgcggaca atccacgag cacagcctac      240 atggagctga gcagcctgag atctgaggac acggccgtgt attactgtgc gaaaccgaga      300
gatggctaca atttggttgc ttttgatatc tggggccaag gacgatggt caccgtctcc      360 tcagctagca ccaagggccc atcggtcttc cccctggcac cctcctccaa gagcacctct      420
gggggcacag cggccctggg ctgcctggtc aaggactact ccccgaacc ggtgacggtg      480 tcgtggaact caggcgccct gaccagcggc gtgcacacct tcccggctgt cctacagtcc      540
tcaggactct actccctcag cagcgtggtg accgtgccct ccagcagcct gggcacccag      600
acctacatct gcaacgtgaa tcacaagccc agcaacacca ggtggacaa gaaagttgag      660 cccaaatctt gtgacaaaac tcacacatgc ccaccgtgcc cagcacctga actcctgggg      720
ggaccgggcg aggtgggag tcagatcgtc ctcactcaaa gtcctgctat tatgtccgca      780
agccctggtg aaaaggttac catgacttgc tccgcatcta gttctgtctc ttacatgaac      840
tggtaccagc aaaagtctgg aacgtccccg aaaaggtgga tatatgatac gagcaaattg      900
gcaagcggag tacccgcgca ttttaggggt tcaggcagcg gtacgtcata tagcctgact      960
attagcggaa tggaggcgga ggatgctgca acatattatt gccaacaatg gtcatcaaat     1020
ccttttactt tcggctcagg cacaaaactt gaaataaata gaaccgtggc tgcaccatct     1080
gtcttcatct cccgccatc tgatgagcag ttgaaatctg gaactgcctc tgttgtgtgc     1140
ctgctgaata acttctatcc cagagaggcc aaagtacagt ggaaggtgga taacgccctc     1200
caatcgggta actcccagga gagtgtcaca gagcaggaca gcaaggacag cacctacagc     1260
ctcagcagca ccctgacgct gagcaaagca gactacgaga acacaaagt ctacgcctgc     1320 gaagtcaccc atcagggcct gagctcgccc gtcacaaaga gcttcaacag gggagagtgt     1380
taa                                                                    1383

<210> SEQ ID NO 107
<211> LENGTH: 657
<212> TYPE: DNA
<213> ORGANISM: Artificial Sequence
<220> FEATURE:
<223> OTHER INFORMATION: ACE-04-LC, ACE-09-LC, ACE-12-LC (anti-PD-L1
      antibody light chain nucleotide sequence)

<400> SEQUENCE: 107
cagctcgtgc tgactcagcc gccctcagtg tctggggccc cagggcagag ggtcaccatc       60
tcctgcactg ggagcagctc caacatcggg gcaggttatg atgtacactg gtatcagcaa      120
cttccaggag cagcccccaa actcctcatc tatgccgaca tcaatcggcc ctcagggggtc     180 cctgaccgat tctctggctc caagtctggc atctcagcct ccctggctat cactgggctc      240
caggctgagg acgaggctga ttattactgc cagtcctatg acagcagcct gagtgggggg      300
gtgttcggcg agggaccaa gctgaccgtc ctaagatctg tggctgcacc atctgtcttc      360
atcttcccgc catctgatga gcagttgaaa tctggaactg cctctgttgt gtgcctgctg      420
aataacttct atcccagaga ggccaaagta cagtggaagg tggataacgc cctccaatcg      480
ggtaactccc aggagagtgt cacagagcag gacagcaagg acagcaccta cagcctcagc      540
agcaccctga cgctgagcaa agcagactac gagaaacaca aagtctacgc ctgcgaagtc      600
acccatcagg gcctgagctc gcccgtcaca aagagcttca caggggaga gtgttag         657

<210> SEQ ID NO 108
<211> LENGTH: 1095
```

```
<212> TYPE: DNA
<213> ORGANISM: Artificial Sequence
<220> FEATURE:
<223> OTHER INFORMATION: ACE-09-VH nucleotide sequence (without G4S
      linker)

<400> SEQUENCE: 108
cagatgcagc tggtgcagtc tggggctgag gtgaagaagc tggggtcctc ggtgaaggtc      60
tcctgcaagg cttctggagg caccttcagc agctatgcta tcagctgggt gcgacaggcc     120
cctggacaag ggcttgagtg gatgggaagg atcatccccta tccttggtat agcaaactac    180
gcacagaagt tccagggcag agtcacgatt accgcggaca aatccacgag cacagcctac    240
atggagctga gcagcctgag atctgaggac acggccgtgt attactgtgc gaaaccgaga    300
gatggctaca atttggttgc ttttgatatc tggggccaag ggacgatggt caccgtctcc    360
tcagctagca ccaagggccc atcggtcttc cccctggcac cctcctccaa gagcacctct    420
gggggcacag cggccctggg ctgcctggtc aaggactact tccccgaacc ggtgacggtg    480
tcgtggaact caggcgccct gaccagcggc gtgcacacct tcccggctgt cctacagtcc    540
tcaggactct actccctcag cagcgtggtg accgtgccct ccagcagcct gggcacccag    600
acctacatct gcaacgtgaa tcacaagccc agcaacacca aggtggacaa gaaagttgag    660
cccaaatctt gtgacaaaac tcacacatgc ccaccgtgcc cagcacctga actcctgggg    720
ggaccggagg tgcagctcca gcagtctgga cctgagctgg tgaagcctgg accttcaatg    780
aagatatcct gcaaggcttc tggttactca ttcactggct acaccatgaa ctgggtgaag    840
cagagtcatg gaaagaacct tgagtggatg gacttatata tccttacaa aggtgttagt    900 acctacaacc agaagttcaa ggacaaggcc acactgactg tagacaagtc atccagcaca    960
gcctacatgg aactcctcag tctgacatct gaggactctg cagtctatta ctgtgcaaga   1020
tcggggtact acgtgatag tgactggtac ttcgatgtct ggggccaggg gaccacgctg   1080
accgtcttct cataa                                                    1095

<210> SEQ ID NO 109
<211> LENGTH: 1053
<212> TYPE: DNA
<213> ORGANISM: Artificial Sequence
<220> FEATURE:
<223> OTHER INFORMATION: ACE-09-VL nucleotide sequence (without G4S
      linker)

<400> SEQUENCE: 109
cagatgcagc tggtgcagtc tggggctgag gtgaagaagc tggggtcctc ggtgaaggtc      60
tcctgcaagg cttctggagg caccttcagc agctatgcta tcagctgggt gcgacaggcc     120
cctggacaag ggcttgagtg gatgggaagg atcatccccta tccttggtat agcaaactac    180
gcacagaagt tccagggcag agtcacgatt accgcggaca aatccacgag cacagcctac    240
atggagctga gcagcctgag atctgaggac acggccgtgt attactgtgc gaaaccgaga    300
gatggctaca atttggttgc ttttgatatc tggggccaag ggacgatggt caccgtctcc    360
tcagctagca ccaagggccc atcggtcttc cccctggcac cctcctccaa gagcacctct    420
gggggcacag cggccctggg ctgcctggtc aaggactact tccccgaacc ggtgacggtg    480
tcgtggaact caggcgccct gaccagcggc gtgcacacct tcccggctgt cctacagtcc    540
tcaggactct actccctcag cagcgtggtg accgtgccct ccagcagcct gggcacccag    600
acctacatct gcaacgtgaa tcacaagccc agcaacacca aggtggacaa gaaagttgag    660
```

```
cccaaatctt gtgacaaaac tcacacatgc ccaccgtgcc cagcacctga actcctgggg      720
ggaccggaca tccagatgac ccagaccacc tcctccctgt ctgcctccct gggcgacaga      780
gtcaccatca gttgcagggc aagtcaggac attagaaatt atttaaactg gtatcaacag      840
aaaccagatg gaactgttaa actcctgatc tactacacat caagattaca ctcaggagtc      900
ccatcaaagt tcagtggcag tgggtctgga acagattatt ctctcaccat tagcaacctg      960
gagcaagagg atattgccac ttactttt gc caacagggta atacgcttcc gtggacgttc     1020
gctggaggca ccaagctgga aatcaaacgg taa                                  1053
```

<210> SEQ ID NO 110
<211> LENGTH: 1125
<212> TYPE: DNA
<213> ORGANISM: Artificial Sequence
<220> FEATURE:
<223> OTHER INFORMATION: ACE-12-VH nucleotide sequence (with 10 residues)

<400> SEQUENCE: 110

```
cagatgcagc tggtgcagtc tggggctgag gtgaagaagc ctgggtcctc ggtgaaggtc       60
tcctgcaagg cttctggagg cacctt cagc agctatgcta tcagctgggt gcgacaggcc     120
cctggacaag ggcttgagtg gatgggaagg atcatccct a tccttggtat agcaaactac     180
gcacagaagt tccagggcag agtcacgatt accgcggaca aatccacgag cacagcctac     240
atggagctga gcagcctgag atctgaggac acggccgtgt attactgtgc gaaaccgaga     300
gatggctaca atttggttgc ttttgatatc tggggccaag gg acgatggt caccgtctcc     360 tcagctagca ccaagggccc atcggtcttc cccctggcac cctcctccaa gagcacctct     420
gggggcacag cggccctggg ctgcctggtc aaggactact tccccgaacc ggtgacggtg     480
tcgtggaact caggcgccct gaccagcggc gtgcacacct tcccggctgt cctacagtcc     540
tcaggactct actccctcag cagcgtggtg accgtgccct ccagcagcct gggcacccag     600
acctacatct gcaacgtgaa tcacaagccc agcaacacca aggtggacaa gaaagttgag     660
cccaaatctt gtgacaaaac tcacacatgc ccaccgtgcc cagcacctga actcctgggg     720
ggaccgggcg gaggtgggag tggaggcgga ggatctgagg tgcagctcca gcagtctgga     780
cctgagctgg tgaagcctgg accttcaatg aagatatcct gcaaggcttc tggttactca     840
ttcactggct acaccatgaa ctgggtgaag cagagtcatg gaaagaacct gagtggatg      900 ggacttatta atccttacaa aggtgttagt acctacaacc agaagttcaa ggacaaggcc     960
acactgactg tagacaagtc atccagcaca gcctacatgg aactcctcag tctgacatct     1020
gaggactctg cagtctatta ctgtgcaaga tcggggtact acggtgatag tgactggtac     1080
ttcgatgtct ggggccaggg gaccacgctg accgtcttct cataa                     1125
```

<210> SEQ ID NO 111
<211> LENGTH: 1080
<212> TYPE: DNA
<213> ORGANISM: Artificial Sequence
<220> FEATURE:
<223> OTHER INFORMATION: ACE-12-VL nucleotide sequence (with 9 residues)

<400> SEQUENCE: 111

```
cagatgcagc tggtgcagtc tggggctgag gtgaagaagc ctgggtcctc ggtgaaggtc       60
tcctgcaagg cttctggagg cacctt cagc agctatgcta tcagctgggt gcgacaggcc     120
cctggacaag ggcttgagtg gatgggaagg atcatccct a tccttggtat agcaaactac     180
```

-continued

```
gcacagaagt tccagggcag agtcacgatt accgcggaca atccacgag cacagcctac    240 atggagctga gcagcctgag atctgaggac acggccgtgt attactgtgc gaaaccgaga    300
gatggctaca atttggttgc ttttgatatc tggggccaag ggacgatggt caccgtctcc    360
tcagctagca ccaagggccc atcggtcttc cccctggcac cctcctccaa gagcacctct    420 ggggcacag cggccctggg ctgcctggtc aaggactact ccccgaacc ggtgacggtg     480 tcgtggaact caggcgccct gaccagcggc gtgcacacct tcccggctgt cctacagtcc    540
tcaggactct actccctcag cagcgtggtg accgtgccct ccagcagcct gggcacccag    600
acctacatct gcaacgtgaa tcacaagccc agcaacacca aggtggacaa gaaagttgag    660
cccaaatctt gtgacaaaac tcacacatgc ccaccgtgcc cagcacctga actcctgggg    720
ggaccgggcg atccggcgg aggcggcagc ggagacatcc agatgaccca gccaccctcc    780
tccctgtctg cctccctggg cgacagagtc accatcagtt gcagggcaag tcaggacatt    840
agaaattatt taaactggta tcaacagaaa ccagatggaa ctgttaaact cctgatctac    900
tacacatcaa gattacactc aggagtccca tcaaagttca gtggcagtgg gtctggaaca    960
gattattctc tcaccattag caacctggag caagaggata ttgccactta cttttgccaa   1020
cagggtaata cgcttccgtg gacgttcgct ggaggcacca agctggaaat caaacggtaa  1080
```

<210> SEQ ID NO 112
<211> LENGTH: 5
<212> TYPE: PRT
<213> ORGANISM: Artificial Sequence
<220> FEATURE:
<223> OTHER INFORMATION: Linker in ACE-05-VH and ACE-05-VL

<400> SEQUENCE: 112

Gly Gly Gly Gly Ser
1               5

<210> SEQ ID NO 113
<211> LENGTH: 10
<212> TYPE: PRT
<213> ORGANISM: Artificial Sequence
<220> FEATURE:
<223> OTHER INFORMATION: Linker in ACE-12-VH

<400> SEQUENCE: 113

Gly Gly Gly Gly Ser Gly Gly Gly Gly Ser
1               5                   10

<210> SEQ ID NO 114
<211> LENGTH: 9
<212> TYPE: PRT
<213> ORGANISM: Artificial Sequence
<220> FEATURE:
<223> OTHER INFORMATION: Linker in ACE-12-VL

<400> SEQUENCE: 114

Gly Gly Ser Gly Gly Gly Gly Ser Gly
1               5

<210> SEQ ID NO 115
<211> LENGTH: 362
<212> TYPE: PRT
<213> ORGANISM: Artificial Sequence
<220> FEATURE:
<223> OTHER INFORMATION: ACE-00-VH amino acid sequence

<400> SEQUENCE: 115

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
            85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Arg Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Glu Val Gln Leu Val Glu Ser Gly Gly Gly Leu Val Gln Pro Gly
            245                 250                 255

Arg Ser Leu Arg Leu Ser Cys Ala Ala Ser Gly Phe Thr Phe Asp Asp
            260                 265                 270

Tyr Ala Met His Trp Val Arg Gln Ala Pro Gly Lys Gly Leu Glu Trp
        275                 280                 285

Val Ser Ala Ile Thr Trp Asn Ser Gly His Ile Asp Tyr Ala Asp Ser
290                 295                 300

Val Glu Gly Arg Phe Thr Ile Ser Arg Asp Asn Ala Lys Asn Ser Leu
305                 310                 315                 320

Tyr Leu Gln Met Asn Ser Leu Arg Ala Glu Asp Thr Ala Val Tyr Tyr
            325                 330                 335

Cys Ala Lys Val Ser Tyr Leu Ser Thr Ala Ser Ser Leu Asp Tyr Trp
            340                 345                 350

Gly Gln Gly Thr Leu Val Thr Val Ser Ser
            355                 360

<210> SEQ ID NO 116
<211> LENGTH: 349
<212> TYPE: PRT
<213> ORGANISM: Artificial Sequence
<220> FEATURE:
<223> OTHER INFORMATION: ACE-00-VL amino acid sequence

<400> SEQUENCE: 116

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
            35                  40                  45

Ala Arg Ile Tyr Pro Thr Asn Gly Tyr Thr Arg Tyr Ala Asp Ser Val
        50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
        180                 185                 190

Ser Ser Ser Leu Gly Thr Gln Thr Tyr Ile Cys Asn Val Asn His Lys
            195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Asp Ile Gln Met Thr Gln Ser Pro Ser Ser Leu Ser Ala Ser Val
            245                 250                 255

Gly Asp Arg Val Thr Ile Thr Cys Arg Ala Ser Gln Gly Ile Arg Asn
        260                 265                 270

Tyr Leu Ala Trp Tyr Gln Gln Lys Pro Gly Lys Ala Pro Lys Leu Leu
        275                 280                 285

Ile Tyr Ala Ala Ser Thr Leu Gln Ser Gly Val Pro Ser Arg Phe Ser
        290                 295                 300

Gly Ser Gly Ser Gly Thr Asp Phe Thr Leu Thr Ile Ser Ser Leu Gln
305                 310                 315                 320

Pro Glu Asp Val Ala Thr Tyr Tyr Cys Gln Arg Tyr Asn Arg Ala Pro
            325                 330                 335

Tyr Thr Phe Gly Gln Gly Thr Lys Val Glu Ile Lys Arg
        340                 345

<210> SEQ ID NO 117
<211> LENGTH: 214
<212> TYPE: PRT
<213> ORGANISM: Artificial Sequence
<220> FEATURE:
<223> OTHER INFORMATION: ACE-00-LC amino acid sequence (anti-CD19
      antibody light chain)

<400> SEQUENCE: 117

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Ser Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 118
<211> LENGTH: 8
<212> TYPE: PRT
<213> ORGANISM: Artificial Sequence
<220> FEATURE:
<223> OTHER INFORMATION: Fab region (Anti-Her2) in CDR H1 of ACE-00

<400> SEQUENCE: 118

Gly Phe Asn Ile Lys Asp Thr Tyr
1               5

<210> SEQ ID NO 119
<211> LENGTH: 8
<212> TYPE: PRT
<213> ORGANISM: Artificial Sequence
<220> FEATURE:
<223> OTHER INFORMATION: Fab region (Anti-Her2) in CDR H2 of ACE-00

<400> SEQUENCE: 119

Ile Tyr Pro Thr Asn Gly Tyr Thr
1               5

<210> SEQ ID NO 120
<211> LENGTH: 13
<212> TYPE: PRT
<213> ORGANISM: Artificial Sequence
<220> FEATURE:
<223> OTHER INFORMATION: Fab region (Anti-Her2) in CDR H3 of ACE-00

<400> SEQUENCE: 120

Ser Arg Trp Gly Gly Asp Gly Phe Tyr Ala Met Asp Tyr
1               5                   10

<210> SEQ ID NO 121
<211> LENGTH: 6
<212> TYPE: PRT
<213> ORGANISM: Artificial Sequence
<220> FEATURE:
<223> OTHER INFORMATION: Fab region (Anti-Her2) in CDR L1 of ACE-00

<400> SEQUENCE: 121

Gln Asp Val Asn Thr Ala
1               5

<210> SEQ ID NO 122
<211> LENGTH: 3
<212> TYPE: PRT
<213> ORGANISM: Artificial Sequence
<220> FEATURE:
<223> OTHER INFORMATION: Fab region (Anti-Her2) in CDR L2 of ACE-00

<400> SEQUENCE: 122

Ser Ala Ser
1

<210> SEQ ID NO 123
<211> LENGTH: 9
<212> TYPE: PRT
<213> ORGANISM: Artificial Sequence
<220> FEATURE:
<223> OTHER INFORMATION: Fab region (Anti-Her2) in CDR L3 of ACE-00

<400> SEQUENCE: 123

Gln Gln His Tyr Thr Thr Pro Pro Thr
1               5

<210> SEQ ID NO 124
<211> LENGTH: 8
<212> TYPE: PRT
<213> ORGANISM: Artificial Sequence
<220> FEATURE:
<223> OTHER INFORMATION: Fv region (Anti-TNF alpha) in CDR H1 of ACE-00

<400> SEQUENCE: 124

Gly Phe Thr Phe Asp Asp Tyr Ala
1               5

<210> SEQ ID NO 125
<211> LENGTH: 8
<212> TYPE: PRT
<213> ORGANISM: Artificial Sequence
<220> FEATURE:
<223> OTHER INFORMATION: Fv region (Anti-TNF alpha) in CDR H2 of ACE-00

<400> SEQUENCE: 125

Ile Thr Trp Asn Ser Gly His Ile
1               5

<210> SEQ ID NO 126
<211> LENGTH: 14
<212> TYPE: PRT
<213> ORGANISM: Artificial Sequence
<220> FEATURE:
<223> OTHER INFORMATION: Fv region (Anti-TNF alpha) in CDR H3 of ACE-00

<400> SEQUENCE: 126

Ala Lys Val Ser Tyr Leu Ser Thr Ala Ser Ser Leu Asp Tyr
1               5                   10

```
<210> SEQ ID NO 127
<211> LENGTH: 6
<212> TYPE: PRT
<213> ORGANISM: Artificial Sequence
<220> FEATURE:
<223> OTHER INFORMATION: Fv region (Anti-TNF alpha) in CDR L1 of ACE-00

<400> SEQUENCE: 127

Gln Gly Ile Arg Asn Tyr
1               5

<210> SEQ ID NO 128
<211> LENGTH: 3
<212> TYPE: PRT
<213> ORGANISM: Artificial Sequence
<220> FEATURE:
<223> OTHER INFORMATION: Fv region (Anti-TNF alpha) in CDR L2 of ACE-00

<400> SEQUENCE: 128

Ala Ala Ser
1

<210> SEQ ID NO 129
<211> LENGTH: 9
<212> TYPE: PRT
<213> ORGANISM: Artificial Sequence
<220> FEATURE:
<223> OTHER INFORMATION: Fv region (Anti-TNF alpha) in CDR L3 of ACE-00

<400> SEQUENCE: 129

Gln Arg Tyr Asn Arg Ala Pro Tyr Thr
1               5

<210> SEQ ID NO 130
<211> LENGTH: 5
<212> TYPE: PRT
<213> ORGANISM: Artificial Sequence
<220> FEATURE:
<223> OTHER INFORMATION: linker

<400> SEQUENCE: 130

Gly Gly Gly Gly Ser
1               5

<210> SEQ ID NO 131
<211> LENGTH: 10
<212> TYPE: PRT
<213> ORGANISM: Artificial Sequence
<220> FEATURE:
<223> OTHER INFORMATION: linker

<400> SEQUENCE: 131

Gly Gly Gly Gly Ser Gly Gly Gly Gly Ser
1               5                   10

<210> SEQ ID NO 132
<211> LENGTH: 9
<212> TYPE: PRT
<213> ORGANISM: Artificial Sequence
<220> FEATURE:
<223> OTHER INFORMATION: linker

<400> SEQUENCE: 132

Gly Gly Ser Gly Gly Gly Gly Ser Gly
1               5

<210> SEQ ID NO 133
```

```
<211> LENGTH: 5
<212> TYPE: PRT
<213> ORGANISM: Artificial Sequence
<220> FEATURE:
<223> OTHER INFORMATION: linker
<220> FEATURE:
<221> NAME/KEY: REPEAT
<222> LOCATION: (1)..(5)
<223> OTHER INFORMATION: The sequence can be repeated one, two, three,
      four or more times

<400> SEQUENCE: 133

Gly Gly Gly Gly Ser
1               5

<210> SEQ ID NO 134
<211> LENGTH: 15
<212> TYPE: PRT
<213> ORGANISM: Artificial Sequence
<220> FEATURE:
<223> OTHER INFORMATION: linker

<400> SEQUENCE: 134

Gly Gly Gly Gly Ser Gly Gly Gly Gly Ser Gly Gly Gly Gly Ser
1               5                   10                  15

<210> SEQ ID NO 135
<211> LENGTH: 20
<212> TYPE: PRT
<213> ORGANISM: Artificial Sequence
<220> FEATURE:
<223> OTHER INFORMATION: linker

<400> SEQUENCE: 135

Gly Gly Gly Gly Ser Gly Gly Gly Gly Ser Gly Gly Gly Gly Ser Gly
1               5                   10                  15

Gly Gly Gly Ser
                20
```

CELL ENGAGING BINDING MOLECULES

CROSS REFERENCE

This application claims the benefit of priority from U.S. Provisional Application No. 62/655,762, filed Apr. 10, 2018, and further claims the benefit of priority from U.S. Provisional Application No. 62/719,484, filed Aug. 17, 2018. Each of the foregoing applications, in their entirety, are incorporated herein by reference.

SEQUENCE LISTING

This application incorporates by reference in its entirety the Computer Readable Form (CRF) of a Sequence Listing in ASCII text format submitted via EFS-Web. The Sequence Listing text file submitted via EFS-Web, entitled 14489-004-999_SUB_SEQ_LISTING.txt, was created on Jul. 3, 2019, and is 142,053 bytes in size.

FIELD

The present disclosure generally relates to cell engaging binding molecules, methods of making the binding molecules, compositions comprising the binding molecules, and uses thereof.

BACKGROUND

Antibodies and/or antibody-based agents are now therapeutic options for a wide variety of diseases and disorders. Currently there are at least 70 antibodies approved in the United States and/or European Union, with large numbers of new molecules in preclinical studies and clinical trials. However, there is a continual search for new, better, and safer therapeutic agents within the research and clinical communities.

A naturally occurring antibody is monospecific and binds to one epitope or antigen. Multispecific antibodies combine specificities of multiple antibodies and have the capability to bind different antigens or epitopes. Many technical hurdles, however, have hampered development of multispecific antibodies; as such, few multispecific antibodies have been approved as therapeutics. Thus, there is still a need for better multispecific antibodies and methods to efficiently produce functional and stable multispecific antibodies.

SUMMARY

The present disclosure provides, in part, cell engaging binding molecules having multiple binding domains, methods of making the binding molecules, and pharmaceutical compositions comprising the binding molecules. Also provided herein are methods of treatment comprising administering the binding molecules.

In one aspect, provided herein are cell engaging binding molecules. In some embodiments, provided is a binding molecule comprising:
(a) a first polypeptide and a second polypeptide, each comprising an antibody light chain,
(b) a third polypeptide comprising, in the order from N-terminus to C-terminus, a first variable heavy (VH) region and a first constant heavy 1 (CH1) region, and a second VH region; and
(c) a fourth polypeptide comprising, in the order from N-terminus to C-terminus, a third VH region and a second CH1 region, and a variable light (VL) region,
wherein the first polypeptide and the first VH region and the first CH1 region of the third polypeptide form a first antigen binding Fab region;
wherein the second polypeptide and the third VH region and the second CH1 region of the fourth polypeptide form a second antigen binding Fab region;
wherein the second VH region of the third polypeptide and the VL region of the fourth polypeptide form an antigen binding Fv region; and
wherein the first Fab region and the second Fab region bind to a first antigen, the Fv region binds to a second antigen, and the first antigen is different from the second antigen.

In some embodiments, with regard to any of the previous binding molecules, the third polypeptide further comprises a constant heavy 3 (CH3) region C-terminal to the second VH region. In some embodiments, with regard to any of the previous binding molecules, the fourth polypeptide further comprises a CH3 region C-terminal to the VL region. In some embodiments, with regard to any of the previous binding molecules, both the third and the fourth polypeptides further comprise CH3 regions C-terminal to the second VH region and the VL region, respectively.

In some embodiments, with regard to any of the previous binding molecules, the third polypeptide further comprises an albumin binding domain or site (ABS) C-terminal to the second VH region. In some embodiments, with regard to any of the previous binding molecules, the fourth polypeptide further comprises an ABS C-terminal to the VL region. In some embodiments, with regard to any of the previous binding molecules, both the third and the fourth polypeptides further comprise ABS C-terminal to the second VH region and the VL region, respectively.

In some embodiments, with regard to any of the previous binding molecules, the third polypeptide further comprises a constant heavy 3 (CH3) region and an ABS C-terminal to the second VH region. In some embodiments, with regard to any of the previous binding molecules, the fourth polypeptide further comprises a CH3 region and an ABS C-terminal to the VL region. In some embodiments, with regard to any of the previous binding molecules, both the third and the fourth polypeptides further comprise CH3 regions and ABSs C-terminal to the second VH region and the VL region, respectively.

In some embodiments, with regard to any of the previous binding molecules, the third polypeptide and/or the four polypeptide further comprise both a CH1 region and an ABS C-terminal to the second VH region and/or to the VL region, respectively.

In some embodiments, with regard to any of the previous binding molecules, the first and/or second polypeptides further comprise an ABS. In some embodiments, with regard to any of the previous binding molecules, the first and/or second polypeptides further comprise an ABS C-terminal to the antibody light chain. In specific embodiments, with regard to any of the previous binding molecules, the first and/or second polypeptides further comprise an ABS at the C-terminus of the antibody light chain.

In some embodiments, provided herein are binding molecules wherein the first Fab region and the second Fab region are linked to the Fv region via a flexible peptide region. In some embodiments, the first Fab region and the second Fab region are linked to the Fv region via fusion.

In some embodiments, the flexible peptide region comprises an antibody hinge region. In some embodiments, the antibody hinge region is an Immunoglobulin G (IgG) hinge region. In some embodiments, the antibody hinge region is selected from the group consisting of IgG1, IgG2, IgG3, and IgG4 hinge regions. In some embodiments, the antibody hinge region comprises an interchain disulfide bond between the third polypeptide and the fourth polypeptide. In some embodiments, the flexible peptide region further comprises a linker. In some embodiments, the linker comprises an amino acid sequence of GGGGS (G4S) (SEQ ID NO.: 130). In some embodiments, the linker comprises two tandem copies of the amino acid sequence of GGGGS (G4S) (SEQ ID NO.: 130).

In some embodiments, the first Fab region and the second Fab region bind to the same epitope of the first antigen. In some embodiments, the second antigen is expressed on an immune cell. In some embodiments, the immune cell is selected from the group consisting of lymphocytes and monocytes. In some embodiments, the immune cell is an effector cell. In some embodiments, the immune cell is selected from the group consisting of a T cell, a B cell, a dendritic cell, a granulocyte, an innate lymphoid cell, a megakaryocyte, a monocyte, a myeloid-derived suppressor cell, and a natural killer (NK) cell.

In some embodiments, the first antigen is a cancer antigen. In some embodiments, the cancer antigen is a tumor associated antigen (TAA) or a tumor specific antigen (TSA). In some embodiments, the first antigen is selected from a group consisting of CD19, CD20, EGFR, Her2, and PD-L1. In some embodiments, the second antigen is CD3 or TNF alpha. In some embodiments, the first antigen is a cancer antigen and the second antigen is CD3. In some embodiments, the cancer antigen is selected from a group consisting of CD19, CD20, EGFR, Her2, and PD-L1.

In another aspect, provided herein are methods of making a binding molecule. In some embodiments, provided is a method of making a binding molecule, comprising:
(i) expressing the binding molecule from one or more vectors in a host cell, wherein the one or more vectors comprise
(a) a first nucleic acid encoding a first polypeptide and a second nucleic acid encoding a second polypeptide, wherein each of the first polypeptide and the second polypeptide is an antibody light chain,
(b) a third nucleic acid encoding a third polypeptide comprising, in the order from N-terminus to C-terminus, a first VH region and a first CH1 region and a second VH region; and
(c) a fourth nucleic acid encoding a fourth polypeptide comprising, in the order from N-terminus to C-terminus, a third VH region and a second CH1 region and a VL region, wherein the first polypeptide and the first VH region and the first CH1 region of the third polypeptide can form a first antigen binding Fab region;
wherein the second polypeptide and the third VH region and the second CH1 region of the fourth polypeptide can form a second antigen binding Fab region; and
wherein the second VH region of the third polypeptide and the VL region of the fourth polypeptide form an antigen binding Fv region; and
wherein the first Fab region and the second Fab region bind to a first antigen, the Fv region binds to a second antigen, and the first antigen is different from the second antigen, and
(ii) purifying the binding molecule.

In some embodiments, with regard to any of the previous methods, the third polypeptide further comprises a constant heavy 3 (CH3) region C-terminal to the second VH region. In some embodiments, with regard to any of the previous methods, the fourth polypeptide further comprises a CH3 region C-terminal to the VL region. In some embodiments, with regard to any of the previous methods, both the third and the fourth polypeptides further comprise CH3 regions C-terminal to the second VH region and the VL region, respectively.

In some embodiments, with regard to any of the previous methods, the third polypeptide further comprises an albumin binding domain or site (ABS) C-terminal to the second VH region. In some embodiments, with regard to any of the previous methods, the fourth polypeptide further comprises an ABS C-terminal to the VL region. In some embodiments, with regard to any of the previous methods, both the third and the fourth polypeptides further comprise ABS C-terminal to the second VH region and the VL region, respectively.

In some embodiments, with regard to any of the previous methods, the third polypeptide further comprises a constant heavy 3 (CH3) region and an ABS C-terminal to the second VH region. In some embodiments, with regard to any of the previous methods, the fourth polypeptide further comprises a CH3 region and an ABS C-terminal to the VL region. In some embodiments, with regard to any of the previous methods, both the third and the fourth polypeptides further comprise CH3 regions and ABSs C-terminal to the second VH region and the VL region, respectively.

In some embodiments, with regard to any of the previous methods, the third polypeptide and/or the four polypeptide further comprise both a CH1 region and an ABS C-terminal to the second VH region and/or to the VL region, respectively.

In some embodiments, with regard to any of the previous methods, the first and/or second polypeptides further comprise an ABS. In some embodiments, with regard to any of the previous methods, the first and/or second polypeptides further comprise an ABS C-terminal to the antibody light chain. In specific embodiments, with regard to any of the previous methods, the first and/or second polypeptides further comprise an ABS at the C-terminus of the antibody light chain.

In some embodiments, provided herein are methods wherein the first Fab region and the second Fab region are linked to the Fv region via a flexible peptide region comprising an antibody hinge region. In some embodiments, the antibody hinge region comprises an interchain disulfide bond formed between the third polypeptide and the fourth polypeptide. In some embodiments, the flexible peptide region further comprises a linker. In some embodiments, the linker comprises an amino acid sequence of GGGGS (G4S) (SEQ ID NO.: 130).

In some embodiments, the first antigen is a cancer antigen and the second antigen is CD3. In some embodiments, the first antigen is selected from a group consisting of CD19, CD20, EGFR, Her2, and PD-L1.

In yet another aspect, provided herein are pharmaceutical compositions comprising a binding molecule. In some embodiments, provided is a pharmaceutical composition comprising a binding molecule and a pharmaceutically acceptable carrier, wherein the binding molecule comprises:
(a) a first polypeptide and a second polypeptide, each comprising an antibody light chain,
(b) a third polypeptide comprising, in the order from N-terminus to C-terminus, a first VH region and a first CH1 region, and a second VH region; and
(c) a fourth polypeptide comprising, in the order from N-terminus to C-terminus, a third VH region and a second CH1 region, and a VL region,
wherein the first polypeptide and the first VH region and the first CH1 region of the third polypeptide form a first antigen binding Fab region;

wherein the second polypeptide and the third VH region and the second CH1 region of the fourth polypeptide form a second antigen Fab region;

wherein the second VH region of the third polypeptide and the VL region of the fourth polypeptide form an antigen binding Fv region; and wherein the first Fab region and the second Fab region bind to a first antigen, the Fv region binds to a second antigen, and the first antigen is different from the second antigen.

In some embodiments, with regard to any of the previous pharmaceutical compositions, the third polypeptide further comprises a constant heavy 3 (CH3) region C-terminal to the second VH region. In some embodiments, with regard to any of the previous pharmaceutical compositions, the fourth polypeptide further comprises a CH3 region C-terminal to the VL region. In some embodiments, with regard to any of the previous pharmaceutical compositions, both the third and the fourth polypeptides further comprise CH3 regions C-terminal to the second VH region and the VL region, respectively.

In some embodiments, with regard to any of the previous pharmaceutical compositions, the third polypeptide further comprises an albumin binding domain or site (ABS) C-terminal to the second VH region. In some embodiments, with regard to any of the previous pharmaceutical compositions, the fourth polypeptide further comprises an ABS C-terminal to the VL region. In some embodiments, with regard to any of the previous pharmaceutical compositions, both the third and the fourth polypeptides further comprise ABS C-terminal to the second VH region and the VL region, respectively.

In some embodiments, with regard to any of the previous pharmaceutical compositions, the third polypeptide further comprises a constant heavy 3 (CH3) region and an ABS C-terminal to the second VH region. In some embodiments, with regard to any of the previous pharmaceutical compositions, the fourth polypeptide further comprises a CH3 region and an ABS C-terminal to the VL region. In some embodiments, with regard to any of the previous pharmaceutical compositions, both the third and the fourth polypeptides further comprise CH3 regions and ABSs C-terminal to the second VH region and the VL region, respectively.

In some embodiments, with regard to any of the previous pharmaceutical compositions, the third polypeptide and/or the four polypeptide further comprise both a CH1 region and an ABS C-terminal to the second VH region and/or to the VL region, respectively.

In some embodiments, with regard to any of the previous pharmaceutical compositions, the first and/or second polypeptides further comprise an ABS. In some embodiments, with regard to any of the previous pharmaceutical compositions, the first and/or second polypeptides further comprise an ABS C-terminal to the antibody light chain. In specific embodiments, with regard to any of the previous pharmaceutical compositions, the first and/or second polypeptides further comprise an ABS at the C-terminus of the antibody light chain.

In yet another aspect, provided herein are methods of treating a disease or condition comprising administering a binding molecule. In some embodiments, provided is a method of treating a disease or condition in a subject comprising administering a therapeutically effective amount of a binding molecule to the subject, wherein the binding molecule comprises:

(a) a first polypeptide and a second polypeptide, each comprising an antibody light chain, (b) a third polypeptide comprising, in the order from N-terminus to C-terminus, a first VH region and a first CH1 region, and a second VH region; and (c) a fourth polypeptide comprising, in the order from N-terminus to C-terminus, a third VH region and a second CH1 region, and a VL region, wherein the first polypeptide and the first VH region and the first CH1 region of the third polypeptide form a first antigen binding Fab region;

wherein the second polypeptide and the third VH region and the second CH1 region of the fourth polypeptide form a second antigen Fab region;

wherein the second VH region of the third polypeptide and the VL region of the fourth polypeptide form an antigen binding Fv region; and wherein the first Fab region and the second Fab region bind to a first antigen, the Fv region binds to a second antigen, and the first antigen is different from the second antigen.

In some embodiments, with regard to any of the previous methods, the third polypeptide further comprises a constant heavy 3 (CH3) region C-terminal to the second VH region. In some embodiments, with regard to any of the previous methods, the fourth polypeptide further comprises a CH3 region C-terminal to the VL region. In some embodiments, with regard to any of the previous methods, both the third and the fourth polypeptides further comprise CH3 regions C-terminal to the second VH region and the VL region, respectively.

In some embodiments, with regard to any of the previous methods, the third polypeptide further comprises an albumin binding domain or site (ABS) C-terminal to the second VH region. In some embodiments, with regard to any of the previous methods, the fourth polypeptide further comprises an ABS C-terminal to the VL region. In some embodiments, with regard to any of the previous methods, both the third and the fourth polypeptides further comprise ABS C-terminal to the second VH region and the VL region, respectively.

In some embodiments, with regard to any of the previous methods, the third polypeptide further comprises a constant heavy 3 (CH3) region and an ABS C-terminal to the second VH region. In some embodiments, with regard to any of the previous methods, the fourth polypeptide further comprises a CH3 region and an ABS C-terminal to the VL region. In some embodiments, with regard to any of the previous methods, both the third and the fourth polypeptides further comprise CH3 regions and ABSs C-terminal to the second VH region and the VL region, respectively.

In some embodiments, with regard to any of the previous methods, the third polypeptide and/or the four polypeptide further comprise both a CH1 region and an ABS C-terminal to the second VH region and/or to the VL region, respectively.

In some embodiments, with regard to any of the previous methods, the first and/or second polypeptides further comprise an ABS. In some embodiments, with regard to any of the previous methods, the first and/or second polypeptides further comprise an ABS C-terminal to the antibody light chain. In specific embodiments, with regard to any of the previous methods, the first and/or second polypeptides further comprise an ABS at the C-terminus of the antibody light chain.

In one aspect, provided herein are cell engaging binding molecules. In some embodiments, provided is a binding molecule comprising:

(a) a first polypeptide and a second polypeptide, each comprising an antibody light chain, (b) a third polypeptide comprising, in the order from N-terminus to C-terminus, a first variable heavy (VH) region and a first constant heavy 1 (CH1) region, and a second VH region; and (c) a fourth polypeptide comprising, in the order from N-terminus to C-terminus, a third VH region and a second CH1 region, and a variable light (VL) region, wherein the first polypeptide and the first VH region and the first CH1 region of the third polypeptide form a first antigen binding Fab region;

wherein the second polypeptide and the third VH region and the second CH1 region of the fourth polypeptide form a second antigen binding Fab region;

wherein the second VH region of the third polypeptide and the VL region of the fourth polypeptide form an antigen binding Fv region; and wherein the first Fab region and the second Fab region binds to Programmed Death-Ligand 1 (PD-L1), and the Fv region binds to Cluster of Differentiation 3 (CD3).

In some embodiments, with regard to any of the previous binding molecules, the third polypeptide further comprises a constant heavy 3 (CH3) region C-terminal to the second VH region. In some embodiments, with regard to any of the previous binding molecules, the fourth polypeptide further comprises a CH3 region C-terminal to the VL region. In some embodiments, with regard to any of the previous binding molecules, both the third and the fourth polypeptides further comprise CH3 regions C-terminal to the second VH region and the VL region, respectively.

In some embodiments, with regard to any of the previous binding molecules, the third polypeptide further comprises an albumin binding domain or site (ABS) C-terminal to the second VH region. In some embodiments, with regard to any of the previous binding molecules, the fourth polypeptide further comprises an ABS C-terminal to the VL region. In some embodiments, with regard to any of the previous binding molecules, both the third and the fourth polypeptides further comprise ABS C-terminal to the second VH region and the VL region, respectively.

In some embodiments, with regard to any of the previous binding molecules, the third polypeptide and/or the four polypeptide further comprise both a CH1 region and an ABS C-terminal to the second VH region and/or to the VL region, respectively.

In some embodiments, with regard to any of the previous binding molecules, the third polypeptide further comprises a constant heavy 3 (CH3) region and an ABS C-terminal to the second VH region. In some embodiments, with regard to any of the previous binding molecules, the fourth polypeptide further comprises a CH3 region and an ABS C-terminal to the VL region. In some embodiments, with regard to any of the previous binding molecules, both the third and the fourth polypeptides further comprise CH3 regions and ABSs C-terminal to the second VH region and the VL region, respectively.

In some embodiments, with regard to any of the previous binding molecules, the first and/or second polypeptides further comprise an ABS. In some embodiments, with regard to any of the previous binding molecules, the first and/or second polypeptides further comprise an ABS C-terminal to the antibody light chain. In specific embodiments, with regard to any of the previous binding molecules, the first and/or second polypeptides further comprise an ABS at the C-terminus of the antibody light chain.

In some embodiments, provided is a binding molecule, wherein:

(a) the antibody light chains of the first and the second polypeptide each comprise three Complementarity Determining Regions (CDRs) having amino acid sequences of SEQ ID NO.: 9, SEQ ID NO.: 10, and SEQ ID NO.: 11;

(b) in the third polypeptide, the first VH region comprises three CDRs having amino acid sequences of SEQ ID NO.: 5, SEQ ID NO.: 6, and SEQ ID NO.: 7, and the second VH region comprises three CDRs having amino acid sequences of SEQ ID NO.: 13, SEQ ID NO.: 14, and SEQ ID NO.: 15; and (c) in the fourth polypeptide, the third VH region comprises three CDRs having amino acid sequences of SEQ ID NO.: 5, SEQ ID NO.: 6, and SEQ ID NO.: 7, and the VL region comprises three CDRs having amino acid sequences of SEQ ID NO.: 17, SEQ ID NO.: 18, and SEQ ID NO.: 19.

In some embodiments, the first Fab region and the second Fab region are linked to the Fv region via a flexible peptide region. In some embodiments, the first Fab region and the second Fab region are linked to the Fv region via fusion.

In some embodiments, the flexible peptide region comprises an antibody hinge region. In some embodiments, the antibody hinge region is an Immunoglobulin G (IgG) hinge region. In some embodiments, the antibody hinge region is selected from the group consisting of IgG1, IgG2, IgG3, and IgG4 hinge regions. In some embodiments, the antibody hinge region comprises an interchain disulfide bond between the third polypeptide and the fourth polypeptide.

In some embodiments, the flexible peptide region further comprises a linker. In some embodiments, the linker comprises an amino acid sequence of GGGGS (G4S) (SEQ ID NO.: 130). In some embodiments, the linker comprises an amino acid sequence of GGGGSGGGGS (SEQ ID NO.: 131) In some embodiments, the linker comprises an amino acid sequence of GGSGGGGSG (SEQ ID NO.: 132).

In some embodiments, provided is a binding molecule, wherein:

(a) the antibody light chains of the first and the second polypeptide each comprise a VL region that comprises the amino acid sequence of SEQ ID NO.: 8;

(b) in the third polypeptide, the first VH region comprises the amino acid sequence of SEQ ID NO.: 4, and the second VH region comprises the amino acid sequence of SEQ ID NO.: 12; and (c) in the fourth polypeptide, the third VH region comprises the amino acid sequence of SEQ ID NO.: 4, and the VL region comprises the amino acid sequence of SEQ ID NO.: 16.

In some embodiments, the first polypeptide and the second polypeptide each comprise the amino acid sequence of SEQ ID NO.: 3; the third polypeptide comprises the amino acid sequence of SEQ ID NO.: 1; and the fourth polypeptide comprises the amino acid sequence of SEQ ID NO.: 2.

In some embodiments, the first polypeptide and the second polypeptide each comprise the amino acid sequence of SEQ ID NO.: 95; the third polypeptide comprises the amino acid sequence of SEQ ID NO.: 96; and the fourth polypeptide comprises the amino acid sequence of SEQ ID NO.: 97.

In some embodiments, the first polypeptide and the second polypeptide each have the amino acid sequence of SEQ ID NO.: 95; the third polypeptide has the amino acid sequence of SEQ ID NO.: 98; and the fourth polypeptide has the amino acid sequence of SEQ ID NO.: 99.

In another aspect, provided herein are methods of making a binding molecule. In some embodiments, provided is a method of making a binding molecule, comprising:
(i) expressing the binding molecule from one or more vectors in a host cell, wherein the one or more vectors comprise
(a) a first nucleic acid encoding a first polypeptide and a second nucleic acid encoding a second polypeptide, wherein each polypeptide comprises an antibody light chain,
(b) a third nucleic acid encoding a third polypeptide comprising, in the order from N-terminus to C-terminus, a first variable heavy (VH) region and a first constant heavy 1 (CH1) region, and a second VH region; and
(c) a fourth nucleic acid encoding a fourth polypeptide comprising, in the order from N-terminus to C-terminus, a third VH region and a second CH1 region, and a variable light (VL) region,
wherein the first polypeptide and the first VH region and the first CH1 region of the third polypeptide form a first antigen binding Fab region;
wherein the second polypeptide and the third VH region and the second CH1 region of the fourth polypeptide form a second antigen binding Fab region;
wherein the second VH region of the third polypeptide and the VL region of the fourth polypeptide form an antigen binding Fv region; and
wherein the first Fab region and the second Fab region bind to PD-L1, and the Fv region binds to CD3, and
(ii) purifying the binding molecule.

In some embodiments, with regard to any of the previous methods, the third polypeptide further comprises a constant heavy 3 (CH3) region C-terminal to the second VH region. In some embodiments, with regard to any of the previous methods, the fourth polypeptide further comprises a CH3 region C-terminal to the VL region. In some embodiments, with regard to any of the previous methods, both the third and the fourth polypeptides further comprise CH3 regions C-terminal to the second VH region and the VL region, respectively.

In some embodiments, with regard to any of the previous methods, the third polypeptide further comprises an albumin binding domain or site (ABS) C-terminal to the second VH region. In some embodiments, with regard to any of the previous methods, the fourth polypeptide further comprises an ABS C-terminal to the VL region. In some embodiments, with regard to any of the previous methods, both the third and the fourth polypeptides further comprise ABS C-terminal to the second VH region and the VL region, respectively.

In some embodiments, with regard to any of the previous methods, the third polypeptide further comprises a constant heavy 3 (CH3) region and an ABS C-terminal to the second VH region. In some embodiments, with regard to any of the previous methods, the fourth polypeptide further comprises a CH3 region and an ABS C-terminal to the VL region. In some embodiments, with regard to any of the previous methods, both the third and the fourth polypeptides further comprise CH3 regions and ABSs C-terminal to the second VH region and the VL region, respectively.

In some embodiments, with regard to any of the previous methods, the third polypeptide and/or the four polypeptide further comprise both a CH1 region and an ABS C-terminal to the second VH region and/or to the VL region, respectively.

In some embodiments, with regard to any of the previous methods, the first and/or second polypeptides further comprise an ABS. In some embodiments, with regard to any of the previous methods, the first and/or second polypeptides further comprise an ABS C-terminal to the antibody light chain. In specific embodiments, with regard to any of the previous methods, the first and/or second polypeptides further comprise an ABS at the C-terminus of the antibody light chain.

In some embodiments, provided is a method, wherein:
(a) the antibody light chains of the first and the second polypeptide each comprise three Complementarity Determining Regions (CDRs) having amino acid sequences of SEQ ID NO.: 9, SEQ ID NO.: 10, and SEQ ID NO.: 11;
(b) in the third polypeptide, the first VH region comprises three CDRs having amino acid sequences of SEQ ID NO.: 5, SEQ ID NO.: 6, and SEQ ID NO.: 7, and the second VH region comprises three CDRs having amino acid sequences of SEQ ID NO.: 13, SEQ ID NO.: 14, and SEQ ID NO.: 15; and
(c) in the fourth polypeptide, the third VH region comprises three CDRs having amino acid sequences of SEQ ID NO.: 5, SEQ ID NO.: 6, and SEQ ID NO.: 7, and the VL region comprises three CDRs having amino acid sequences of SEQ ID NO.: 17, SEQ ID NO.: 18, and SEQ ID NO.: 19.

In some embodiments, the first Fab region and the second Fab region are linked to the Fv region via a flexible peptide region. In some embodiments, the flexible peptide region comprises an antibody hinge region. In some embodiments, the antibody hinge region comprises an interchain disulfide bond between the third polypeptide and the fourth polypeptide.

In some embodiments, the flexible peptide region further comprises a linker. In some embodiments, the linker comprises an amino acid sequence of GGGGS (G4S) (SEQ ID NO.: 130). In some embodiments, the linker comprises an amino acid sequence of GGGGSGGGGS (SEQ ID NO.: 131). In some embodiments, the linker comprises an amino acid sequence of GGSGGGGSG (SEQ ID NO.: 132).

In some embodiments, provided is a method, wherein the VH region of each of the first and second Fab regions comprises an amino acid sequence of SEQ ID NO.: 4;
wherein the VL region of each of the first and second Fab regions comprises an amino acid sequence of SEQ ID NO.: 8;
wherein the VH region of the Fv region comprises an amino acid sequence of SEQ ID NO.: 12; and
wherein the VL region of the Fv region comprises an amino acid sequence of SEQ ID NO.: 16.

In some embodiments, the first polypeptide and the second polypeptide each have the amino acid sequence of SEQ ID NO.: 3; the third polypeptide has the amino acid sequence of SEQ ID NO.: 1; and the fourth polypeptide has the amino acid sequence of SEQ ID NO.: 2.

In yet another aspect, provided herein are pharmaceutical compositions comprising a binding molecule. In some embodiments, provided is a pharmaceutical composition comprising a binding molecule and a pharmaceutically acceptable carrier, wherein the binding molecule comprises:
(a) a first polypeptide and a second polypeptide, each comprising an antibody light chain,
(b) a third polypeptide comprising, in the order from N-terminus to C-terminus, a first variable heavy (VH) region and a first constant heavy 1 (CH1) region, and a second VH region; and
(c) a fourth polypeptide comprising, in the order from N-terminus to C-terminus, a third VH region and a second CH1 region, and a variable light (VL) region, wherein the first polypeptide and the first VH region and the first CH1 region of the third polypeptide form a first antigen binding Fab region;

wherein the second polypeptide and the third VH region and the second CH1 region of the fourth polypeptide form a second antigen binding Fab region;

wherein the second VH region of the third polypeptide and the VL region of the fourth polypeptide form an antigen binding Fv region; and wherein the first Fab region and the second Fab region binds to PD-L1, and the Fv region binds to CD3.

In some embodiments, with regard to any of the previous pharmaceutical compositions, the third polypeptide further comprises a constant heavy 3 (CH3) region C-terminal to the second VH region. In some embodiments, with regard to any of the previous pharmaceutical compositions, the fourth polypeptide further comprises a CH3 region C-terminal to the VL region. In some embodiments, with regard to any of the previous pharmaceutical compositions, both the third and the fourth polypeptides further comprise CH3 regions C-terminal to the second VH region and the VL region, respectively.

In some embodiments, with regard to any of the previous pharmaceutical compositions, the third polypeptide further comprises an albumin binding domain or site (ABS) C-terminal to the second VH region. In some embodiments, with regard to any of the previous pharmaceutical compositions, the fourth polypeptide further comprises an ABS C-terminal to the VL region. In some embodiments, with regard to any of the previous pharmaceutical compositions, both the third and the fourth polypeptides further comprise ABS C-terminal to the second VH region and the VL region, respectively.

In some embodiments, with regard to any of the previous pharmaceutical compositions, the third polypeptide further comprises a constant heavy 3 (CH3) region and an ABS C-terminal to the second VH region. In some embodiments, with regard to any of the previous pharmaceutical compositions, the fourth polypeptide further comprises a CH3 region and an ABS C-terminal to the VL region. In some embodiments, with regard to any of the previous pharmaceutical compositions, both the third and the fourth polypeptides further comprise CH3 regions and ABSs C-terminal to the second VH region and the VL region, respectively.

In some embodiments, with regard to any of the previous pharmaceutical compositions, the third polypeptide and/or the four polypeptide further comprise both a CH1 region and an ABS C-terminal to the second VH region and/or to the VL region, respectively.

In some embodiments, with regard to any of the previous pharmaceutical compositions, the first and/or second polypeptides further comprise an ABS. In some embodiments, with regard to any of the previous pharmaceutical compositions, the first and/or second polypeptides further comprise an ABS C-terminal to the antibody light chain. In specific embodiments, with regard to any of the previous pharmaceutical compositions, the first and/or second polypeptides further comprise an ABS at the C-terminus of the antibody light chain.

In yet another aspect, provided herein are methods of treating a disease or condition comprising administering a binding molecule. In some embodiments, provided is a method of treating a disease or condition in a subject comprising administering a therapeutically effective amount of a binding molecule to the subject, wherein the binding molecule comprises:

(a) a first polypeptide and a second polypeptide, each comprising an antibody light chain, (b) a third polypeptide comprising, in the order from N-terminus to C-terminus, a first variable heavy (VH) region and a first constant heavy 1 (CH1) region, and a second VH region; and (c) a fourth polypeptide comprising, in the order from N-terminus to C-terminus, a third VH region and a second CH1 region, and a variable light (VL) region, wherein the first polypeptide and the first VH region and the first CH1 region of the third polypeptide form a first antigen binding Fab region;

wherein the second polypeptide and the third VH region and the second CH1 region of the fourth polypeptide form a second antigen binding Fab region;

wherein the second VH region of the third polypeptide and the VL region of the fourth polypeptide form an antigen binding Fv region; and wherein the first Fab region and the second Fab region binds to PD-L1, and the Fv region binds to CD3.

In some embodiments, with regard to any of the previous methods, the third polypeptide further comprises a constant heavy 3 (CH3) region C-terminal to the second VH region. In some embodiments, with regard to any of the previous methods, the fourth polypeptide further comprises a CH3 region C-terminal to the VL region. In some embodiments, with regard to any of the previous methods, both the third and the fourth polypeptides further comprise CH3 regions C-terminal to the second VH region and the VL region, respectively.

In some embodiments, with regard to any of the previous methods, the third polypeptide further comprises an albumin binding domain or site (ABS) C-terminal to the second VH region. In some embodiments, with regard to any of the previous methods, the fourth polypeptide further comprises an ABS C-terminal to the VL region. In some embodiments, with regard to any of the previous methods, both the third and the fourth polypeptides further comprise ABS C-terminal to the second VH region and the VL region, respectively.

In some embodiments, with regard to any of the previous methods, the third polypeptide further comprises a constant heavy 3 (CH3) region and an ABS C-terminal to the second VH region. In some embodiments, with regard to any of the previous methods, the fourth polypeptide further comprises a CH3 region and an ABS C-terminal to the VL region. In some embodiments, with regard to any of the previous methods, both the third and the fourth polypeptides further comprise CH3 regions and ABSs C-terminal to the second VH region and the VL region, respectively.

In some embodiments, with regard to any of the previous methods, the third polypeptide and/or the four polypeptide further comprise both a CHI region and an ABS C-terminal to the second VH region and/or to the VL region, respectively.

In some embodiments, with regard to any of the previous methods, the first and/or second polypeptides further comprise an ABS. In some embodiments, with regard to any of the previous methods, the first and/or second polypeptides further comprise an ABS C-terminal to the antibody light chain. In specific embodiments, with regard to any of the previous methods, the first and/or second polypeptides further comprise an ABS at the C-terminus of the antibody light chain.

In one aspect, provided herein are cell engaging binding molecules. In some embodiments, provided is a binding molecule comprising:

(a) a first polypeptide and a second polypeptide, each comprising an antibody light chain, (b) a third polypeptide comprising, in the order from N-terminus to C-terminus, a first variable heavy (VH) region and a first constant heavy 1 (CH1) region, and a second VH region; and (c) a fourth polypeptide comprising, in the order from N-terminus to C-terminus, a third VH region and a second CH1 region, and a variable light (VL) region, wherein the first polypeptide and the first VH region and the first CH1 region of the third polypeptide form a first antigen binding Fab region;

wherein the second polypeptide and the third VH region and the second CH1 region of the fourth polypeptide form a second antigen binding Fab region;

wherein the second VH region of the third polypeptide and the VL region of the fourth polypeptide form an antigen binding Fv region; and wherein the first Fab region and the second Fab region each binds to CD20 or epidermal growth factor receptor (EGFR), and the Fv region binds to CD3.

In some embodiments, with regard to any of the previous binding molecules, the third polypeptide further comprises a constant heavy 3 (CH3) region C-terminal to the second VH region. In some embodiments, with regard to any of the previous binding molecules, the fourth polypeptide further comprises a CH3 region C-terminal to the VL region. In some embodiments, with regard to any of the previous binding molecules, both the third and the fourth polypeptides further comprise CH3 regions C-terminal to the second VH region and the VL region, respectively.

In some embodiments, with regard to any of the previous binding molecules, the third polypeptide further comprises an albumin binding domain or site (ABS) C-terminal to the second VH region. In some embodiments, with regard to any of the previous binding molecules, the fourth polypeptide further comprises an ABS C-terminal to the VL region. In some embodiments, with regard to any of the previous binding molecules, both the third and the fourth polypeptides further comprise ABS C-terminal to the second VH region and the VL region, respectively.

In some embodiments, with regard to any of the previous binding molecules, the third polypeptide further comprises a constant heavy 3 (CH3) region and an ABS C-terminal to the second VH region. In some embodiments, with regard to any of the previous binding molecules, the fourth polypeptide further comprises a CH3 region and an ABS C-terminal to the VL region. In some embodiments, with regard to any of the previous binding molecules, both the third and the fourth polypeptides further comprise CH3 regions and ABSs C-terminal to the second VH region and the VL region, respectively.

In some embodiments, with regard to any of the previous binding molecules, the third polypeptide and/or the four polypeptide further comprise both a CH1 region and an ABS C-terminal to the second VH region and/or to the VL region, respectively.

In some embodiments, with regard to any of the previous binding molecules, the first and/or second polypeptides further comprise an ABS. In some embodiments, with regard to any of the previous binding molecules, the first and/or second polypeptides further comprise an ABS C-terminal to the antibody light chain. In specific embodiments, with regard to any of the previous binding molecules, the first and/or second polypeptides further comprise an ABS at the C-terminus of the antibody light chain.

In some embodiments, the first Fab region and the second Fab region bind to CD20, and (a) the antibody light chains of the first and the second polypeptide each comprise three Complementarity Determining Regions (CDRs) having amino acid sequences of SEQ ID NO.: 31, SEQ ID NO.: 32, and SEQ ID NO.: 33;

(b) in the third polypeptide, the first VH region comprises three CDRs having amino acid sequences of SEQ ID NO.: 27, SEQ ID NO.: 28, and SEQ ID NO.: 29, and the second VH region comprises three CDRs having amino acid sequences of SEQ ID NO.: 13, SEQ ID NO.: 14, and SEQ ID NO.: 15; and (c) in the fourth polypeptide, the third VH region comprises three CDRs having amino acid sequences of SEQ ID NO.: 27, SEQ ID NO.: 28, and SEQ ID NO.: 29, and the VL region comprises three CDRs having amino acid sequences of SEQ ID NO.: 17, SEQ ID NO.: 18, and SEQ ID NO.: 19.

In some embodiments, the first Fab region and the second Fab region are linked to the Fv region via a flexible peptide region. In some embodiments, the flexible peptide region comprises an antibody hinge region. In some embodiments, the antibody hinge region comprises an interchain disulfide bond between the third polypeptide and the fourth polypeptide. In some embodiments, the flexible peptide region further comprises a linker.

In some embodiments, provided is a binding molecule, wherein:

(a) the antibody light chains of the first and the second polypeptide each comprise a VL region that comprises the amino acid sequence of SEQ ID NO.: 30;

(b) in the third polypeptide, the first VH region comprises the amino acid sequence of SEQ ID NO.: 26, and the second VH region comprises the amino acid sequence of SEQ ID NO.: 12; and (c) in the fourth polypeptide, the third VH region comprises the amino acid sequence of SEQ ID NO.: 26, and the VL region comprises the amino acid sequence of SEQ ID NO.: 16.

In some embodiments, the first polypeptide and the second polypeptide each have the amino acid sequence of SEQ ID NO.: 25; the third polypeptide has the amino acid sequence of SEQ ID NO.: 23; and the fourth polypeptide has the amino acid sequence of SEQ ID NO.: 24.

In some embodiments, the first Fab region and the second Fab region bind to EGFR, and (a) the antibody light chains of the first and the second polypeptide each comprise three CDRs having amino acid sequences of SEQ ID NO.: 45, SEQ ID NO.: 46, and SEQ ID NO.: 47;

(b) in the third polypeptide, the first VH region comprises three CDRs having amino acid sequences of SEQ ID NO.: 41, SEQ ID NO.: 42, and SEQ ID NO.: 43, and the second VH region comprises three CDRs having amino acid sequences of SEQ ID NO.: 13, SEQ ID NO.: 14, and SEQ ID NO.: 15; and (c) in the fourth polypeptide, the third VH region comprises three CDRs having amino acid sequences of SEQ ID NO.: 41, SEQ ID NO.: 42, and SEQ ID NO.: 43, and the VL region comprises three CDRs having amino acid sequences of SEQ ID NO.: 17, SEQ ID NO.: 18, and SEQ ID NO.: 19.

In some embodiments, the first Fab region and the second Fab region are linked to the Fv region via a flexible peptide region. In some embodiments, the flexible peptide region comprises an antibody hinge region. In some embodiments, the antibody hinge region comprises an interchain disulfide bond between the third polypeptide and the fourth polypeptide. In some embodiments, the flexible peptide region further comprises a linker.

In some embodiments, provided is a binding molecule, wherein:
(a) the antibody light chains of the first and the second polypeptide each comprise a VL region that comprises the amino acid sequence of SEQ ID NO.: 44;
(b) in the third polypeptide, the first VH region comprises the amino acid sequence of SEQ ID NO.: 40, and the second VH region comprises the amino acid sequence of SEQ ID NO.: 12; and
(c) in the fourth polypeptide, the third VH region comprises the amino acid sequence of SEQ ID NO.: 40, and the VL region comprises the amino acid sequence of SEQ ID NO.: 16.

In some embodiments, the first polypeptide and the second polypeptide each have the amino acid sequence of SEQ ID NO.: 39; the third polypeptide has the amino acid sequence of SEQ ID NO.: 37; and the fourth polypeptide has the amino acid sequence of SEQ ID NO.: 38.

In another aspect, provided herein are methods of making a binding molecule. In some embodiments, provided is a method of making a binding molecule, comprising:
(i) expressing the binding molecule from one or more vectors in a host cell, wherein the one or more vectors comprise
(a) a first nucleic acid encoding a first polypeptide and a second nucleic acid encoding a second polypeptide, wherein each of the first polypeptide and the second polypeptide is an antibody light chain,
(b) a third nucleic acid encoding a third polypeptide comprising, in the order from N-terminus to C-terminus, a first VH region and a first CH1 region, and a second VH region; and
(c) a fourth nucleic acid encoding a fourth polypeptide comprising, in the order from N-terminus to C-terminus, a third VH region and a second CH1 region, and a VL region,
wherein the first polypeptide and the first VH region and the first CH1 region of the third polypeptide form a first antigen binding Fab region;
wherein the second polypeptide and the third VH region and the second CH1 region of the fourth polypeptide form a second antigen binding Fab region;
wherein the second VH region of the third polypeptide and the VL region of the fourth polypeptide form an antigen binding Fv region; and
wherein the first Fab region and the second Fab region each binds to CD20 or EGFR, and the Fv region binds to CD3, and
(ii) purifying the binding molecule.

In some embodiments, with regard to any of the previous methods, the third polypeptide further comprises a constant heavy 3 (CH3) region C-terminal to the second VH region. In some embodiments, with regard to any of the previous methods, the fourth polypeptide further comprises a CH3 region C-terminal to the VL region. In some embodiments, with regard to any of the previous methods, both the third and the fourth polypeptides further comprise CH3 regions C-terminal to the second VH region and the VL region, respectively.

In some embodiments, with regard to any of the previous methods, the third polypeptide further comprises an albumin binding domain or site (ABS) C-terminal to the second VH region. In some embodiments, with regard to any of the previous methods, the fourth polypeptide further comprises an ABS C-terminal to the VL region. In some embodiments, with regard to any of the previous methods, both the third and the fourth polypeptides further comprise ABS C-terminal to the second VH region and the VL region, respectively.

In some embodiments, with regard to any of the previous methods, the third polypeptide further comprises a constant heavy 3 (CH3) region and an ABS C-terminal to the second VH region. In some embodiments, with regard to any of the previous methods, the fourth polypeptide further comprises a CH3 region and an ABS C-terminal to the VL region. In some embodiments, with regard to any of the previous methods, both the third and the fourth polypeptides further comprise CH3 regions and ABSs C-terminal to the second VH region and the VL region, respectively.

In some embodiments, with regard to any of the previous methods, the third polypeptide and/or the four polypeptide further comprise both a CH1 region and an ABS C-terminal to the second VH region and/or to the VL region, respectively.

In some embodiments, with regard to any of the previous methods, the first and/or second polypeptides further comprise an ABS. In some embodiments, with regard to any of the previous methods, the first and/or second polypeptides further comprise an ABS C-terminal to the antibody light chain. In specific embodiments, with regard to any of the previous methods, the first and/or second polypeptides further comprise an ABS at the C-terminus of the antibody light chain.

In some embodiments, the first Fab region and the second Fab region bind to CD20, and
(a) the antibody light chains of the first and the second polypeptide each comprise three Complementarity Determining Regions (CDRs) having amino acid sequences of SEQ ID NO.: 31, SEQ ID NO.: 32, and SEQ ID NO.: 33;
(b) in the third polypeptide, the first VH region comprises three CDRs having amino acid sequences of SEQ ID NO.: 27, SEQ ID NO.: 28, and SEQ ID NO.: 29, and the second VH region comprises three CDRs having amino acid sequences of SEQ ID NO.: 13, SEQ ID NO.: 14, and SEQ ID NO.: 15; and
(c) in the fourth polypeptide, the third VH region comprises three CDRs having amino acid sequences of SEQ ID NO.: 27, SEQ ID NO.: 28, and SEQ ID NO.: 29, and the VL region comprises three CDRs having amino acid sequences of SEQ ID NO.: 17, SEQ ID NO.: 18, and SEQ ID NO.: 19.

In some embodiments, the first Fab region and the second Fab region are linked to the Fv region via a flexible peptide region. In some embodiments, the flexible peptide region comprises an antibody hinge region. In some embodiments, the flexible peptide region further comprises a linker.

In some embodiment, provided is a method, wherein:
(a) the antibody light chains of the first and the second polypeptide each comprise a VL region that comprises the amino acid sequence of SEQ ID NO.: 30;
(b) in the third polypeptide, the first VH region comprises the amino acid sequence of SEQ ID NO.: 26, and the second VH region comprises the amino acid sequence of SEQ ID NO.: 12; and
(c) in the fourth polypeptide, the third VH region comprises the amino acid sequence of SEQ ID NO.: 26, and the VL region comprises the amino acid sequence of SEQ ID NO.: 16.

In some embodiments, the first polypeptide and the second polypeptide each have the amino acid sequence of SEQ ID NO.: 25; the third polypeptide has the amino acid sequence of SEQ ID NO.: 23; and the fourth polypeptide has the amino acid sequence of SEQ ID NO.: 24.

In some embodiments, the first Fab region and the second Fab region bind to CD20, and
(a) the antibody light chains of the first and the second polypeptide each comprise three CDRs having amino acid sequences of SEQ ID NO.: 45, SEQ ID NO.: 46, and SEQ ID NO.: 47;
(b) in the third polypeptide, the first VH region comprises three CDRs having amino acid sequences of SEQ ID NO.: 41, SEQ ID NO.: 42, and SEQ ID NO.: 43, and the second VH region comprises three CDRs having amino acid sequences of SEQ ID NO.: 13, SEQ ID NO.: 14, and SEQ ID NO.: 15; and
(c) in the fourth polypeptide, the third VH region comprises three CDRs having amino acid sequences of SEQ ID NO.: 41, SEQ ID NO.: 42, and SEQ ID NO.: 43, and the VL region comprises three CDRs having amino acid sequences of SEQ ID NO.: 17, SEQ ID NO.: 18, and SEQ ID NO.: 19.

In some embodiments, the first Fab region and the second Fab region are linked to the Fv region via a flexible peptide region. In some embodiments, the flexible peptide region comprises an antibody hinge region. In some embodiments, the flexible peptide region further comprises a linker.

In some embodiment, provided is a method, wherein:
(a) the antibody light chains of the first and the second polypeptide each comprise a VL region that comprises the amino acid sequence of SEQ ID NO.: 44;
(b) in the third polypeptide, the first VH region comprises the amino acid sequence of SEQ ID NO.: 40, and the second VH region comprises the amino acid sequence of SEQ ID NO.: 12; and
(c) in the fourth polypeptide, the third VH region comprises the amino acid sequence of SEQ ID NO.: 40, and the VL region comprises the amino acid sequence of SEQ ID NO.: 16.

In some embodiments, the first polypeptide and the second polypeptide each have the amino acid sequence of SEQ ID NO.: 39; the third polypeptide has the amino acid sequence of SEQ ID NO.: 37; and the fourth polypeptide has the amino acid sequence of SEQ ID NO.: 38.

In yet another aspect, provided herein are pharmaceutical compositions comprising a binding molecule. In some embodiments, provided is a pharmaceutical composition comprising a therapeutically effective amount of a binding molecule and a pharmaceutically acceptable carrier, wherein the binding molecule comprises:
(a) a first polypeptide and a second polypeptide, each comprising an antibody light chain,
(b) a third polypeptide comprising, in the order from N-terminus to C-terminus, a first variable heavy (VH) region and a first constant heavy 1 (CH1) region, and a second VH region; and
(c) a fourth polypeptide comprising, in the order from N-terminus to C-terminus, a third VH region and a second CH1 region, and a variable light (VL) region,
wherein the first polypeptide and the first VH region and the first CH1 region of the third polypeptide form a first antigen binding Fab region;
wherein the second polypeptide and the third VH region and the second CH1 region of the fourth polypeptide form a second antigen binding Fab region;
wherein the second VH region of the third polypeptide and the VL region of the fourth polypeptide form an antigen binding Fv region; and
wherein the first Fab region and the second Fab region each binds to CD20 or EGFR, and the Fv region binds to CD3.

In some embodiments, with regard to any of the previous pharmaceutical compositions, the third polypeptide further comprises a constant heavy 3 (CH3) region C-terminal to the second VH region. In some embodiments, with regard to any of the previous pharmaceutical compositions, the fourth polypeptide further comprises a CH3 region C-terminal to the VL region. In some embodiments, with regard to any of the previous pharmaceutical compositions, both the third and the fourth polypeptides further comprise CH3 regions C-terminal to the second VH region and the VL region, respectively.

In some embodiments, with regard to any of the previous pharmaceutical compositions, the third polypeptide further comprises an albumin binding domain or site (ABS) C-terminal to the second VH region. In some embodiments, with regard to any of the previous pharmaceutical compositions, the fourth polypeptide further comprises an ABS C-terminal to the VL region. In some embodiments, with regard to any of the previous pharmaceutical compositions, both the third and the fourth polypeptides further comprise ABS C-terminal to the second VH region and the VL region, respectively.

In some embodiments, with regard to any of the previous pharmaceutical compositions, the third polypeptide further comprises a constant heavy 3 (CH3) region and an ABS C-terminal to the second VH region. In some embodiments, with regard to any of the previous pharmaceutical compositions, the fourth polypeptide further comprises a CH3 region and an ABS C-terminal to the VL region. In some embodiments, with regard to any of the previous pharmaceutical compositions, both the third and the fourth polypeptides further comprise CH3 regions and ABSs C-terminal to the second VH region and the VL region, respectively.

In some embodiments, with regard to any of the previous pharmaceutical compositions, the third polypeptide and/or the four polypeptide further comprise both a CH1 region and an ABS C-terminal to the second VH region and/or to the VL region, respectively.

In some embodiments, with regard to any of the previous pharmaceutical compositions, the first and/or second polypeptides further comprise an ABS. In some embodiments, with regard to any of the previous pharmaceutical compositions, the first and/or second polypeptides further comprise an ABS C-terminal to the antibody light chain. In specific embodiments, with regard to any of the previous pharmaceutical compositions, the first and/or second polypeptides further comprise an ABS at the C-terminus of the antibody light chain.

In yet another aspect, provided herein are methods of treating a disease or condition comprising administering a binding molecule. In some embodiments, provided is a method of treating a disease or condition in a subject comprising administering a therapeutically effective amount of a binding molecule to the subject, wherein the binding molecule comprises:
(a) a first polypeptide and a second polypeptide, each comprising an antibody light chain,
(b) a third polypeptide comprising, in the order from N-terminus to C-terminus, a first variable heavy (VH) region and a first constant heavy 1 (CH1) region, and a second VH region; and
(c) a fourth polypeptide comprising, in the order from N-terminus to C-terminus, a third VH region and a second CH1 region, and a variable light (VL) region, wherein the first polypeptide and the first VH region and the first CH1 region of the third polypeptide form a first antigen binding Fab region;

wherein the second polypeptide and the third VH region and the second CH1 region of the fourth polypeptide form a second antigen binding Fab region;

wherein the second VH region of the third polypeptide and the VL region of the fourth polypeptide form an antigen binding Fv region; and wherein the first Fab region and the second Fab region each binds to CD20 or EGFR, and the Fv region binds to CD3.

In some embodiments, with regard to any of the previous methods, the third polypeptide further comprises a constant heavy 3 (CH3) region C-terminal to the second VH region. In some embodiments, with regard to any of the previous methods, the fourth polypeptide further comprises a CH3 region C-terminal to the VL region. In some embodiments, with regard to any of the previous methods, both the third and the fourth polypeptides further comprise CH3 regions C-terminal to the second VH region and the VL region, respectively.

In some embodiments, with regard to any of the previous methods, the third polypeptide further comprises an albumin binding domain or site (ABS) C-terminal to the second VH region. In some embodiments, with regard to any of the previous methods, the fourth polypeptide further comprises an ABS C-terminal to the VL region. In some embodiments, with regard to any of the previous methods, both the third and the fourth polypeptides further comprise ABS C-terminal to the second VH region and the VL region, respectively.

In some embodiments, with regard to any of the previous methods, the third polypeptide further comprises a constant heavy 3 (CH3) region and an ABS C-terminal to the second VH region. In some embodiments, with regard to any of the previous methods, the fourth polypeptide further comprises a CH3 region and an ABS C-terminal to the VL region. In some embodiments, with regard to any of the previous methods, both the third and the fourth polypeptides further comprise CH3 regions and ABSs C-terminal to the second VH region and the VL region, respectively.

In some embodiments, with regard to any of the previous methods, the third polypeptide and/or the four polypeptide further comprise both a CH1 region and an ABS C-terminal to the second VH region and/or to the VL region, respectively.

In some embodiments, with regard to any of the previous methods, the first and/or second polypeptides further comprise an ABS. In some embodiments, with regard to any of the previous methods, the first and/or second polypeptides further comprise an ABS C-terminal to the antibody light chain. In specific embodiments, with regard to any of the previous methods, the first and/or second polypeptides further comprise an ABS at the C-terminus of the antibody light chain.

The present disclosure provides, in part, cell engaging binding molecules having multiple binding domains. In one aspect, provided herein is a binding molecule comprising:

(a) a first antigen binding domain comprising two antibody Fab regions, each comprising:
  (i) a first portion comprising an antibody variable heavy (VH) region and an antibody CH1 region, wherein the first portion does not contain an antibody CH2 region and an antibody CH3 region; and
  (ii) a second portion comprising an antibody light chain (LC) comprising an antibody variable light (VL) region and an antibody light chain constant region (CL), wherein the two antibody Fab regions each bind to an antigen, and (b) a second antigen binding domain comprising an antibody Fv region comprising a VH region and an antibody variable light (VL) region, wherein the second antigen binding domain binds to an antigen present on an immune cell; and wherein the first antigen binding domain and the second antigen binding domain are linked.

In certain embodiments, the first portion and the second portion of each Fab region of the first antigen binding domain are on the same polypeptide. In some embodiments, at least one Fab region is oriented from N-terminus to C-terminus in the following order: VH-CH1-VL-CL. In other embodiments, at least one Fab region is oriented from N-terminus to C-terminus in the following order: VL-CL-VH-CH1.

In certain embodiments, the first portion and the second portion of each Fab region are present on separate polypeptides.

In certain embodiments, the VH region and the VL region of the Fv region are on the same polypeptide. In some embodiments, the Fv region is oriented from N-terminus to C-terminus in the following order: VH-VL. In other embodiments, the Fv region is oriented from N-terminus to C-terminus in the following order: VL-VH.

In certain embodiments, the VH region and the VL region of the Fv region are on separate polypeptides.

In some embodiments, the first antigen binding domain and the second antigen binding domain are linked by a flexible peptide region. In some embodiments, the flexible peptide region comprises an antibody hinge region. In some specific embodiments, the antibody hinge region is a IgG hinge region. In some more specific embodiments, the IgG hinge region is of IgG1 subtype. In other more specific embodiments, the IgG hinge region is of IgG2 subtype. In yet other more specific embodiments, the IgG hinge region is of IgG3 subtype. In yet other more specific embodiments, the IgG hinge region is of IgG4 subtype.

In certain embodiments, the flexible peptide region comprise additional amino acids. For example, in some embodiments, the flexible peptide region further comprises a linker between the antibody hinge region and the second antigen binding domain. In some embodiments, the linker comprises an amino acid sequence of GGGGS (G4S)( SEQ ID NO.: 130).

In some embodiments, the second antigen binding domain further comprises a first CH3 region linked to the VH region of the Fv region and a second CH3 region linked to the VL region of the Fv region.

In some embodiments, the binding molecule further comprises one or more albumin binding domain or site (ABS). In some embodiments, the ABS is linked to the C-terminus of the VH region of the Fv region. In other embodiments, the ABS is linked to the C-terminus of the VL region of the Fv region. In yet other embodiments, the C-terminus of each of the VL and VH regions of the Fv region is linked to ABS. In other embodiments, the ABS is linked to the CL region of at least one of the Fab regions. In yet other embodiments, the binding molecule further comprises one or more albumin domain.

In some embodiments, the two Fab regions bind to different antigens. In other embodiments, the two Fab regions bind to the same antigen. In some embodiments, the two Fab regions bind to the same epitope of the same antigen. In other embodiments, the two Fab regions bind to different epitopes of the same antigen.

In some embodiments, the first antigen binding domain and the second antigen binding domain bind to the same antigen. In some embodiments, the second antigen binding domain binds to the same epitope as at least one of the epitopes bound by the first antigen binding domain.

In other embodiments, the first antigen binding domain and the second antigen binding domain bind to different antigens, and wherein the first antigen binding domain binds to a first antigen and the second antigen binding domain binds to a second antigen.

In some embodiments, the first antigen is a cancer antigen. In other embodiments, the first antigen is not a cancer antigen.

In some embodiments, the second antigen is expressed on an immune cells including lymphocytes and monocytes. In some embodiments, the second antigen is expressed on a T cell. In some embodiments, the second antigen is expressed on a B cell. In other embodiments, the second antigen is expressed on a dendritic cell. In other embodiments, the second antigen is expressed on a granulocyte. In yet other embodiments, the second antigen is expressed on an innate lymphoid cell. In yet other embodiments, the second antigen is expressed on a megakaryocyte. In yet other embodiments, the second antigen is expressed on a monocyte. In yet other embodiments, the second antigen is expressed on a myeloid-derived suppressor cell. In yet other embodiments, the second antigen is expressed on a NK cell.

In some embodiments, the second antigen is expressed on an effector cell. In some embodiments, the second antigen is expressed on a T cell. In some embodiments, the second antigen is expressed on a T helper cell, a regulatory T cell, or a cytotoxic T cell. In some embodiments, the second antigen is expressed on a T helper cell. In some embodiments, the second antigen is expressed on a regulatory T cell. In some embodiments, the second antigen is expressed on a cytotoxic T cell. In some embodiments, the second antigen is expressed on a CD8+ T cell. In some embodiments, the second antigen is expressed on a CD4+ T cell. In some embodiments, the second antigen comprises an extracellular domain.

In some embodiments, the VH region of the first portion of each Fab region comprise the same CDR amino acid sequences. In other embodiments, the VH region of the first portion of each Fab region comprise different CDR amino acid sequences.

In some embodiments, the VL region of the second portion of each Fab region comprise the same CDR amino acid sequences. In other embodiments, the VL region of the second portion of each Fab region comprise different CDR amino acid sequence In some embodiments, the VH region of the first portion of each Fab region comprise the same CDR amino acid sequences, and the VL region of the second portion of each Fab region comprise the same CDR amino acid sequences. In some embodiments, the VH region of the first portion of each Fab region comprise the same CDR amino acid sequences, and the VL region of the second portion of each Fab region comprise different CDR amino acid sequences. In some embodiments, the VH region of the first portion of each Fab region comprise different CDR amino acid sequences, and the VL region of the second portion of each Fab region comprise the same CDR amino acid sequences. In some embodiments, the VH region of the first portion of each Fab region comprise different CDR amino acid sequences, and the VL region of the second portion of each Fab region comprise different CDR amino acid sequences.

In some specific embodiments, the second antigen is CD3. In some embodiments, the first antigen is a cancer antigen and the second antigen is CD3.

In some more specific embodiments, the first antigen is PD-L1 and the second antigen is CD3.

In some embodiments, the VH region of the first portion of each Fab region comprises three CDRs having amino acid sequences of SEQ ID NO.: 5, SEQ ID NO.: 6, and SEQ ID NO.: 7; the VL region of the second portion of each Fab region comprises three CDRs having amino acid sequences of SEQ ID NO.: 9, SEQ ID NO.: 10, and SEQ ID NO.: 11; the VH region of the Fv region comprises three CDRs having amino acid sequences of SEQ ID NO.: 13, SEQ ID NO.: 14, SEQ ID NO.: 15; and the VL region of the Fv region comprises three CDRs having amino acid sequences of SEQ ID NO.: 17, SEQ ID NO.: 18, and SEQ ID NO.: 19.

In some embodiments, the VH region of the first portion of each Fab region has an amino acid sequence of SEQ ID NO.: 4; the VL region of the second portion of each Fab region has an amino acid sequence of SEQ ID NO.: 8; the VH region of the Fv region has an amino acid sequence of SEQ ID NO.: 12; and the VL region of the Fv region has an amino acid sequence of SEQ ID NO.: 16.

In other more specific embodiments, the first antigen is CD20 and the second antigen is CD3.

In some embodiments, the VH region of the first portion of each Fab region comprises three CDRs having amino acid sequences of SEQ ID NO.: 27, SEQ ID NO.: 28, SEQ ID NO.: 29; the VL region of the second portion of each Fab region comprises three CDRs having amino acid sequences of SEQ ID NO.: 31, SEQ ID NO.: 32, and SEQ ID NO.: 33; the VH region of the Fv region comprises three CDRs having amino acid sequences of SEQ ID NO.: 13, SEQ ID NO.: 14, SEQ ID NO.: 15; and the VL region of the Fv region comprises three CDRs having amino acid sequences of SEQ ID NO.: 17, SEQ ID NO.: 18, and SEQ ID NO.: 19.

In some embodiments, the VH region of the first portion of each Fab region has an amino acid sequence of SEQ ID NO.: 26; the VL region of the second portion of each Fab region has an amino acid sequence of SEQ ID NO.: 30; the VH region of the Fv region has an amino acid sequence of SEQ ID NO.: 12; and the VL region of the Fv region has an amino acid sequence of SEQ ID NO.: 16.

In other more specific embodiments, the first antigen is EGFR and the second antigen is CD3.

In some embodiments, the VH region of the first portion of each Fab region comprises three CDRs having amino acid sequences of SEQ ID NO.: 41, SEQ ID NO.: 42, and SEQ ID NO.: 43; the VL region of the second portion of each Fab region comprises three CDRs having amino acid sequences of SEQ ID NO.: 45, SEQ ID NO.: 46, and SEQ ID NO.: 47; the VH region of the Fv region comprises three CDRs having amino acid sequences of SEQ ID NO.: 13, SEQ ID NO.: 14, and SEQ ID NO.: 15 and the VL region of the Fv region comprises three CDRs having amino acid sequences of SEQ ID NO.: 17, SEQ ID NO.: 18, and SEQ ID NO.: 19.

In some embodiments, the VH region of the first portion of each Fab region has an amino acid sequence of SEQ ID NO.: 40; the VL region of the second portion of each Fab region has an amino acid sequence of SEQ ID NO.: 44; the VH region of the Fv region has an amino acid sequence of SEQ ID NO.: 12; and the VL region of the Fv region has an amino acid sequence of SEQ ID NO.: 16.

In other more specific embodiments, the first antigen is Her2 and the second antigen is TNF alpha. In some embodiments, the VH region of the first portion of each Fab region has an amino acid sequence of SEQ ID NO.: 51; the VL region of the second portion of each Fab region has an amino acid sequence of SEQ ID NO.: 52; the VH region of the Fv region has an amino acid sequence of SEQ ID NO.: 53; and the VL region of the Fv region has an amino acid sequence of SEQ ID NO.: 54.

In another aspect, provide herein is a binding molecule, comprising:
(a) a first polypeptide and a second polypeptide, each comprising an antibody light chain,
(b) a third polypeptide comprising a first VH region and a first CH1 region, and a second VH region; and
(c) a fourth polypeptide comprising a third VH region and a second CH1, and a VL region,
wherein the first polypeptide and the first VH region and the first CH1 region of the third polypeptide form a first antigen binding Fab region;
wherein the second polypeptide and the third VH region and the second CH1 region of the fourth polypeptide form a second antigen Fab region; and
wherein the second VH region of the third polypeptide and the VL region of the fourth polypeptide form an antigen binding Fv region.

In some embodiments, the first Fab region and the second Fab region are linked to the Fv region via a flexible peptide region. In some embodiments, the flexible peptide region comprises an antibody hinge region. In some specific embodiments, the antibody hinge region is a IgG hinge region. In some more specific embodiments, the IgG hinge region is of IgG1 subtype. In other more specific embodiments, the IgG hinge region is of IgG2 subtype. In yet other more specific embodiments, the IgG hinge region is of IgG3 subtype. In yet other more specific embodiments, the IgG hinge region is of IgG4 subtype. In some embodiments, the flexible peptide region further comprises a linker between the antibody hinge region and the second antigen binding domain. In some embodiments, the linker comprises an amino acid sequence of GGGGS (G4S) (SEQ ID NO.: 130).

In some embodiments, the first Fab region and the second Fab region bind to different antigens. In other embodiments, the first Fab region and the second Fab region bind to the same antigen. In some embodiments, the first Fab region and the second Fab region bind to the same epitope of the same antigen. In other embodiments, the first Fab region and the second Fab region bind to different epitopes of the same antigen.

In certain embodiments, the first Fab region and the second Fab region form a first antigen binding domain, and the Fv region forms a second antigen binding domain.

In some embodiments, the first antigen binding domain and the second antigen binding domain bind to the same antigen. In some embodiments, the second antigen binding domain binds to the same epitope as at least one of the epitopes bound by the first antigen binding domain.

In other embodiments, the first antigen binding domain and the second antigen binding domain bind to different antigens, and wherein the first antigen binding domain binds to a first antigen and the second antigen binding domain binds to a second antigen.

In some embodiments, the first antigen is a cancer antigen. In other embodiments, the first antigen is not a cancer antigen.

In some embodiments, the second antigen is expressed on an immune cells including lymphocytes and monocytes. In some embodiments, the second antigen is expressed on a T cell. In some embodiments, the second antigen is expressed on a B cell. In other embodiments, the second antigen is expressed on a dendritic cell. In other embodiments, the second antigen is expressed on a granulocyte. In yet other embodiments, the second antigen is expressed on an innate lymphoid cell. In yet other embodiments, the second antigen is expressed on a megakaryocyte. In yet other embodiments, the second antigen is expressed on a monocyte. In yet other embodiments, the second antigen is expressed on a myeloid-derived suppressor cell. In yet other embodiments, the second antigen is expressed on a NK cell.

In some embodiments, the second antigen is expressed on an effector cell. In some embodiments, the second antigen is expressed on a T cell. In some embodiments, the second antigen is expressed on a T helper cell, a regulatory T cell, or a cytotoxic T cell. In some embodiments, the second antigen is expressed on a T helper cell. In some embodiments, the second antigen is expressed on a regulatory T cell. In some embodiments, the second antigen is expressed on a cytotoxic T cell. In some embodiments, the second antigen is expressed on a CD8+ T cell. In some embodiments, the second antigen is expressed on a CD4+ T cell. In some embodiments, the second antigen comprises an extracellular domain.

In some specific embodiments, the second antigen is CD3. In some embodiments, the first antigen is a cancer antigen and the second antigen is CD3.

In some more specific embodiments, the first antigen is PD-L1 and the second antigen is CD3.

In some embodiments, the VH region of the first portion of each Fab region comprises three CDRs having amino acid sequences of SEQ ID NO.: 5, SEQ ID NO.: 6, and SEQ ID NO.: 7; the VL region of the second portion of each Fab region comprises three CDRs having amino acid sequences of SEQ ID NO.: 9, SEQ ID NO.: 10, and SEQ ID NO.: 11; the VH region of the Fv region comprises three CDRs having amino acid sequences of SEQ ID NO.: 13, SEQ ID NO.: 14, and SEQ ID NO.: 15; and the VL region of the Fv region comprises three CDRs having amino acid sequences of SEQ ID NO.: 16, SEQ ID NO.: 17, and SEQ ID NO.: 19.

In some embodiments, the VH region of the first portion of each Fab region has an amino acid sequence of SEQ ID NO.: 4; the VL region of the second portion of each Fab region has an amino acid sequence of SEQ ID NO.: 8; the VH region of the Fv region has an amino acid sequence of SEQ ID NO.: 12; and the VL region of the Fv region has an amino acid sequence of SEQ ID NO.: 16.

In some embodiments, the first polypeptide and the second polypeptide each have the amino acid sequence of SEQ ID NO.: 3; the third polypeptide has the amino acid sequence of SEQ ID NO.: 1; and the fourth polypeptide has the amino acid sequence of SEQ ID NO.: 2.

In other more specific embodiments, the first antigen is CD20 and the second antigen is CD3.

In some embodiments, the VH region of the first portion of each Fab region comprises three CDRs having amino acid sequences of SEQ ID NO.: 27, SEQ ID NO.: 28, and SEQ ID NO.: 29; the VL region of the second portion of each Fab region comprises three CDRs having amino acid sequences of SEQ ID NO.: 31, SEQ ID NO.: 32, and SEQ ID NO.: 33; the VH region of the Fv region comprises three CDRs having amino acid sequences of SEQ ID NO.: 13, SEQ ID NO.: 14, and SEQ ID NO.: 15; and the VL region of the Fv region comprises three CDRs having amino acid sequences of SEQ ID NO.: 17, SEQ ID NO.: 18, and SEQ ID NO.: 19.

In some embodiments, the VH region of the first portion of each Fab region has an amino acid sequence of SEQ ID NO.: 26; the VL region of the second portion of each Fab region has an amino acid sequence of SEQ ID NO.: 30; the VH region of the Fv region has an amino acid sequence of SEQ ID NO.: 12; and the VL region of the Fv region has an amino acid sequence of SEQ ID NO.: 16.

In some embodiments, the first polypeptide and the second polypeptide each have the amino acid sequence of SEQ ID NO.: 25; the third polypeptide has the amino acid sequence of SEQ ID NO.: 23; and the fourth polypeptide has the amino acid sequence of SEQ ID NO.: 24.

In other more specific embodiments, the first antigen is EGFR and the second antigen is CD3.

In some embodiments, the VH region of the first portion of each Fab region comprises three CDRs having amino acid sequences of SEQ ID NO.: 41, SEQ ID NO.: 42, SEQ ID NO.: 43; the VL region of the second portion of each Fab region comprises three CDRs having amino acid sequences of SEQ ID NO.: 45, SEQ ID NO.: 46, and SEQ ID NO.: 47; the VH region of the Fv region comprises three CDRs having amino acid sequences of SEQ ID NO.: 13, SEQ ID NO.: 14, and SEQ ID NO.: 15; and the VL region of the Fv region comprises three CDRs having amino acid sequences of SEQ ID NO.: 17, SEQ ID NO.: 18, and SEQ ID NO.: 19.

In some embodiments, the VH region of the first portion of each Fab region has an amino acid sequence of SEQ ID NO.: 40; the VL region of the second portion of each Fab region has an amino acid sequence of SEQ ID NO.: 44; the VH region of the Fv region has an amino acid sequence of SEQ ID NO.: 12; and the VL region of the Fv region has an amino acid sequence of SEQ ID NO.: 16.

In some embodiments, the first polypeptide and the second polypeptide each have the amino acid sequence of SEQ ID NO.: 39; the third polypeptide has the amino acid sequence of SEQ ID NO.: 37; and the fourth polypeptide has the amino acid sequence of SEQ ID NO.: 38.

In other more specific embodiments, the first antigen is Her2 and the second antigen is TNF alpha. In some embodiments, the VH region of the first portion of each Fab region has an amino acid sequence of SEQ ID NO.: 51; the VL region of the second portion of each Fab region has an amino acid sequence of SEQ ID NO.: 52; the VH region of the Fv region has an amino acid sequence of SEQ ID NO.: 53; and the VL region of the Fv region has an amino acid sequence of SEQ ID NO.: 54.

In yet another aspect, provided herein are methods for making the binding molecules provided herein. In some embodiments, provided herein is a method of making a binding molecule comprising transfecting one or more vectors into a host cell, wherein the one or more vectors comprise:
(a) a first nucleic acid encoding a first polypeptide and a second polypeptide, each being an antibody light chain,
(b) a second nucleic acid encoding a third polypeptide comprising a first VH region and a first CH1 region and a second VH region; and
(c) a third nucleic acid encoding a fourth polypeptide comprising a third VH region and a second CH1 and a VL region,
wherein the first polypeptide and the first VH region and the first CH1 region of the third polypeptide can form a first antigen binding Fab region;
wherein the second polypeptide and the third VH region and the second CH1 region of the fourth polypeptide can form a second antigen binding Fab region; and
wherein the second VH region of the third polypeptide and the VL region of the fourth polypeptide can form an antigen binding Fv region.

In some embodiments, the first Fab region and the second Fab region are linked to the Fv region via a flexible peptide region. In some embodiments, the flexible peptide region comprises an antibody hinge region. In some specific embodiments, the antibody hinge region is a IgG hinge region. In some more specific embodiments, the IgG hinge region is of IgG1 subtype. In other more specific embodiments, the IgG hinge region is of IgG2 subtype. In yet other more specific embodiments, the IgG hinge region is of IgG3 subtype. In yet other more specific embodiments, the IgG hinge region is of IgG4 subtype. In some embodiments, the flexible peptide region further comprises a linker between the antibody hinge region and the second antigen binding domain. In some embodiments, the linker comprises an amino acid sequence of GGGGS (G4S) (SEQ ID NO.: 130).

In some embodiments, the first Fab region and the second Fab region bind to different antigens. In other embodiments, the first Fab region and the second Fab region bind to the same antigen. In some embodiments, the first Fab region and the second Fab region bind to the same epitope of the same antigen. In other embodiments, the first Fab region and the second Fab region bind to different epitopes of the same antigen.

In certain embodiments, the first Fab region and the second Fab region form a first antigen binding domain, and the Fv region forms a second antigen binding domain.

In some embodiments, the first antigen binding domain and the second antigen binding domain bind to the same antigen. In some embodiments, the second antigen binding domain binds to the same epitope as at least one of the epitopes bound by the first antigen binding domain.

In other embodiments, the first antigen binding domain and the second antigen binding domain bind to different antigens, and wherein the first antigen binding domain binds to a first antigen and the second antigen binding domain binds to a second antigen.

In some embodiments, the first antigen is a cancer antigen. In other embodiments, the first antigen is not a cancer antigen.

In some embodiments, the second antigen is expressed on an immune cells including lymphocytes and monocytes. In some embodiments, the second antigen is expressed on a T cell. In some embodiments, the second antigen is expressed on a B cell. In other embodiments, the second antigen is expressed on a dendritic cell. In other embodiments, the second antigen is expressed on a granulocyte. In yet other embodiments, the second antigen is expressed on an innate lymphoid cell. In yet other embodiments, the second antigen is expressed on a megakaryocyte. In yet other embodiments, the second antigen is expressed on a monocyte. In yet other embodiments, the second antigen is expressed on a myeloid-derived suppressor cell. In yet other embodiments, the second antigen is expressed on a NK cell.

In some embodiments, the second antigen is expressed on an effector cell. In some embodiments, the second antigen is expressed on a T cell. In some embodiments, the second antigen is expressed on a T helper cell, a regulatory T cell, or a cytotoxic T cell. In some embodiments, the second antigen is expressed on a T helper cell. In some embodiments, the second antigen is expressed on a regulatory T cell. In some embodiments, the second antigen is expressed on a cytotoxic T cell. In some embodiments, the second antigen is expressed on a CD8+ T cell. In some embodiments, the second antigen is expressed on a CD4+ T cell. In some embodiments, the second antigen comprises an extracellular domain.

In some specific embodiments, the second antigen is CD3. In some embodiments, the first antigen is a cancer antigen and the second antigen is CD3.

In some more specific embodiments, the first antigen is PD-L1 and the second antigen is CD3.

In some embodiments, the VH region of the first portion of each Fab region comprises three CDRs having amino acid sequences of SEQ ID NO.: 5, SEQ ID NO.: 6, and SEQ ID NO.: 7; the VL region of the second portion of each Fab region comprises three CDRs having amino acid sequences of SEQ ID NO.: 9, SEQ ID NO.: 10, and SEQ ID NO.: 11; the VH region of the Fv region comprises three CDRs having amino acid sequences of SEQ ID NO.: 13, SEQ ID NO.: 14, and SEQ ID NO.: 15; and the VL region of the Fv region comprises three CDRs having amino acid sequences of SEQ ID NO.: 17, SEQ ID NO.: 18, and SEQ ID NO.: 19.

In some embodiments, the VH region of the first portion of each Fab region has an amino acid sequence of SEQ ID NO.: 4; the VL region of the second portion of each Fab region has an amino acid sequence of SEQ ID NO.: 8; the VH region of the Fv region has an amino acid sequence of SEQ ID NO.: 12; and the VL region of the Fv region has an amino acid sequence of SEQ ID NO.: 16.

In some embodiments, the first polypeptide and the second polypeptide each have the amino acid sequence of SEQ ID NO.: 3; the third polypeptide has the amino acid sequence of SEQ ID NO.: 1; and the fourth polypeptide has the amino acid sequence of SEQ ID NO.: 2.

In some embodiments, the first nucleic acid has a nucleotide sequence of SEQ ID NO.: 22; the second nucleic acid has a nucleotide sequence of SEQ ID NO.: 20; and the third nucleic acid has a nucleotide sequence of SEQ ID NO.: 21.

In other more specific embodiments, the first antigen is CD20 and the second antigen is CD3.

In some embodiments, the VH region of the first portion of each Fab region comprises three CDRs having amino acid sequences of SEQ ID NO.: 27, SEQ ID NO.: 28, SEQ ID NO.: 29; the VL region of the second portion of each Fab region comprises three CDRs having amino acid sequences of SEQ ID NO.: 31, SEQ ID NO.: 32, and SEQ ID NO.: 33; the VH region of the Fv region comprises three CDRs having amino acid sequences of SEQ ID NO.: 13, SEQ ID NO.: 14, and SEQ ID NO.: 15; and the VL region of the Fv region comprises three CDRs having amino acid sequences of SEQ ID NO.: 17, SEQ ID NO.: 18, and SEQ ID NO.: 19.

In some embodiments, the VH region of the first portion of each Fab region has an amino acid sequence of SEQ ID NO.: 26; the VL region of the second portion of each Fab region has an amino acid sequence of SEQ ID NO.: 30; the VH region of the Fv region has an amino acid sequence of SEQ ID NO.: 12; and the VL region of the Fv region has an amino acid sequence of SEQ ID NO.: 16.

In some embodiments, the first polypeptide and the second polypeptide each have the amino acid sequence of SEQ ID NO.: 25; the third polypeptide has the amino acid sequence of SEQ ID NO.: 23; and the fourth polypeptide has the amino acid sequence of SEQ ID NO.: 24.

In some embodiments, the first nucleic acid has a nucleotide sequence of SEQ ID NO.: 36; the second nucleic acid has a nucleotide sequence of SEQ ID NO.: 34; and the third nucleic acid has a nucleotide sequence of SEQ ID NO.: 35.

In other more specific embodiments, the first antigen is EGFR and the second antigen is CD3.

In some embodiments, the VH region of the first portion of each Fab region comprises three CDRs having amino acid sequences of SEQ ID NO.: 41, SEQ ID NO.: 42, and SEQ ID NO.: 43; the VL region of the second portion of each Fab region comprises three CDRs having amino acid sequences of SEQ ID NO.: 45, SEQ ID NO.: 46, and SEQ ID NO.: 47; the VH region of the Fv region comprises three CDRs having amino acid sequences of SEQ ID NO.: 13, SEQ ID NO.: 14, and SEQ ID NO.: 15; and the VL region of the Fv region comprises three CDRs having amino acid sequences of SEQ ID NO.: 17, SEQ ID NO.: 18, and SEQ ID NO.: 19.

In some embodiments, the VH region of the first portion of each Fab region has an amino acid sequence of SEQ ID NO.: 40; the VL region of the second portion of each Fab region has an amino acid sequence of SEQ ID NO.: 44; the VH region of the Fv region has an amino acid sequence of SEQ ID NO.: 12; and the VL region of the Fv region has an amino acid sequence of SEQ ID NO.: 16.

In some embodiments, the first polypeptide and the second polypeptide each have the amino acid sequence of SEQ ID NO.: 39; the third polypeptide has the amino acid sequence of SEQ ID NO.: 37; and the fourth polypeptide has the amino acid sequence of SEQ ID NO.: 38.

In some embodiments, the first nucleic acid has a nucleotide sequence of SEQ ID NO.: 50; the second nucleic acid has a nucleotide sequence of SEQ ID NO.: 48; and the third nucleic acid has a nucleotide sequence of SEQ ID NO.: 49.

In other more specific embodiments, the first antigen is Her2 and the second antigen is TNF alpha. In some embodiments, the VH region of the first portion of each Fab region has an amino acid sequence of SEQ ID NO.: 51; the VL region of the second portion of each Fab region has an amino acid sequence of SEQ ID NO.: 52; the VH region of the Fv region has an amino acid sequence of SEQ ID NO.: 53; and the VL region of the Fv region has an amino acid sequence of SEQ ID NO.: 54.

In yet another aspect, provided herein is a pharmaceutical composition comprising a therapeutically effective amount of the binding molecule provided herein and a pharmaceutically acceptable carrier. In some embodiments, the pharmaceutical composition is for use in treating a disease or condition in a subject. In some embodiments, the disease or condition is a cancer. In other embodiments, cancer is lung cancer. In some embodiments, the cancer is Non Small Cell Lung Carcinoma (NSCLC). In some embodiments, the cancer is a Diffuse Large B cell Lymphoma (DLBCL). In other embodiments, the disease or condition is a PD-L1 positive cancer.

In yet another aspect, provided herein is a method of treating a disease or condition in a subject comprising administering a therapeutically effective amount of the binding molecule provided herein to the subject. In some embodiments, the disease or condition is a cancer. In other embodiments, cancer is lung cancer. In some embodiments, the cancer is Non Small Cell Lung Carcinoma (NSCLC). In some embodiments, the cancer is a Diffuse Large B cell Lymphoma (DLBCL). In other embodiments, the disease or condition is a PD-L1 positive cancer.

Where aspects or embodiments of the disclosure are described in terms of a Markush group or other grouping of alternatives, the present disclosure encompasses not only the entire group listed as a whole, but also each member of the group individually and all possible subgroups of the main group, and also the main group absent one or more of the group members. The present disclosure also envisages the explicit exclusion of one or more of any of the group members in the claimed disclosure.

ILLUSTRATIVE EMBODIMENTS

1. A binding molecule, comprising:
(a) a first polypeptide and a second polypeptide, each comprising an antibody light chain, (b) a third polypeptide comprising, in the order from N-terminus to C-terminus, a first variable heavy (VH) region and a first constant heavy 1 (CH1) region, and a second VH region; and (c) a fourth polypeptide comprising, in the order from N-terminus to C-terminus, a third VH region and a second CH1 region, and a variable light (VL) region, wherein the first polypeptide and the first VH region and the first CH1 region of the third polypeptide form a first antigen binding Fab region;

wherein the second polypeptide and the third VH region and the second CH1 region of the fourth polypeptide form a second antigen binding Fab region;

wherein the second VH region of the third polypeptide and the VL region of the fourth polypeptide form an antigen binding Fv region; and wherein the first Fab region and the second Fab region bind to a first antigen, the Fv region binds to a second antigen, and the first antigen is different from the second antigen.

2. The binding molecule of embodiment 1, wherein the first Fab region and the second Fab region are linked to the Fv region via a flexible peptide region.

3. The binding molecule of embodiment 2, wherein the first Fab region and the second Fab region are linked to the Fv region via fusion.

4. The binding molecule of embodiment 2, wherein the flexible peptide region comprises an antibody hinge region.

5. The binding molecule of embodiment 4, wherein the antibody hinge region is an Immunoglobulin G (IgG) hinge region.

6. The binding molecule of embodiment 5, wherein the antibody hinge region is selected from the group consisting of IgG1, IgG2, IgG3, and IgG4 hinge regions.

7. The binding molecule of embodiment 4, wherein the antibody hinge region comprises an interchain disulfide bond between the third polypeptide and the fourth polypeptide.

8. The binding molecule of embodiment 4, wherein the flexible peptide region further comprises a linker.

9. The binding molecule of embodiment 8, wherein the linker comprises an amino acid sequence of GGGGS (G4S) (SEQ ID NO: 130).

10. The binding molecule of embodiment 9, wherein the linker comprises two tandem copies of the amino acid sequence of GGGGS (G4S) (SEQ ID NO: 130).

11. The binding molecule of embodiment 1, wherein the first Fab region and the second Fab region bind to the same epitope of the first antigen.

12. The binding molecule of embodiment 1, wherein the second antigen is expressed on an immune cell.

13. The binding molecule of embodiment 12, wherein the immune cell is selected from the group consisting of lymphocytes and monocytes.

14. The binding molecule of embodiment 12, wherein the immune cell is an effector cell.

15. The binding molecule of embodiment 12, wherein the immune cell is selected from the group consisting of a T cell, a B cell, a dendritic cell, a granulocyte, an innate lymphoid cell, a megakaryocyte, a monocyte, a myeloid-derived suppressor cell, and a natural killer (NK) cell.

16. The binding molecule of embodiment 1, wherein the first antigen is a cancer antigen.

17. The binding molecule of embodiment 16, wherein the cancer antigen is a tumor associated antigen (TAA) or a tumor specific antigen (TSA).

18. The binding molecule of embodiment 1, wherein the first antigen is selected from a group consisting of CD19, CD20, EGFR, Her2, and PD-L1.

19. The binding molecule of embodiment 12, wherein the second antigen is CD3 or TNF alpha.

20. The binding molecule of embodiment 16, wherein the first antigen is a cancer antigen and the second antigen is CD3.

21. The binding molecule of embodiment 20, wherein the cancer antigen is selected from a group consisting of CD19, CD20, EGFR, Her2, and PD-L1.

22. A method of making a binding molecule, comprising:

(i) expressing the binding molecule from one or more vectors in a host cell, wherein the one or more vectors comprise (a) a first nucleic acid encoding a first polypeptide and a second nucleic acid encoding a second polypeptide, wherein each of the first polypeptide and the second polypeptide is an antibody light chain, (b) a third nucleic acid encoding a third polypeptide comprising, in the order from N-terminus to C-terminus, a first VH region and a first CH1 region and a second VH region; and (c) a fourth nucleic acid encoding a fourth polypeptide comprising, in the order from N-terminus to C-terminus, a third VH region and a second CH1 region and a VL region, wherein the first polypeptide and the first VH region and the first CH1 region of the third polypeptide can form a first antigen binding Fab region;

wherein the second polypeptide and the third VH region and the second CH1 region of the fourth polypeptide can form a second antigen binding Fab region; and wherein the second VH region of the third polypeptide and the VL region of the fourth polypeptide form an antigen binding Fv region; and wherein the first Fab region and the second Fab region bind to a first antigen, the Fv region binds to a second antigen, and the first antigen is different from the second antigen, and 23. The method of embodiment 22, wherein the first Fab region and the second Fab region are linked to the Fv region via a flexible peptide region comprising an antibody hinge region.

24. The method of embodiment 23, wherein the antibody hinge region comprises an interchain disulfide bond formed between the third polypeptide and the fourth polypeptide.

25. The method of embodiment 23, wherein the flexible peptide region further comprises a linker.

26. The method of embodiment 25, wherein the linker comprises an amino acid sequence of GGGGS (G4S) (SEQ ID NO: 130).

27. The method of embodiment 22, wherein the first antigen is a cancer antigen and the second antigen is CD3.

28. The method of embodiment 22, wherein the first antigen is selected from a group consisting of CD19, CD20, EGFR, Her2, and PD-L1.

29. A pharmaceutical composition comprising a binding molecule and a pharmaceutically acceptable carrier, wherein the binding molecule comprises:

(a) a first polypeptide and a second polypeptide, each comprising an antibody light chain, (b) a third polypeptide comprising, in the order from N-terminus to C-terminus, a first VH region and a first CH1 region, and a second VH region; and (c) a fourth polypeptide comprising, in the order from N-terminus to C-terminus, a third VH region and a second CH1 region, and a VL region, wherein the first polypeptide and the first VH region and the first CH1 region of the third polypeptide form a first antigen binding Fab region;

wherein the second polypeptide and the third VH region and the second CH1 region of the fourth polypeptide form a second antigen Fab region;

wherein the second VH region of the third polypeptide and the VL region of the fourth polypeptide form an antigen binding Fv region; and wherein the first Fab region and the second Fab region bind to a first antigen, the Fv region binds to a second antigen, and the first antigen is different from the second antigen.

30. A method of treating a disease or condition in a subject comprising administering a therapeutically effective amount of a binding molecule to the subject, wherein the binding molecule comprises:

(a) a first polypeptide and a second polypeptide, each comprising an antibody light chain, (b) a third polypeptide comprising, in the order from N-terminus to C-terminus, a first VH region and a first CH1 region, and a second VH region; and (c) a fourth polypeptide comprising, in the order from N-terminus to C-terminus, a third VH region and a second CH1 region, and a VL region, wherein the first polypeptide and the first VH region and the first CH1 region of the third polypeptide form a first antigen binding Fab region;

wherein the second polypeptide and the third VH region and the second CH1 region of the fourth polypeptide form a second antigen Fab region;

wherein the second VH region of the third polypeptide and the VL region of the fourth polypeptide form an antigen binding Fv region; and wherein the first Fab region and the second Fab region bind to a first antigen, the Fv region binds to a second antigen, and the first antigen is different from the second antigen.

31. A binding molecule, comprising:

(a) a first polypeptide and a second polypeptide, each comprising an antibody light chain, (b) a third polypeptide comprising, in the order from N-terminus to C-terminus, a first variable heavy (VH) region and a first constant heavy 1 (CH1) region, and a second VH region; and (c) a fourth polypeptide comprising, in the order from N-terminus to C-terminus, a third VH region and a second CH1 region, and a variable light (VL) region, wherein the first polypeptide and the first VH region and the first CH1 region of the third polypeptide form a first antigen binding Fab region;

wherein the second polypeptide and the third VH region and the second CH1 region of the fourth polypeptide form a second antigen binding Fab region;

wherein the second VH region of the third polypeptide and the VL region of the fourth polypeptide form an antigen binding Fv region; and wherein the first Fab region and the second Fab region binds to Programmed Death-Ligand 1 (PD-L1), and the Fv region binds to Cluster of Differentiation 3 (CD3).

32. The binding molecule of embodiment 31, wherein:

(a) the antibody light chains of the first and the second polypeptide each comprise three Complementarity Determining Regions (CDRs) having amino acid sequences of SEQ ID NO.: 9, SEQ ID NO.: 10, and SEQ ID NO.: 11;

(b) in the third polypeptide, the first VH region comprises three CDRs having amino acid sequences of SEQ ID NO.: 5, SEQ ID NO.: 6, and SEQ ID NO.: 7, and the second VH region comprises three CDRs having amino acid sequences of SEQ ID NO.: 13, SEQ ID NO.: 14, and SEQ ID NO.: 15; and (c) in the fourth polypeptide, the third VH region comprises three CDRs having amino acid sequences of SEQ ID NO.: 5, SEQ ID NO.: 6, and SEQ ID NO.: 7, and the VL region comprises three CDRs having amino acid sequences of SEQ ID NO.: 17, SEQ ID NO.: 18, and SEQ ID NO.: 19.

33. The binding molecule of embodiment 32, wherein the first Fab region and the second Fab region are linked to the Fv region via a flexible peptide region.

34. The binding molecule of embodiment 33, wherein the first Fab region and the second Fab region are linked to the Fv region via fusion.

35. The binding molecule of embodiment 33, wherein the flexible peptide region comprises an antibody hinge region.

36. The binding molecule of embodiment 35, wherein the antibody hinge region is an Immunoglobulin G (IgG) hinge region.

37. The binding molecule of embodiment 36, wherein the antibody hinge region is selected from the group consisting of IgG1, IgG2, IgG3, and IgG4 hinge regions.

38. The binding molecule of embodiment 35, wherein the antibody hinge region comprises an interchain disulfide bond between the third polypeptide and the fourth polypeptide.

39. The binding molecule of embodiment 35, wherein the flexible peptide region further comprises a linker.

40. The binding molecule of embodiment 39, wherein the linker comprises an amino acid sequence of GGGGS (G4S) (SEQ ID NO: 130).

41. The binding molecule of embodiment 40, wherein the linker comprises an amino acid sequence of GGGGSGGGGS (SEQ ID NO: 131).

42. The binding molecule of embodiment 40, wherein the linker comprises an amino acid sequence of GGSGGGGSG (SEQ ID NO: 132).

43. The binding molecule of embodiment 32, wherein:

(a) the antibody light chains of the first and the second polypeptide each comprise a VL region that comprises the amino acid sequence of SEQ ID NO.: 8;

(b) in the third polypeptide, the first VH region comprises the amino acid sequence of SEQ ID NO.: 4, and the second VH region comprises the amino acid sequence of SEQ ID NO.: 12; and (c) in the fourth polypeptide, the third VH region comprises the amino acid sequence of SEQ ID NO.: 4, and the VL region comprises the amino acid sequence of SEQ ID NO.: 16.

44. The binding molecule of embodiment 32, wherein the first polypeptide and the second polypeptide each comprise the amino acid sequence of SEQ ID NO.: 3; the third polypeptide comprises the amino acid sequence of SEQ ID NO.: 1; and the fourth polypeptide comprises the amino acid sequence of SEQ ID NO.: 2.

45. The binding molecule of embodiment 32, wherein the first polypeptide and the second polypeptide each comprise the amino acid sequence of SEQ ID NO.: 95; the third polypeptide comprises the amino acid sequence of SEQ ID NO.: 96; and the fourth polypeptide comprises the amino acid sequence of SEQ ID NO.: 97.

46. The binding molecule of embodiment 32, wherein the first polypeptide and the second polypeptide each have the amino acid sequence of SEQ ID NO.: 95; the third polypeptide has the amino acid sequence of SEQ ID NO.: 98; and the fourth polypeptide has the amino acid sequence of SEQ ID NO.: 99.

47. A method of making a binding molecule, comprising:
(i) expressing the binding molecule from one or more vectors in a host cell, wherein the one or more vectors comprise
(a) a first nucleic acid encoding a first polypeptide and a second nucleic acid encoding a second polypeptide, wherein each polypeptide comprises an antibody light chain,
(b) a third nucleic acid encoding a third polypeptide comprising, in the order from N-terminus to C-terminus, a first variable heavy (VH) region and a first constant heavy 1 (CH1) region, and a second VH region; and
(c) a fourth nucleic acid encoding a fourth polypeptide comprising, in the order from N-terminus to C-terminus, a third VH region and a second CH1 region, and a variable light (VL) region,
wherein the first polypeptide and the first VH region and the first CH1 region of the third polypeptide form a first antigen binding Fab region;
wherein the second polypeptide and the third VH region and the second CH1 region of the fourth polypeptide form a second antigen binding Fab region;
wherein the second VH region of the third polypeptide and the VL region of the fourth polypeptide form an antigen binding Fv region; and
wherein the first Fab region and the second Fab region bind to PD-L1, and the Fv region binds to CD3, and
(ii) purifying the binding molecule.

48. A method of embodiment 47, wherein:
(a) the antibody light chains of the first and the second polypeptide each comprise three Complementarity Determining Regions (CDRs) having amino acid sequences of SEQ ID NO.: 9, SEQ ID NO.: 10, and SEQ ID NO.: 11;
(b) in the third polypeptide, the first VH region comprises three CDRs having amino acid sequences of SEQ ID NO.: 5, SEQ ID NO.: 6, and SEQ ID NO.: 7, and the second VH region comprises three CDRs having amino acid sequences of SEQ ID NO.: 13, SEQ ID NO.: 14, and SEQ ID NO.: 15; and
(c) in the fourth polypeptide, the third VH region comprises three CDRs having amino acid sequences of SEQ ID NO.: 5, SEQ ID NO.: 6, and SEQ ID NO.: 7, and the VL region comprises three CDRs having amino acid sequences of SEQ ID NO.: 17, SEQ ID NO.: 18, and SEQ ID NO.: 19.

49. The method of embodiment 48, wherein the first Fab region and the second Fab region are linked to the Fv region via a flexible peptide region.

50. The method of embodiment 49, wherein the flexible peptide region comprises an antibody hinge region.

51. The method of embodiment 50, wherein the antibody hinge region comprises an interchain disulfide bond between the third polypeptide and the fourth polypeptide.

52. The method of embodiment 50, wherein the antibody hinge region is an Immunoglobulin G (IgG) hinge region.

53. The method of embodiment 20, wherein the flexible peptide region further comprises a linker.

54. The method of embodiment 53, wherein the linker comprises an amino acid sequence of GGGGS (G4S) (SEQ ID NO: 130).

55. The method of embodiment 54, wherein the linker comprises an amino acid sequence of GGGGSGGGGS (SEQ ID NO: 131).

56. The method of embodiment 54, wherein the linker comprises an amino acid sequence of GGSGGGGSG (SEQ ID NO: 132).

57. The method of embodiment 48,
wherein the VH region of each of the first and second Fab regions comprises an amino acid sequence of SEQ ID NO.: 4;
wherein the VL region of each of the first and second Fab regions comprises an amino acid sequence of SEQ ID NO.: 8;
wherein the VH region of the Fv region comprises an amino acid sequence of SEQ ID NO.: 12; and
wherein the VL region of the Fv region comprises an amino acid sequence of SEQ ID NO.: 16.

58. The method of embodiment 48, wherein the first polypeptide and the second polypeptide each have the amino acid sequence of SEQ ID NO.: 3; the third polypeptide has the amino acid sequence of SEQ ID NO.: 1; and the fourth polypeptide has the amino acid sequence of SEQ ID NO.: 2.

59. A pharmaceutical composition comprising a binding molecule and a pharmaceutically acceptable carrier, wherein the binding molecule comprises:
(a) a first polypeptide and a second polypeptide, each comprising an antibody light chain,
(b) a third polypeptide comprising, in the order from N-terminus to C-terminus, a first variable heavy (VH) region and a first constant heavy 1 (CH1) region, and a second VH region; and
(c) a fourth polypeptide comprising, in the order from N-terminus to C-terminus, a third VH region and a second CH1 region, and a variable light (VL) region,
wherein the first polypeptide and the first VH region and the first CH1 region of the third polypeptide form a first antigen binding Fab region;
wherein the second polypeptide and the third VH region and the second CH1 region of the fourth polypeptide form a second antigen binding Fab region;
wherein the second VH region of the third polypeptide and the VL region of the fourth polypeptide form an antigen binding Fv region; and
wherein the first Fab region and the second Fab region binds to PD-L1, and the Fv region binds to CD3.

60. A method of treating a disease or condition in a subject comprising administering a therapeutically effective amount of a binding molecule to the subject, wherein the binding molecule comprises:
(a) a first polypeptide and a second polypeptide, each comprising an antibody light chain,
(b) a third polypeptide comprising, in the order from N-terminus to C-terminus, a first variable heavy (VH) region and a first constant heavy 1 (CH1) region, and a second VH region; and
(c) a fourth polypeptide comprising, in the order from N-terminus to C-terminus, a third VH region and a second CH1 region, and a variable light (VL) region,
wherein the first polypeptide and the first VH region and the first CH1 region of the third polypeptide form a first antigen binding Fab region;
wherein the second polypeptide and the third VH region and the second CH1 region of the fourth polypeptide form a second antigen binding Fab region;
wherein the second VH region of the third polypeptide and the VL region of the fourth polypeptide form an antigen binding Fv region; and
wherein the first Fab region and the second Fab region binds to PD-L1, and the Fv region binds to CD3.

61. A binding molecule, comprising:
   (a) a first polypeptide and a second polypeptide, each comprising an antibody light chain,
   (b) a third polypeptide comprising, in the order from N-terminus to C-terminus, a first variable heavy (VH) region and a first constant heavy 1 (CH1) region, and a second VH region; and
   (c) a fourth polypeptide comprising, in the order from N-terminus to C-terminus, a third VH region and a second CH1 region, and a variable light (VL) region,
   wherein the first polypeptide and the first VH region and the first CH1 region of the third polypeptide form a first antigen binding Fab region;
   wherein the second polypeptide and the third VH region and the second CH1 region of the fourth polypeptide form a second antigen binding Fab region;
   wherein the second VH region of the third polypeptide and the VL region of the fourth polypeptide form an antigen binding Fv region; and
   wherein the first Fab region and the second Fab region each binds to CD20 or epidermal growth factor receptor (EGFR), and the Fv region binds to CD3.

62. The binding molecule of embodiment 61, wherein the first Fab region and the second Fab region bind to CD20, and
   (a) the antibody light chains of the first and the second polypeptide each comprise three Complementarity Determining Regions (CDRs) having amino acid sequences of SEQ ID NO.: 31, SEQ ID NO.: 32, and SEQ ID NO.: 33;
   (b) in the third polypeptide, the first VH region comprises three CDRs having amino acid sequences of SEQ ID NO.: 27, SEQ ID NO.: 28, and SEQ ID NO.: 29, and the second VH region comprises three CDRs having amino acid sequences of SEQ ID NO.: 13, SEQ ID NO.: 14, and SEQ ID NO.: 15; and
   (c) in the fourth polypeptide, the third VH region comprises three CDRs having amino acid sequences of SEQ ID NO.: 27, SEQ ID NO.: 28, and SEQ ID NO.: 29, and the VL region comprises three CDRs having amino acid sequences of SEQ ID NO.: 17, SEQ ID NO.: 18, and SEQ ID NO.: 19.

63. The binding molecule of embodiment 62, wherein the first Fab region and the second Fab region are linked to the Fv region via a flexible peptide region.

64. The binding molecule of embodiment 63, wherein the flexible peptide region comprises an antibody hinge region.

65. The binding molecule of embodiment 64, wherein the antibody hinge region comprises an interchain disulfide bond between the third polypeptide and the fourth polypeptide.

66. The binding molecule of embodiment 64, wherein the flexible peptide region further comprises a linker.

67. The binding molecule of embodiment 62, wherein:
   (a) the antibody light chains of the first and the second polypeptide each comprise a VL region that comprises the amino acid sequence of SEQ ID NO.: 30;
   (b) in the third polypeptide, the first VH region comprises the amino acid sequence of SEQ ID NO.: 26, and the second VH region comprises the amino acid sequence of SEQ ID NO.: 12; and
   (c) in the fourth polypeptide, the third VH region comprises the amino acid sequence of SEQ ID NO.: 26, and the VL region comprises the amino acid sequence of SEQ ID NO.: 16.

68. The binding molecule of embodiment 62, wherein the first polypeptide and the second polypeptide each have the amino acid sequence of SEQ ID NO.: 25; the third polypeptide has the amino acid sequence of SEQ ID NO.: 23; and the fourth polypeptide has the amino acid sequence of SEQ ID NO.: 24.

69. The binding molecule of embodiment 61, wherein the first Fab region and the second Fab region bind to EGFR, and
   (a) the antibody light chains of the first and the second polypeptide each comprise three CDRs having amino acid sequences of SEQ ID NO.: 45, SEQ ID NO.: 46, and SEQ ID NO.: 47;
   (b) in the third polypeptide, the first VH region comprises three CDRs having amino acid sequences of SEQ ID NO.: 41, SEQ ID NO.: 42, and SEQ ID NO.: 43, and the second VH region comprises three CDRs having amino acid sequences of SEQ ID NO.: 13, SEQ ID NO.: 14, and SEQ ID NO.: 15; and
   (c) in the fourth polypeptide, the third VH region comprises three CDRs having amino acid sequences of SEQ ID NO.: 41, SEQ ID NO.: 42, and SEQ ID NO.: 43, and the VL region comprises three CDRs having amino acid sequences of SEQ ID NO.: 17, SEQ ID NO.: 18, and SEQ ID NO.: 19.

70. The binding molecule of embodiment 69, wherein the first Fab region and the second Fab region are linked to the Fv region via a flexible peptide region.

71. The binding molecule of embodiment 70, wherein the flexible peptide region comprises an antibody hinge region.

72. The binding molecule of embodiment 71, wherein the antibody hinge region comprises an interchain disulfide bond between the third polypeptide and the fourth polypeptide.

73. The binding molecule of embodiment 70, wherein the flexible peptide region further comprises a linker.

74. The binding molecule of embodiment 69, wherein:
   (a) the antibody light chains of the first and the second polypeptide each comprise a VL region that comprises the amino acid sequence of SEQ ID NO.: 44;
   (b) in the third polypeptide, the first VH region comprises the amino acid sequence of SEQ ID NO.: 40, and the second VH region comprises the amino acid sequence of SEQ ID NO.: 12; and
   (c) in the fourth polypeptide, the third VH region comprises the amino acid sequence of SEQ ID NO.: 40, and the VL region comprises the amino acid sequence of SEQ ID NO.: 16.

75. The binding molecule of embodiment 69, wherein the first polypeptide and the second polypeptide each have the amino acid sequence of SEQ ID NO.: 39; the third polypeptide has the amino acid sequence of SEQ ID NO.: 37; and the fourth polypeptide has the amino acid sequence of SEQ ID NO.: 38.

76. A method of making a binding molecule comprising:
   (i) expressing the binding molecule from one or more vectors in a host cell, wherein the one or more vectors comprise
   (a) a first nucleic acid encoding a first polypeptide and a second nucleic acid encoding a second polypeptide, wherein each of the first polypeptide and the second polypeptide is an antibody light chain,
   (b) a third nucleic acid encoding a third polypeptide comprising, in the order from N-terminus to C-terminus, a first VH region and a first CH1 region, and a second VH region; and
   (c) a fourth nucleic acid encoding a fourth polypeptide comprising, in the order from N-terminus to C-terminus, a third VH region and a second CH1 region, and a VL region, wherein the first polypeptide and the first VH region and the first CH1 region of the third polypeptide form a first antigen binding Fab region;

wherein the second polypeptide and the third VH region and the second CH1 region of the fourth polypeptide form a second antigen binding Fab region;

wherein the second VH region of the third polypeptide and the VL region of the fourth polypeptide form an antigen binding Fv region; and wherein the first Fab region and the second Fab region each binds to CD20 or EGFR, and the Fv region binds to CD3, and (ii) purifying the binding molecule.

77. The method of embodiment 76, wherein the first Fab region and the second Fab region bind to CD20, and (a) the antibody light chains of the first and the second polypeptide each comprise three Complementarity Determining Regions (CDRs) having amino acid sequences of SEQ ID NO.: 31, SEQ ID NO.: 32, and SEQ ID NO.: 33;

(b) in the third polypeptide, the first VH region comprises three CDRs having amino acid sequences of SEQ ID NO.: 27, SEQ ID NO.: 28, and SEQ ID NO.: 29, and the second VH region comprises three CDRs having amino acid sequences of SEQ ID NO.: 13, SEQ ID NO.: 14, and SEQ ID NO.: 15; and (c) in the fourth polypeptide, the third VH region comprises three CDRs having amino acid sequences of SEQ ID NO.: 27, SEQ ID NO.: 28, and SEQ ID NO.: 29, and the VL region comprises three CDRs having amino acid sequences of SEQ ID NO.: 17, SEQ ID NO.: 18, and SEQ ID NO.: 19.

78. The method of embodiment 77, wherein the first Fab region and the second Fab region are linked to the Fv region via a flexible peptide region.

79. The binding molecule of embodiment 78, wherein the flexible peptide region comprises an antibody hinge region.

80. The binding molecule of embodiment 79, wherein the flexible peptide region further comprises a linker.

81. The method of embodiment 77, wherein:

(a) the antibody light chains of the first and the second polypeptide each comprise a VL region that comprises the amino acid sequence of SEQ ID NO.: 30;

(b) in the third polypeptide, the first VH region comprises the amino acid sequence of SEQ ID NO.: 26, and the second VH region comprises the amino acid sequence of SEQ ID NO.: 12; and (c) in the fourth polypeptide, the third VH region comprises the amino acid sequence of SEQ ID NO.: 26, and the VL region comprises the amino acid sequence of SEQ ID NO.: 16.

82. The method of embodiment 77, wherein the first polypeptide and the second polypeptide each have the amino acid sequence of SEQ ID NO.: 25; the third polypeptide has the amino acid sequence of SEQ ID NO.: 23; and the fourth polypeptide has the amino acid sequence of SEQ ID NO.: 24.

83. The method of embodiment 87, wherein the first Fab region and the second Fab region bind to CD20, and (a) the antibody light chains of the first and the second polypeptide each comprise three CDRs having amino acid sequences of SEQ ID NO.: 45, SEQ ID NO.: 46, and SEQ ID NO.: 47;

(b) in the third polypeptide, the first VH region comprises three CDRs having amino acid sequences of SEQ ID NO.: 41, SEQ ID NO.: 42, and SEQ ID NO.: 43, and the second VH region comprises three CDRs having amino acid sequences of SEQ ID NO.: 13, SEQ ID NO.: 14, and SEQ ID NO.: 15; and (c) in the fourth polypeptide, the third VH region comprises three CDRs having amino acid sequences of SEQ ID NO.: 41, SEQ ID NO.: 42, and SEQ ID NO.: 43, and the VL region comprises three CDRs having amino acid sequences of SEQ ID NO.: 17, SEQ ID NO.: 18, and SEQ ID NO.: 19.

84. The method of embodiment 83, wherein the first Fab region and the second Fab region are linked to the Fv region via a flexible peptide region.

85. The method of embodiment 84, wherein the flexible peptide region comprises an antibody hinge region.

86. The method of embodiment 85, wherein the flexible peptide region further comprises a linker.

87. The method of embodiment 83, wherein:

(a) the antibody light chains of the first and the second polypeptide each comprise a VL region that comprises the amino acid sequence of SEQ ID NO.: 44;

(b) in the third polypeptide, the first VH region comprises the amino acid sequence of SEQ ID NO.: 40, and the second VH region comprises the amino acid sequence of SEQ ID NO.: 12; and (c) in the fourth polypeptide, the third VH region comprises the amino acid sequence of SEQ ID NO.: 40, and the VL region comprises the amino acid sequence of SEQ ID NO.: 16.

88. The method of embodiment 83, wherein the first polypeptide and the second polypeptide each have the amino acid sequence of SEQ ID NO.: 39; the third polypeptide has the amino acid sequence of SEQ ID NO.: 37; and the fourth polypeptide has the amino acid sequence of SEQ ID NO.: 38.

89. A pharmaceutical composition comprising a therapeutically effective amount of a binding molecule and a pharmaceutically acceptable carrier, wherein the binding molecule comprises:

(a) a first polypeptide and a second polypeptide, each comprising an antibody light chain, (b) a third polypeptide comprising, in the order from N-terminus to C-terminus, a first variable heavy (VH) region and a first constant heavy 1 (CH1) region, and a second VH region; and (c) a fourth polypeptide comprising, in the order from N-terminus to C-terminus, a third VH region and a second CH1 region, and a variable light (VL) region, wherein the first polypeptide and the first VH region and the first CH1 region of the third polypeptide form a first antigen binding Fab region;

wherein the second polypeptide and the third VH region and the second CH1 region of the fourth polypeptide form a second antigen binding Fab region;

wherein the second VH region of the third polypeptide and the VL region of the fourth polypeptide form an antigen binding Fv region; and wherein the first Fab region and the second Fab region each binds to CD20 or EGFR, and the Fv region binds to CD3.

90. A method of treating a disease or condition in a subject comprising administering a therapeutically effective amount of a binding molecule to the subject, wherein the binding molecule comprises:

(a) a first polypeptide and a second polypeptide, each comprising an antibody light chain, (b) a third polypeptide comprising, in the order from N-terminus to C-terminus, a first variable heavy (VH) region and a first constant heavy 1 (CH1) region, and a second VH region; and (c) a fourth polypeptide comprising, in the order from N-terminus to C-terminus, a third VH region and a second CH1 region, and a variable light (VL) region, wherein the first polypeptide and the first VH region and the first CH1 region of the third polypeptide form a first antigen binding Fab region;

wherein the second polypeptide and the third VH region and the second CH1 region of the fourth polypeptide form a second antigen binding Fab region;

wherein the second VH region of the third polypeptide and the VL region of the fourth polypeptide form an antigen binding Fv region; and wherein the first Fab region and the second Fab region each binds to CD20 or EGFR, and the Fv region binds to CD3

BRIEF DESCRIPTION OF THE FIGURES

FIG. 4A illustrates the structure of ACE-04. "A" refers to anti-PD-L1. UCHT1 is an anti-CD3 antibody. FIG. 4B illustrates the structure of ACE-05. "A" refers to anti-PD-L1. OKT3 is an anti-CD3 antibody. FIG. 4C show the results of SDS-PAGE performed to identify the assembly pattern of ACE-04, ACE-04-VL2, ACE-05, and ACE-05-VL2. The arrows indicate the bands of ACE-04 and ACE-05 under reducing and non-reducing conditions.

In FIG. 6B, the arrows indicate the bands of ACE-10 under reducing and non-reducing conditions. "ACE-10 dialysis" represents ACE-10 generated via transfection with dialyzed DNA. In FIG. 6C, the arrow in the results from the anti-kappa condition indicates ACE-10-VL/ACE-10-LC dimer and ACE-10-VH/ACE-10-LC dimer complex under non reducing condition; the arrow in the results from the anti-CH1 condition indicates the assembled ACE-10 under non reducing condition.

FIGS. 12A-12C show the analysis of binding kinetics of ACE-05 to PD-L1 (12A, 12C) and CD3 (12B, 12C) using Surface Plasmon Resonance (SPR).

FIG. 18A shows dose response of anti-tumor efficacy for ACE-05 and BiTE-05. FIG. 18B and FIG. 18C show anti-tumor efficacy of individual mice in each dose group for ACE-05 and BiTE-05, respectively. FIG. 18D shows individual body weight loss (%) (side-effect) of ACE-05 and BiTE-05 treated group.

DETAILED DESCRIPTION

Figure 1A:
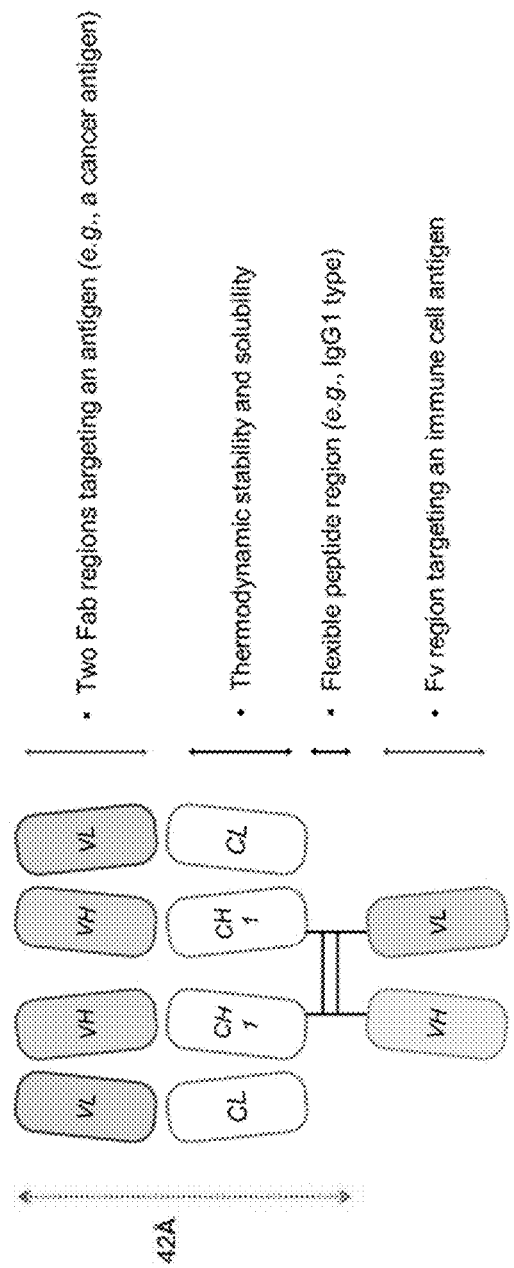
FIG. 1A illustrates a binding molecule (ALiCE) provided herein.

The present disclosure provides novel cell engaging binding molecules having multiple binding domains. These binding molecules are referred to herein as "antibody like cell engagers" (ALiCE). ALiCE molecules provided herein have two antigen binding domains. The first antigen binding domain has two Fab regions. The second antigen binding domain has a Fv region. A typical ALiCE molecule is depicted in FIG. 1A. Generally, in such a molecule the first antigen binding domain comprises Fab regions, and the second antigen binding domain is attached (directly or indirectly) to the first antigen binding domain generally at the position where CH2 and CH3 domains would generally be located in a native antibody structure. For example, in the depicted embodiment, the C terminus of heavy chain comprises a VH domain rather than a CH2 domain and the C-terminus of the second heavy chain comprises a VL domain rather than a domain.

The binding molecules disclosed herein provide many advantages over conventional antibodies and existing multispecific antibodies (e.g., bispecific antibodies). Due to its multiple antigen binding domains and overall configuration design, the binding molecules provided herein can be used as a cell engager to bring multiple cells together. For example, the first antigen binding domain can bind to an antigen expressed on a first cell and the second antigen binding domain can bind to an antigen expressed on a second cell, and thereby bring the two cells together.

In certain embodiments, one of the engaged cells is an immune cell, e.g., a cytotoxic T cell. In these embodiments, the binding molecules provided herein are particularly useful for directing and activating an immune cell. For example, in certain embodiments, while the bivalent Fab portion of ALiCE molecule retains the functionality of conventional antibodies, the second Fc-less monovalent antigen-binding region (i.e., the Fv region) can recognize, engage, redirect, and/or activate effector cells of the immune system, such as T cells. For example, as demonstrated in the Example section below, ACE-05, an ALiCE molecule composed of anti-PD-L1 and anti-CD3 domains, shows synergistic effects for both PD-L1-dependent (mediated) T cell activation and PD-1 and PD-L1 blockade efficacy.

In certain embodiments, the absence of a fully functional Fc region, or the absence of complete CH2 and/or CH3 region abolishes or reduces certain undesirable Fc-mediated effector cytotoxicity. In certain embodiment, the native interaction between the VH and VL chains of the Fv portion facilitates heterodimerization of the ALiCE molecule without imparting undesirable immunogenicity through artificial engineering.

Pharmacokinetic (PK) studies presented herein indicate higher stability of ALiCE molecules than other formats such as BiTE (bispecific T-cell engager) or DART (dual-affinity re-targeting) (Campagne O. et al. Integrated Pharmacokinetic/Pharmacodynamic Model of a Bispecific CD3×CD123 DART Molecule in Nonhuman Primates: Evaluation of Activity and Impact of Immunogenicity. *Clin Cancer Res.* 2018 Jun. 1; 24(11):2631-2641; Moore P. A. et al. Application of dual affinity retargeting molecules to achieve optimal redirected T-cell killing of B-cell lymphoma. *Blood.* 2011 Apr. 28; 117(17):4542-51; Moore P. A. et al. Development of MGD007, a gpA33×CD3-Bispecific DART Protein for T-Cell Immunotherapy of Metastatic Colorectal Cancer. *Mol*

Cancer Ther. 2018 August; 17(8):1761-1772; Yuraszeck T. et al. Translation and Clinical Development of Bispecific T-cell Engaging Antibodies for Cancer Treatment. *Clin Pharmacol Ther.* 2017 May; 101(5):634-645. Each of these is incorporated herein by reference in its entirety). Further, in vivo efficacy study of an exemplary ALiCE molecule shows significant anti-cancer effects. These results demonstrate that ALiCE is an advantageous platform technology in antibody engineering, e.g., for cancer therapy.

I. Definitions

Techniques and procedures described or referenced herein include those that are generally well understood and/or commonly employed using conventional methodology by those skilled in the art, such as, for example, the widely utilized methodologies described in Sambrook et al., *Molecular Cloning: A Laboratory Manual* (3d ed. 2001); *Current Protocols in Molecular Biology* (Ausubel et al. eds., 2003); *Therapeutic Monoclonal Antibodies: From Bench to Clinic* (An ed. 2009); *Monoclonal Antibodies: Methods and Protocols* (Albitar ed. 2010); and *Antibody Engineering* Vols 1 and 2 (Kontermann and Dübel eds., 2d ed. 2010).

Unless otherwise defined herein, technical and scientific terms used in the present description have the meanings that are commonly understood by those of ordinary skill in the art. For purposes of interpreting this specification, the following description of terms will apply and whenever appropriate, terms used in the singular will also include the plural and vice versa. In the event that any description of a term set forth conflicts with any document incorporated herein by reference, the description of the term set forth below shall control.

The term "binding molecule" refers to a protein comprising a portion (e.g., one or more binding regions such as CDRs) that binds to a target or an antigen and, optionally, a scaffold or framework portion (e.g., one or more scaffold or framework regions) that allows the binding portion to adopt a conformation that promotes binding of the binding protein to a polypeptide, fragment, or epitope. In the context of the present disclosure, a binding molecule is said to specifically bind or selectively bind to an antigen, for example, when the dissociation constant ($K_D$) is $\leq 10^{-7}$ M. In some embodiments, the binding molecule may specifically bind to an antigen with a $K_D$ of from about $10^{-7}$ M to about $10^{-12}$ M. In certain embodiments, the binding molecule may specifically bind to an antigen with high affinity when the $K_D$ is $\leq 10^{-8}$ M or $K_D$ is $\leq 10^{-9}$ M. In one embodiment, the binding molecule may specifically bind to a purified human antigen with a $K_D$ of from $1 \times 10^{-9}$ M to $10 \times 10^{-9}$ M as measured by OCTET®. In yet another embodiment, the binding molecule specifically binds to a human antigen expressed on cells with a $K_D$ of from $0.1 \times 10^{-9}$ M to $10 \times 10^{-9}$ M. In certain embodiments, the binding molecule specifically binds to a human antigen expressed on cells with a $K_D$ of about $0.1 \times 10^{-9}$ M, about $0.5 \times 10^{-9}$ M, about $1 \times 10^{-9}$ M, about $5 \times 10^{-9}$ M, about $10 \times 10^{-9}$ M, or any range or interval thereof. The term "binding molecule" includes antibodies and molecules derived from antibodies.

The term "antibody," "immunoglobulin," or "Ig" is used interchangeably herein, and is used in the broadest sense and specifically covers, for example, monoclonal antibodies (including agonist, antagonist, neutralizing antibodies, full length or intact monoclonal antibodies), antibody compositions with polyepitopic or monoepitopic specificity, polyclonal or monovalent antibodies, multivalent antibodies, multispecific antibodies (e.g., bispecific antibodies so long as they exhibit the desired biological activity), formed from at least two intact antibodies, single chain antibodies, and fragments thereof, as described below. An antibody can be human, humanized, chimeric and/or affinity matured, as well as an antibody from other species, for example, mouse and rabbit, etc. The term "antibody" is intended to include a polypeptide product of B cells within the immunoglobulin class of polypeptides that is able to bind to a specific molecular antigen and is composed of two identical pairs of polypeptide chains, wherein each pair has one heavy chain (about 50-70 kDa) and one light chain (about 25 kDa), each amino-terminal portion of each chain includes a variable region of about 100 to about 130 or more amino acids, and each carboxy-terminal portion of each chain includes a constant region. See, e.g., *Antibody Engineering* (Borrebaeck ed., 2d ed. 1995); and Kuby, *Immunology* (3d ed. 1997). In specific embodiments, the specific molecular antigen can be bound by an antibody provided herein, including a polypeptide or an epitope. Antibodies also include, but are not limited to, synthetic antibodies, recombinantly produced antibodies, camelized antibodies, intrabodies, anti-idiotypic (anti-Id) antibodies, and functional fragments (e.g., antigen-binding fragments) of any of the above, which refers to a portion of an antibody heavy or light chain polypeptide that retains some or all of the binding activity of the antibody from which the fragment was derived. Non-limiting examples of functional fragments (e.g., antigen-binding fragments) include single-chain Fvs (scFv) (e.g., including monospecific, bispecific, etc.), Fab fragments, F(ab') fragments, F(ab)$_2$ fragments, F(ab')$_2$ fragments, disulfide-linked Fvs (dsFv), Fd fragments, Fv fragments, diabody, triabody, tetrabody, and minibody. In particular, antibodies provided herein include immunoglobulin molecules and immunologically active portions of immunoglobulin molecules, for example, antigen-binding domains or molecules that contain an antigen-binding site that binds to an antigen (e.g., one or more CDRs of an antibody). Such antibody fragments can be found in, for example, Harlow and Lane, *Antibodies: A Laboratory Manual* (1989); *Mol. Biology and Biotechnology: A Comprehensive Desk Reference* (Myers ed., 1995); Huston et al., 1993, Cell Biophysics 22:189-224; Plückthun and Skerra, 1989, Meth. Enzymol. 178:497-515; and Day, *Advanced Immunochemistry* (2d ed. 1990). The antibodies provided herein can be of any class (e.g., IgG, IgE, IgM, IgD, and IgA) or any subclass (e.g., IgG1, IgG2, IgG3, IgG4, IgA1, and IgA2) of immunoglobulin molecule. Antibodies may be agonistic antibodies or antagonistic antibodies.

An "antigen" is a structure to which an antibody can selectively bind. A target antigen may be a polypeptide, carbohydrate, nucleic acid, lipid, hapten, or other naturally occurring or synthetic compound. In some embodiments, the target antigen is a polypeptide. In certain embodiments, an antigen is associated with a cell, for example, is present on or in a cell, for example, an immune cell.

The terms "antigen-binding fragment," "antigen-binding domain," "antigen-binding region," and similar terms refer to that portion of a binding molecule, which comprises the amino acid residues that interact with an antigen and confer on the binding agent its specificity and affinity for the antigen (e.g., the CDRs).

The terms "binds" or "binding" refer to an interaction between molecules including, for example, to form a complex. Interactions can be, for example, non-covalent interactions including hydrogen bonds, ionic bonds, hydrophobic interactions, and/or van der Waals interactions. A complex can also include the binding of two or more molecules held together by covalent or non-covalent bonds, interactions, or forces. The strength of the total non-covalent interactions between a single antigen-binding site on an antibody and a single epitope of a target molecule, such as an antigen, is the affinity of the antibody or functional fragment for that epitope. The ratio of dissociation rate ($k_{off}$) to association rate ($k_{on}$) of a binding molecule (e.g., an antibody) to a monovalent antigen ($k_{off}/k_{on}$) is the dissociation constant $K_D$, which is inversely related to affinity. The lower the $K_D$ value, the higher the affinity of the antibody. The value of $K_D$ varies for different complexes of antibody and antigen and depends on both $k_{on}$ and $k_{off}$. The dissociation constant $K_D$ for an antibody provided herein can be determined using any method provided herein or any other method well known to those skilled in the art. The affinity at one binding site does not always reflect the true strength of the interaction between an antibody and an antigen. When complex antigens containing multiple, repeating antigenic determinants, such as a polyvalent antigen, come in contact with antibodies containing multiple binding sites, the interaction of antibody with antigen at one site will increase the probability of a reaction at a second site. The strength of such multiple interactions between a multivalent antibody and antigen is called the avidity.

In connection with the binding molecules described herein terms such as "bind to," "that specifically bind to," and analogous terms are also used interchangeably herein and refer to binding molecules of antigen binding domains that specifically bind to an antigen, such as a polypeptide. A binding molecule or antigen binding domain that binds to or specifically binds to an antigen may be cross-reactive with related antigens. In certain embodiments, a binding molecule or antigen binding domain that binds to or specifically binds to an antigen does not cross-react with other antigens. A binding molecule or antigen binding domain that binds to or specifically binds to an antigen can be identified, for example, by immunoassays, Octet®, Biacore®, or other techniques known to those of skill in the art. A binding molecule or antigen binding domain binds to or specifically binds to an antigen when it binds to an antigen with higher affinity than to any cross-reactive antigen as determined using experimental techniques, such as radioimmunoassays (RIA) and enzyme linked immunosorbent assays (ELISAs). Typically, a specific or selective reaction will be at least twice background signal or noise and may be more than 10 times background. See, e.g., *Fundamental Immunology* 332-36 (Paul ed., 2d ed. 1989) for a discussion regarding binding specificity. In certain embodiments, the extent of binding of a binding molecule or antigen binding domain to a "non-target" protein is less than about 10% of the binding of the binding molecule or antigen binding domain to its particular target antigen, for example, as determined by fluorescence activated cell sorting (FACS) analysis or RIA. With regard terms such as "specific binding," "specifically binds to," or "is specific for" means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target, for example, an excess of non-labeled target. In this case, specific binding is indicated if the binding of the labeled target to a probe is competitively inhibited by excess unlabeled target. A binding molecule or antigen binding domain that binds to an antigen includes one that is capable of binding the antigen with sufficient affinity such that the binding molecule is useful, for example, as a diagnostic agent in targeting the antigen. In certain embodiments, a binding molecule or antigen binding domain that binds to an antigen has a dissociation constant ($K_D$) of less than or equal to 10 nM, 5 nM, 4 nM, 3 nM, 2 nM, 1 nM, 0.9 nM, 0.8 nM, 0.7 nM, 0.6 nM, 0.5 nM, 0.4 nM, 0.3 nM, 0.2 nM, or 0.1 nM. In certain embodiments, a binding molecule or antigen binding domain binds to an epitope of an antigen that is conserved among the antigen from different species (e.g., between human and cyno species).

"Binding affinity" generally refers to the strength of the sum total of noncovalent interactions between a single binding site of a molecule (e.g., a binding protein such as an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The term "Bmax" refers to the maximum binding affinity extrapolated from experimental results. Bmax can be calculated using known curve fitting methods in the art, for example, curve fitting methods provided in GraphPad Prism software 7. The affinity of a binding molecule X for its binding partner Y can generally be represented by the dissociation constant ($K_D$). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present disclosure. Specific illustrative embodiments include the following. In one embodiment, the "$K_D$" or "$K_D$ value" may be measured by assays known in the art, for example by a binding assay. The $K_D$ may be measured in a RIA, for example, performed with the Fab version of an antibody of interest and its antigen (Chen et al., 1999, J. Mol Biol 293:865-81). The $K_D$ or $K_D$ value may also be measured by using biolayer interferometry (BLI) or surface plasmon resonance (SPR) assays by Octet®, using, for example, a Octet® QK384 system, or by Biacore®, using, for example, a Biacore® TM-2000 or a Biacore® TM-3000. An "on-rate" or "rate of association" or "association rate" or "$k_{on}$" may also be determined with the same biolayer interferometry (BLI) or surface plasmon resonance (SPR) techniques described above using, for example, the Octet® QK384, the Biacore® TM-2000, or the Biacore® TM-3000 system.

The term "reducing" used herein refers to a condition in which interchain or intrachain disulfide (S—S) bridges within a protein are denatured or reduced, for example, by the addition of 2-Mercaptoethanol (2-ME) or dithiothreitol (DTT), resulting in multiple polypeptide chains. The term "non reducing" used herein refers to a condition in which interchain or intrachain disulfide (S—S) bridges within a protein remain intact in the absence of denaturing or reducing agents such as 2-Mercaptoethanol (2-ME) or dithiothreitol (DTT).

In certain embodiments, the binding molecules or antigen binding domains can comprise "chimeric" sequences in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see U.S. Pat. No. 4,816,567; and Morrison et al., 1984, Proc. Natl. Acad. Sci. USA 81:6851-55).

In certain embodiments, the binding molecules or antigen binding domains can comprise portions of "humanized" forms of nonhuman (e.g., murine) antibodies that are chimeric antibodies that include human immunoglobulins (e.g., recipient antibody) in which the native CDR residues are replaced by residues from the corresponding CDR of a nonhuman species (e.g., donor antibody) such as mouse, rat, rabbit, or nonhuman primate having the desired specificity, affinity, and capacity. In some instances, one or more FR region residues of the human immunoglobulin are replaced by corresponding nonhuman residues. Furthermore, humanized antibodies can comprise residues that are not found in the recipient antibody or in the donor antibody. These modifications are made to further refine antibody performance. A humanized antibody heavy or light chain can comprise substantially all of at least one or more variable regions, in which all or substantially all of the CDRs correspond to those of a nonhuman immunoglobulin and all or substantially all of the FRs are those of a human immunoglobulin sequence. In certain embodiments, the humanized antibody will comprise at least a portion of an immunoglobulin constant region (Fc), typically that of a human immunoglobulin. For further details, see, Jones et al., 1986, Nature 321:522-25; Riechmann et al., 1988, Nature 332:323-29; Presta, 1992, Curr. Op. Struct. Biol. 2:593-96; Carter et al., 1992, Proc. Natl. Acad. Sci. USA 89:4285-89; U.S. Pat. Nos. 6,800,738; 6,719,971; 6,639,055; 6,407,213; and 6,054,297.

In certain embodiments, the binding molecules or antigen binding domains can comprise portions of a "fully human antibody" or "human antibody," wherein the terms are used interchangeably herein and refer to an antibody that comprises a human variable region and, for example, a human constant region. In specific embodiments, the terms refer to an antibody that comprises a variable region and constant region of human origin. "Fully human" antibodies, in certain embodiments, can also encompass antibodies which bind polypeptides and are encoded by nucleic acid sequences which are naturally occurring somatic variants of human germline immunoglobulin nucleic acid sequence. The term "fully human antibody" includes antibodies having variable and constant regions corresponding to human germline immunoglobulin sequences as described by Kabat et al. (see Kabat et al. (1991) *Sequences of Proteins of Immunological Interest*, Fifth Edition, U.S. Department of Health and Human Services, NIH Publication No. 91-3242). A "human antibody" is one that possesses an amino acid sequence which corresponds to that of an antibody produced by a human and/or has been made using any of the techniques for making human antibodies. This definition of a human antibody specifically excludes a humanized antibody comprising non-human antigen-binding residues. Human antibodies can be produced using various techniques known in the art, including phage-display libraries (Hoogenboom and Winter, 1991, J. Mol. Biol. 227:381; Marks et al., 1991, J. Mol. Biol. 222:581) and yeast display libraries (Chao et al., 2006, Nature Protocols 1: 755-68). Also available for the preparation of human monoclonal antibodies are methods described in Cole et al., *Monoclonal Antibodies and Cancer Therapy* 77 (1985); Boerner et al., 1991, J. Immunol. 147(1):86-95; and van Dijk and van de Winkel, 2001, Curr. Opin. Pharmacol. 5: 368-74. Human antibodies can be prepared by administering the antigen to a transgenic animal that has been modified to produce such antibodies in response to antigenic challenge, but whose endogenous loci have been disabled, e.g., mice (see, e.g., Jakobovits, 1995, Curr. Opin. Biotechnol. 6(5):561-66; Bruggemann and Taussing, 1997, Curr. Opin. Biotechnol. 8(4):455-58; and U.S. Pat. Nos. 6,075,181 and 6,150,584 regarding XENO-MOUSE™ technology). See also, for example, Li et al., 2006, Proc. Natl. Acad. Sci. USA 103:3557-62 regarding human antibodies generated via a human B-cell hybridoma technology.

In certain embodiments, the binding molecules or antigen binding domains can comprise portions of a "recombinant human antibody," wherein the phrase includes human antibodies that are prepared, expressed, created or isolated by recombinant means, such as antibodies expressed using a recombinant expression vector transfected into a host cell, antibodies isolated from a recombinant, combinatorial human antibody library, antibodies isolated from an animal (e.g., a mouse or cow) that is transgenic and/or transchromosomal for human immunoglobulin genes (see, e.g., Taylor, L. D. et al. (1992) *Nucl. Acids Res.* 20:6287-6295) or antibodies prepared, expressed, created or isolated by any other means that involves splicing of human immunoglobulin gene sequences to other DNA sequences. Such recombinant human antibodies can have variable and constant regions derived from human germline immunoglobulin sequences (see Kabat, E. A. et al. (1991) *Sequences of Proteins of Immunological Interest*, Fifth Edition, U.S. Department of Health and Human Services, NIH Publication No. 91-3242). In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

In certain embodiments, the binding molecules or antigen binding domains can comprise a portion of a "monoclonal antibody," wherein the term as used herein refers to an antibody obtained from a population of substantially homogeneous antibodies, e.g., the individual antibodies comprising the population are identical except for possible naturally occurring mutations that may be present in minor amounts, and each monoclonal antibody will typically recognize a single epitope on the antigen. In specific embodiments, a "monoclonal antibody," as used herein, is an antibody produced by a single hybridoma or other cell. The term "monoclonal" is not limited to any particular method for making the antibody. For example, the monoclonal antibodies useful in the present disclosure may be prepared by the hybridoma methodology first described by Kohler et al., 1975, Nature 256:495, or may be made using recombinant DNA methods in bacterial or eukaryotic animal or plant cells (see, e.g., U.S. Pat. No. 4,816,567). The "monoclonal antibodies" may also be isolated from phage antibody libraries using the techniques described in Clackson et al., 1991, Nature 352:624-28 and Marks et al., 1991, J. Mol. Biol. 222:581-97, for example. Other methods for the preparation of clonal cell lines and of monoclonal antibodies expressed thereby are well known in the art. See, e.g., *Short Protocols in Molecular Biology* (Ausubel et al. eds., 5th ed. 2002).

A typical 4-chain antibody unit is a heterotetrameric glycoprotein composed of two identical light (L) chains and two identical heavy (H) chains. In the case of IgGs, the 4-chain unit is generally about 150,000 daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain (VH) followed by three constant domains (CH) for each of the α and γ chains and four CH domains for μ and ε isotypes. Each L chain has at the N-terminus, a variable domain (VL) followed by a constant domain (CL) at its other end. The VL is aligned with the VH, and the CL is aligned with the first constant domain of the heavy chain (CH1). Particular amino acid residues are believed to form an interface between the light chain and heavy chain variable domains. The pairing of a VH and VL together forms a single antigen-binding site. For the structure and properties of the different classes of antibodies, see, for example, *Basic and Clinical Immunology* 71 (Stites et al. eds., 8th ed. 1994); and *Immunobiology* (Janeway et al. eds., 5$^{th}$ ed. 2001).

The term "Fab" or "Fab region" refers to an antibody region that binds to antigens. A conventional IgG usually comprises two Fab regions, each residing on one of the two arms of the Y-shaped IgG structure. Each Fab region is typically composed of one variable region and one constant region of each of the heavy and the light chain. More specifically, the variable region and the constant region of the heavy chain in a Fab region are VH and CH1 regions, and the variable region and the constant region of the light chain in a Fab region are VL and CL regions. The VH, CH1, VL, and CL in a Fab region can be arranged in various ways to confer an antigen binding capability according to the present disclosure. For example, VH and CH1 regions can be on one polypeptide, and VL and CL regions can be on a separate polypeptide, similarly to a Fab region of a conventional IgG. Alternatively, VH, CH1, VL and CL regions can all be on the same polypeptide and oriented in different orders as described in more detail the sections below.

The term "variable region," "variable domain," "V region," or "V domain" refers to a portion of the light or heavy chains of an antibody that is generally located at the amino-terminal of the light or heavy chain and has a length of about 120 to 130 amino acids in the heavy chain and about 100 to 110 amino acids in the light chain, and are used in the binding and specificity of each particular antibody for its particular antigen. The variable region of the heavy chain may be referred to as "VH." The variable region of the light chain may be referred to as "VL." The term "variable" refers to the fact that certain segments of the variable regions differ extensively in sequence among antibodies. The V region mediates antigen binding and defines specificity of a particular antibody for its particular antigen. However, the variability is not evenly distributed across the 110-amino acid span of the variable regions. Instead, the V regions consist of less variable (e.g., relatively invariant) stretches called framework regions (FRs) of about 15-30 amino acids separated by shorter regions of greater variability (e.g., extreme variability) called "hypervariable regions" that are each about 9-12 amino acids long. The variable regions of heavy and light chains each comprise four FRs, largely adopting a β sheet configuration, connected by three hypervariable regions, which form loops connecting, and in some cases form part of, the β sheet structure. The hypervariable regions in each chain are held together in close proximity by the FRs and, with the hypervariable regions from the other chain, contribute to the formation of the antigen-binding site of antibodies (see, e.g., Kabat et al., *Sequences of Proteins of Immunological Interest* (5th ed. 1991)). The constant regions are not involved directly in binding an antibody to an antigen, but exhibit various effector functions, such as participation of the antibody in antibody dependent cellular cytotoxicity (ADCC) and complement dependent cytotoxicity (CDC). The variable regions differ extensively in sequence between different antibodies. In specific embodiments, the variable region is a human variable region.

The term "variable region residue numbering according to Kabat" or "amino acid position numbering as in Kabat", and variations thereof, refer to the numbering system used for heavy chain variable regions or light chain variable regions of the compilation of antibodies in Kabat et al., supra. Using this numbering system, the actual linear amino acid sequence may contain fewer or additional amino acids corresponding to a shortening of, or insertion into, an FR or CDR of the variable domain. For example, a heavy chain variable domain may include a single amino acid insert (residue 52a according to Kabat) after residue 52 and three inserted residues (e.g., residues 82a, 82b, and 82c, etc. according to Kabat) after residue 82. The Kabat numbering of residues may be determined for a given antibody by alignment at regions of homology of the sequence of the antibody with a "standard" Kabat numbered sequence. The Kabat numbering system is generally used when referring to a residue in the variable domain (approximately residues 1-107 of the light chain and residues 1-113 of the heavy chain) (e.g., Kabat et al., supra). The "EU numbering system" or "EU index" is generally used when referring to a residue in an immunoglobulin heavy chain constant region (e.g., the EU index reported in Kabat et al., supra). The "EU index as in Kabat" refers to the residue numbering of the human IgG 1 EU antibody. Other numbering systems have been described, for example, by AbM, Chothia, Contact, IMGT, and AHon.

An "intact" antibody is one comprising an antigen-binding site as well as a CL and at least heavy chain constant regions, CH1, CH2 and CH3. The constant regions may include human constant regions or amino acid sequence variants thereof. In certain embodiments, an intact antibody has one or more effector functions.

"Antibody fragments" comprise a portion of an intact antibody, such as the antigen-binding or variable region of the intact antibody. Examples of antibody fragments include, without limitation, Fab, Fab', F(ab')2, and Fv fragments; diabodies and di-diabodies (see, e.g., Holliger et al., 1993, Proc. Natl. Acad. Sci. 90:6444-48; Lu et al., 2005, J. Biol. Chem. 280:19665-72; Hudson et al., 2003, Nat. Med. 9:129-34; WO 93/11161; and U.S. Pat. Nos. 5,837,242 and 6,492,123); single-chain antibody molecules (see, e.g., U.S. Pat. Nos. 4,946,778; 5,260,203; 5,482,858; and 5,476,786); dual variable domain antibodies (see, e.g., U.S. Pat. No. 7,612,181); single variable domain antibodies (sdAbs) (see, e.g., Woolven et al., 1999, Immunogenetics 50: 98-101; and Streltsov et al., 2004, Proc Natl Acad Sci USA. 101:12444-49); and multispecific antibodies formed from antibody fragments.

The term "heavy chain" when used in reference to an antibody refers to a polypeptide chain of about 50-70 kDa, wherein the amino-terminal portion includes a variable region of about 120 to 130 or more amino acids, and a carboxy-terminal portion includes a constant region. The constant region can be one of five distinct types, (e.g., isotypes) referred to as alpha (α), delta (δ), epsilon (ε), gamma (γ), and mu (μ), based on the amino acid sequence of the heavy chain constant region. The distinct heavy chains differ in size: α, δ, and γ contain approximately 450 amino acids, while μ and ε contain approximately 550 amino acids. When combined with a light chain, these distinct types of heavy chains give rise to five well known classes (e.g., isotypes) of antibodies, IgA, IgD, IgE, IgG, and IgM, respectively, including four subclasses of IgG, namely IgG1, IgG2, IgG3, and IgG4.

The term "light chain" when used in reference to an antibody refers to a polypeptide chain of about 25 kDa, wherein the amino-terminal portion includes a variable region of about 100 to about 110 or more amino acids, and a carboxy-terminal portion includes a constant region. The approximate length of a light chain is 211 to 217 amino acids. There are two distinct types, referred to as kappa (κ) or lambda (λ) based on the amino acid sequence of the constant domains.

As used herein, the terms "hypervariable region," "HVR," "Complementarity Determining Region," and "CDR" are used interchangeably. A "CDR" refers to one of three hypervariable regions (H1, H2 or H3) within the non-framework region of the immunoglobulin (Ig or antibody) VH β-sheet framework, or one of three hypervariable regions (L1, L2 or L3) within the non-framework region of the antibody VL β-sheet framework. Accordingly, CDRs are variable region sequences interspersed within the framework region sequences.

CDR regions are well known to those skilled in the art and have been defined by well-known numbering systems. For example, the Kabat Complementarity Determining Regions (CDRs) are based on sequence variability and are the most commonly used (see, e.g., Kabat et al., supra). Chothia refers instead to the location of the structural loops (see, e.g., Chothia and Lesk, 1987, J. Mol. Biol. 196:901-17). The end of the Chothia CDR-H1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). The AbM hypervariable regions represent a compromise between the Kabat CDRs and Chothia structural loops, and are used by Oxford Molecular's AbM antibody modeling software (see, e.g., *Antibody Engineering* Vol. 2 (Kontermann and Dübel eds., 2d ed. 2010)). The "contact" hypervariable regions are based on an analysis of the available complex crystal structures. Another universal numbering system that has been developed and widely adopted is ImMunoGeneTics (IMGT) Information System® (Lafranc et al., 2003, Dev. Comp. Immunol. 27(1):55-77). IMGT is an integrated information system specializing in immunoglobulins (Ig), T cell receptors (TCR), and major histocompatibility complex (MHC) of human and other vertebrates. Herein, the CDRs are referred to in terms of both the amino acid sequence and the location within the light or heavy chain. As the "location" of the CDRs within the structure of the immunoglobulin variable domain is conserved between species and present in structures called loops, by using numbering systems that align variable domain sequences according to structural features, CDR and framework residues are readily identified. This information can be used in grafting and replacement of CDR residues from immunoglobulins of one species into an acceptor framework from, typically, a human antibody. An additional numbering system (AHon) has been developed by Honegger and Plückthun, 2001, J. Mol. Biol. 309: 657-70. Correspondence between the numbering system, including, for example, the Kabat numbering and the IMGT unique numbering system, is well known to one skilled in the art (see, e.g., Kabat, supra; Chothia and Lesk, supra; Martin, supra; Lefranc et al., supra). The residues from each of these hypervariable regions or CDRs are noted below.

TABLE 1

Residues of hypervariable regions or CDRs

| Loop | Kabat | AbM | Chothia | Contact | IMGT |
| --- | --- | --- | --- | --- | --- |
| CDR L1 | L24 - - - L34 | L24 - - - L34 | L24 - - - L34 | L30 - - - L36 | L27 - - - L38 |
| CDR L2 | L50 - - - L56 | L50 - - - L56 | L50 - - - L56 | L46 - - - L55 | L56 - - - L65 |
| CDR L3 | L89 - - - L97 | L89 - - - L97 | L89 - - - L97 | L89 - - - L96 | L105-L117 |
| CDR H1 | H31 - - - H35B (Kabat Numbering) | H26 - - - H35B | H26 - - - H32 . . . 34 | | H27 - - - H38 |
| CDR H1 | H31 - - - H35 (Chothia Numbering) | H26 - - - H35 | H26 - - - H32 | H30 - - - H35 | |
| CDR H2 | H50 - - - H65 | H50 - - - H58 | H52 - - - H56 | H47 - - - H58 | H56 - - - H65 |
| CDR H3 | H95 - - - H102 | H95 - - - H102 | H95 - - - H102 | H93 - - - H101 | H105-H117 |

The boundaries of a given CDR may vary depending on the scheme used for identification. Thus, unless otherwise specified, the terms "CDR" and "complementary determining region" of a given antibody or region thereof, such as a variable region, as well as individual CDRs (e.g., "CDR-H1, CDR-H2) of the antibody or region thereof, should be understood to encompass the complementary determining region as defined by any of the known schemes described herein above. In some instances, the scheme for identification of a particular CDR or CDRs is specified, such as the CDR as defined by the Kabat, Chothia, or Contact method. In other cases, the particular amino acid sequence of a CDR is given.

Hypervariable regions may comprise "extended hypervariable regions" as follows: 24-36 or 24-34 (L1), 46-56 or 50-56 (L2), and 89-97 or 89-96 (L3) in the VL, and 26-35 or 26-35A (H1), 50-65 or 49-65 (H2), and 93-102, 94-102, or 95-102 (H3) in the VH.

The term "constant region" or "constant domain" refers to a carboxy terminal portion of the light and heavy chain which is not directly involved in binding of the antibody to antigen but exhibits various effector function, such as interaction with the Fc receptor. The term refers to the portion of an immunoglobulin molecule having a more conserved amino acid sequence relative to the other portion of the immunoglobulin, the variable region, which contains the antigen binding site. The constant region may contain the CH1, CH2, and CH3 regions of the heavy chain and the CL region of the light chain.

The term "framework" or "FR" refers to those variable region residues flanking the CDRs. FR residues are present, for example, in chimeric, humanized, human, domain antibodies, diabodies, linear antibodies, and bispecific antibodies. FR residues are those variable domain residues other than the hypervariable region residues or CDR residues.

The term "Fc region" herein is used to define a C-terminal region of an immunoglobulin heavy chain, including, for example, native sequence Fc regions, recombinant Fc regions, and variant Fc regions. Although the boundaries of the Fc region of an immunoglobulin heavy chain might vary, the human IgG heavy chain Fc region is often defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue. A "functional Fc region" possesses an "effector function" of a native sequence Fc region. Exemplary "effector functions" include C1q binding; CDC; Fc receptor binding; ADCC; phagocytosis; downregulation of cell surface receptors (e.g., B cell receptor), etc. Such effector functions generally require the Fc region to be combined with a binding region or binding domain (e.g., an antibody variable region or domain) and can be assessed using various assays known to those skilled in the art. A "variant Fc region" comprises an amino acid sequence which differs from that of a native sequence Fc region by virtue of at least one amino acid modification (e.g., substituting, addition, or deletion). In certain embodiments, the variant Fc region has at least one amino acid substitution compared to a native sequence Fc region or to the Fc region of a parent polypeptide, for example, from about one to about ten amino acid substitutions, or from about one to about five amino acid substitutions in a native sequence Fc region or in the Fc region of a parent polypeptide. The variant Fc region herein can possess at least about 80% homology with a native sequence Fc region and/or with an Fc region of a parent polypeptide, or at least about 90% homology therewith, for example, at least about 95% homology therewith.

A polypeptide "extracellular domain" or "ECD" refers to a form or a portion of the polypeptide that is essentially free of the transmembrane and cytoplasmic domains. For example, an ECD may have less than 1% of such transmembrane and/or cytoplasmic domains and can have less than 0.5% of such domains.

As used herein, an "epitope" is a term in the art and refers to a localized region of an antigen to which a binding molecule (e.g., an antibody) can specifically bind. An epitope can be a linear epitope or a conformational, non-linear, or discontinuous epitope. In the case of a polypeptide antigen, for example, an epitope can be contiguous amino acids of the polypeptide (a "linear" epitope) or an epitope can comprise amino acids from two or more non-contiguous regions of the polypeptide (a "conformational," "non-linear" or "discontinuous" epitope). It will be appreciated by one of skill in the art that, in general, a linear epitope may or may not be dependent on secondary, tertiary, or quaternary structure. For example, in some embodiments, a binding molecule binds to a group of amino acids regardless of whether they are folded in a natural three dimensional protein structure. In other embodiments, a binding molecule requires amino acid residues making up the epitope to exhibit a particular conformation (e.g., bend, twist, turn or fold) in order to recognize and bind the epitope.

The terms "polypeptide" and "peptide" and "protein" are used interchangeably herein and refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification. Also included within the definition are, for example, polypeptides containing one or more analogs of an amino acid, including but not limited to, unnatural amino acids, as well as other modifications known in the art. It is understood that, because the polypeptides of this disclosure may be based upon antibodies or other members of the immunoglobulin superfamily, in certain embodiments, a "polypeptide" can occur as a single chain or as two or more associated chains.

The term "vector" refers to a substance that is used to carry or include a nucleic acid sequence, including for example, a nucleic acid sequence encoding a binding molecule (e.g., an antibody) as described herein, in order to introduce a nucleic acid sequence into a host cell. Vectors applicable for use include, for example, expression vectors, plasmids, phage vectors, viral vectors, episomes, and artificial chromosomes, which can include selection sequences or markers operable for stable integration into a host cell's chromosome. Additionally, the vectors can include one or more selectable marker genes and appropriate expression control sequences. Selectable marker genes that can be included, for example, provide resistance to antibiotics or toxins, complement auxotrophic deficiencies, or supply critical nutrients not in the culture media. Expression control sequences can include constitutive and inducible promoters, transcription enhancers, transcription terminators, and the like, which are well known in the art. When two or more nucleic acid molecules are to be co-expressed (e.g., both an antibody heavy and light chain or an antibody VH and VL), both nucleic acid molecules can be inserted, for example, into a single expression vector or in separate expression vectors. For single vector expression, the encoding nucleic acids can be operationally linked to one common expression control sequence or linked to different expression control sequences, such as one inducible promoter and one constitutive promoter. The introduction of nucleic acid molecules into a host cell can be confirmed using methods well known in the art. Such methods include, for example, nucleic acid analysis such as Northern blots or polymerase chain reaction (PCR) amplification of mRNA, immunoblotting for expression of gene products, or other suitable analytical methods to test the expression of an introduced nucleic acid sequence or its corresponding gene product. It is understood by those skilled in the art that the nucleic acid molecules are expressed in a sufficient amount to produce a desired product and it is further understood that expression levels can be optimized to obtain sufficient expression using methods well known in the art.

The term "host" as used herein refers to an animal, such as a mammal (e.g., a human).

The term "host cell" as used herein refers to a particular subject cell that may be transfected with a nucleic acid molecule and the progeny or potential progeny of such a cell. Progeny of such a cell may not be identical to the parent cell transfected with the nucleic acid molecule due to mutations or environmental influences that may occur in succeeding generations or integration of the nucleic acid molecule into the host cell genome.

An "isolated nucleic acid" is a nucleic acid, for example, an RNA, DNA, or a mixed nucleic acids, which is substantially separated from other genome DNA sequences as well as proteins or complexes such as ribosomes and polymerases, which naturally accompany a native sequence. An "isolated" nucleic acid molecule is one which is separated from other nucleic acid molecules which are present in the natural source of the nucleic acid molecule. Moreover, an "isolated" nucleic acid molecule, such as a cDNA molecule, can be substantially free of other cellular material, or culture medium when produced by recombinant techniques, or substantially free of chemical precursors or other chemicals when chemically synthesized. In a specific embodiment, one or more nucleic acid molecules encoding an antibody as described herein are isolated or purified. The term embraces nucleic acid sequences that have been removed from their naturally occurring environment, and includes recombinant or cloned DNA isolates and chemically synthesized analogues or analogues biologically synthesized by heterologous systems. A substantially pure molecule may include isolated forms of the molecule.

"Polynucleotide" or "nucleic acid," as used interchangeably herein, refers to polymers of nucleotides of any length and includes DNA and RNA. The nucleotides can be deoxyribonucleotides, ribonucleotides, modified nucleotides or bases, and/or their analogs, or any substrate that can be incorporated into a polymer by DNA or RNA polymerase or by a synthetic reaction. A polynucleotide may comprise modified nucleotides, such as methylated nucleotides and their analogs. "Oligonucleotide," as used herein, refers to short, generally single-stranded, synthetic polynucleotides that are generally, but not necessarily, fewer than about 200 nucleotides in length. The terms "oligonucleotide" and "polynucleotide" are not mutually exclusive. The description above for polynucleotides is equally and fully applicable to oligonucleotides. A cell that produces a binding molecule of the present disclosure may include a parent hybridoma cell, as well as bacterial and eukaryotic host cells into which nucleic acids encoding the antibodies have been introduced. Unless specified otherwise, the left-hand end of any single-stranded polynucleotide sequence disclosed herein is the 5' end; the left-hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA transcript that are 5' to the 5' end of the RNA transcript are referred to as "upstream sequences"; sequence regions on the DNA strand having the same sequence as the RNA transcript that are 3' to the 3' end of the RNA transcript are referred to as "downstream sequences."

"Carriers" as used herein include pharmaceutically acceptable carriers, excipients, or stabilizers that are non-toxic to the cell or mammal being exposed thereto at the dosages and concentrations employed. Often the physiologically acceptable carrier is an aqueous pH buffered solution. Examples of physiologically acceptable carriers include buffers, such as phosphate, citrate, and other organic acids; antioxidants, including ascorbic acid; low molecular weight (e.g., fewer than about 10 amino acid residues) polypeptide; proteins, such as serum albumin, gelatin, or immunoglobulins; hydrophilic polymers, such as polyvinylpyrrolidone; amino acids, such as glycine, glutamine, asparagine, arginine, or lysine; monosaccharides, disaccharides, and other carbohydrates, including glucose, mannose, or dextrins; chelating agents, such as EDTA; sugar alcohols, such as mannitol or sorbitol; salt-forming counterions, such as sodium; and/or nonionic surfactants, such as TWEEN™, polyethylene glycol (PEG), and PLURONICS™. The term "carrier" can also refer to a diluent, adjuvant (e.g., Freund's adjuvant (complete or incomplete)), excipient, or vehicle. Such carriers, including pharmaceutical carriers, can be sterile liquids, such as water and oils, including those of petroleum, animal, vegetable, or synthetic origin, such as peanut oil, soybean oil, mineral oil, sesame oil, and the like. Water is an exemplary carrier when a composition (e.g., a pharmaceutical composition) is administered intravenously. Saline solutions and aqueous dextrose and glycerol solutions can also be employed as liquid carriers, particularly for injectable solutions. Suitable excipients (e.g., pharmaceutical excipients) include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The composition, if desired, can also contain minor amounts of wetting or emulsifying agents, or pH buffering agents. Compositions can take the form of solutions, suspensions, emulsion, tablets, pills, capsules, powders, sustained-release formulations, and the like. Oral compositions, including formulations, can include standard carriers such as pharmaceutical grades of mannitol, lactose, starch, magnesium stearate, sodium saccharine, cellulose, magnesium carbonate, etc. Examples of suitable pharmaceutical carriers are described in Remington and Gennaro, *Remington's Pharmaceutical Sciences* (18th ed. 1990). Compositions, including pharmaceutical compounds, may contain a binding molecule (e.g., an antibody), for example, in isolated or purified form, together with a suitable amount of carriers.

The term "pharmaceutically acceptable" as used herein means being approved by a regulatory agency of the Federal or a state government, or listed in *United States Pharmacopeia, European Pharmacopeia*, or other generally recognized Pharmacopeia for use in animals, and more particularly in humans.

The term "effective amount" as used herein refers to the amount of binding molecule (e.g., an antibody) or pharmaceutical composition provided herein which is sufficient to result in the desired outcome.

The terms "subject" and "patient" may be used interchangeably. As used herein, in certain embodiments, a subject is a mammal, such as a non-primate (e.g., cow, pig, horse, cat, dog, rat, etc.) or a primate (e.g., monkey and human). In specific embodiments, the subject is a human. In one embodiment, the subject is a mammal, e.g., a human, diagnosed with a condition or disorder. In another embodiment, the subject is a mammal, e.g., a human, at risk of developing a condition or disorder.

"Administer" or "administration" refers to the act of injecting or otherwise physically delivering a substance as it exists outside the body into a patient, such as by mucosal, intradermal, intravenous, intramuscular delivery, and/or any other method of physical delivery described herein or known in the art.

As used herein, the terms "treat," "treatment" and "treating" refer to the reduction or amelioration of the progression, severity, and/or duration of a disease or condition resulting from the administration of one or more therapies.

The terms "about" and "approximately" mean within 20%, within 15%, within 10%, within 9%, within 8%, within 7%, within 6%, within 5%, within 4%, within 3%, within 2%, within 1%, or less of a given value or range.

As used in the present disclosure and claims, the singular forms "a", "an" and "the" include plural forms unless the context clearly dictates otherwise.

It is understood that wherever embodiments are described herein with the term "comprising" otherwise analogous embodiments described in terms of "consisting of" and/or "consisting essentially of" are also provided. It is also understood that wherever embodiments are described herein with the phrase "consisting essentially of" otherwise analogous embodiments described in terms of "consisting of" are also provided.

The term "and/or" as used in a phrase such as "A and/or B" herein is intended to include both A and B; A or B; A (alone); and B (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

II. Binding Molecules

Provided herein are binding molecules (ALiCE) comprising multiple antigen binding domains (e.g., two antigen binding domains). In some embodiments, the multiple antigen binding domains of the binding molecules provided herein are useful for engaging cells, bringing a cell to an immune cell, or redirecting an immune cell.

In certain embodiments, the binding molecules provided herein comprises two antigen binding domains, wherein the first antigen binding domain comprises two antibody Fab regions and the second antigen binding domain comprises an antibody Fv region. Each of the two Fab regions contains two portions: a first portion having an antibody variable heavy (VH) region and an antibody CH1 region; and a second portion having a second portion comprising an antibody light chain (LC) comprising an antibody variable light (VL) region and an antibody light chain constant region (CL). Each of the two Fab regions binds to an antigen. The Fv region in the second antigen binding domain comprises a VH region and an antibody variable light (VL) region. The two Fab regions are linked to the Fv region.

Thus, in one aspect, the present disclosure provides a binding molecule comprising:

(a) a first antigen binding domain comprising two antibody Fab regions, each comprising:
  (i) a first portion comprising an antibody variable heavy (VH) region and an antibody CH1 region, wherein the first portion does not contain an antibody CH2 region and an antibody CH3 region; and
  (ii) a second portion comprising an antibody light chain (LC) comprising an antibody variable light (VL) region and an antibody light chain constant region (CL),
  wherein the two antibody Fab regions each bind to an antigen, and
(b) a second antigen binding domain comprising an antibody Fv region comprising a VH region and an antibody variable light (VL) region,
wherein the second antigen binding domain binds to an antigen present on an immune cell; and
wherein the first antigen binding domain and the second antigen binding domain are linked.

A Fab region (i.e., antigen-binding fragment) is an antibody region that binds to antigens. A conventional IgG usually comprises two Fab regions, each residing on one of the two arms of the Y-shaped IgG structure. Each Fab region is typically composed of one variable region and one constant region of each of the heavy and the light chain. More specifically, the variable region and the constant region of the heavy chain in a Fab region are VH and CH1 regions, and the variable region and the constant region of the light chain in a Fab region are VL and CL regions. The VH, CH1, VL, and CL in a Fab region can be arranged in various ways to confer an antigen binding capability according to the present disclosure. For example, VH and CH1 regions can be on one polypeptide, and VL and CL regions can be on a separate polypeptide, similarly to a Fab region of a conventional IgG. Alternatively, VH, CH1, VL and CL regions can all be on the same polypeptide and oriented in different orders as described in more detail below.

A Fv region is an antigen binding region that comprises a VH region and a VL region. The VH and VL regions in a Fv region can be arranged in various ways to confer an antigen binding capability according to the present disclosure. For example, VH and VL region can be on the same or separate polypeptides. If the VH and VL regions are on the same polypeptide, they can be oriented in different orders as described in more detail below.

As explained in Section I above, the term "variable region" refers to a portion of the light or heavy chains of an antibody that is generally located at the amino-terminal of the light or heavy chain and has a length of about 120 to 130 amino acids in the heavy chain and about 100 to 110 amino acids in the light chain, and are used in the binding and specificity of each particular antibody for its particular antigen. The variable region of the heavy chain may be referred to as "VH." The variable region of the light chain may be referred to as "VL."

The term "constant region" refers to a carboxy terminal portion of the light and heavy chain which is not directly involved in binding of the antibody to antigen but exhibits various effector function, such as interaction with the Fc receptor. The term refers to the portion of an immunoglobulin molecule having a more conserved amino acid sequence relative to the other portion of the immunoglobulin, the variable region, which contains the antigen binding site. The constant region can determine the mechanism used to destroy antigen. Antibodies are divided into five major classes, IgM, IgG, Iga, IgD, and IgE, based on their constant region structure and immune function. IgG is the class of immunoglobulin characterized by γ heavy chains. It is the most abundant class of immunoglobulin found in the plasma. The constant region of a light chain is referred to as "CL." The multiple heavy-chain C domains (CH domains) are numbered from the amino-terminal end to the carboxy terminus, for example CH1, CH2, CH3 and so on. Any CL and CH1 regions of these antibody classes can be used in the present disclosure. In a specific embodiment, CL and CH1 regions provided herein are of IgG type (e.g., IgG1). A representative CL region of the Fab region provided herein has the following amino acid sequence:

(SEQ ID NO.: 59)
TVAAPSVFIFPPSDEQLKSGTASVVCLLNNFYPREAKVQWKVDNALQSG

NSQESVTEQDSKDSTYSLSSTLTLSKADYEKHKVYACEVTHQGLSSPVT

KSFNRGEC.

A representative CH1 region of the Fab region provided herein has the following amino acid sequence:

(SEQ ID NO.: 60)
ASTKGPSVFPLAPSSKSTSGGTAALGCLVKDYFPEPVTVSWNSGALTSG

VHTFPAVLQSSGLYSLSSVVTVPSSSLGTQTYICNVNHKPSNTKVDKKV

The language that "the first portion does not contain an antibody CH2 region and an antibody CH3 region" is used herein to mean that the first portion does not contain a complete antibody CH2 region or a complete CH3 region. However, this language does not exclude the embodiments wherein a part of a CH2 region and/or a CH3 region is included in the first portion. In addition, in certain embodiments, CH2 and/or CH3 variants or truncations that do not exhibit full CH2 and/or CH3 activity (e.g., effector function) may be included. Assays such as Fc receptor binding assays or ADCC activity assays or other well-known assays for determining Fc region related functions may be used herein to determine if CH2 and/or CH3 activities (or Fc region activities) are fully retained.

In some embodiments, the first portion and the second portion of each Fab region are present on separate polypeptides. Each of the two Fab regions can also be optionally a single chain Fab region. Thus, in other embodiments, the first portion and the second portion of both Fab regions of the first antigen binding domain are on the same polypeptide. In other embodiments, the first portion and the second portion of one of the two Fab regions are on the same polypeptide. In those embodiments wherein a Fab region is a single chain Fab (i.e., the first portion and the second portion of the Fab region are on the same polypeptide), the Fab region can be oriented from N-terminus to C-terminus in the following order: VH-CH1-VL-CL. Alternatively, a single chain Fab region can be oriented from N-terminus to C-terminus in the following order: VL-CL-VH-CH1.

Similarly, in certain embodiments, the VH region and the VL region of the Fv region are on separate polypeptides. In other embodiments, the Fv region of the second antigen binding domain is a single chain Fv (i.e., the VH region and the VL region of the Fv region are on the same polypeptide). In such single chain Fv embodiments, the Fv region can be oriented from N-terminus to C-terminus in the following order: VH-VL, or can be oriented from N-terminus to C-terminus in the following order: VL-VH.

In some specific embodiments, the two portions of each Fab region are on separate polypeptides and the VH and VL regions of the Fv region are also on separate polypeptides.

In some embodiments, the first antigen binding domain and the second antigen binding domain are linked by a flexible peptide region. In some embodiments, the flexible peptide region comprises an antibody hinge region. In some specific embodiments, the antibody hinge region is an IgG hinge region. The IgG hinge region provided herein may be selected from antibody hinge regions of various IgG subtypes. Table 2 below lists exemplary IgG subtypes with core hinge sequences that may be included in the flexible peptide region provided herein.

TABLE 2

Exemplary IgG subtypes

| IgG subtype | Core hinge sequence | SEQ ID NO: |
|---|---|---|
| IgG1 | EPKSCDKTHTCPPCP | 55 |
| IgG2 | ERKCCVECPPCP | 56 |
| IgG3 | ELKTPLDTTHTCPRCP (EPKSCDTPPPCPRCP)3 | 57 |
| IgG4 | ESKYGPPCPSCP | 58 |

Thus, in some more specific embodiments, the IgG hinge region is of IgG1 subtype. In other more specific embodiments, the IgG hinge region is of IgG2 subtype. In yet other more specific embodiments, the IgG hinge region is of IgG3 subtype. In yet other more specific embodiments, the IgG hinge region is of IgG4 subtype. In some specific embodiments, the flexible peptide region provided herein comprises an amino acid sequence of SEQ ID NO: 55. In some specific embodiments, the flexible peptide region provided herein comprises an amino acid sequence of SEQ ID NO: 56. In other specific embodiments, the flexible peptide region provided herein comprises an amino acid sequence of SEQ ID NO.: 57. In some specific embodiments, the flexible peptide region provided herein comprises an amino acid sequence of SEQ ID NO.: 58.

In certain embodiments, the flexible peptide region comprise additional amino acids. For example, in some embodiments, the flexible peptide region further comprises a linker (e.g., G4S (SEQ ID NO: 130)) between the antibody hinge region and the second Fv antigen binding domain. Flexible linker between antibody hinge region and second Fv domain may influence binding affinity of the second Fv domain. Improved binding affinity of second Fv domain can lead to increased redirectional efficiency of immune cells (e.g., effector cells including T cells) to target cells (e.g., cancer cells). The second Fv domain need to bend to be able to interact with and bind to a surface antigen presented on immune cells (e.g., effector cells including T cells), because the paratope of the second Fv domain of ALiCE is structurally masked by the first Fab domain of ALiCE. Therefore, to reduce steric hindrance and optimize the binding of the second Fv domain to immune cells (e.g., effector cells including T cells), flexible linker such as G4S (SEQ ID NO: 130) can be introduced between the antibody hinge region and the second Fv domain. In some embodiments, the linker comprises an amino acid sequence of GGGGS (G4S) (SEQ ID NO: 130). In some embodiments, the linker comprises an amino acid sequence of (G4S)n (SEQ ID NO: 133) where n is an integer. In some specific embodiments, the linker comprises an amino acid sequence of $(G4S)_1$ (SEQ ID NO: 130). In some more specific embodiments, the linker comprises an amino acid sequence of $(G4S)_2$ (SEQ ID NO: 131). In other more specific embodiments, the linker comprises an amino acid sequence of $(G4S)_3$ (SEQ ID NO: 134). In yet other more specific embodiments, the linker comprises an amino acid sequence of $(G4S)_4$ (SEQ ID NO: 135). Other methods for designing and constructing linkers with different flexibilities are described in more detail in, e.g., Klein et al., Protein Engineering, Design & Selection, 2014, 27(10): 325-330, and DiGiammarino et al., Landes Bioscience, 2011, 3(5): 487-494, each of which is incorporated herein by reference in its entirety.

Figure 1B:
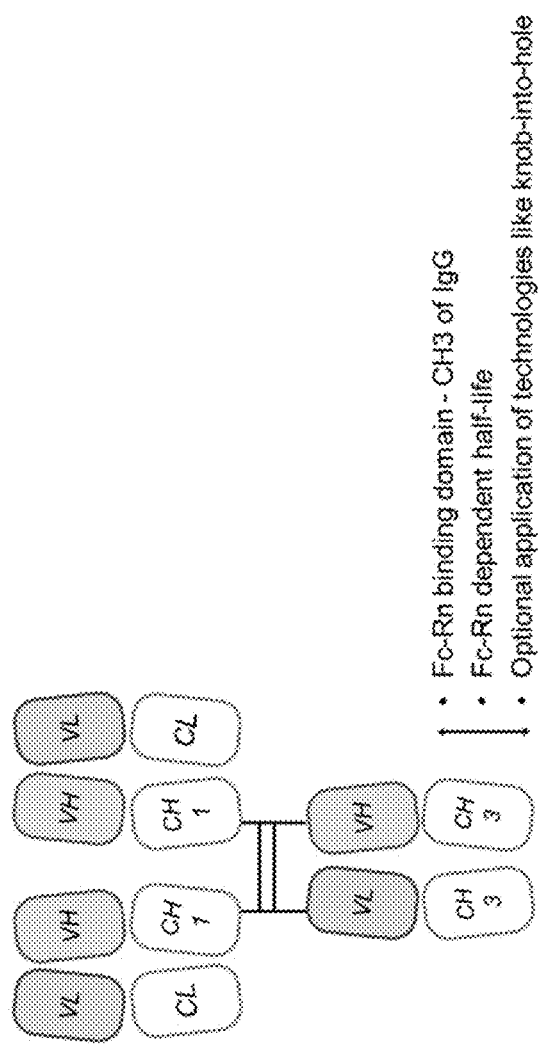
FIG. 1B illustrates an exemplary binding molecule provided herein that contains CH3 regions.

The binding molecules provided herein can optionally comprise a CH3 domain. FIG. 1B illustrates such an exemplary binding molecule. In some embodiments, the second antigen binding domain further comprise a first CH3 region linked to the VH region of the Fv region and a second CH3 region linked to the VL region of the Fv region. In some embodiments, the CH regions are linked to the C-terminus of the VH and VL regions of the Fv region. The presence of the CH3 regions provides the Fc receptor binding capability of the binding molecules provided herein. In some embodiments, the CH3 regions linked to the Fv region are engineered to facilitate or enforce the association between the two CH3 regions using existing technologies such as knobs-into-holes (KiH) technology or electrostatic steering. For example, knobs-into-holes was originally proposed as a model for the packing of amino acid side chains between adjacent α-helices, and was later demonstrated to be an effective design strategy for engineering antibody heavy chain homodimers for heterodimerization. Briefly, in certain embodiments of this approach, a 'knob' variant can be first obtained by replacement of a small amino acid with a larger one in one IgG CH3 domain (e.g., T to Y substitution). The knob was designed to insert into a 'hole' in another IgG CH3 domain created by replacement of a large residue with a smaller one (e.g., Y to T substitution). The knob-into-holes technology is described in detail with several examples in e.g., WO 96/027011, Ridgway et al., Protein Eng 9 (1996) 617-621, and Merchant et al., Nat Biotechnol 16 (1998) 677-681, each of which is incorporated herein by reference in its entirety. Other well-known technologies for modifying CH3 regions to facilitate or enforce the association between the two CH3 regions are also contemplated in the present disclosure.

Albumin (e.g., human serum albumin) has been used to increase the serum half-life of biological drugs. See Dennis et al., *The Journal of Biological Chemistry*, 2002, 277 (38): 35035-35043; Adams et al., *MABS*, 2016, 8(7): 1336-1346. For example, human serum albumin (HSA) has been utilized. HSA is the most abundant protein in blood, and is widely distributed in tissues and has a non-acute function. It has a half like of 19 days. Therefore, in some embodiments, albumin (e.g., HSA) can be used herein to increase half-life of the binding molecules provided herein. Alumin can be used in a few ways. One exemplary approach is to directly couple an albumin domain (e.g., HSA) to the binding molecule provided herein, either genetically or chemically. Another exemplary approach is to use an albumin binding domain or site (ABD or ABS).

Figure 1C:
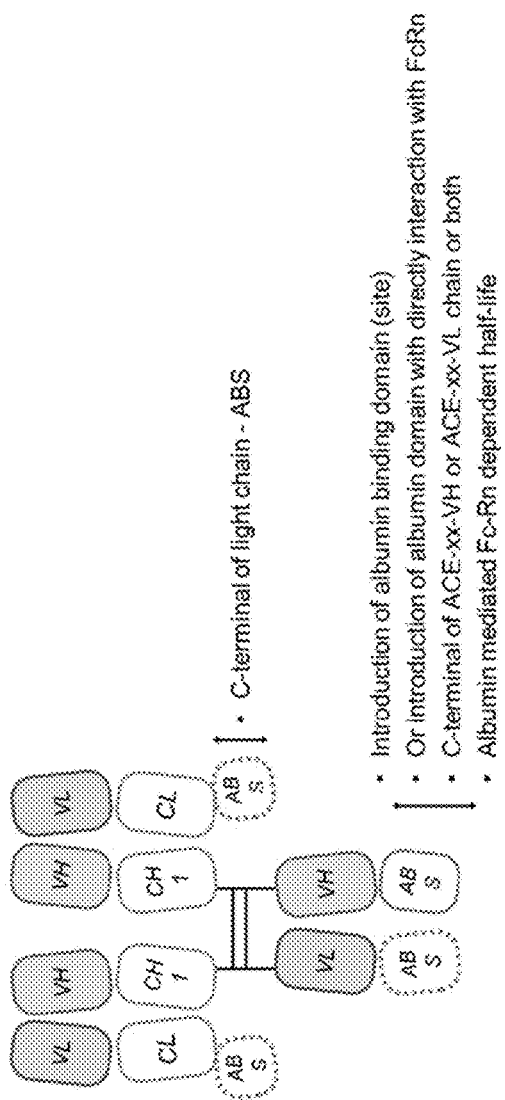
FIG. 1C illustrates an exemplary binding molecule provided herein that contains albumin binding sites (ABS).
Figure 1D:
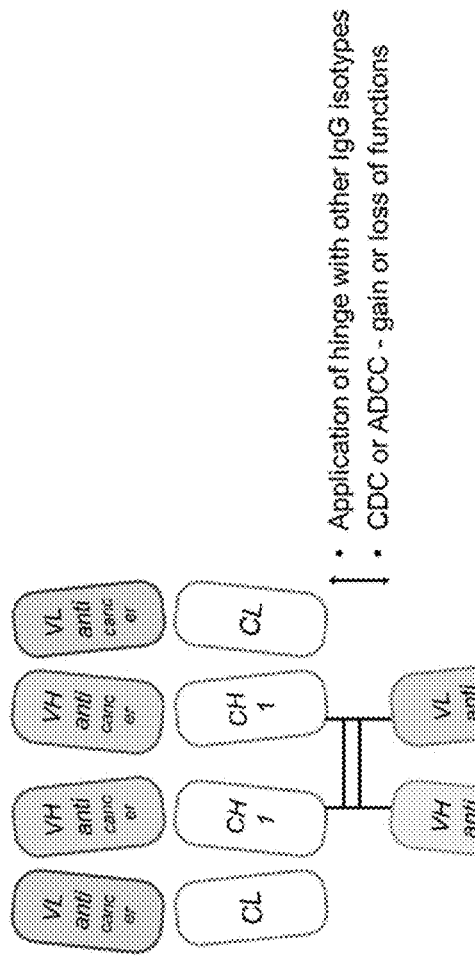
FIG. 1D illustrates an exemplary binding molecule provided herein that has a binding domain targeting a cancer antigen and also illustrates exemplary options for the flexible peptide region provided herein.

Thus, the binding molecules provided herein may also optionally include one or more albumin binding domain or albumin binding site (ABD or ABS). FIG. 1C illustrates such exemplary binding molecules. In some embodiments, the ABS of the binding molecules provided herein mediates binding with endogenous albumin, thereby helping prolong the half-life and/or enhancing the therapeutic effects of the binding molecules provided herein. In some embodiments, the ABS of the binding molecules provided herein may also help improve the pharmacokinetics, through the non-covalent association to albumin. In some embodiments, the ABS is linked to the C-terminus of the VH region of the Fv region. In other embodiments, the ABS is linked to the C-terminus of the VL region of the Fv region. In yet other embodiments, the C-terminus of each of the VL and VH regions of the Fv region is linked to ABS. In other embodiments, the ABS is linked to the CL region of at least one of the Fab regions.

In certain embodiments, the binding molecule can further optionally comprises one or more albumin domain (e.g., HSA). In some embodiments, an albumin domain is linked to the C-terminus of the VH region of the Fv region. In other embodiments, an albumin domain is linked to the C-terminus of the VL region of the Fv region. In yet other embodiments, the C-terminus of each of the VL and VH regions of the Fv region is linked to an albumin domain. In other embodiments, an albumin domain is linked to the CL region of at least one of the Fab regions.

The two Fab regions and Fv region of the binding molecules provided herein can each bind to an antigen. In some embodiments, the two Fab regions bind to different antigens.

In other embodiments, the two Fab regions bind to the same antigen. In some embodiments, the two Fab regions bind to the same epitope of the same antigen. In other embodiments, the two Fab regions bind to different epitopes of the same antigen.

When two Fab regions bind to the same antigen—a first antigen, the first antigen can be the same or different from the antigen (a second antigen) bound by the Fv region. Thus, in some embodiments, the first antigen binding domain and the second antigen binding domain bind to the same antigen.

In some embodiments, the second antigen binding domain binds to the same epitope as at least one of the epitopes bound by the first antigen binding domain.

Figure 1E:
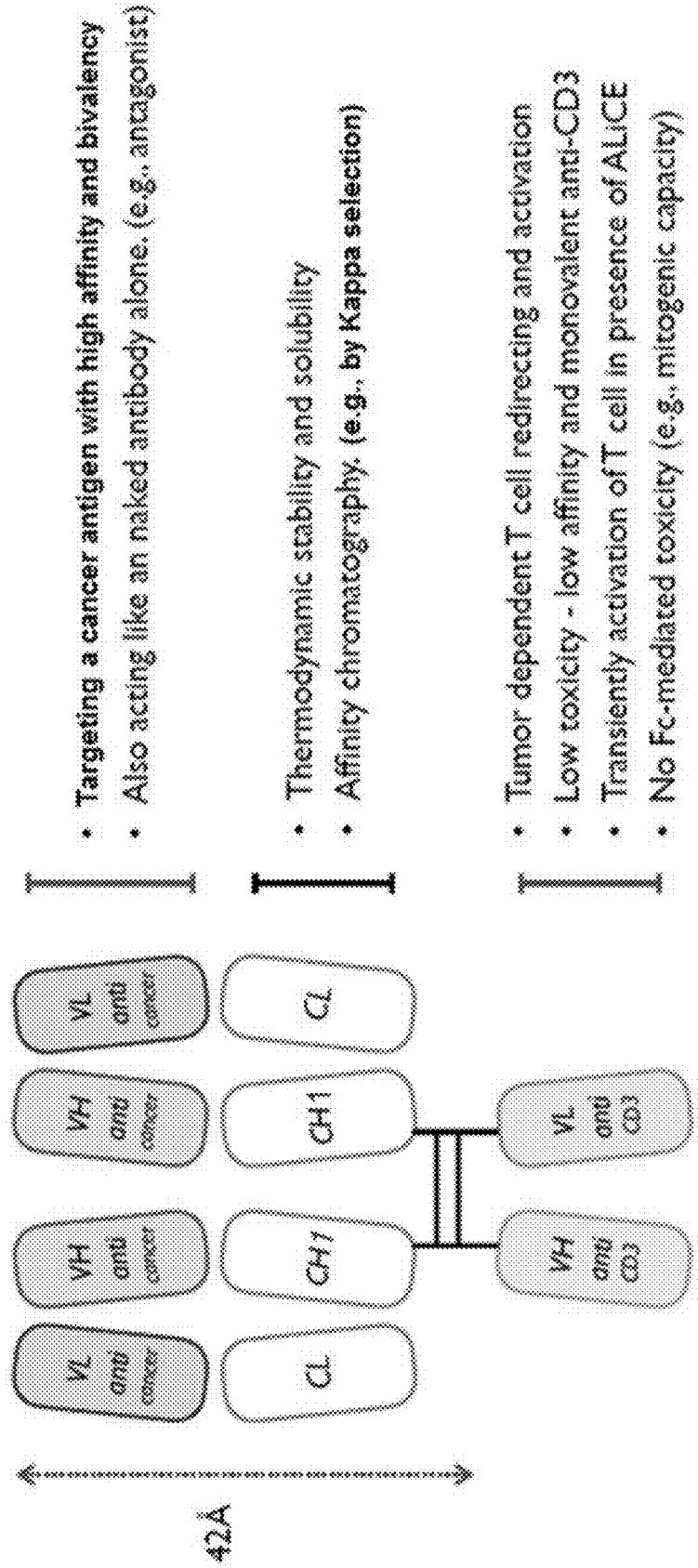
FIG. 1E illustrates an exemplary binding molecule provided herein that has a binding domain targeting a cancer antigen and a binding domain targeting CD3.

In other embodiments, the first antigen binding domain and the second antigen binding domain bind to different antigens, and wherein the first antigen binding domain binds to a first antigen and the second antigen binding domain binds to a second antigen. FIG. 1E provides an illustration of such an ALiCE molecule wherein the first antigen binding domain (the two Fab regions) binds to a cancer antigen, and the second antigen binding domain binds to an immune cell such as a T cell through an antigen like CD3. Such ALiCE molecules can engage an immune cell (e.g., T cell) to a cancer cell and thus be used as a therapeutic for cancer treatment.

Thus, in some embodiments, the binding molecules provided herein are bispecific binding molecules which comprises (a) two Fab regions (in the first antigen binding domain) that provides the binding affinity to the first antigen and (b) a Fv region (in the second antigen binding domain) that provides the binding affinity to the second antigen. The first antigen binding domain can bind to an extracellular domain of a surface protein on one cell, and the second antigen binding domain can bind to an extracellular domain of a surface protein on an immune cell, and thereby bring the two cells together.

The first antigen binding domain (with the two Fab regions) can bind to a cancer cell. It can also bind to a non-cancer cell. Thus, in some embodiments, the first antigen is a cancer antigen (e.g., PD-L1). In other embodiments, the first antigen is not a cancer antigen.

In some embodiments, the second antigen is expressed on an immune cells including lymphocytes and monocytes. In some embodiments, the second antigen is expressed on a T cell. In some embodiments, the second antigen is expressed on a B cell. In other embodiments, the second antigen is expressed on a dendritic cell. In other embodiments, the second antigen is expressed on a granulocyte. In yet other embodiments, the second antigen is expressed on an innate lymphoid cell. In yet other embodiments, the second antigen is expressed on a megakaryocyte. In yet other embodiments, the second antigen is expressed on a monocyte. In yet other embodiments, the second antigen is expressed on a myeloid-derived suppressor cell. In yet other embodiments, the second antigen is expressed on a NK cell.

In some embodiments, the second antigen is expressed on an effector cell. In some embodiments, the second antigen is expressed on a T cell. In some embodiments, the second antigen is expressed on a T helper cell, a regulatory T cell, or a cytotoxic T cell. In some embodiments, the second antigen is expressed on a T helper cell. In some embodiments, the second antigen is expressed on a regulatory T cell. In some embodiments, the second antigen is expressed on a cytotoxic T cell. In some embodiments, the second antigen is expressed on a CD8+ T cell. In some embodiments, the second antigen is expressed on a CD4+ T cell. In some embodiments, the second antigen comprises an extracellular domain.

In some specific embodiments, the second antigen is CD3. In some embodiments, the first antigen is a cancer antigen and the second antigen is CD3.

In some more specific embodiments, the first antigen is PD-L1 and the second antigen is CD3.

In some embodiments, the VH region of the first portion of each Fab region comprises three CDRs having amino acid sequences of SEQ ID NO.: 5, SEQ ID NO.: 6, and SEQ ID NO.: 7; the VL region of the second portion of each Fab region comprises three CDRs having amino acid sequences of SEQ ID NO.: 9, SEQ ID NO.: 10, and SEQ ID NO.: 11; the VH region of the Fv region comprises three CDRs having amino acid sequences of SEQ ID NO.: 13, SEQ ID NO.: 14, SEQ ID NO.: 15; and the VL region of the Fv region comprises three CDRs having amino acid sequences of SEQ ID NO.: 17, SEQ ID NO.: 18, and SEQ ID NO.: 19.

In some embodiments, the VH region of the first portion of each Fab region has an amino acid sequence of SEQ ID NO.: 4; the VL region of the second portion of each Fab region has an amino acid sequence of SEQ ID NO.: 8; the VH region of the Fv region has an amino acid sequence of SEQ ID NO.: 12; and the VL region of the Fv region has an amino acid sequence of SEQ ID NO.: 16.

In other more specific embodiments, the first antigen is CD20 and the second antigen is CD3.

In some embodiments, the VH region of the first portion of each Fab region comprises three CDRs having amino acid sequences of SEQ ID NO.: 27, SEQ ID NO.: 28, SEQ ID NO.: 29; the VL region of the second portion of each Fab region comprises three CDRs having amino acid sequences of SEQ ID NO.: 31, SEQ ID NO.: 32, and SEQ ID NO.: 33; the VH region of the Fv region comprises three CDRs having amino acid sequences of SEQ ID NO.: 13, SEQ ID NO.: 14, SEQ ID NO.: 15; and the VL region of the Fv region comprises three CDRs having amino acid sequences of SEQ ID NO.: 17, SEQ ID NO.: 18, and SEQ ID NO.: 19.

In some embodiments, the VH region of the first portion of each Fab region has an amino acid sequence of SEQ ID NO.: 26; the VL region of the second portion of each Fab region has an amino acid sequence of SEQ ID NO.: 30; the VH region of the Fv region has an amino acid sequence of SEQ ID NO.: 12; and the VL region of the Fv region has an amino acid sequence of SEQ ID NO.: 16.

In other more specific embodiments, the first antigen is EGFR and the second antigen is CD3.

In some embodiments, the VH region of the first portion of each Fab region comprises three CDRs having amino acid sequences of SEQ ID NO.: 41, SEQ ID NO.: 42, and SEQ ID NO.: 43; the VL region of the second portion of each Fab region comprises three CDRs having amino acid sequences of SEQ ID NO.: 45, SEQ ID NO.: 46, and SEQ ID NO.: 47; the VH region of the Fv region comprises three CDRs having amino acid sequences of SEQ ID NO.: 13, SEQ ID NO.: 14, and SEQ ID NO.: 15 and the VL region of the Fv region comprises three CDRs having amino acid sequences of SEQ ID NO.: 17, SEQ ID NO.: 18, and SEQ ID NO.: 19.

In some embodiments, the VH region of the first portion of each Fab region has an amino acid sequence of SEQ ID NO.: 40; the VL region of the second portion of each Fab region has an amino acid sequence of SEQ ID NO.: 44; the VH region of the Fv region has an amino acid sequence of SEQ ID NO.: 12; and the VL region of the Fv region has an amino acid sequence of SEQ ID NO.: 16.

In other more specific embodiments, the first antigen is Her2 and the second antigen is TNF alpha. In some embodiments, the VH region of the first portion of each Fab region has an amino acid sequence of SEQ ID NO.: 51; the VL region of the second portion of each Fab region has an amino acid sequence of SEQ ID NO.: 52; the VH region of the Fv region has an amino acid sequence of SEQ ID NO.: 53; and the VL region of the Fv region has an amino acid sequence of SEQ ID NO.: 54.

In some specific embodiment, the first antigen binding domain is at the N-terminus and maintains the native antibody structure at the N-terminus, while the second antigen binding domain is at the C-terminus and C-terminal CH2 and CH3 domains of both heavy chains are each substituted with a single VH and VL domain, respectively. FIG. 1A is an illustration of such an exemplary ALiCE molecule. More specifically, the first portion and the second portion of each Fab region are on separate polypeptides, the first antigen binding domain binds to a first antigen, the VH region and the VL region of the Fv region are on separate polypeptides, the second antigen binding domain binds to a second antigen present on an immune cell, and the first antigen and the second antigen are different antigens.

Thus, in one specific embodiment, the binding molecule provided herein comprises:

(a) a first antigen binding domain comprising two antibody Fab regions, each comprising:
  (i) a first portion comprising an antibody variable heavy (VH) region and an antibody CH1 region, wherein the first portion does not contain an antibody CH2 region and an antibody CH3 region; and
  (ii) a second portion comprising an antibody light chain (LC) comprising an antibody variable light (VL) region and an antibody light chain constant region (CL),
wherein the first portion and the second portion are on separate polypeptides; and
wherein the first antigen binding domain binds to a first antigen.

(b) a second antigen binding domain comprising an antibody Fv region comprising a VH region and an antibody variable light (VL) region, wherein the VH region and the VL region are on separate polypeptides; wherein the second antigen binding domain binds to a second antigen present on an immune cell,
wherein the first antigen and the second antigen are different antigens.

In some embodiments, the first portion of one Fab region and the VH region of the Fv region are on the same polypeptide, and the portion of the other Fab region and the VL region of the Fv region are on the same polypeptide. Thus, in some specific embodiments, the binding molecule provided herein comprises:

(a) a first antigen binding domain comprising a first antibody Fab region and a second antibody Fab region, each comprising:
  (i) a first portion comprising an antibody variable heavy (VH) region and an antibody CH1 region, wherein the first portion does not contain an antibody CH2 region and an antibody CH3 region; and
  (ii) a second portion comprising an antibody light chain (LC) comprising an antibody variable light (VL) region and an antibody light chain constant region (CL),
wherein the first antigen binding domain binds to a first antigen.

(b) a second antigen binding domain comprising an antibody Fv region comprising a VH region and an antibody variable light (VL) region, wherein the second antigen binding domain binds to a second antigen present on an immune cell,
wherein the first antigen and the second antigen are different antigens; and
wherein the first portion of the first Fab region and the VH region of the Fv region are on the same polypeptide; and the first portion of the second Fab region and the VL region of the Fv region are on the same polypeptide.

In some embodiments, the first antigen is a cancer antigen (e.g., PD-L1). In other embodiments, the first antigen is not a cancer antigen.

In some embodiments, the second antigen is expressed on an immune cells including lymphocytes and monocytes. In some embodiments, the second antigen is expressed on a T cell. In some embodiments, the second antigen is expressed on a B cell. In other embodiments, the second antigen is expressed on a dendritic cell. In other embodiments, the second antigen is expressed on a granulocyte. In yet other embodiments, the second antigen is expressed on an innate lymphoid cell. In yet other embodiments, the second antigen is expressed on a megakaryocyte. In yet other embodiments, the second antigen is expressed on a monocyte. In yet other embodiments, the second antigen is expressed on a myeloid-derived suppressor cell. In yet other embodiments, the second antigen is expressed on a NK cell.

In some embodiments, the second antigen is expressed on an effector cell. In some embodiments, the second antigen is expressed on a T cell. In some embodiments, the second antigen is expressed on a T helper cell, a regulatory T cell, or a cytotoxic T cell. In some embodiments, the second antigen is expressed on a T helper cell. In some embodiments, the second antigen is expressed on a regulatory T cell. In some embodiments, the second antigen is expressed on a cytotoxic T cell. In some embodiments, the second antigen is expressed on a CD8+ T cell. In some embodiments, the second antigen is expressed on a CD4+ T cell. In some embodiments, the second antigen comprises an extracellular domain.

In some specific embodiments, the second antigen is CD3. In some embodiments, the first antigen is a cancer antigen and the second antigen is CD3.

In some more specific embodiments, the first antigen is PD-L1 and the second antigen is CD3.

In some embodiments, the VH region of the first portion of each Fab region comprises three CDRs having amino acid sequences of SEQ ID NO.: 5, SEQ ID NO.: 6, and SEQ ID NO.: 7; the VL region of the second portion of each Fab region comprises three CDRs having amino acid sequences of SEQ ID NO.: 9, SEQ ID NO.: 10, and SEQ ID NO.: 11; the VH region of the Fv region comprises three CDRs having amino acid sequences of SEQ ID NO.: 13, SEQ ID NO.: 14, SEQ ID NO.: 15; and the VL region of the Fv region comprises three CDRs having amino acid sequences of SEQ ID NO.: 17, SEQ ID NO.: 18, and SEQ ID NO.: 19.

In some embodiments, the VH region of the first portion of each Fab region has an amino acid sequence of SEQ ID NO.: 4; the VL region of the second portion of each Fab region has an amino acid sequence of SEQ ID NO.: 8; the VH region of the Fv region has an amino acid sequence of SEQ ID NO.: 12; and the VL region of the Fv region has an amino acid sequence of SEQ ID NO.: 16.

In other more specific embodiments, the first antigen is CD20 and the second antigen is CD3.

In some embodiments, the VH region of the first portion of each Fab region comprises three CDRs having amino acid sequences of SEQ ID NO.: 27, SEQ ID NO.: 28, SEQ ID NO.: 29; the VL region of the second portion of each Fab region comprises three CDRs having amino acid sequences of SEQ ID NO.: 31, SEQ ID NO.: 32, and SEQ ID NO.: 33; the VH region of the Fv region comprises three CDRs having amino acid sequences of SEQ ID NO.: 13, SEQ ID NO.: 14, SEQ ID NO.: 15; and the VL region of the Fv region comprises three CDRs having amino acid sequences of SEQ ID NO.: 17, SEQ ID NO.: 18, and SEQ ID NO.: 19.

In some embodiments, the VH region of the first portion of each Fab region has an amino acid sequence of SEQ ID NO.: 26; the VL region of the second portion of each Fab region has an amino acid sequence of SEQ ID NO.: 30; the VH region of the Fv region has an amino acid sequence of SEQ ID NO.: 12; and the VL region of the Fv region has an amino acid sequence of SEQ ID NO.: 16.

In other more specific embodiments, the first antigen is EGFR and the second antigen is CD3.

In some embodiments, the VH region of the first portion of each Fab region comprises three CDRs having amino acid sequences of SEQ ID NO.: 41, SEQ ID NO.: 42, and SEQ ID NO.: 43; the VL region of the second portion of each Fab region comprises three CDRs having amino acid sequences of SEQ ID NO.: 45, SEQ ID NO.: 46, and SEQ ID NO.: 47; the VH region of the Fv region comprises three CDRs having amino acid sequences of SEQ ID NO.: 13, SEQ ID NO.: 14, and SEQ ID NO.: 15 and the VL region of the Fv region comprises three CDRs having amino acid sequences of SEQ ID NO.: 17, SEQ ID NO.: 18, and SEQ ID NO.: 19.

In some embodiments, the VH region of the first portion of each Fab region has an amino acid sequence of SEQ ID NO.: 40; the VL region of the second portion of each Fab region has an amino acid sequence of SEQ ID NO.: 44; the VH region of the Fv region has an amino acid sequence of SEQ ID NO.: 12; and the VL region of the Fv region has an amino acid sequence of SEQ ID NO.: 16.

In other more specific embodiments, the first antigen is Her2 and the second antigen is TNF alpha. In some embodiments, the VH region of the first portion of each Fab region has an amino acid sequence of SEQ ID NO.: 51; the VL region of the second portion of each Fab region has an amino acid sequence of SEQ ID NO.: 52; the VH region of the Fv region has an amino acid sequence of SEQ ID NO.: 53; and the VL region of the Fv region has an amino acid sequence of SEQ ID NO.: 54.

In another aspect, the binding molecules provided herein include four peptides (two antibody light chains and two heavy chain like chains), and their overall structure is similar to a traditional IgG except that the Fc region of the IgG is replaced with a Fv region. This structure can be further modified to generate variations that confer various properties. More specifically, in some embodiments, the binding molecule provided herein comprises:

(a) a first polypeptide and a second polypeptide, each comprising an antibody light chain,
(b) a third polypeptide comprising a first VH region and a first CH1 region, and a second VH region; and
(c) a fourth polypeptide comprising a third VH region and a second CH1, and a VL region, wherein the first polypeptide and the first VH region and the first CH1 region of the third polypeptide form a first antigen binding Fab region;
wherein the second polypeptide and the third VH region and the second CH1 region of the fourth polypeptide form a second antigen Fab region; and
wherein the second VH region of the third polypeptide and the VL region of the fourth polypeptide form an antigen binding Fv region.

In some embodiments, the first polypeptide and the second polypeptide have the same amino acid sequence. In these embodiments, the binding molecules provided herein comprise two identical light chains (the first and second polypeptides) and two different heavy chain like chains (the third and fourth polypeptides).

In some embodiments, the first Fab region and the second Fab region are linked to the Fv region via a flexible peptide region. In some embodiments, the flexible peptide region comprises an antibody hinge region. In some specific embodiments, the antibody is an IgG hinge region. In some more specific embodiments, the IgG hinge region is of IgG1 subtype. In other more specific embodiments, the IgG hinge region is of IgG2 subtype. In yet other more specific embodiments, the IgG hinge region is of IgG3 subtype. In yet other more specific embodiments, the IgG hinge region is of IgG4 subtype. In some specific embodiments, the flexible peptide region provided herein comprises an amino acid sequence of SEQ ID NO.: 55. In some specific embodiments, the flexible peptide region provided herein comprises an amino acid sequence of SEQ ID NO.: 56. In other specific embodiments, the flexible peptide region provided herein comprises an amino acid sequence of SEQ ID NO.: 57. In some specific embodiments, the flexible peptide region provided herein comprises an amino acid sequence of SEQ ID NO.: 58.

In certain embodiments, the flexible peptide region comprise additional amino acids. For example, in some embodiments, the flexible peptide region further comprises a linker (e.g., G4S (SEQ ID NO: 130)) between the antibody hinge region and the second Fv antigen binding domain. Flexible linker between antibody hinge region and second Fv domain may influence binding affinity of the second Fv domain. Improved binding affinity of second Fv domain can lead to increased redirectional efficiency of immune cells (e.g., effector cells including T cells) to target cells (e.g., cancer cells). The second Fv domain need to bend to be able to interact with and bind to a surface antigen presented on immune cells (e.g., effector cells including T cells), because the paratope of the second Fv domain of ALiCE is structurally masked by the first Fab domain of ALiCE. Therefore, to reduce streic hinderance and optimize the binding of the second Fv domain to immune cells (e.g., effector cells including T cells), flexible linker such as G4S (SEQ ID NO: 130) can be introduced between the antibody hinge region and the second Fv domain. In some embodiments, the linker comprises an amino acid sequence of GGGGS (G4S) (SEQ ID NO: 130). In some embodiments, the linker comprises an amino acid sequence of (G4S)n (SEQ ID NO: 133) where n is an integer. In some specific embodiments, the linker comprises an amino acid sequence of (G4S)$_1$ (SEQ ID NO: 130). In some more specific embodiments, the linker comprises an amino acid sequence of (G4S)$_2$ (SEQ ID NO: 131). In other more specific embodiments, the linker comprises an amino acid sequence of (G4S)$_3$ (SEQ ID NO: 134) . In yet other more specific embodiments, the linker comprises an amino acid sequence of (G4S)$_4$ (SEQ ID NO: 135).

In some embodiments, the first Fab region and the second Fab region bind to different antigens. In other embodiments, the first Fab region and the second Fab region bind to the same antigen. In some embodiments, the first Fab region and the second Fab region bind to the same epitope of the same antigen. In other embodiments, the first Fab region and the second Fab region bind to different epitopes of the same antigen.

In certain embodiments, the first Fab region and the second Fab region form a first antigen binding domain, and the Fv region forms a second antigen binding domain.

In some embodiments, the first antigen binding domain and the second antigen binding domain bind to the same antigen. In some embodiments, the second antigen binding domain binds to the same epitope as at least one of the epitopes bound by the first antigen binding domain.

In other embodiments, the first antigen binding domain and the second antigen binding domain bind to different antigens, and wherein the first antigen binding domain binds to a first antigen and the second antigen binding domain binds to a second antigen.

In some embodiments, the first antigen is a cancer antigen. In other embodiments, the first antigen is not a cancer antigen.

In some embodiments, the second antigen is expressed on an immune cells including lymphocytes and monocytes. In some embodiments, the second antigen is expressed on a T cell. In some embodiments, the second antigen is expressed on a B cell. In other embodiments, the second antigen is expressed on a dendritic cell. In other embodiments, the second antigen is expressed on a granulocyte. In yet other embodiments, the second antigen is expressed on an innate lymphoid cell. In yet other embodiments, the second antigen is expressed on a megakaryocyte. In yet other embodiments, the second antigen is expressed on a monocyte. In yet other embodiments, the second antigen is expressed on a myeloid-derived suppressor cell. In yet other embodiments, the second antigen is expressed on a NK cell.

In some embodiments, the second antigen is expressed on an effector cell. In some embodiments, the second antigen is expressed on a T cell. In some embodiments, the second antigen is expressed on a T helper cell, a regulatory T cell, or a cytotoxic T cell. In some embodiments, the second antigen is expressed on a T helper cell. In some embodiments, the second antigen is expressed on a regulatory T cell. In some embodiments, the second antigen is expressed on a cytotoxic T cell. In some embodiments, the second antigen is expressed on a CD8+ T cell. In some embodiments, the second antigen is expressed on a CD4+ T cell. In some embodiments, the second antigen comprises an extracellular domain.

In some specific embodiments, the second antigen is CD3. In some embodiments, the first antigen is a cancer antigen and the second antigen is CD3.

In some more specific embodiments, the first antigen is PD-L1 and the second antigen is CD3.

In some embodiments, the VH region of the first portion of each Fab region comprises three CDRs having amino acid sequences of SEQ ID NO.: 5, SEQ ID NO.: 6, and SEQ ID NO.: 7; the VL region of the second portion of each Fab region comprises three CDRs having amino acid sequences of SEQ ID NO.: 9, SEQ ID NO.: 10, and SEQ ID NO.: 11; the VH region of the Fv region comprises three CDRs having amino acid sequences of SEQ ID NO.: 13, SEQ ID NO.: 14, and SEQ ID NO.: 15; and the VL region of the Fv region comprises three CDRs having amino acid sequences of SEQ ID NO.: 16, SEQ ID NO.: 17, and SEQ ID NO.: 19.

In some embodiments, the VH region of the first portion of each Fab region has an amino acid sequence of SEQ ID NO.: 4; the VL region of the second portion of each Fab region has an amino acid sequence of SEQ ID NO.: 8; the VH region of the Fv region has an amino acid sequence of SEQ ID NO.: 12; and the VL region of the Fv region has an amino acid sequence of SEQ ID NO.: 16.

In some embodiments, the first polypeptide and the second polypeptide each have the amino acid sequence of SEQ ID NO.: 3; the third polypeptide has the amino acid sequence of SEQ ID NO.: 1; and the fourth polypeptide has the amino acid sequence of SEQ ID NO.: 2.

In other more specific embodiments, the first antigen is CD20 and the second antigen is CD3.

In some embodiments, the VH region of the first portion of each Fab region comprises three CDRs having amino acid sequences of SEQ ID NO.: 27, SEQ ID NO.: 28, and SEQ ID NO.: 29; the VL region of the second portion of each Fab region comprises three CDRs having amino acid sequences of SEQ ID NO.: 31, SEQ ID NO.: 32, and SEQ ID NO.: 33; the VH region of the Fv region comprises three CDRs having amino acid sequences of SEQ ID NO.: 13, SEQ ID NO.: 14, and SEQ ID NO.: 15; and the VL region of the Fv region comprises three CDRs having amino acid sequences of SEQ ID NO.: 17, SEQ ID NO.: 18, and SEQ ID NO.: 19.

In some embodiments, the VH region of the first portion of each Fab region has an amino acid sequence of SEQ ID NO.: 26; the VL region of the second portion of each Fab region has an amino acid sequence of SEQ ID NO.: 30; the VH region of the Fv region has an amino acid sequence of SEQ ID NO.: 12; and the VL region of the Fv region has an amino acid sequence of SEQ ID NO.: 16.

In some embodiments, the first polypeptide and the second polypeptide each have the amino acid sequence of SEQ ID NO.: 25; the third polypeptide has the amino acid sequence of SEQ ID NO.: 23; and the fourth polypeptide has the amino acid sequence of SEQ ID NO.: 24.

In other more specific embodiments, the first antigen is EGFR and the second antigen is CD3.

In some embodiments, the VH region of the first portion of each Fab region comprises three CDRs having amino acid sequences of SEQ ID NO.: 41, SEQ ID NO.: 42, SEQ ID NO.: 43; the VL region of the second portion of each Fab region comprises three CDRs having amino acid sequences of SEQ ID NO.: 45, SEQ ID NO.: 46, and SEQ ID NO.: 47; the VH region of the Fv region comprises three CDRs having amino acid sequences of SEQ ID NO.: 13, SEQ ID NO.: 14, and SEQ ID NO.: 15; and the VL region of the Fv region comprises three CDRs having amino acid sequences of SEQ ID NO.: 17, SEQ ID NO.: 18, and SEQ ID NO.: 19.

In some embodiments, the VH region of the first portion of each Fab region has an amino acid sequence of SEQ ID NO.: 40; the VL region of the second portion of each Fab region has an amino acid sequence of SEQ ID NO.: 44; the VH region of the Fv region has an amino acid sequence of SEQ ID NO.: 12; and the VL region of the Fv region has an amino acid sequence of SEQ ID NO.: 16.

In some embodiments, the first polypeptide and the second polypeptide each have the amino acid sequence of SEQ ID NO.: 39; the third polypeptide has the amino acid sequence of SEQ ID NO.: 37; and the fourth polypeptide has the amino acid sequence of SEQ ID NO.: 38.

In other more specific embodiments, the first antigen is Her2 and the second antigen is TNF alpha. In some embodiments, the VH region of the first portion of each Fab region has an amino acid sequence of SEQ ID NO.: 51; the VL region of the second portion of each Fab region has an amino acid sequence of SEQ ID NO.: 52; the VH region of the Fv region has an amino acid sequence of SEQ ID NO.: 53; and the VL region of the Fv region has an amino acid sequence of SEQ ID NO.: 54.

As described above, in certain embodiments, the binding molecules provided herein comprise two identical light chains and two different heavy chain like chains. To make recombinant protein in mammalian cells like CHO or HEK293, understanding antibody assembly and quality control system happened in ER is very important. Antibody is assembled and secreted as a tetramer $H_2L_2$ and the quality control machinery is very tightly regulated in ER by BiP and PDI. It was known that unfolded CH1 domain of heavy chain has a role of regulation of antibody assembly in BiP dependent manner. As described below in the Example section, the present disclosure demonstrates that antibody VH domain also has a role of antibody assembly, and shows that the heavy chain like chain of the binding molecule provided herein that contains two VH regions (one in a Fab region and one in a Fv region) contributes to the proper assembly of the binding molecule.

C-terminal Fv also has an important role of heterodimerization of two different heavy chain like chains (the third and fourth polypeptides). Because the interaction between VH and VL regions is much stronger than VL-VL interaction, the VH-VL interaction was selected to make heterodimerization between the two different heavy chain like chains (the third and fourth polypeptides). The efficiency of heterodimerization was found very high and most of the binding molecules expressed and purified in mammalian cells were heterodimerized form (close to 99% heterodimerization efficiency).

In addition, this structure provides for the optimal synaptic distance between target and effector cells. The distance of N-terminal two Fab region and the C-terminal Fv region was estimated to be 40 Å. Furthermore, the binding molecule provided herein has more folding complexity (molecular size) than other known bispecific antibodies such as BiTE, DART and other ScFv based bispecific antibody formats and thus are expected to have improved thermodynamic stability.

Furthermore, in certain embodiments, the binding molecules provided herein are bispecific binding molecules, in which the two Fab regions (N-terminal F(ab')$_2$) bind to the first antigen (e.g., a cancer antigen) and the Fv region binds to an immune cell (e.g., T cell). In certain embodiments, the binding molecules provided herein are designed and constructed in Y-shape to provide synergistic effect of antibody function and immune redirecting (e.g., T cell redirecting), for example, for the maximum anti-tumor activity. The configuration of ALiCE molecules (predominantly reside in Y-shape) is designed to confer optimal immunological synaptic distance between the two antigen binding domains (two target paratopes) and maximize functional redirection of a cell (e.g., T cell) to other cells (e.g., tumor cells). In addition, high affinity and bivalent N-terminal (two Fab regions) is provided and, at the same time, unwanted target independent T cell activation is reduced due to the monovalent and low affinity of the Fv region to an immune cell antigen.

It has been reported that a binding molecule can have different configurations, which may affect the distance between the domains in the binding molecule (Zhang X. et al. 3D Structural Fluctuation of IgG1 Antibody Revealed by Individual Particle Electron Tomography. *Scientific Reports* 5, Article number: 9803 (2015); Klein J. S. et al. Examination of the contributions of size and avidity to the neutralization mechanisms of the anti-HIV antibodies b12 and 4E10. *Proc Natl Acad Sci USA*. 2009 May 5; 106(18):7385-90; both references incorporated by reference in their entirety). In certain embodiments, ALiCE molecules may have different configurations, for example ALiCE molecules may reside in a Y-shape, or in a T-shape. In certain embodiments, the different configurations of ALiCE molecules may contribute to different distance between N-terminal two Fab region and the C-terminal Fv region in the ALiCE molecules. In certain embodiments, the distance between N-terminal two Fab region and the C-terminal Fv region in the binding molecules provided herein may be estimated to be in a range of between around 40 Å and around 70 Å. In certain embodiments, the distance between N-terminal two Fab region and the C-terminal Fv region in the binding molecules provided herein may be estimated to be around 42 Å. In some other embodiments, the distance between N-terminal two Fab region and the C-terminal Fv region in the binding molecules provided herein may be estimated to be around 60 Å.

Thus, in the various bispecific binding molecules provided herein, the binding affinity of the first antigen binding domain to the first antigen is higher than the binding affinity of the second antigen binding domain to the second antigen. For example, as shown in Example 3 below, the binding kinetics of ACE-05 to human PD-L1 was comparable to the parental anti-PD-L1 antibody (i.e., YBL-007 from Y-Biologics, Inc.) (see FIGS. 12A-12C). In contrast, the binding affinity of ACE-05 to CD3 was much lower than the parental anti-CD3 antibody (UCHT1 from BioLegend, USA) (see FIGS. 12A-12C).

Generally speaking, antigen-antibody interactions are non-covalent and reversible, formed by a combination of hydrogen bonds, hydrophobic interactions, electrostatic and van der Waals forces. When describing the strength of an antigen-antibody complex, affinity and/or avidity are usually mentioned. As mentioned above, the binding of an antibody to its antigen is a reversible process, and the affinity of the binding is typically reported as an equilibrium dissociation constant ($K_D$). $K_D$ is the ratio of an antibody dissociation rate ($k_{off}$ or $k_d$) (how quickly it dissociates from its antigen) to the antibody association rate ($k_{on}$ or $k_a$) (how quickly it binds to its antigen). In some embodiments, $K_D$ values are determined by measuring the $k_{on}$ and $k_{off}$ rates of a specific antibody/antigen interaction and then using a ratio of these values to calculate the $K_D$ value. $K_D$ values may be used to evaluate and rank order the strength of individual antibody/antigen interactions. The lower the $K_D$ of an antibody, the higher the affinity of the antibody for its target. Avidity gives a measure of the overall strength of an antibody-antigen complex. It is dependent on three major parameters: (i) affinity of the antibody for the epitope, (ii) valency of both the antibody and antigen, and (iii) structural arrangement of the parts that interact.

In certain embodiments, the binding molecule provided herein binds one or more targets, antigens, or epitopes with a dissociation constant ($K_D$) of about 1 μM or less, about 100 nM or less, about 40 nM or less, about 20 nM or less, about 10 nM or less, about 1 nM or less, about 0.1 nM or less, 50 pM or less, 10 pM or less, or 1 pM or less. In some embodiments, the binding molecule provided herein binds a target, antigen, or epitope with a $K_D$ of about 20 nM or less. In some embodiments, the binding molecule binds a target, antigen, or epitope with a $K_D$ of about 10 nM or less. In some embodiments, the binding molecule binds a target, antigen, or epitope with a $K_D$ of about 1 nM or less. In some embodiments, the binding molecule binds a target, antigen, or epitope with a $K_D$ of about 0.5 nM or less. In some embodiments, the binding molecule provided herein binds a target, antigen, or epitope with a $K_D$ of about 0.1 nM or less. In some embodiments, the binding molecule provided herein binds a target, antigen, or epitope with a $K_D$ of about 50 pM or less. In some embodiments, the binding molecule provided herein binds a target, antigen, or epitope with a $K_D$ of about 25 pM or less. In some embodiments, the binding molecule provided herein binds a target, antigen, or epitope with a $K_D$ of about 10 pM or less. In some embodiments, the binding molecule provided herein binds a target, antigen, or epitope with a $K_D$ of about 1 pM or less. In some embodiments, the dissociation constant of a binding molecule provided herein to a target or an antigen is the dissociation constant determined using a fusion protein comprising at least a portion of the target protein immobilized on an Octet® chip. In some embodiments, the dissociation constant of a binding molecule provided herein to a target or an antigen is the dissociation constant determined using the binding agent captured by an anti-human IgG antibody on an Octet® chip and a soluble target protein.

In certain embodiments, the binding molecule provided herein binds a target, antigen, or epitope with a half maximal effective concentration ($EC_{50}$) of about 1 μM or less, about 100 nM or less, about 40 nM or less, about 20 nM or less, about 10 nM or less, about 1 nM or less, or about 0.1 nM or less. In certain embodiments, a binding molecule provided herein binds a target, antigen, or epitope with an EC50 of about 1 μM or less, about 100 nM or less, about 40 nM or less, about 20 nM or less, about 10 nM or less, about 1 nM or less, or about 0.1 nM or less.

In certain embodiments, the $K_D$ for the binding molecule to the first antigen is about 2 fold, 3 fold, 4 fold, 5 fold, 6 fold, 7 fold, 8 fold, 9 fold, 10 fold, 15 fold, 20 fold, 50 fold or more of the $K_D$ for the binding molecule to the second antigen. In some embodiments, the $K_D$ for the binding molecule to the first antigen is about 10, $10^2$, $10^3$, or $10^4$ fold of the $K_D$ for the binding molecule to the second antigen.

In certain embodiments, the binding molecule provided herein (e.g., a bispecific binding molecule) comprises at least a portion of one or more "parental" antibodies. In some embodiments, a parental antibody is a recombinant antibody. In some embodiments, a parental antibody is a monoclonal antibody. In some embodiments, the parental antibody is a polyclonal antibody. In some embodiments, a parental antibody is a chimeric antibody. In some embodiments, a parental antibody is a humanized antibody. In some embodiments, a parental antibody is a human antibody or fully human antibody. In some embodiments, a parental antibody is an IgA, IgD, IgE, IgG, or IgM antibody. In certain embodiments, a parental antibody is an IgG1 antibody. In certain embodiments, a parental antibody is an IgG2 antibody. In some embodiments, the parental antibody is an IgG3 antibody. In some embodiments, a parental antibody is an IgG4 antibody.

In some embodiments, the binding molecule provided herein (e.g., a bispecific binding molecule) is isolated. In some embodiments, the binding molecule provided herein (e.g., a bispecific binding molecule) is substantially pure.

In some embodiments, the binding molecule provided herein (e.g., a bispecific binding molecule) or a portion thereof is derived from at least one monoclonal antibody. In some embodiments, a monoclonal antibody is prepared using hybridoma methods known to one of skill in the art. For example, using the hybridoma method, a mouse, rat, rabbit, hamster, or other appropriate host animal, is immunized as described above to elicit the production of antibodies that specifically bind the immunizing antigen. In some embodiments, lymphocytes are immunized in vitro. In some embodiments, the immunizing antigen is a human protein or a fragment thereof. In some embodiments, the immunizing antigen is a mouse protein or a fragment thereof.

Following immunization, lymphocytes are isolated and fused with a suitable myeloma cell line using, for example, polyethylene glycol. The hybridoma cells are selected using specialized media as known in the art and unfused lymphocytes and myeloma cells do not survive the selection process. Hybridomas that produce monoclonal antibodies directed specifically against a chosen antigen can be identified by a variety of methods including, but not limited to, immunoprecipitation, immunoblotting, and in vitro binding assays (e.g., flow cytometry, FACS, ELISA, and radioimmunoassay). Once hybridoma cells that produce antibodies of the desired specificity, affinity, and/or activity are identified, the clones may be subcloned by limiting dilution techniques. The hybridomas can be propagated either in in vitro culture using standard methods or in vivo as ascites tumors in an animal. The monoclonal antibodies can be purified from the culture medium or ascites fluid according to standard methods in the art including, but not limited to, affinity chromatography, ion-exchange chromatography, gel electrophoresis, and dialysis.

In certain embodiments, monoclonal antibodies can be made using recombinant DNA techniques as known to one skilled in the art. For example, in certain examples, polynucleotides encoding a monoclonal antibody are isolated from mature B-cells or hybridoma cells, such as by RT-PCR using oligonucleotide primers that specifically amplify the genes encoding the heavy and light chains of the antibody, and their sequence is determined using standard techniques. The isolated polynucleotides encoding the heavy and light chains are then cloned into suitable expression vectors which produce the monoclonal antibodies when transfected into host cells such as E. coli, simian COS cells, Chinese hamster ovary (CHO) cells, or myeloma cells that do not otherwise produce immunoglobulin proteins.

In certain other embodiments, recombinant monoclonal antibodies, or fragments thereof, can be isolated from phage display libraries expressing variable domains or CDRs of a desired species. Screening of phage libraries can be accomplished by various techniques known in the art.

In some embodiments, a monoclonal antibody is modified, for example, by using recombinant DNA technology to generate alternative antibodies. In some embodiments, the constant domains of the light chain and heavy chain of, for example, a mouse monoclonal antibody can be substituted for constant regions of, for example, a human antibody to generate a chimeric antibody, or for a non-immunoglobulin polypeptide to generate a fusion antibody. In some embodiments, the constant regions are truncated or removed to generate a desired antibody fragment of a monoclonal antibody. In some embodiments, site-directed or high-density mutagenesis of the variable region(s) is used to optimize specificity and/or affinity of a monoclonal antibody.

In some embodiments, the binding molecule provided herein (e.g., a bispecific binding molecule) or a portion thereof is derived from a humanized antibody. Various methods for generating humanized antibodies are known in the art. In some embodiments, humanization is performed by substituting one or more non-human CDR sequences for the corresponding CDR sequences of a human antibody. In some embodiments, humanized antibodies are generated by substituting all six CDRs of a parent non-human antibody (e.g., rodent) for the corresponding CDR sequences of a human antibody.

The choice of which human heavy chain variable region and light chain variable region to be used in generating humanized antibodies can be made based on a variety of factors and by a variety of methods. In some embodiments, the "best-fit" method is used where the sequence of the variable region of a non-human (e.g., rodent) antibody is screened against the entire library of known human variable region sequences. The human sequence that is most similar to that of the non-human sequence is selected as the human variable region backbone for the humanized antibody. In some embodiments, a method is used wherein a particular variable region backbone derived from a consensus sequence of all human antibodies of a particular subgroup of light or heavy chains is selected. In some embodiments, the framework is derived from the consensus sequences of the most abundant human subclasses. In some embodiments, human germline genes are used as the source of the variable region framework sequences.

Other methods for humanization include, but are not limited to, a method called "superhumanization" which is described as the direct transfer of CDRs to a human germline framework, a method called Human String Content (HSC) which is based on a metric of antibody "humanness", methods based on generation of large libraries of humanized variants (including phage, ribosomal, and yeast display libraries), and methods based on framework region shuffling.

In certain embodiments, the binding molecule provided herein (e.g., a bispecific binding molecule) or a portion thereof is derived from a human antibody. Human antibodies can be directly prepared using various techniques known in the art. In some embodiments, human antibodies are generated from immortalized human B lymphocytes immunized in vitro. In some embodiments, human antibodies are generated from lymphocytes isolated from an immunized individual. In any case, cells that produce an antibody directed against a target antigen can be generated and isolated. In some embodiments, a human antibody is selected from a phage library, where that phage library expresses human antibodies. Alternatively, phage display technology may be used to produce human antibodies and antibody fragments in vitro, from immunoglobulin variable region gene repertoires from unimmunized donors. Techniques for the generation and use of antibody phage libraries are well known in the art. Once antibodies are identified, affinity maturation strategies known in the art, including but not limited to, chain shuffling and site-directed mutagenesis, may be employed to generate higher affinity human antibodies.

In some embodiments, human antibodies are produced in transgenic mice that contain human immunoglobulin loci. Upon immunization, these mice are capable of producing the full repertoire of human antibodies in the absence of endogenous immunoglobulin production.

In some embodiments, the binding molecule provided herein (e.g., a bispecific binding molecule) or a portion thereof described herein are derived from antibodies (e.g., full-length antibodies or fragments thereof) that comprise modifications in at least one or more of the constant regions. In some embodiments, the antibodies comprise modifications to one or more of the three heavy chain constant regions (e.g., CH1) and/or to the light chain constant region (CL). In some embodiments, the heavy chain constant region of the modified antibodies comprises at least one human constant region. In some embodiments, the heavy chain constant region of the modified antibodies comprises more than one human constant region. In some embodiments, modifications to the constant region comprise additions, deletions, or substitutions of one or more amino acids in one or more regions. In some embodiments, one or more regions are partially or entirely deleted from the constant regions of the modified antibodies. In some embodiments, the entire CH2 domain has been removed from an antibody (ΔCH2 constructs). In some embodiments, the entire CH3 domain has been removed from an antibody (ΔCH3 constructs). In some embodiments, an omitted constant region is replaced by a short amino acid spacer (e.g., 10 amino acid residues) that provides some of the molecular flexibility typically imparted by the absent constant region.

Modifications to the constant region of antibodies (e.g., parental antibody) and/or the binding molecule provided herein (e.g., a bispecific antibody) described herein may be made using well known biochemical or molecular engineering techniques. In some embodiments, variants can be prepared by introducing appropriate nucleotide changes into the encoding DNA, and/or by direct synthesis of the desired polypeptide or agent. In this respect it may be possible to disrupt the activity or effector function provided by a specific sequence or region while substantially maintaining the structure, binding activity, and other desired characteristics of the modified binding agent.

The present disclosure further embraces additional variants and equivalents which are substantially homologous to the binding molecules described herein. In some embodiments, it is desirable to improve the binding affinity and/or other biological properties of the binding molecules, including but not limited to, specificity, thermostability, expression level, effector functions, glycosylation, reduced immunogenicity, or solubility. Those skilled in the art will appreciate that amino acid changes may alter post-translational processes of a polypeptide.

Variations may be a substitution, deletion, or insertion of one or more nucleotides encoding a multispecific binding agent that results in a change in the amino acid sequence as compared with the sequence of the parental binding agent. Amino acid substitutions can be the result of replacing one amino acid with another amino acid having similar structural and/or chemical properties, such as the replacement of a leucine with a serine, e.g., conservative amino acid replacements. In some embodiments, insertions or deletions are in the range of about 1 to 5 amino acids. In certain embodiments, the substitution, deletion, or insertion includes less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the parent molecule. Variations in the amino acid sequence that are biologically useful and/or relevant may be determined by systematically making insertions, deletions, or substitutions in the sequence and testing the resulting variant proteins for activity as compared to the parental protein.

In some embodiments, variants may include the addition of amino acid residues at the amino- and/or carboxyl-terminal end of one or more polypeptides that make up the binding molecules provided herein. The length of additional amino acids residues may range from one residue to a hundred or more residues. In some embodiments, a variant comprises an N-terminal methionyl residue. In some embodiments, the variant comprising an additional polypeptide/protein, i.e., a fusion protein. In certain embodiments, a variant is engineered to be detectable and may comprise a detectable label and/or protein (e.g., an enzyme).

In some embodiments, a cysteine residue not involved in maintaining the proper conformation of the binding molecule provided herein is substituted or deleted to modulate the agent's characteristics, for example, to improve oxidative stability and/or prevent aberrant disulfide crosslinking. Conversely, in some embodiments, one or more cysteine residues are added to create disulfide bond(s) to improve stability.

In some embodiments, the binding molecule of the present disclosure is "deimmunized". The deimmunization of agents such as antibodies generally consists of introducing specific mutations to remove T cell epitopes without significantly reducing the binding affinity or other desired activities of the agent.

The variant binding molecules or polypeptides described herein may be generated using methods known in the art, including but not limited to, site-directed mutagenesis, alanine scanning mutagenesis, and PCR mutagenesis.

In some embodiments, a binding molecule described herein is chemically modified. In some embodiments, a binding molecule is a bispecific antibody that has been chemically modified by glycosylation, acetylation, pegylation, phosphorylation, amidation, derivatization by known protecting/blocking groups, proteolytic cleavage, and/or linkage to a cellular ligand or other protein. Any of numerous chemical modifications may be carried out by known techniques.

The polypeptides that make up the multispecific binding agents described herein can be produced by any suitable method known in the art and described in more detail in Section III and Section IV below.

The present disclosure also provides conjugates comprising any one of the binding molecules (e.g., bispecific antibodies) described herein. In some embodiments, the binding molecule provided herein is attached to an additional molecule. In some embodiments, the binding molecule provided herein is conjugated to a cytotoxic agent or moiety. In some embodiments, the binding molecule provided herein is conjugated to a cytotoxic agent to form an ADC (antibody-drug conjugate). In some embodiments, the cytotoxic moiety is a chemotherapeutic agent including, but not limited to, methotrexate, adriamycin/doxorubicin, melphalan, mitomycin C, chlorambucil, duocarmycin, daunorubicin, pyrrolobenzodiazepines (PBDs), or other intercalating agents. In some embodiments, the cytotoxic moiety is a microtubule inhibitor including, but not limited to, auristatins, maytansinoids (e.g., DM1 and DM4), and tubulysins. In some embodiments, the cytotoxic moiety is an enzymatically active toxin of bacterial, fungal, plant, or animal origin, or fragments thereof, including, but not limited to, diphtheria A chain, non-binding active fragments of diphtheria toxin, exotoxin A chain, ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and tricothecenes. In some embodiments, the binding molecule provided herein is conjugated to one or more small molecule toxins, such as calicheamicins, maytansinoids, trichothenes, and CC1065. The derivatives of any one of these toxins can be used in a conjugate as long as the derivative retains the cytotoxic activity.

Conjugates comprising the binding molecule provided herein may be made using any suitable methods as known in the art. In some embodiments, conjugates are made using a variety of bifunctional protein-coupling agents such as N-succinimidyl-3-(2-pyridyidithiol) propionate (SPDP), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene).

In some embodiments, the binding molecule (e.g., a bispecific antibody) described herein is conjugated to detectable substances or molecules that allow the antibodies to be used for diagnosis and/or detection. The detectable substances may include but not limited to, enzymes, such as horseradish peroxidase, alkaline phosphatase, beta-galactosidase, and acetylcholinesterase; prosthetic groups, such as biotin and flavine(s); fluorescent materials, such as, umbelliferone, fluorescein, fluorescein isothiocyanate (FITC), rhodamine, tetramethylrhodamine isothiocyanate (TRITC), dichlorotriazinylamine fluorescein, dansyl chloride, cyanine (Cy3), and phycoerythrin; bioluminescent materials, such as luciferase; radioactive materials, such as $^{212}$Bi, $^{14}$C, $^{57}$Co, $^{51}$Cr, $^{67}$Cu, $^{18}$F, $^{68}$Ga, $^{67}$Ga, $^{153}$Gd, $^{159}$Gd, $^{68}$Ge, $^{3}$H, $^{166}$Ho, $^{131}$I, $^{125}$I, $^{123}$I, $^{121}$I, $^{115}$In, $^{113}$In, $^{112}$In, $^{111}$In, $^{140}$La, $^{177}$Lu, $^{54}$Mn, $^{99}$Mo, $^{32}$P, $^{103}$Pd, $^{149}$Pm, $^{142}$Pr, $^{186}$Re, $^{188}$Re, $^{105}$Rh, $^{97}$Ru, $^{35}$S, $^{47}$Sc, $^{75}$Se, $^{153}$Sm, $^{113}$Sn, $^{117}$Sn, $^{85}$Sr, $^{99m}$Tc, $^{201}$Ti, $^{133}$Xe, $^{90}$Y, $^{69}$Yb, $^{175}$Yb, $^{65}$Zn; positron emitting metals; and magnetic metal ions.

In some embodiments, the binding molecule provided herein described herein is attached to a solid support, that are particularly useful for immunoassays or purification of a target antigen(s). Such solid supports include, but are not limited to, glass, cellulose, polyacrylamide, nylon, polystyrene, polyvinyl chloride, or polypropylene.

In some embodiments, the binding molecules provided herein is formulated in a pharmaceutical composition. Therefore, in yet another aspect, provided herein is a pharmaceutical composition comprising a therapeutically effective amount of the binding molecule provided herein and a pharmaceutically acceptable carrier. The pharmaceutical composition provided herein is described in more detail in Section V below. In some embodiments, the pharmaceutical composition is for use in treating a disease or condition in a subject. In some embodiments, the disease or condition is a cancer. In other embodiments, the cancer is a PD-L1 positive cancer. In some embodiments, the cancer is a lung cancer. In some embodiments, the cancer is a Non Small Cell Lung Carcinoma (NSCLC). In some embodiments, the cancer is a Diffuse Large B cell Lymphoma (DLBCL). In some embodiments, the cancer is a colorectal cancer. In some embodiments, the cancer is a breast cancer. In some embodiments, the cancer is a lymphoma. In some embodiments, the cancer is a melanoma. In some embodiments, the cancer is ovarian cancer.

In some embodiments, the binding molecules provided herein is used for treating a disease or condition. Therefore, in yet another aspect, provided herein is a method of treating a disease or condition in a subject comprising administering a therapeutically effective amount of the binding molecule provided herein to the subject. In some embodiments, the disease or condition is a cancer. In other embodiments, the cancer is a PD-L1 positive cancer. In some embodiments, the cancer is a lung cancer. In some embodiments, the cancer is a Non Small Cell Lung Carcinoma (NSCLC). In some embodiments, the cancer is a Diffuse Large B cell Lymphoma (DLBCL). In some embodiments, the cancer is a colorectal cancer. In some embodiments, the cancer is a breast cancer. In some embodiments, the cancer is a lymphoma. In some embodiments, the cancer is a melanoma. In some embodiments, the cancer is ovarian cancer. A more detail description of methods for administering the present binding molecules is in Section VI below.

III. Polynucleotides

In certain embodiments, the disclosure encompasses polynucleotides that encode the binding molecule described herein. The term "polynucleotides that encode a polypeptide" encompasses a polynucleotide that includes only coding sequences for the polypeptide as well as a polynucleotide which includes additional coding and/or non-coding sequences. The polynucleotides of the disclosure can be in the form of RNA or in the form of DNA. DNA includes cDNA, genomic DNA, and synthetic DNA; and can be double-stranded or single-stranded, and if single stranded can be the coding strand or non-coding (anti-sense) strand.

In certain embodiments, a polynucleotide comprises the coding sequence for a polypeptide fused in the same reading frame to a polynucleotide which aids, for example, in expression and secretion of a polypeptide from a host cell (e.g., a leader sequence which functions as a secretory sequence for controlling transport of a polypeptide). The polypeptide can have the leader sequence cleaved by the host cell to form a "mature" form of the polypeptide.

In certain embodiments, a polynucleotide comprises the coding sequence for a polypeptide fused in the same reading frame to a marker or tag sequence. For example, in some embodiments, a marker sequence is a hexa-histidine tag supplied by a vector that allows efficient purification of the polypeptide fused to the marker in the case of a bacterial host. In some embodiments, a marker is used in conjunction with other affinity tags.

The present disclosure further relates to variants of the polynucleotides described herein, wherein the variant encodes, for example, fragments, analogs, and/or derivatives of a polypeptide. In certain embodiments, the present disclosure provides a polynucleotide comprising a polynucleotide having a nucleotide sequence at least about 80% identical, at least about 85% identical, at least about 90% identical, at least about 95% identical, and in some embodiments, at least about 96%, 97%, 98% or 99% identical to a polynucleotide encoding a polypeptide comprising a binding molecule described herein.

As used herein, the phrase "a polynucleotide having a nucleotide sequence at least, for example, 95% "identical" to a reference nucleotide sequence" is intended to mean that the nucleotide sequence of the polynucleotide is identical to the reference sequence except that the polynucleotide sequence can include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence can be deleted or substituted with another nucleotide, or a number of nucleotides up to 5% of the total nucleotides in the reference sequence can be inserted into the reference sequence. These mutations of the reference sequence can occur at the 5' or 3' terminal positions of the reference nucleotide sequence or anywhere between those terminal positions, interspersed either individually among nucleotides in the reference sequence or in one or more contiguous groups within the reference sequence.

The polynucleotide variants can contain alterations in the coding regions, non-coding regions, or both. In some embodiments, a polynucleotide variant contains alterations which produce silent substitutions, additions, or deletions, but does not alter the properties or activities of the encoded polypeptide. In some embodiments, a polynucleotide variant comprises silent substitutions that results in no change to the amino acid sequence of the polypeptide (due to the degeneracy of the genetic code). Polynucleotide variants can be produced for a variety of reasons, for example, to optimize codon expression for a particular host (i.e., change codons in the human mRNA to those preferred by a bacterial host such as *E. coli*). In some embodiments, a polynucleotide variant comprises at least one silent mutation in a non-coding or a coding region of the sequence.

In some embodiments, a polynucleotide variant is produced to modulate or alter expression (or expression levels) of the encoded polypeptide. In some embodiments, a polynucleotide variant is produced to increase expression of the encoded polypeptide. In some embodiments, a polynucleotide variant is produced to decrease expression of the encoded polypeptide. In some embodiments, a polynucleotide variant has increased expression of the encoded polypeptide as compared to a parental polynucleotide sequence. In some embodiments, a polynucleotide variant has decreased expression of the encoded polypeptide as compared to a parental polynucleotide sequence.

In certain embodiments, a polynucleotide is isolated. In certain embodiments, a polynucleotide is substantially pure.

Vectors and cells comprising the polynucleotides described herein are also provided. In some embodiments, an expression vector comprises a polynucleotide molecule. In some embodiments, a host cell comprises an expression vector comprising the polynucleotide molecule. In some embodiments, a host cell comprises one or more expression vectors comprising polynucleotide molecules. In some embodiments, a host cell comprises a polynucleotide molecule. In some embodiments, a host cell comprises one or more polynucleotide molecules.

IV. Methods of Making the Binding Molecules

In yet another aspect, provided herein are methods for making the various binding molecules provided herein. In some embodiments, provided herein is a method of making a binding molecule comprising transfecting one or more vectors into a host cell, wherein the one or more vectors comprise:

(a) a first nucleic acid encoding a first polypeptide and a second polypeptide, each being an antibody light chain,
(b) a second nucleic acid encoding a third polypeptide comprising a first VH region and a first CH1 region and a second VH region; and
(c) a third nucleic acid encoding a fourth polypeptide comprising a third VH region and a second CH1 and a VL region, wherein the first polypeptide and the first VH region and the first CH1 region of the third polypeptide can form a first antigen binding Fab region;
wherein the second polypeptide and the third VH region and the second CH1 region of the fourth polypeptide can form a second antigen binding Fab region; and
wherein the second VH region of the third polypeptide and the VL region of the fourth polypeptide can form an antigen binding Fv region.

In some embodiments, the first Fab region and the second Fab region are linked to the Fv region via a flexible peptide region. In some embodiments, the flexible peptide region comprises an antibody hinge region. In some specific embodiments, the antibody hinge region is an IgG hinge region. In some more specific embodiments, the IgG hinge region is of IgG1 subtype. In other more specific embodiments, the IgG hinge region is of IgG2 subtype. In yet other more specific embodiments, the IgG hinge region is of IgG3 subtype. In yet other more specific embodiments, the IgG hinge region is of IgG4 subtype. In some embodiments, the flexible peptide region further comprises a linker between the antibody hinge region and the second antigen binding domain. In some embodiments, the linker comprises an amino acid sequence of GGGGS (G4S) (SEQ ID NO: 130). In some embodiments, the linker comprises an amino acid sequence of (G4S)n (SEQ ID NO: 133) where n is an integer. In some specific embodiments, the linker comprises an amino acid sequence of (G4S)$_1$ (SEQ ID NO: 130). In some more specific embodiments, the linker comprises an amino acid sequence of (G4S)$_2$ (SEQ ID NO: 131). In other more specific embodiments, the linker comprises an amino acid sequence of (G4S)$_3$ (SEQ ID NO: 134). In yet other more specific embodiments, the linker comprises an amino acid sequence of (G4S)$_4$ (SEQ ID NO: 135).

In some embodiments, the first Fab region and the second Fab region bind to different antigens. In other embodiments, the first Fab region and the second Fab region bind to the same antigen. In some embodiments, the first Fab region and the second Fab region bind to the same epitope of the same antigen. In other embodiments, the first Fab region and the second Fab region bind to different epitopes of the same antigen.

In certain embodiments, the first Fab region and the second Fab region form a first antigen binding domain, and the Fv region forms a second antigen binding domain.

In some embodiments, the first antigen binding domain and the second antigen binding domain bind to the same antigen. In some embodiments, the second antigen binding domain binds to the same epitope as at least one of the epitopes bound by the first antigen binding domain.

In other embodiments, the first antigen binding domain and the second antigen binding domain bind to different antigens, and wherein the first antigen binding domain binds to a first antigen and the second antigen binding domain binds to a second antigen.

In some embodiments, the first antigen is a cancer antigen. In other embodiments, the first antigen is not a cancer antigen.

In some embodiments, the second antigen is expressed on an immune cells including lymphocytes and monocytes. In some embodiments, the second antigen is expressed on a T cell. In some embodiments, the second antigen is expressed on a B cell. In other embodiments, the second antigen is expressed on a dendritic cell. In other embodiments, the second antigen is expressed on a granulocyte. In yet other embodiments, the second antigen is expressed on an innate lymphoid cell. In yet other embodiments, the second antigen is expressed on a megakaryocyte. In yet other embodiments, the second antigen is expressed on a monocyte. In yet other embodiments, the second antigen is expressed on a myeloid-derived suppressor cell. In yet other embodiments, the second antigen is expressed on a NK cell.

In some specific embodiments, the second antigen is CD3. In some embodiments, the first antigen is a cancer antigen and the second antigen is CD3.

In some more specific embodiments, the first antigen is PD-L1 and the second antigen is CD3.

In some embodiments, the VH region of the first portion of each Fab region comprises three CDRs having amino acid sequences of SEQ ID NO.: 5, SEQ ID NO.: 6, and SEQ ID NO.: 7; the VL region of the second portion of each Fab region comprises three CDRs having amino acid sequences of SEQ ID NO.: 9, SEQ ID NO.: 10, and SEQ ID NO.: 11; the VH region of the Fv region comprises three CDRs having amino acid sequences of SEQ ID NO.: 13, SEQ ID NO.: 14, and SEQ ID NO.: 15; and the VL region of the Fv region comprises three CDRs having amino acid sequences of SEQ ID NO.: 17, SEQ ID NO.: 18, and SEQ ID NO.: 19.

In some embodiments, the VH region of the first portion of each Fab region has an amino acid sequence of SEQ ID NO.: 4; the VL region of the second portion of each Fab region has an amino acid sequence of SEQ ID NO.: 8; the VH region of the Fv region has an amino acid sequence of SEQ ID NO.: 12; and the VL region of the Fv region has an amino acid sequence of SEQ ID NO.: 16.

In some embodiments, the first polypeptide and the second polypeptide each have the amino acid sequence of SEQ ID NO.: 3; the third polypeptide has the amino acid sequence of SEQ ID NO.: 1; and the fourth polypeptide has the amino acid sequence of SEQ ID NO.: 2.

In some embodiments, the first nucleic acid has a nucleotide sequence of SEQ ID NO.: 22; the second nucleic acid has a nucleotide sequence of SEQ ID NO: 20; and the third nucleic acid has a nucleotide sequence of SEQ ID NO.: 21.

In other more specific embodiments, the first antigen is CD20 and the second antigen is CD3.

In some embodiments, the VH region of the first portion of each Fab region comprises three CDRs having amino acid sequences of SEQ ID NO.: 27, SEQ ID NO.: 28, SEQ ID NO.: 29; the VL region of the second portion of each Fab region comprises three CDRs having amino acid sequences of SEQ ID NO.: 31, SEQ ID NO.: 32, and SEQ ID NO.: 33; the VH region of the Fv region comprises three CDRs having amino acid sequences of SEQ ID NO.: 13, SEQ ID NO.: 14, and SEQ ID NO.: 15; and the VL region of the Fv region comprises three CDRs having amino acid sequences of SEQ ID NO.: 17, SEQ ID NO.: 18, and SEQ ID NO.: 19.

In some embodiments, the VH region of the first portion of each Fab region has an amino acid sequence of SEQ ID NO.: 26; the VL region of the second portion of each Fab region has an amino acid sequence of SEQ ID NO.: 30; the VH region of the Fv region has an amino acid sequence of SEQ ID NO.: 12; and the VL region of the Fv region has an amino acid sequence of SEQ ID NO.: 16.

In some embodiments, the first polypeptide and the second polypeptide each have the amino acid sequence of SEQ ID NO.: 25; the third polypeptide has the amino acid sequence of SEQ ID NO.: 23; and the fourth polypeptide has the amino acid sequence of SEQ ID NO.: 24.

In some embodiments, the first nucleic acid has a nucleotide sequence of SEQ ID NO.: 36; the second nucleic acid has a nucleotide sequence of SEQ ID NO.: 34; and the third nucleic acid has a nucleotide sequence of SEQ ID NO.: 35.

In other more specific embodiments, the first antigen is EGFR and the second antigen is CD3.

In some embodiments, the VH region of the first portion of each Fab region comprises three CDRs having amino acid sequences of SEQ ID NO.: 41, SEQ ID NO.: 42, and SEQ ID NO.: 43; the VL region of the second portion of each Fab region comprises three CDRs having amino acid sequences of SEQ ID NO.: 45, SEQ ID NO.: 46, and SEQ ID NO.: 47; the VH region of the Fv region comprises three CDRs having amino acid sequences of SEQ ID NO.: 13, SEQ ID NO.: 14, and SEQ ID NO.: 15; and the VL region of the Fv region comprises three CDRs having amino acid sequences of SEQ ID NO.: 17, SEQ ID NO.: 18, and SEQ ID NO.: 19.

In some embodiments, the VH region of the first portion of each Fab region has an amino acid sequence of SEQ ID NO.: 40; the VL region of the second portion of each Fab region has an amino acid sequence of SEQ ID NO.: 44; the VH region of the Fv region has an amino acid sequence of SEQ ID NO.: 12; and the VL region of the Fv region has an amino acid sequence of SEQ ID NO.: 16.

In some embodiments, the first polypeptide and the second polypeptide each have the amino acid sequence of SEQ ID NO.: 39; the third polypeptide has the amino acid sequence of SEQ ID NO.: 37; and the fourth polypeptide has the amino acid sequence of SEQ ID NO.: 38.

In some embodiments, the first nucleic acid has a nucleotide sequence of SEQ ID NO.: 50; the second nucleic acid has a nucleotide sequence of SEQ ID NO.: 48; and the third nucleic acid has a nucleotide sequence of SEQ ID NO.: 49.

In other more specific embodiments, the first antigen is Her2 and the second antigen is TNF alpha. In some embodiments, the VH region of the first portion of each Fab region has an amino acid sequence of SEQ ID NO.: 51; the VL region of the second portion of each Fab region has an amino acid sequence of SEQ ID NO.: 52; the VH region of the Fv region has an amino acid sequence of SEQ ID NO.: 53; and the VL region of the Fv region has an amino acid sequence of SEQ ID NO.: 54.

Recombinant expression of a binding molecule provided herein may require construction of an expression vector containing a polynucleotide that encodes the binding molecule or a fragment thereof. Once a polynucleotide encoding a binding molecule, an antibody heavy or light chain, or fragment thereof (such as, but not necessarily, containing the heavy and/or light chain variable domain) provided herein has been obtained, the vector for the production of the binding molecule may be produced by recombinant DNA technology using techniques well-known in the art. Thus, methods for preparing a protein by expressing a polynucleotide containing an encoding nucleotide sequence are described herein. Methods which are well known to those skilled in the art can be used to construct expression vectors containing coding sequences and appropriate transcriptional and translational control signals. These methods include, for example, in vitro recombinant DNA techniques, synthetic techniques, and in vivo genetic recombination. Also provided are replicable vectors comprising a nucleotide sequence encoding a binding molecule provided herein, or a fragment thereof, or a heavy or light chain CDR, operably linked to a promoter. Such vectors may include the nucleotide sequence encoding the constant region of an antibody molecule (see, e.g., International Publication Nos. WO 86/05807 and WO 89/01036; and U.S. Pat. No. 5,122,464) and the variable domain of an antibody may be cloned into such a vector for expression of the entire heavy, the entire light chain, or both the entire heavy and light chains.

The expression vector is transferred to a host cell by conventional techniques and the transfected cells are then cultured by conventional techniques to produce a binding molecule provided herein. Thus, also provided herein are host cells containing a polynucleotide encoding a binding molecule provided herein or fragments thereof, or a heavy or light chain thereof, or fragment thereof, operably linked to a heterologous promoter. In certain embodiments, multiple vectors comprising polynucleotides encoding different portions of a binding molecule provided herein may be co-expressed in the host cell for expression of the entire binding molecule, as detailed below.

A variety of host-expression vector systems may be utilized to express the binding molecules provided herein (see, e.g., U.S. Pat. No. 5,807,715). Such host-expression systems represent vehicles by which the coding sequences of interest may be produced and subsequently purified, but also represent cells which may, when transformed or transfected with the appropriate nucleotide coding sequences, express a binding molecule provided herein in situ. These include but are not limited to microorganisms such as bacteria (e.g., *E. coli* and *B. subtilis*) transformed with recombinant bacteriophage DNA, plasmid DNA or cosmid DNA expression vectors containing coding sequences; yeast (e.g., *Saccharomyces pichia*) transformed with recombinant yeast expression vectors containing coding sequences; insect cell systems infected with recombinant virus expression vectors (e.g., baculovirus) containing coding sequences; plant cell systems infected with recombinant virus expression vectors (e.g., cauliflower mosaic virus, CaMV, tobacco mosaic virus, TMV) or transformed with recombinant plasmid expression vectors (e.g., Ti plasmid) containing coding sequences; or mammalian cell systems (e.g., COS, CHO, BHK, 293, NS0, and 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Bacterial cells such as *Escherichia coli*, or, eukaryotic cells, especially for the expression of whole recombinant antibody molecule, can be used for the expression of a recombinant binding molecule. For example, mammalian cells such as Chinese hamster ovary cells (CHO), in conjunction with a vector such as the major intermediate early gene promoter element from human cytomegalovirus is an effective expression system for antibodies or variants thereof (Foecking et al., 1986, Gene 45:101; and Cockett et al., 1990, Bio/Technology 8:2). In some embodiments, antibodies provided herein are produced in CHO cells. In a specific embodiment, the expression of nucleotide sequences encoding binding molecules provided herein is regulated by a constitutive promoter, inducible promoter or tissue specific promoter.

In bacterial systems, a number of expression vectors may be advantageously selected depending upon the use intended for the binding molecule being expressed. For example, when a large quantity of such a binding molecule is to be produced, for the generation of pharmaceutical compositions of a binding molecule, vectors which direct the expression of high levels of fusion protein products that are readily purified may be desirable. Such vectors include, but are not limited to, the E. coli expression vector pUR278 (Ruther et al., 1983, EMBO 12:1791), in which the coding sequence may be ligated individually into the vector in frame with the lac Z coding region so that a fusion protein is produced; pIN vectors (Inouye & Inouye, 1985, Nucleic Acids Res. 13:3101-3109; Van Heeke & Schuster, 1989, J. Biol. Chem. 24:5503-5509); and the like. pGEX vectors may also be used to express foreign polypeptides as fusion proteins with glutathione 5-transferase (GST). In general, such fusion proteins are soluble and can easily be purified from lysed cells by adsorption and binding to matrix glutathione agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the binding molecule in infected hosts (e.g., see Logan & Shenk, 1984, Proc. Natl. Acad. Sci. USA 8 1:355-359). Specific initiation signals may also be required for efficient translation of inserted coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see, e.g., Bittner et al., 1987, Methods in Enzymol. 153:51-544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 3T3, W138, BT483, Hs578T, HTB2, BT2O and T47D, NS0 (a murine myeloma cell line that does not endogenously produce any immunoglobulin chains), CRL7O3O and HsS78Bst cells.

For long-term, high-yield production of recombinant proteins, stable expression can be utilized. For example, cell lines which stably express the binding molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the binding molecule. Such engineered cell lines may be particularly useful in screening and evaluation of compositions that interact directly or indirectly with the binding molecule.

A number of selection systems may be used, including but not limited to, the herpes simplex virus thymidine kinase (Wigler et al., 1977, Cell 11:223), hypoxanthineguanine phosphoribosyltransferase (Szybalska & Szybalski, 1992, Proc. Natl. Acad. Sci. USA 48:202), and adenine phosphoribosyltransferase (Lowy et al., 1980, Cell 22:8-17) genes can be employed in tk-, hgprt- or aprt-cells, respectively. Also, antimetabolite resistance can be used as the basis of selection for the following genes: dhfr, which confers resistance to methotrexate (Wigler et al., 1980, Natl. Acad. Sci. USA 77:357; O'Hare et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Wu and Wu, 1991, Biotherapy 3:87-95; Tolstoshev, 1993, Ann. Rev. Pharmacol. Toxicol. 32:573-596; Mulligan, 1993, Science 260:926-932; and Morgan and Anderson, 1993, Ann. Rev. Biochem. 62:191-217; May, 1993, TIB TECH 11(5):155-2 15); and hygro, which confers resistance to hygromycin (Santerre et al., 1984, Gene 30:147). Methods commonly known in the art of recombinant DNA technology may be routinely applied to select the desired recombinant clone, and such methods are described, for example, in Ausubel et al. (eds.), *Current Protocols in Molecular Biology*, John Wiley & Sons, NY (1993); Kriegler, *Gene Transfer and Expression*, A Laboratory Manual, Stockton Press, NY (1990); and in Chapters 12 and 13, Dracopoli et al. (eds.), *Current Protocols in Human Genetics*, John Wiley & Sons, NY (1994); Colberre-Garapin et al., 1981, J. Mol. Biol. 150:1, which are incorporated by reference herein in their entireties.

The expression levels of a binding molecule can be increased by vector amplification (for a review, see Bebbington and Hentschel, The use of vectors based on gene amplification for the expression of cloned genes in mammalian cells in DNA cloning, Vol. 3 (Academic Press, New York, 1987)). When a marker in the vector system expressing a binding molecule is amplifiable, increase in the level of inhibitor present in culture of host cell will increase the number of copies of the marker gene. Since the amplified region is associated with the binding molecule gene, production of the binding molecule will also increase (Crouse et al., 1983, Mol. Cell. Biol. 3:257).

The host cell may be co-transfected with multiple expression vectors provided herein. The vectors may contain identical selectable markers which enable equal expression of respective encoding polypeptides. Alternatively, a single vector may be used which encodes, and is capable of expressing multiple polypeptides. The coding sequences may comprise cDNA or genomic DNA.

Once a binding molecule provided herein has been produced by recombinant expression, it may be purified by any method known in the art for purification of an immunoglobulin molecule, for example, by chromatography (e.g., ion exchange, affinity, particularly by affinity for the specific antigen after Protein A, sizing column chromatography, and kappa-select affinity chromatography), centrifugation, differential solubility, or by any other standard technique for the purification of proteins. In a specific embodiment, kappa-select (e.g., KappaSelect developed by GE Healthcare Life Science) is used for the purification of Fab (kappa) fragments or binding molecules that contain the Fab fragments. Further, the binding molecules provided herein can be fused to heterologous polypeptide sequences described herein or otherwise known in the art to facilitate purification.

V. Pharmaceutical Compositions

In one aspect, the present disclosure further provides pharmaceutical compositions comprising at least one binding molecule of the present disclosure. In some embodiments, a pharmaceutical composition comprises therapeutically effective amount of a binding molecule provided herein and a pharmaceutically acceptable carrier.

Pharmaceutical compositions comprising a binding molecule are prepared for storage by mixing the binding molecule having the desired degree of purity with optional physiologically acceptable carriers, excipients, or stabilizers (see, e.g., Remington, *Remington's Pharmaceutical Sciences* (18th ed. 1980)) in the form of aqueous solutions or lyophilized or other dried forms.

The binding molecule of the present disclosure may be formulated in any suitable form for delivery to a target cell/tissue, e.g., as microcapsules or macroemulsions (Remington, supra; Park et al., 2005, Molecules 10:146-61; Malik et al., 2007, Curr. Drug. Deliv. 4:141-51), as sustained release formulations (Putney and Burke, 1998, Nature Biotechnol. 16:153-57), or in liposomes (Maclean et al., 1997, Int. J. Oncol. 11:325-32; Kontermann, 2006, Curr. Opin. Mol. Ther. 8:39-45).

A binding molecule provided herein can also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles, and nano-capsules) or in macroemulsions. Such techniques are disclosed, for example, in Remington, supra.

Various compositions and delivery systems are known and can be used with a binding molecule as described herein, including, but not limited to, encapsulation in liposomes, microparticles, microcapsules, recombinant cells capable of expressing the binding molecule, receptor-mediated endocytosis (see, e.g., Wu and Wu, 1987, J. Biol. Chem. 262: 4429-32), construction of a nucleic acid as part of a retroviral or other vector, etc. In another embodiment, a composition can be provided as a controlled release or sustained release system. In one embodiment, a pump may be used to achieve controlled or sustained release (see, e.g., Langer, supra; Sefton, 1987, Crit. Ref. Biomed. Eng. 14:201-40; Buchwald et al., 1980, Surgery 88:507-16; and Saudek et al., 1989, N. Engl. J. Med. 321:569-74). In another embodiment, polymeric materials can be used to achieve controlled or sustained release of a prophylactic or therapeutic agent (e.g., a binding molecule as described herein) or a composition provided herein (see, e.g., *Medical Applications of Controlled Release* (Langer and Wise eds., 1974); *Controlled Drug Bioavailability, Drug Product Design and Performance* (Smolen and Ball eds., 1984); Ranger and Peppas, 1983, J. Macromol. Sci. Rev. Macromol. Chem. 23:61-126; Levy et al., 1985, Science 228:190-92; During et al., 1989, Ann. Neurol. 25:351-56; Howard et al., 1989, J. Neurosurg. 71:105-12; U.S. Pat. Nos. 5,679,377; 5,916,597; 5,912,015; 5,989,463; and 5,128,326; PCT Publication Nos. WO 99/15154 and WO 99/20253). Examples of polymers used in sustained release formulations include, but are not limited to, poly(2-hydroxy ethyl methacrylate), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. In one embodiment, the polymer used in a sustained release formulation is inert, free of leachable impurities, stable on storage, sterile, and biodegradable.

In yet another embodiment, a controlled or sustained release system can be placed in proximity of a particular target tissue, for example, the nasal passages or lungs, thus requiring only a fraction of the systemic dose (see, e.g., Goodson, *Medical Applications of Controlled Release* Vol. 2, 115-38 (1984)). Controlled release systems are discussed, for example, by Langer, 1990, Science 249:1527-33. Any technique known to one of skill in the art can be used to produce sustained release formulations comprising one or more binding molecule as described herein (see, e.g., U.S. Pat. No. 4,526,938, PCT publication Nos. WO 91/05548 and WO 96/20698, Ning et al., 1996, Radiotherapy & Oncology 39:179-89; Song et al., 1995, PDA J. of Pharma. Sci. & Tech. 50:372-97; Cleek et al., 1997, Pro. Int'l. Symp. Control. Rel. Bioact. Mater. 24:853-54; and Lam et al., 1997, Proc. Int'l. Symp. Control Rel. Bioact. Mater. 24:759-60).

VI. Methods of Administration

In a specific embodiment, provided herein is a composition for use in the prevention, management, treatment and/or amelioration of a disease or condition comprising a binding molecule provided herein. In one embodiment, provided herein is a composition for use in the prevention of a disease or condition, wherein the composition comprises a binding molecule provided herein. In one embodiment, provided herein is a composition for use in the management of a disease or condition, wherein the composition comprises a binding molecule provided herein. In one embodiment, provided herein is a composition for use in the treatment of a disease or condition, wherein the composition comprises a binding molecule provided herein. In one embodiment, provided herein is a composition for use in the amelioration of a disease or condition, wherein the composition comprises a binding molecule provided herein. In some embodiments, the disease or condition is a cancer. In other embodiments, the cancer is a PD-L1 positive cancer. In some embodiments, the cancer is a lung cancer. In some embodiments, the cancer is a Non Small Cell Lung Carcinoma (NSCLC). In some embodiments, the cancer is a Diffuse Large B cell Lymphoma (DLBCL). In some embodiments, the cancer is a colorectal cancer. In some embodiments, the cancer is a breast cancer. In some embodiments, the cancer is a lymphoma. In some embodiments, the cancer is a melanoma. In some embodiments, the cancer is ovarian cancer. In certain embodiments, the subject is a subject in need thereof. In some embodiments, the subject has the disease or condition. In other embodiments, the subject is at risk of having the disease or condition. In some embodiments, the administration results in the prevention, management, treatment or amelioration of the disease or condition.

In one embodiment, provided herein is a composition for use in the prevention, management, treatment and/or amelioration of a symptom of a disease or condition, wherein the composition comprises a binding molecule provided herein. In one embodiment, provided herein is a composition for use in the prevention of a symptom of a disease or condition, wherein the composition comprises a binding molecule provided herein. In one embodiment, provided herein is a composition for use in the management of a symptom of a disease or condition, wherein the composition comprises a binding molecule provided herein. In one embodiment, provided herein is a composition for use in the treatment of a symptom of a disease or condition, wherein the composition comprises an a binding molecule provided herein. In one embodiment, provided herein is a composition for use in the amelioration of a symptom of a disease or condition, wherein the composition comprises a binding molecule provided herein. In one embodiment, the disease is cancer. In certain embodiments, the subject is a subject in need thereof. In some embodiments, the subject has the disease or condition. In other embodiments, the subject is at risk of having the disease or condition. In some embodiments, the administration results in the prevention, management, treatment or amelioration of the symptom of the disease or condition.

In another embodiment, provided herein is a method of preventing, managing, treating and/or ameliorating a disease or condition in a subject, comprising administering an effective amount of a binding molecule provided herein. In one embodiment, provided herein is a method of preventing a disease or condition in a subject, comprising administering an effective amount of a binding molecule provided herein. In one embodiment, provided herein is a method of managing a disease or condition in a subject, comprising administering an effective amount of a binding molecule provided herein. In one embodiment, provided herein is a method of treating a disease or condition in a subject, comprising administering an effective amount of a binding molecule provided herein. In one embodiment, provided herein is a method of ameliorating a disease or condition in a subject, comprising administering an effective amount of a binding molecule provided herein. In one embodiment, the disease or condition is cancer. In certain embodiments, the subject is a subject in need thereof. In some embodiments, the subject has the disease or condition. In other embodiments, the subject is at risk of having the disease or condition. In some embodiments, the administration results in the prevention, management, treatment or amelioration of the disease or condition.

In another embodiment, provided herein is a method of preventing, managing, treating and/or ameliorating a symptom of a disease or condition in a subject, comprising administering an effective amount of a binding molecule provided herein. In one embodiment, provided herein is a method of preventing a symptom of a disease or condition in a subject, comprising administering an effective amount of a binding molecule provided herein. In one embodiment, provided herein is a method of managing a symptom of a disease or condition in a subject, comprising administering an effective amount of a binding molecule provided herein. In one embodiment, provided herein is a method of treating a symptom of a disease or condition in a subject, comprising administering an effective amount of a binding molecule provided herein. In one embodiment, provided herein is a method of ameliorating a disease or condition in a subject, comprising administering an effective amount of a binding molecule provided herein. In one embodiment, the disease or condition is cancer. In certain embodiments, the subject is a subject in need thereof. In some embodiments, the subject has the disease or condition. In other embodiments, the subject is at risk of having the disease or condition. In some embodiments, the administration results in the prevention, management, treatment or amelioration of the symptom of the disease or condition.

Also provided herein are methods of preventing, managing, treating and/or ameliorating a disease or condition by administrating to a subject of an effective amount of a binding molecule provided herein, or pharmaceutical composition comprising a binding molecule provided herein. In one aspect, the binding molecule is substantially purified (i.e., substantially free from substances that limit its effect or produce undesired side effects). In certain embodiments, the binding molecule is derived from one or more fully human monoclonal antibodies. The subject administered a therapy can be a mammal such as non-primate (e.g., cows, pigs, horses, cats, dogs, rats etc.) or a primate (e.g., a monkey, such as a cynomolgous monkey, or a human). In a one embodiment, the subject is a human. In another embodiment, the subject is a human with a disease or condition, e.g., cancer.

Various delivery systems are known and can be used to administer a prophylactic or therapeutic agent (e.g., a binding molecule provided herein), including, but not limited to, encapsulation in liposomes, microparticles, microcapsules, recombinant cells capable of expressing the binding molecule, receptor-mediated endocytosis (see, e.g., Wu and Wu, J. Biol. Chem. 262:4429-4432 (1987)), construction of a nucleic acid as part of a retroviral or other vector, etc. Methods of administering a prophylactic or therapeutic agent (e.g., a binding molecule provided herein), or pharmaceutical composition include, but are not limited to, parenteral administration (e.g., intradermal, intramuscular, intraperitoneal, intravenous and subcutaneous), epidural, and mucosal (e.g., intranasal and oral routes). In a specific embodiment, a prophylactic or therapeutic agent (e.g., a binding molecule provided herein), or a pharmaceutical composition is administered intranasally, intramuscularly, intravenously, or subcutaneously. The prophylactic or therapeutic agents, or compositions may be administered by any convenient route, for example by infusion or bolus injection, by absorption through epithelial or mucocutaneous linings (e.g., oral mucosa, intranasal mucosa, rectal and intestinal mucosa, etc.) and may be administered together with other biologically active agents. Administration can be systemic or local. In addition, pulmonary administration can also be employed, e.g., by use of an inhaler or nebulizer, and formulation with an aerosolizing agent. See, e.g., U.S. Pat. Nos. 6,019,968, 5,985,320, 5,985,309, 5,934,272, 5,874, 064, 5,855,913, 5,290,540, and 4,880,078; and PCT Publication Nos. WO 92/19244, WO 97/32572, WO 97/44013, WO 98/31346, and WO 99/66903, each of which is incorporated herein by reference their entirety.

In a specific embodiment, it may be desirable to administer a prophylactic or therapeutic agent, or a pharmaceutical composition provided herein locally to the area in need of treatment. This may be achieved by, for example, and not by way of limitation, local infusion, by topical administration (e.g., by intranasal spray), by injection, or by means of an implant, said implant being of a porous, non-porous, or gelatinous material, including membranes, such as sialastic membranes, or fibers. In some embodiments, when administering an antibody provided herein, care must be taken to use materials to which the antibody does not absorb.

In another embodiment, a prophylactic or therapeutic agent, or a composition provided herein can be delivered in a vesicle, in particular a liposome (see Langer, 1990, Science 249:1527-1533; Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.).

In another embodiment, a prophylactic or therapeutic agent, or a composition provided herein can be delivered in a controlled release or sustained release system. In one embodiment, a pump may be used to achieve controlled or sustained release (see Langer, supra; Sefton, 1987, CRC Crit. Ref. Biomed. Eng. 14:20; Buchwald et al., 1980, Surgery 88:507; Saudek et al., 1989, N. Engl. J. Med. 321:574). In another embodiment, polymeric materials can be used to achieve controlled or sustained release of a prophylactic or therapeutic agent (e.g., an antibody provided herein) or a composition provided herein (see e.g., Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, J., Macromol. Sci. Rev. Macromol. Chem. 23:61; see also Levy et al., 1985, Science 228:190; During et al., 1989, Ann. Neurol. 25:351; Howard et al., 1989, J. Neurosurg. 7 1:105); U.S. Pat. Nos. 5,679,377; 5,916,597; 5,912,015; 5,989,463; 5,128,326; PCT Publication No. WO 99/15154; and PCT Publication No. WO 99/20253. Examples of polymers used in sustained release formulations include, but are not limited to, poly(2-hydroxy ethyl methacrylate), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. In an embodiment, the polymer used in a sustained release formulation is inert, free of leachable impurities, stable on storage, sterile, and biodegradable. In yet another embodiment, a controlled or sustained release system can be placed in proximity of the therapeutic target, i.e., the nasal passages or lungs, thus requiring only a fraction of the systemic dose (see, e.g., Goodson, in Medical Applications of Controlled Release, supra, vol. 2, pp. 115-138 (1984)). Controlled release systems are discussed in the review by Langer (1990, Science 249:1527-1533). Any technique known to one of skill in the art can be used to produce sustained release formulations comprising one or more binding molecule provided herein. See, e.g., U.S. Pat. No. 4,526,938, PCT publication WO 91/05548, PCT publication WO 96/20698, Ning et al., 1996, "Intratumoral Radioimmunotherapy of a Human Colon Cancer Xenograft Using a Sustained-Release Gel," Radiotherapy & Oncology 39:179-189, Song et al., 1995, "Antibody Mediated Lung Targeting of Long-Circulating Emulsions," PDA Journal of Pharmaceutical Science & Technology 50:372-397, Cleek et al., 1997, "Biodegradable Polymeric Carriers for a bFGF Antibody for Cardiovascular Application," Pro. Int'l. Symp. Control. Rel. Bioact. Mater. 24:853-854, and Lam et al., 1997, "Microencapsulation of Recombinant Humanized Monoclonal Antibody for Local Delivery," Proc. Int'l. Symp. Control Rel. Bioact. Mater. 24:759-760, each of which is incorporated herein by reference in their entirety.

In a specific embodiment, where the composition provided herein is a nucleic acid encoding a prophylactic or therapeutic agent (e.g., a binding molecule provided herein), the nucleic acid can be administered in vivo to promote expression of its encoded prophylactic or therapeutic agent, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell surface receptors or transfecting agents, or by administering it in linkage to a homeobox-like peptide which is known to enter the nucleus (see, e.g., Joliot et al., 1991, Proc. Natl. Acad. Sci. USA 88:1864-1868), etc. Alternatively, a nucleic acid can be introduced intracellularly and incorporated within host cell DNA for expression by homologous recombination.

In a specific embodiment, a composition provided herein comprises one, two or more binding molecules provided herein. In another embodiment, a composition provided herein comprises one, two or more binding molecules provided herein and a prophylactic or therapeutic agent other than a binding molecule provided herein. In one embodiment, the agents are known to be useful for or have been or are currently used for the prevention, management, treatment and/or amelioration of a disease or condition. In addition to prophylactic or therapeutic agents, the compositions provided herein may also comprise a carrier.

The compositions provided herein include bulk drug compositions useful in the manufacture of pharmaceutical compositions (e.g., compositions that are suitable for administration to a subject or patient) that can be used in the preparation of unit dosage forms. In an embodiment, a composition provided herein is a pharmaceutical composition. Such compositions comprise a prophylactically or therapeutically effective amount of one or more prophylactic or therapeutic agents (e.g., a binding molecule provided herein or other prophylactic or therapeutic agent), and a pharmaceutically acceptable carrier. The pharmaceutical compositions can be formulated to be suitable for the route of administration to a subject.

In a specific embodiment, the term "carrier" refers to a diluent, adjuvant (e.g., Freund's adjuvant (complete and incomplete)), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is an exemplary carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in *Remington's Pharmaceutical Sciences* (1990) Mack Publishing Co., Easton, Pa. Such compositions will contain a prophylactically or therapeutically effective amount of the binding molecule provided herein, such as in purified form, together with a suitable amount of carrier so as to provide the form for proper administration to the patient. The formulation should suit the mode of administration.

In an embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Such compositions, however, may be administered by a route other than intravenous.

Generally, the ingredients of compositions provided herein are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

An binding molecule provided herein can be packaged in a hermetically sealed container such as an ampoule or sachette indicating the quantity of antibody. In one embodiment, the binding molecule is supplied as a dry sterilized lyophilized powder or water free concentrate in a hermetically sealed container and can be reconstituted, e.g., with water or saline to the appropriate concentration for administration to a subject. The lyophilized binding molecule can be stored at between 2 and 8° C. in its original container and the binding molecule can be administered within 12 hours, such as within 6 hours, within 5 hours, within 3 hours, or within 1 hour after being reconstituted. In an alternative embodiment, a binding molecule provided herein is supplied in liquid form in a hermetically sealed container indicating the quantity and concentration of the antibody.

The compositions provided herein can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The amount of a prophylactic or therapeutic agent (e.g., a binding molecule provided herein), or a composition provided herein that will be effective in the prevention, management, treatment and/or amelioration of a disease or condition can be determined by standard clinical techniques. In addition, in vitro assays may optionally be employed to help identify optimal dosage ranges. The precise dose to be employed in the formulation will also depend on the route of administration, and the seriousness of a disease or condition, and should be decided according to the judgment of the practitioner and each patient's circumstances.

Effective doses may be extrapolated from dose-response curves derived from in vitro or animal model test systems.

In certain embodiments, the route of administration for a dose of a binding molecule provided herein to a patient is intranasal, intramuscular, intravenous, or a combination thereof, but other routes described herein are also acceptable. Each dose may or may not be administered by an identical route of administration. In some embodiments, a binding molecule provided herein may be administered via multiple routes of administration simultaneously or subsequently to other doses of the same or a different binding molecule provided herein.

In certain embodiments, binding molecules provided herein are administered prophylactically or therapeutically to a subject. Antibodies provided herein can be prophylactically or therapeutically administered to a subject so as to prevent, lessen or ameliorate a disease or symptom thereof.

For the sake of conciseness, certain abbreviations are used herein. One example is the single letter abbreviation to represent amino acid residues. The amino acids and their corresponding three letter and single letter abbreviations are as follows:

| | | |
|---|---|---|
| alanine | Ala | (A) |
| arginine | Arg | (R) |
| asparagine | Asn | (N) |
| aspartic acid | Asp | (D) |
| cysteine | Cys | (C) |
| glutamic acid | Glu | (E) |
| glutamine | Gln | (Q) |
| glycine | Gly | (G) |
| histidine | His | (H) |
| isoleucine | Ile | (I) |
| leucine | Leu | (L) |
| lysine | Lys | (K) |
| methionine | Met | (M) |
| phenylalanine | Phe | (F) |
| proline | Pro | (P) |
| serine | Ser | (S) |
| threonine | Thr | (T) |
| tryptophan | Trp | (W) |
| tyrosine | Tyr | (Y) |
| valine | Val | (V) |

The invention is generally disclosed herein using affirmative language to describe the numerous embodiments. The invention also specifically includes embodiments in which particular subject matter is excluded, in full or in part, such as substances or materials, method steps and conditions, protocols, procedures, assays or analysis. Thus, even though the invention is generally not expressed herein in terms of what the invention does not include, aspects that are not expressly included in the invention are nevertheless disclosed herein.

A number of embodiments of the invention have been described. Nevertheless, it will be understood that various modifications may be made without departing from the spirit and scope of the invention. Accordingly, the following examples are intended to illustrate but not limit the scope of invention described in the claims.

EXAMPLES

Example 1

Construction and Expression of Exemplary Binding Molecules

This example illustrates the construction and expression of exemplary binding molecules as provided herein (illustrated in FIGS. 1A-1E), in particular, binding molecules ACE-00, ACE-02, ACE-03, ACE-04, ACE-05, ACE-09, ACE-10, ACE-11, and ACE-12. The components targeting first and second antigens in each of the exemplary binding molecules are summarized in the table below.

TABLE 3

Components targeting first and second antigens in exemplary binding molecules

| Binding molecule | Targeting component | |
|---|---|---|
| | First antigen | Second antigen |
| ACE-00 | Trastuzumab | Adalimumab |
| ACE-02 | Anti-CD19 Ab | Anti-CD3 humanized 12F6 |
| ACE-03 | Anti-CD19 Ab | Anti-CD3 humanized OKT3 |
| ACE-04 | Anti-PD-L1 Ab | Anti-CD3 chimetic (xi) OKT3 Fab |
| ACE-05 | Anti-PD-L1 Ab | Anti-CD3 UCHT1 |
| ACE-09 | Anti-PD-L1 Ab | Anti-CD3 UCHT1 |
| ACE-10 | Anti-CD20 | Anti-CD3 |
| ACE-11 | Anti-EGFR | Anti-CD3 |
| ACE-12 | Anti-PD-L1 Ab | Anti-CD3 UCHT1 |

Formats used in amino acid sequences:
BOLD: VH or VL;
BOLD and UNDERLINED: CDR;
ITALICIZED: antibody hinge region;
lower case: flexible linker;
[BRACKET]: CH1;
[BRACKET and UNDERLINED]: CL.

1.1. Construction and Expression of ACE-00

Figure 2A:
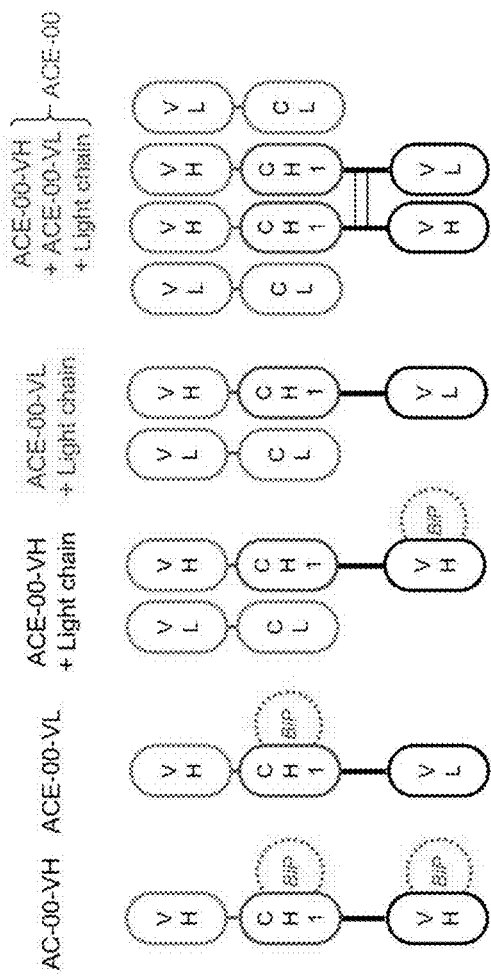
FIG. 2A illustrates the assembly pattern of ACE-00. "BiP" illustrates the binding immunoglobulin protein (BiP), which binds CH1 or VH domains of ACE-00 that are exposed.
Figure 2B:
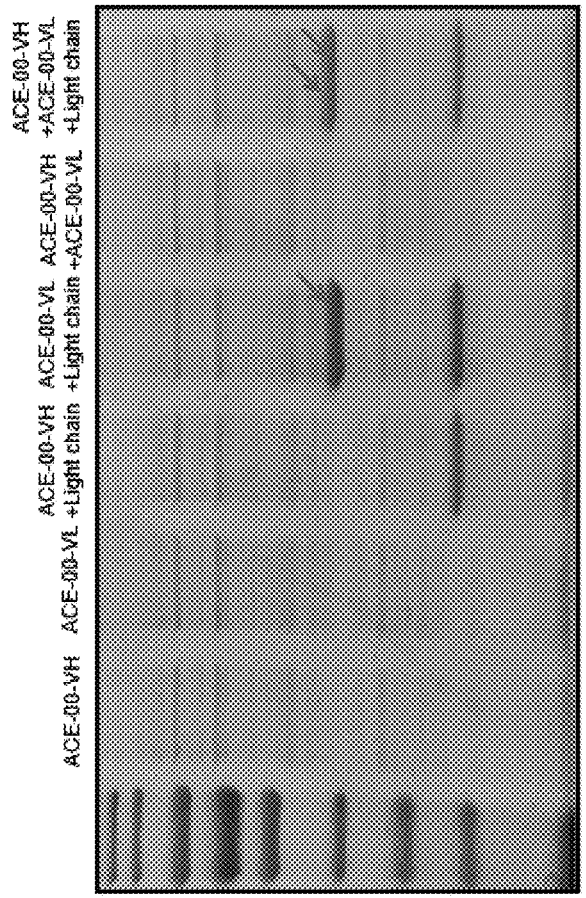
FIG. 2B shows the results of the SDS-PAGE performed to identify the assembly pattern of ACE-00. The arrows indicate the band of ACE-00-VL in the "ACE-00+ Light chain" sample and the two bands of ACE-00-VH and ACE-00-VL in the "ACE-00-VH+ACE-00-VL+ Light chain" samples under the reducing condition.
Figure 2E:
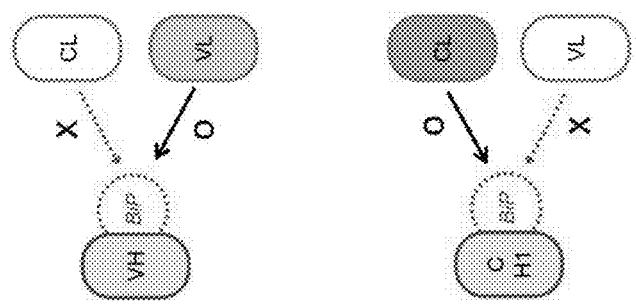
FIG. 2E illustrates contribution of the antibody VH domain to antibody assembly and contribution of the ACE-00-VH chain to the proper assembly of ACE-00 molecule. "X" represents no assembly; "O" represents assembly.
Figure 2D:
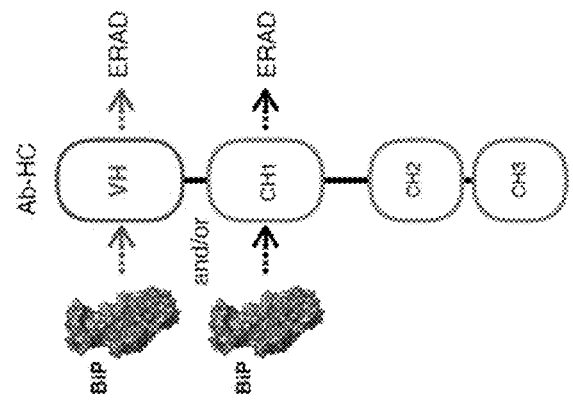
FIG. 2D illustrates that BiP can regulate the assembly and secretion of heavy chain by interaction with VH and/or CH1 domain of heavy chain. "ERAD" represents endoplasmic-reticulum-associated protein degradation.
Figure 2C:
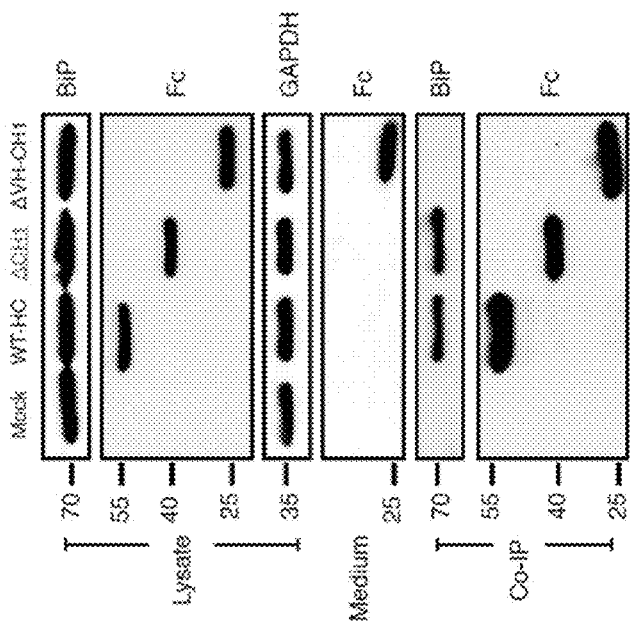
FIG. 2C shows the co-immunoprecipitation (co-IP) results of wild-type heavy chain (HC), CH1-truncated heavy chain (ΔCH1) and VH-CH1-truncated heavy chain (ΔVH-CH1) of adalimumab.
Figure 2G:
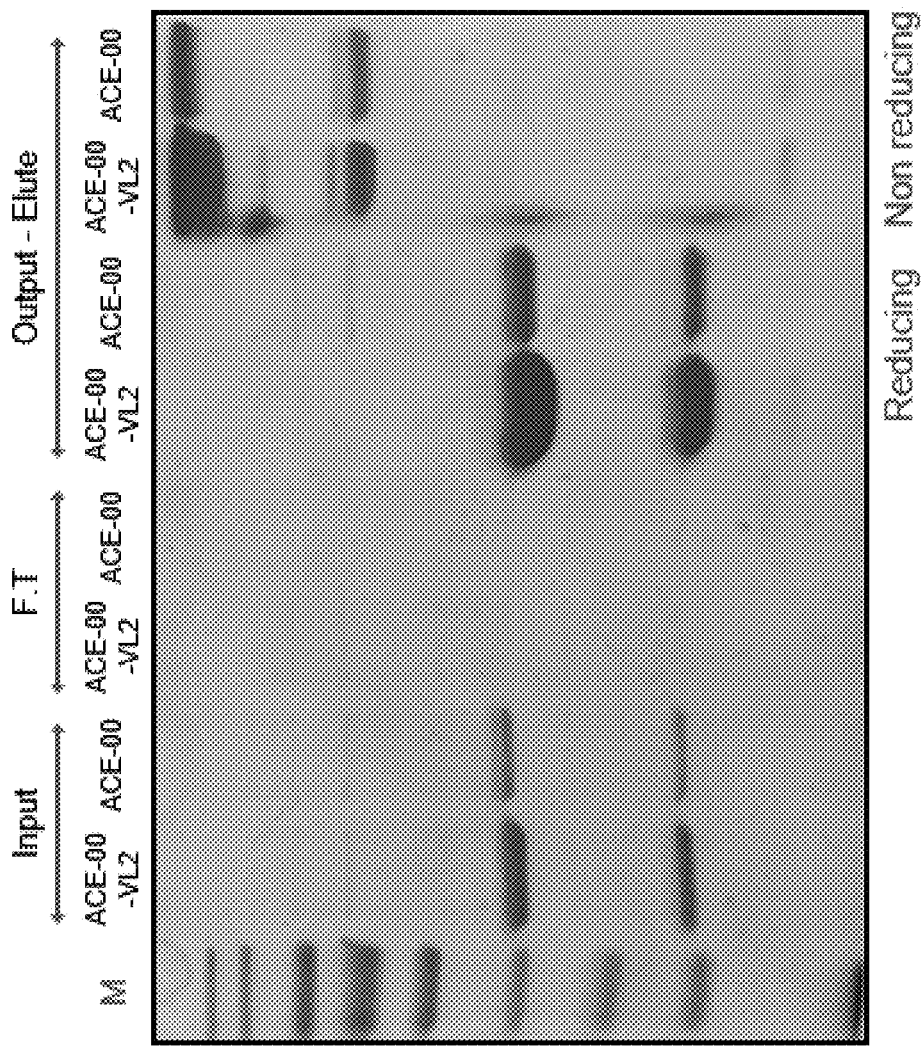
FIG. 2G shows the results of affinity chromatography for ACE-00 and ACE-00-VL2 proteins using Hitrap™ KappaSelect (GE healthcare, USA).
Figure 2F:
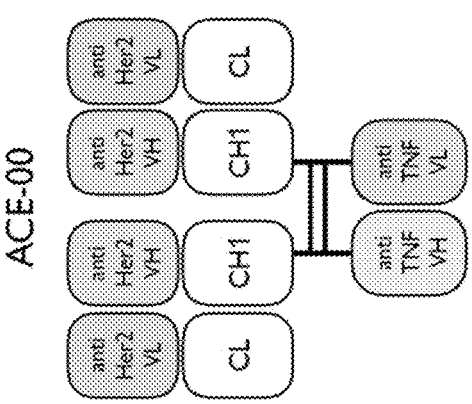
FIG. 2F illustrates the structure of ACE-00.

A HEK-293 transient expression system (Invitrogen, USA) was used for expressing ACE-00, whose second antigen binding Fv region binds to TNF alpha, and whose first antigen binding domain (Fab regions) binds to Her2 antigen (see FIG. 2F). ACE-00 has the same overall structure as the exemplary binding molecule illustrated in FIG. 1A. Briefly, ACE-00 contains two different heavy chain like chains (ACE-00-VH and ACE-00-VL) and two identical light chains (ACE-00-LC). The parental antibody used for constructing the anti-Her2 domain of ACE-00 is trastuzumab and the parental antibody used for constructing the anti-TNF alpha domain of ACE-00 is adalimumab. The amino acid sequences of these three type of polypeptides are as follows:

ACE-00-VH amino acid sequence:
(SEQ ID NO: 115)
EVQLVESGGGLVQPGGSLRLSCAAS<u>GFNIKDTY</u>IHWVRQAPGKGLEWVAR

<u>IYPTNGYTRYADSVKGRFT</u>ISADTSKNTAYLQMNSLRAEDTAVYYC<u>SRWG</u>

<u>GDGFYAMDY</u>WGQGTLVTVSS[ASTKGPSVFPLAPSSKSTSGGTAALGC

LVKDYFPEPVTVSWNSGALTSGVHTFPAVLQSSGLYSLSSVVTVPSSSLG

TQTYICNVNHKPSNTKVDKRVEPKSC]*DKTHTCPPCPAPELLGGP*EVQ

LVESGGGLVQPGRSLRLSCAAS<u>GFTFDDYA</u>MHWVRQAPGKGLEWVSA<u>ITW</u>

<u>NSGHIDYADSVEGRFT</u>ISRDNAKNSLYLQMNSLRAEDTAVYYC<u>AKVSYLS</u>

<u>TASSLDY</u>WGQGTLVTVSS

ACE-00-VL amino acid sequence:
(SEQ ID NO: 116)
EVQLVESGGGLVQPGGSLRLSCAAS<u>GFNIKDTY</u>IHWVRQAPGKGLEWVAR

<u>IYPTNGYTRYADSVKGRFT</u>ISADTSKNTAYLQMNSLRAEDTAVYYC<u>SRWG</u>

<u>GDGFYAMDY</u>WGQGTLVTVSS[ASTKGPSVFPLAPSSKSTSGGTAALGC

LVKDYFPEPVTVSWNSGALTSGVHTFPAVLQSSGLYSLSSVVTVPSSSLG

TQTYICNVNHKPSNTKVDKRVEPKSC]*DKTHTCPPCPAPELLGGP*DIQ

MTQSPSSLSASVGDRVTITCRAS<u>QGIRNY</u>LAWYQQKPGKAPKLLIY<u>AAST</u>

LQSGVPSRFSGSGSGTDFTLTISSLQPEDVATYYC<u>QRYNRAPYT</u>FGQGTK

VEIKR

ACE-00-LC amino acid sequence (anti-CD19 antibody light chain):
(SEQ ID NO: 117)
DIQMTQSPSSLSASVGDRVTITCRAS<u>QDVNTA</u>VAWYQQKPGKAPKLLIY<u>S</u>

<u>ASFLYS</u>GVPSRFSGSRSGTDFTLTISSLQPEDFATYYC<u>QQHYTTPPT</u>FGQ

GTKVEIK[<u>RSVAAPSVFIFPPSDEQLKSGTASVVCLLNNFYPREAKVQ</u>

<u>WKVDNALQSGNSQESVTEQDSKDSTYSLSSTLTLSKADYEKHKVYACEVT</u>

<u>HQGLSSPVTKSFNRGEC</u>]

The VH and VL amino acid sequences for the bivalent Fab region targeting Her2 and the monovalent Fv region targeting TNF alpha are listed in the table below:

TABLE 4

| VHs and VLs of ACE-00 | | |
|---|---|---|
| Fab region | VH: | VL: |
| (Anti-Her2) | EVQLVESGGGLVQPGGSLRLSCA ASGFNIKDTYIHWVRQAPGKGLE WVARIYPTNGYTRYADSVKGRFT ISADTSKNTAYLQMNSLRAEDTA VYYCSRWGGDGFYAMDYWGQG TLVTVSS (SEQ ID NO: 51) | DIQMTQSPSSLSASVGDRVTITCR ASQDVNTAVAWYQQKPGKAPKL LIYSASFLYSGVPSRFSGSRSGTDF TLTISSLQPEDFATYYCQQHYTTP PTFGQGTKVEIKR (SEQ ID NO: 52) |
| | CDR H1: GFNIKDTY (SEQ ID NO: 118) | CDR L1: QDVNTA (SEQ ID NO: 121) |
| | CDR H2: IYPTNGYT (SEQ ID NO: 119) | CDR L2: SAS (SEQ ID NO: 122) |

TABLE 4-continued

VHs and VLs of ACE-00

| | | | |
|---|---|---|---|
| | CDR H3: SRWGGDGFYAMDY (SEQ ID NO: 120) | | CDR L3: QQHYTTPPT (SEQ ID NO: 123) |
| Fv region (Anti-TNF alpha) | VH: EVQLVESGGGLVQPGRSLRLSCA ASGFTFDDYAMHWVRQAPGKGL EWVSAITWNSGHIDYADSVEGRF TISRDNAKNSLYLQMNSLRAEDT AVYYCAKVSYLSTASSLDYWGQ GTLVTVSS (SEQ ID NO: 53) | | VL: DIQMTQSPSSLSASVGDRVTITCR ASQGIRNYLAWYQQKPGKAPKLL IYAASTLQSGVPSRFSGSGSGTDF TLTISSLQPEDVATYYCQRYNRAP YTFGQGTKVEIKR (SEQ ID NO: 54) |
| | CDR H1: GFTFDDYA (SEQ ID NO: 124) | | CDR L1: QGIRNY (SEQ ID NO: 127) |
| | CDR H2: ITWNSGHI (SEQ ID NO: 125) | | CDR L2: AAS (SEQ ID NO: 128) |
| | CDR H3: AKVSYLSTASSLDY (SEQ ID NO: 126) | | CDR L3: QRYNRAPYT (SEQ ID NO: 129) |

Tri-transfection of DNAs encoding ACE-00-VH, ACE-00-VL, and ACE-00-LC were performed as briefly described below. Polyethylenimine (PEI) was used as a transfection reagent (used at a ratio of DNA:PEI=1:4 (w/w)). Six to seven days after the transfection when the cell survival rate was measured to be about 60% to 70%, the batch culture was discontinued, and the expression medium was collected and centrifuged (4,800 rpm, 30 min, 4° C.) to remove the debris. The supernatant was then filtered by using a 0.22 µm TOP-filter (Millipore, USA). Subsequently, the filtered supernatant including ACE-00 molecules underwent an affinity chromatography purification process using Hitrap™ KappaSelect (GE healthcare, USA), followed by dialysis with pH 7.4 PBS using Slide-A Lyzer Dialysis Cassette (Thermo, USA) for elution buffer change. Purified proteins were analyzed by SDS-PAGE, capillary electrophoresis, and size exclusion chromatography (SEC). The purified ACE-00 molecules were also analyzed for their purity using Agilent 2100 Bioanalyzer (Agilent Technologies, Germany) and SEC-HPLC (ThermoFisher, USA). The purity analysis was performed using the protocols provided by the manufactures.

As a control, bi-transfection of DNAs encoding ACE-00-VL and ACE-00-LC into HEK-293 cells was performed. SDS-PAGE was performed to identify the difference of assembly pattern of ACE-00 (containing two different heavy chain like chains ACE-00-VH and ACE-00-VL) and ACE-00-VL2 (containing two identical heavy chain like chains ACE-00-VL) (FIGS. 2A-2B).

Antibody is assembled and secreted as a tetramer $H_2L_2$ and the quality control machinery is very tightly regulated in Endoplasmic Reticulum (ER) by ER chaperones such as luminal binding protein (BiP) and protein disulfide isomerase (PDI). It was known that unfolded CH1 domain of heavy chain has a role of regulation of antibody assembly in BiP dependent manner. BiP may play a role in the heterodimer formation of CH1 and CL as well as in quality control mechanisms in antibody assembly by regulation of endoplasmic-reticulum-associated protein degradation (ERAD) (Lee Y. K. et al. BiP and immunoglobulin light chain cooperate to control the folding of heavy chain and ensure the fidelity of immunoglobulin assembly. *Mol Biol Cell*. 1999 July; 10(7):2209-19; Feige M. J. et al. An unfolded CH1 domain controls the assembly and secretion of IgG antibodies. *Mol Cell*. 2009 Jun. 12; 34(5):569-79; Feige M. J. et al. How antibodies fold. *Trends Biochem Sci.* 2010 April; 35(4):189-98. Each of these is incorporated herein by reference in its entirety). The possible interaction between VH domain and BiP was investigated to examine if two different ALiCE heavy chains can form heterodimer by specific interaction of VH-VL. CH1 or VH-CH1 truncated heavy chains, ΔCH1 or ΔVH-CH1, was cloned and delivered into HEK293 cells. Wild-type HC or truncated HC constructs was delivered into HEK293 cell. Cell lysates obtained from each transfectant were pulled down with protein A bead in order to identify antibody domains that may bind to BiP using anti-Fc-HRP (Thermo Fisher) and anti-BiP-HRP (R&D systems).

Without wishing to be bound by any particular mechanism or theory, the following results were obtained. Co-precipitated BiP was found by Western blot in ΔCH1 and WT-HC clone transfected lysate, indicating VH and BiP interaction (FIG. 2C). Furthermore, secreted polypeptide was detected in ΔVH-CH1 transfected expression medium, indicating that BiP can regulate the assembly and secretion of heavy chain by interaction with VH and/or CH1 domain of heavy chain (FIGS. 2C-2E). Potentially, antibody VH domain was also found to have a role of antibody assembly in BiP dependent manner in this study (see FIGS. 2C-2E). As shown in FIG. 2F, the heavy chain like chain of the binding molecule provided herein that contains two VH regions (one in a Fab region and one in a Fv region), i.e., ACE-00-VH in this study, contributes to the proper assembly of the binding molecule provided herein in mammalian expression system. Without this quality control system, many unwanted different combinations of polypeptide chains will be found in expression medium.

KappaSelect was used for affinity chromatography for ACE-00 and ACE-00-VL2 proteins. As shown in FIG. 2G, no unbound ACE was detected in flow through (F.T) lanes.

Figure 2H:
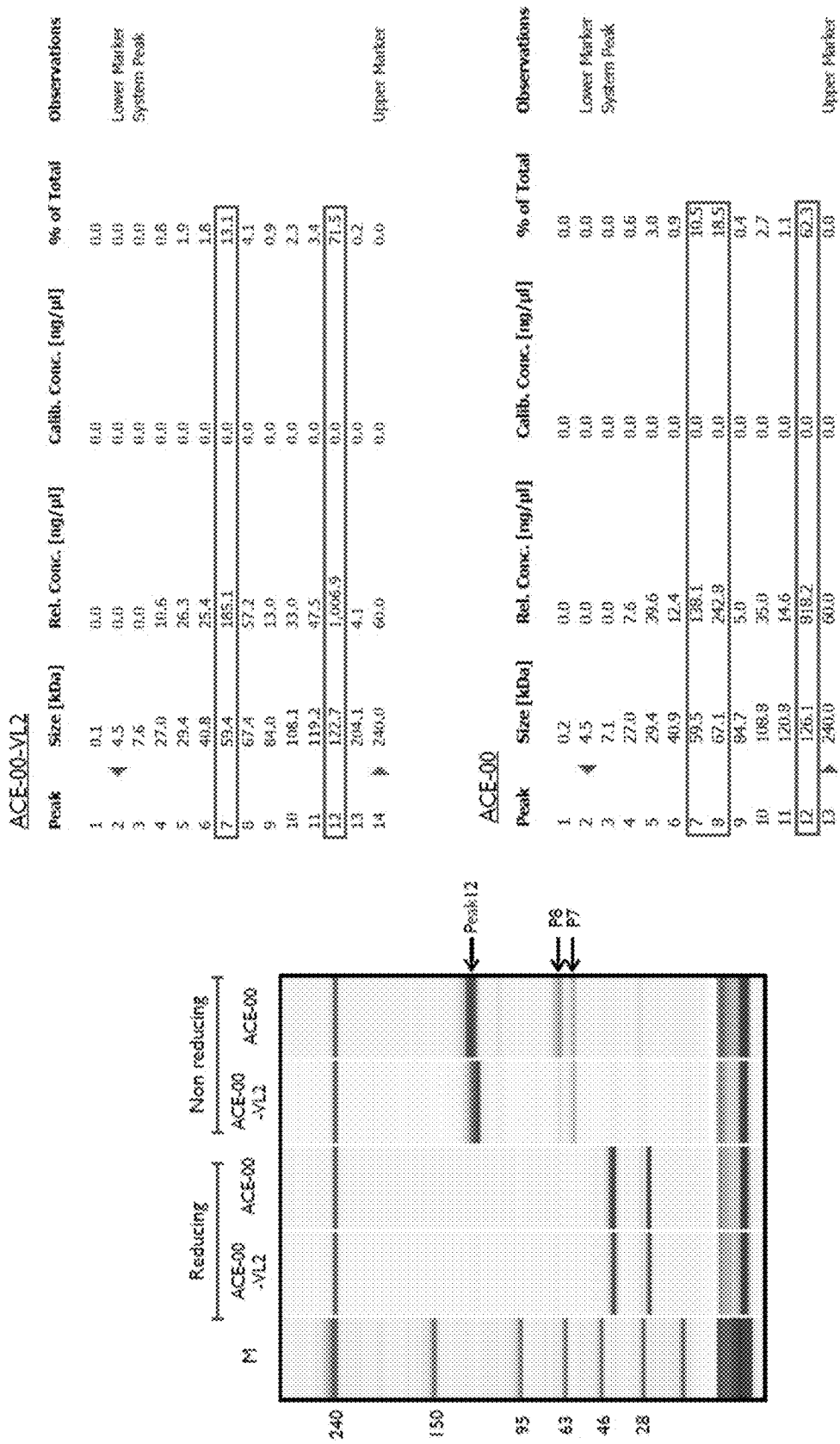
FIG. 2H shows the results of capillary electrophoresis performed to identify the molecular size differentiation between ACE-00-VL2 and ACE-00.

Capillary electrophoresis was then performed to identify the molecular size differentiation between ACE-00-VL2 and ACE-00. In FIG. 2H, the size of each peak in the figure (left) is shown in the table (right). Peak 7 represents ACE-00-VL/ACE-00-LC dimer complex and peak 8 represents ACE-00-VH/ACE-00-LC dimer complex. The molecular weight of ACE-00 is 4 kDa higher than ACE-00-VL2 (peak 12).

Figure 2I:
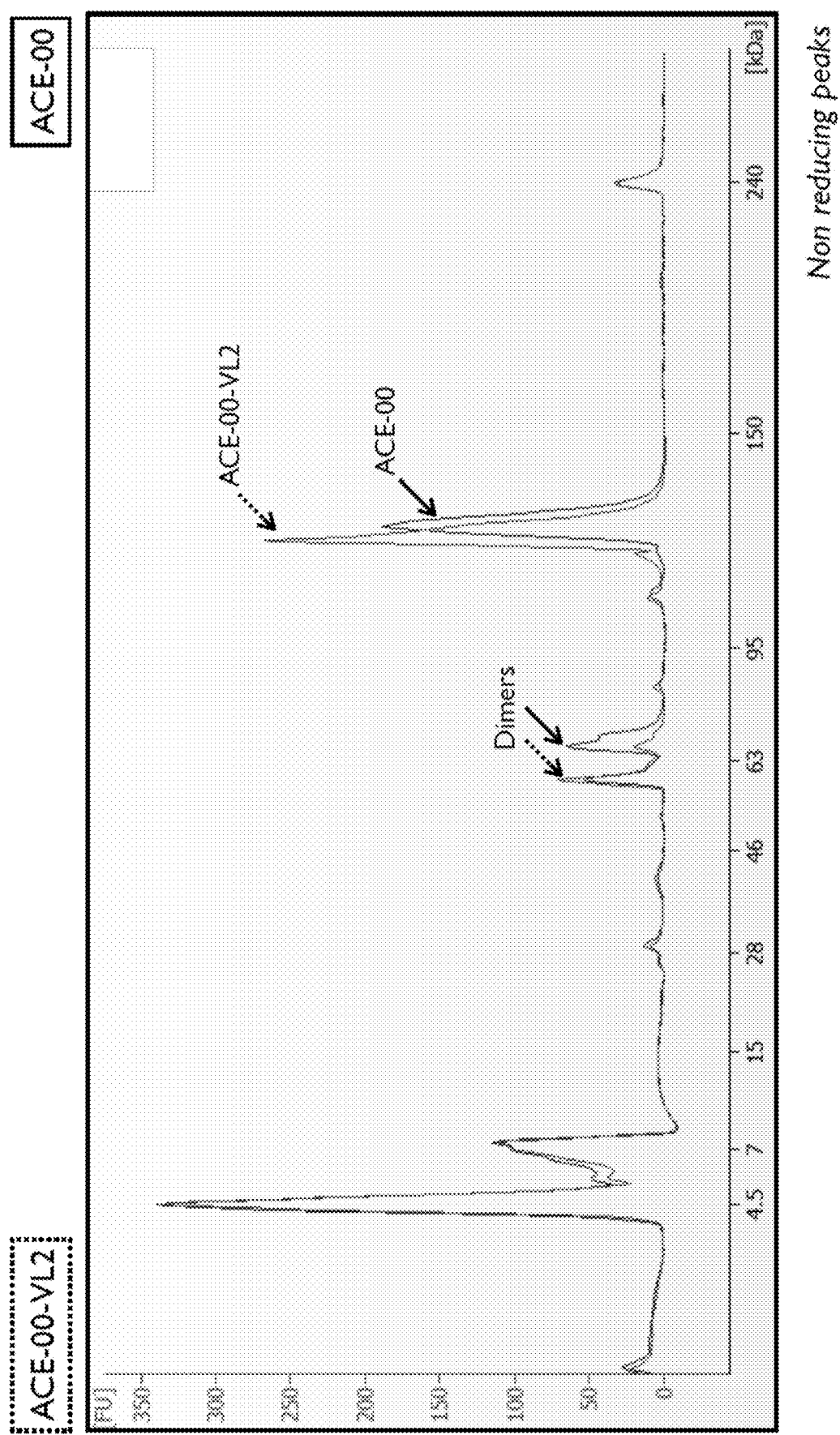
FIG. 2I shows the results of capillary electrophoresis showing the conformation of ACE-00 and ACE-00-VL2 molecules. Solid arrows indicate results of ACE-00; dashed arrows indicate results of ACE-00-VL2.
Figure 2J:
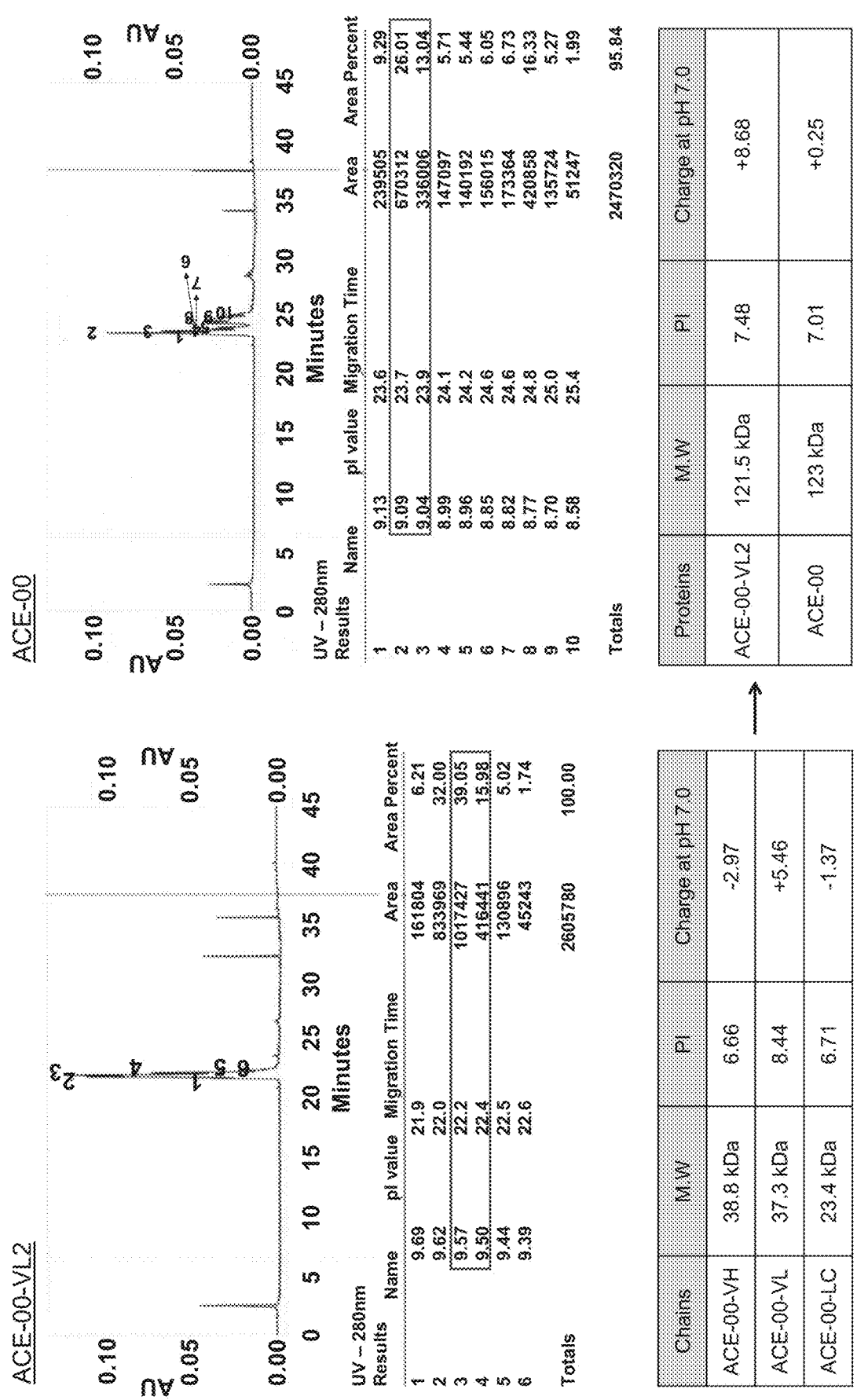
FIG. 2J shows the results of capillary isoelectric focusing performed to corroborate the heterodimerization between ACE-00-VH chain and ACE-00-VL chain.
Figure 2K:
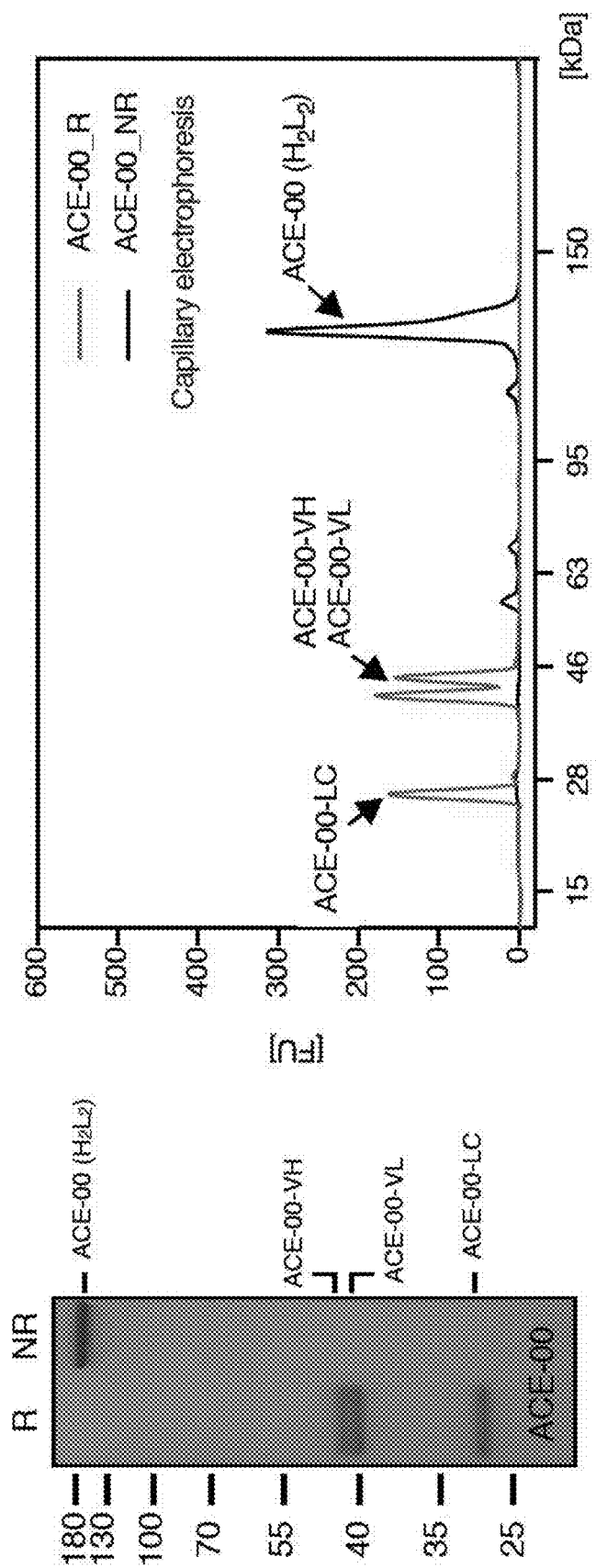
FIG. 2K shows the results of SDS-PAGE and capillary electrophoresis performed to identify the assembly pattern of ACE-00. "R" represents reducing; "NR" represents non reducing.
Figure 2L:
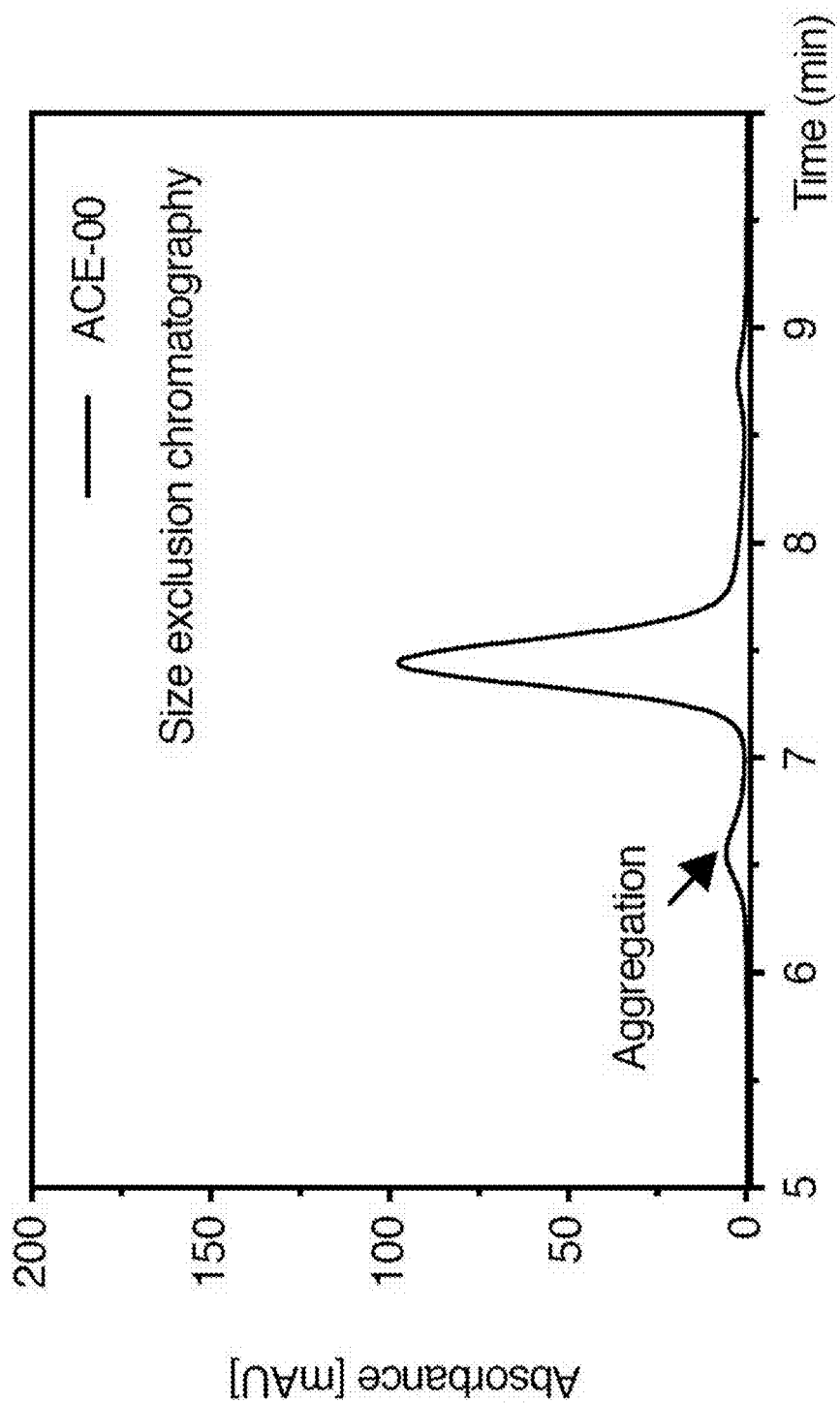
FIG. 2L shows the results of size exclusion chromatography of ACE-00.

Capillary electrophoresis results also showed the conformation of ACE-00 and ACE-00-VL2 molecules. As shown in FIG. 2I, most (almost 99%) of ACE-00 molecules were existed in a heterodimerized form. Capillary Isoelectric focusing was then performed and corroborated the heterodimerization between ACE-00-VH chain and ACE-00-VL chain. pI value was measured by cIEF for each of ACE-00 and ACE-00-VL2. The result is shown in FIG. 2J. The high efficiency of heterodimerization between ACE-00-VH and ACE-00-VL chains was corroborated in the SDS-PAGE and capillary electrophoresis results shown in FIG. 2K. As shown in FIG. 2L, a small portion of protein aggregates were found in size exclusion chromatography of ACE-00, and most ACE-00 was in soluble and uniform structure, which further corroborated the high efficiency of heterodimerization.

These results indicate that ACE-00 was properly expressed and assembled. These results also indicate that the heavy chain like chain of the binding molecule provided herein that contains two VH regions (one in a Fab region and one in a Fv region) contributes to the proper assembly of the binding molecule provided herein in mammalian expression system, and that VH-VL interaction in the Fv region is a major driving force to facilitate heterodimerization of two heavy chain like chains. Similar tests were performed for other exemplary binding molecules (e.g., ACE-05, ACE-10, and ACE-11) described below and same conclusions were arrived with for these molecules.

1.2. Construction and Expression of ACE-02

A HEK-293 transient expression system (Invitrogen, USA) was used for expressing ALiCE molecule ACE-02 provided herein. ACE-02 is composed of anti-CD19 and humanized anti-CD3 12F6 domains. ACE-02 contains two different heavy chain like chains (ACE-02-VH and ACE-02-VL) and two identical light chains (ACE-02-LC). The amino acid sequences of these three type of polypeptides are as follows:

ACE-02-VH amino acid sequence:
(SEQ ID NO: 88)
QVQLQQSGAELVRPGSSVKISCKASGYAFS<u>SYWMN</u>WVKQRPGQGLEWIGQ <u>IWPGDGDTNYNGKFKG</u>KATLTADESSSTAYMQLSSLASEDSAVYFCAR<u>RE</u>

<u>TTTVGRYYYAMDY</u>WGQGTTVTVSS[ASTKGPSVFPLAPSSKSTSGGTA

ALGCLVKDYFPEPVTVSWNSGALTSGVHTFPAVLQSSGLYSLSSVVTVPS

SSLGTQTYICNVNHKPSNTKVDKRVEPKSC]*DKTHTCPPCPAPELLGG*

*P*QVQLVQSGGGVVQPGRSLRLSCKAS<u>GYTFTSYT</u>MHWVRQAPGKGLEWIG

<u>YINPSSGYT</u>KYNQKFKDRFTISADKSKSTAFLQMDSLRPEDTGVYFCAR<u>W</u>

<u>QDYDVYFDY</u>WGQGTPVTVSS

ACE-02-VL amino acid sequence:
(SEQ ID NO: 89)
QVQLQQSGAELVRPGSSVKISCKASGYAFS<u>SYWMN</u>WVKQRPGQGLEWIGQ <u>IWPGDGDTNYNGKFKG</u>KATLTADESSSTAYMQLSSLASEDSAVYFCAR<u>RE</u>

<u>TTTVGRYYYAMDY</u>WGQGTTVTVSS[ASTKGPSVFPLAPSSKSTSGGTA

ALGCLVKDYFPEPVTVSWNSGALTSGVHTFPAVLQSSGLYSLSSVVTVPS

SSLGTQTYICNVNHKPSNTKVDKRVEPKSC]*DKTHTCPPCPAPELLGG*

*P*DIQMTQSPSSLSASVGDRVTMTCRA<u>SSSVSYMH</u>WYQQTPGKAPKPWIYA

<u>TSNLASG</u>VPSRFSGSGSGTDYTLTISSLQPEDIATYYC<u>QQWSSNPPT</u>FGQ

GTKLQITR

ACE-02-LC amino acid sequence (anti-CD19 antibody light chain):
(SEQ ID NO: 90)
DIQLTQSPASLAVSLGQRATISCKAS<u>QSVDYDGDSYLN</u>WYQQIPGQPPKL LIY<u>DASNLVS</u>GIPPRFSGSGSGTDFTLNIHPVEKVDAATYHC<u>QQSTEDPW</u>

<u>T</u>FGGGTKLEIK[RTVAAPSVFIFPPSDEQLKSGTASVVCLLNNFYPRE

AKVQWKVDNALQSGNSQESVTEQDSKDSTYSLSSTLTLSKADYEKHKVYA

CEVTHQGLSSPVTKSFNRGEC]

The VH and VL amino acid sequences and CDR sequences therein for the first antigen binding domain bivalent Fab region targeting CD19 and the second antigen binding domain monovalent Fv region of humanized 12F6 are listed in the table below:

TABLE 5

| | | VHs, VLs and CDRs of ACE-02 | |
|---|---|---|---|
| Fab region (Anti-CD19) | VH: QVQLQQSGAELVRPGSSVKISCKA SGYAFSSYWMNWVKQRPGQGLE WIGQIWPGDGDTNYNGKFKGKAT LTADESSSTAYMQLSSLASEDSAV YFCARRETTTVGRYYYAMDYWG QGTTVTVSS (SEQ ID NO: 61) | | VL: DIQLTQSPASLAVSLGQRATISCK ASQSVDYDGDSYLNWYQQIPGQP PKLLIYDASNLVSGIPPRFSGSGSG TDFTLNIHPVEKVDAATYHCQQS TEDPWTFGGGTKLEIK (SEQ ID NO: 65) |
| | CDR H1: SYWMN (SEQ ID NO: 62) | | CDR L1: QSVDYDGDSY (SEQ ID NO: 66) |
| | CDR H2: QIWPGDGDTNYNGKFKG (SEQ ID NO: 63) | | CDR L2: DAS (SEQ ID NO: 67) |
| | CDR H3: RETTTVGRYYYAMDY (SEQ ID NO: 64) | | CDR L3: QQSTEDPWT (SEQ ID NO: 68) |
| Fv region (Anti-CD3) | VH: QVQLVQSGGGVVQPGRSLRLSCK ASGYTFTSYTMHWVRQAPGKGLE WIGYINPSSGYTKYNQKFKDRFTIS ADKSKSTAFLQMDSLRPEDTGVYF CARWQDYDVYFDYWGQGTPVTV SS (SEQ ID NO: 69) | | VL: DIQMTQSPSSLSASVGDRVTMTC RASSSVSYMHWYQQTPGKAPKP WIYATSNLASGVPSRFSGSGSGTD YTLTISSLQPEDIATYYCQQWSSN PPTFGQGTKLQITR (SEQ ID NO: 73) |
| | CDR H1: GYTFTSYT (SEQ ID NO: 70) | | CDR L1: SSSVSY (SEQ ID NO: 74) |
| | CDR H2: INPSSGYT (SEQ ID NO: 71) | | CDR L2: ATS (SEQ ID NO: 75) |
| | CDR H3: ARWQDYDVYFDY (SEQ ID NO: 72) | | CDR L3: QQWSSNPPT (SEQ ID NO: 76) |

DNA sequences encoding ACE-02-VH, ACE-02-VL and ACE-02-LC are as follows:

ACE-02-VH nucleotide sequence:
(SEQ ID NO: 100)
CAGGTTCAATTGCAGCAAAGCGGGGCTGAGTTGGTACGGCCTGGGTCCAG CGTGAAGATATCATGTAAGGCTtctGGATATGCCTTCTCCTCTTACTGGA

TGAACTGGGTCAAGCAACGGCCAGGACAAGGCCTGGAGTGGATTGGGCAA

ATATGGCCCGGGGACGGAGATACTAATTATAATGGCAAGTTTAAGGGGAA

AGCTACACTGACCGCAGACGAAAGCTCCTCTACGGCCTATATGCAGCTCT

CATCTCTTGCGTCCGAAGATAGTGCAGTATATTTTTGTGCGCGCCGCGAG

ACCACCACGGTTGGGAGGTACTATTACGCGATGGATTACTGGGGCCAGGG

GACTACAGTTACGGTTTCATCAGCTAGCACCAAGGGCCCATCGGTCTTCC

CCCTGGCACCCTCCTCCAAGAGCACCTCTGGGGGCACAGCGGCCCTGGGC

TGCCTGGTCAAGGACTACTTCCCCGAACCGGTGACGGTGTCGTGGAACTC

AGGCGCCCTGACCAGCGGCGTGCACACCTTCCCGGCTGTCCTACAGTCCT

CAGGACTCTACTCCCTCAGCAGCGTGGTGACCGTGCCCTCCAGCAGCCTG

GGCACCCAGACCTACATCTGCAACGTGAATCACAAGCCCAGCAACACCAA

GGTGGACAAGAGAGTTGAGCCCAAATCTTGTGACAAAACTCACACATGCC

CACCGTGCCCAGCACCTGAACTCCTGGGGGGAccGCAGGTGCAGCTGGTG

CAGAGCGGCGGCGGCGTGGTGCAGCCCGGCCGCAGCCTGCGCCTGAGCTG

CAAGGCCAGCGGCTACACCTTCACCAGCTACACCATGCACTGGGTGCGCC

AGGCCCCCGGCAAGGGCCTGGAGTGGATCGGCTACATCAACCCCAGCAGC

GGCTACACCAAGTACAACCAGAAGTTCAAGGACCGCTTCACCATCAGCGC

CGACAAGAGCAAGAGCACCGCCTTCCTGCAGATGGACAGCCTGCGCCCCG

AGGACACCGGCGTGTACTTCTGCGCCCGCTGGCAGGACTACGACGTGTAC

TTCGACTACTGGGGCCAGGGCACCCCCGTGACCGTGAGCAGCTAA

ACE-02-VL nucleotide sequence:
(SEQ ID NO: 101)
CAGGTTCAATTGCAGCAAAGCGGGGCTGAGTTGGTACGGCCTGGGTCCAG

CGTGAAGATATCATGTAAGGCTTCTGGATATGCCTTCTCCTCTTACTGGA

TGAACTGGGTCAAGCAACGGCCAGGACAAGGCCTGGAGTGGATTGGGCAA

ATATGGCCCGGGGACGGAGATACTAATTATAATGGCAAGTTTAAGGGGAA

AGCTACACTGACCGCAGACGAAAGCTCCTCTACGGCCTATATGCAGCTCT

CATCTCTTGCGTCCGAAGATAGTGCAGTATATTTTTGTGCGCGCCGCGAG

ACCACCACGGTTGGGAGGTACTATTACGCGATGGATTACTGGGGCCAGGG

GACTACAGTTACGGTTTCATCAGCTAGCACCAAGGGCCCATCGGTCTTCC

CCCTGGCACCCTCCTCCAAGAGCACCTCTGGGGGCACAGCGGCCCTGGGC

TGCCTGGTCAAGGACTACTTCCCCGAACCGGTGACGGTGTCGTGGAACTC

AGGCGCCCTGACCAGCGGCGTGCACACCTTCCCGGCTGTCCTACAGTCCT

CAGGACTCTACTCCCTCAGCAGCGTGGTGACCGTGCCCTCCAGCAGCCTG

GGCACCCAGACCTACATCTGCAACGTGAATCACAAGCCCAGCAACACCAA

GGTGGACAAGAGAGTTGAGCCCAAATCTTGTGACAAAACTCACACATGCC

CACCGTGCCCAGCACCTGAACTCCTGGGGGGACCGGACATCCAGATGACC

CAGAGCCCCAGCAGCCTGAGCGCCAGCGTGGGCGACCGCGTGACCATGAC

CTGCCGCGCCAGCAGCAGCGTGAGCTACATGCACTGGTACCAGCAGACCC

CCGGCAAGGCCCCCAAGCCCTGGATCTACGCCACCAGCAACCTGGCCAGC

GGCGTGCCCAGCCGCTTCAGCGGCAGCGGCAGCGGCACCGACTACACCCT

GACCATCAGCAGCCTGCAGCCCGAGGACATCGCCACCTACTACTGCCAGC

AGTGGAGCAGCAACCCCCCCACCTTCGGCCAGGGCACCAAGCTGCAGATC

ACCCGCTAA

ACE-02-LC nucleotide sequence (anti-CD19 antibody light chain nucleotide sequence):
(SEQ ID NO: 102)
GATATTCAACTCACGCAATCTCCAGCAAGTCTCGCAGTTAGTTTGGGGCA

GCGAGCTACAATAAGTTGCAAGGCGAGCCAATCCGTGGATTATGATGGAG

ACAGCTATCTTAACTGGTATCAGCAAATTCCAGGCCAGCCACCCAAGTTG

CTGATCTACGACGCGTCAAACCTGGTCTCAGGGATCCCTCCAAGATTTAG

CGGCTCAGGTTCAGGTACGGATTTTACGCTCAATATCCATCCTGTAGAGA

AGGTTGATGCAGCTACATACCACTGTCAACAGAGTACCGAGGATCCTTGG

ACCTTCGGAGGCGGTACAAAGCTGGAGATCAAGAGAACCGTGGCTGCACC

ATCTGTCTTCATCTTCCCGCCATCTGATGAGCAGTTGAAATCTGGAACTG

CCTCTGTTGTGTGCCTGCTGAATAACTTCTATCCCAGAGAGGCCAAAGTA

CAGTGGAAGGTGGATAACGCCCTCCAATCGGGTAACTCCCAGGAGAGTGT

CACAGAGCAGGACAGCAAGGACAGCACCTACAGCCTCAGCAGCACCCTGA

CGCTGAGCAAAGCAGACTACGAGAAACACAAAGTCTACGCCTGCGAAGTC

ACCCATCAGGGCCTGAGCTCGCCCGTCACAAAGAGCTTCAACAGGGGAGA

GTGTTAA

Figure 3:
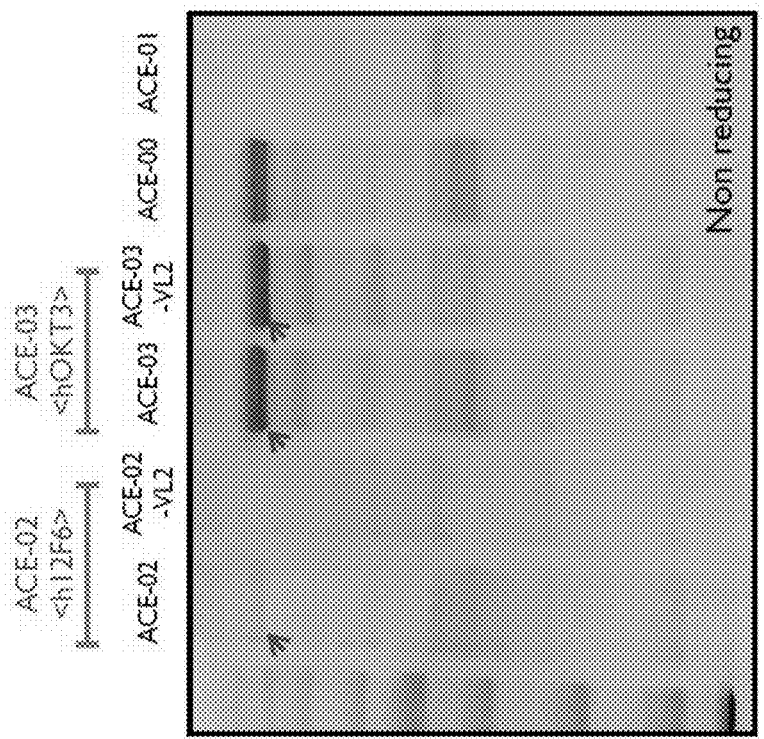
FIG. 3 shows the result of SDS-PAGE (under reducing (left) and non-reducing (right) conditions) performed to identify the expression and assembly of ACE-02, ACE-02-VL2, ACE-03, ACE-03-VL2, ACE-00 and ACE-01. ACE-02 contains the second antigen as humanized 12F6 (h12F6, an anti-CD3 antibody), and ACE-03 contains the second antigen as humanized OKT3 (hOKT3, an anti-CD3 antibody). The arrows indicate the bands of assembled ACE-02, ACE-03 and ACE-03-VL2 respectively under non-reducing condition.
Figure 3:
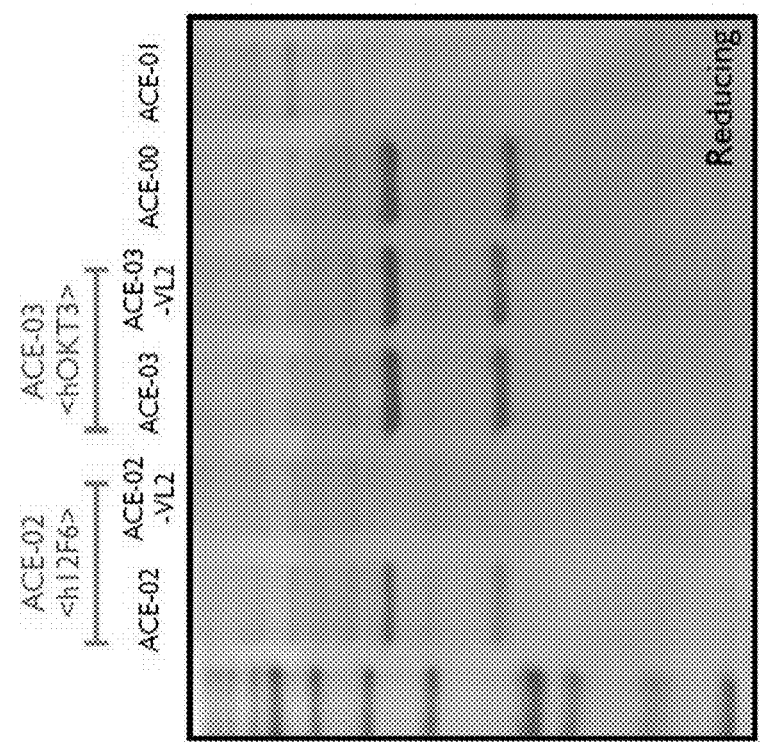

In FIG. 3, the SDS-PAGE results show the expression of ACE-02, ACE-03, ACE-00 and ACE-01. It also shows the difference in assembly patterns of ACE-02 and ACE-02-VL2 and the difference in assembly patterns of ACE-03 and ACE-03-VL2. ACE-01 has parent antibodies of anti-CD19 Ab targeting the first antigen and murine OKT3 targeting the second antigen. These results suggest that ACE-02 was properly expressed and assembled.

1.3. Construction and Expression of ACE-03

A HEK-293 transient expression system (Invitrogen, USA) was used for expressing ALiCE molecule ACE-03 provided herein. ACE-03 is composed of anti-CD19 and humanized anti-CD3 OKT3 domains. ACE-03 contains two different heavy chain like chains (ACE-03-VH and ACE-03-VL) and two identical light chains (ACE-03-LC). The amino acid sequences of these three type of polypeptides are as follows:

ACE-03-VH amino acid sequence:
(SEQ ID NO: 91)
QVQLQQSGAELVRPGSSVKISCKASGYAFS<u>SYWMN</u>WVKQRPGQGLEWIGQ IWPGDGDTNYNGKFKGKATLTADESSSTAYMQLSSLASEDSAVYFCAR<u>RE</u>

<u>TTTVGRYYYAMDY</u>WGQGTTVTVSS[ASTKGPSVFPLAPSSKSTSGGTA

ALGCLVKDYFPEPVTVSWNSGALTSGVHTFPAVLQSSGLYSLSSVVTVPS

SSLGTQTYICNVNHKPSNTKVDKRVEPKSC]*DKTHTCPPCPAPELLGG*

-continued

PVQLVQSGGGVVQPGRSLRLSCKAS<u>GYTFTRYTMHW</u>VRQAPGKGLEWIGY

<u>INPSRGYT</u>NYNQKVKDRFTISTDKSKSTAFLQMDSLRPEDTAVYYC<u>ARYY</u>

<u>DDHYCLDY</u>WGQGTPVTVSS

ACE-03-VL amino acid sequence:
(SEQ ID NO: 92)
QVQLQQSGAELVRPGSSVKISCKASGYAFS<u>SYWMN</u>WVKQRPGQGLEWIGQ <u>IWPGDGDTNYNGKFKG</u>KATLTADESSSTAYMQLSSLASEDSAVYFCARRE <u>TTTVGRYYYAMDY</u>WGQGTTVTVSS[ASTKGPSVFPLAPSSKSTSGGTA

ALGCLVKDYFPEPVTVSWNSGALTSGVHTFPAVLQSSGLYSLSSVVTVPS

SSLGTQTYICNVNHKPSNTKVDKRVEPKSC]*DKTHTCPPCPAPELLGG*

*P*DIQMTQSPSSLSASVGDRVTITCSAS<u>SSVSY</u>MNWYQQTPGKAPKRWIY<u>D</u>

<u>TS</u>KLASGVPSRFSGSGSGTDYTFTISSLQPEDIATYYC<u>QQWSSNPFT</u>FGQ

GTKLQITR

ACE-03-LC amino acid sequence (anti-CD19 antibody light chain):
(SEQ ID NO: 90)
DIQLTQSPASLAVSLGQRATISCKAS<u>QSVDYDGDSY</u>LNWYQQIPGQPPKL LIY<u>DAS</u>NLVSGIPPRFSGSGSGTDFTLNIHPVEKVDAATYHC<u>QQSTEDPW</u>

<u>T</u>FGGGTKLEIK[RTVAAPSVFIFPPSDEQLKSGTASVVCLLNNFYPRE

AKVQWKVDNALQSGNSQESVTEQDSKDSTYSLSSTLTLSKADYEKHKVYA

CEVTHQGLSSPVTKSFNRGEC]

The VH and VL amino acid sequences and CDR sequences therein for the first antigen binding domain bivalent Fab region targeting CD19 and the second antigen binding domain monovalent Fv region of humanized OKT3 are listed in the table below:

TABLE 6

VHs, VLs and CDRs of ACE-03

| | | |
|---|---|---|
| Fab region (Anti-CD19) | VH: QVQLQQSGAELVRPGSSVKISCKA SGYAFSSYWMNWVKQRPGQGLE WIGQIWPGDGDTNYNGKFKGKAT LTADESSSTAYMQLSSLASEDSAV YFCARRETTTVGRYYYAMDYWG QGTTVTVSS (SEQ ID NO: 61) CDR H1: SYWMN (SEQ ID NO: 62) CDR H2: QIWPGDGDTNYNGKFKG (SEQ ID NO: 63) CDR H3: RETTTVGRYYYAMDY (SEQ ID NO: 64) | VL: DIQLTQSPASLAVSLGQRATISCK ASQSVDYDGDSYLNWYQQIPGQP PKLLIYDASNLVSGIPPRFSGSGSG TDFTLNIHPVEKVDAATYHCQQS TEDPWTFGGGTKLEIK (SEQ ID NO: 65) CDR L1: QSVDYDGDSY (SEQ ID NO: 66) CDR L2: DAS (SEQ ID NO: 67) CDR L3: QQSTEDPWT (SEQ ID NO: 68) |
| Fv region (Anti-CD3) | VH: VQLVQSGGGVVQPGRSLRLSCKA SGYTFTRYTMHWVRQAPGKGLE WIGYINPSRGYTNYNQKVKDRFTI STDKSKSTAFLQMDSLRPEDTAVY YCARYYDDHYCLDYWGQGTPVT VSS (SEQ ID NO: 77) CDR H1: GYTFTRYT (SEQ ID NO: 78) CDR H2: INPSRGYT (SEQ ID NO: 79) CDR H3: ARYYDDHYCLDY (SEQ ID NO: 80) | VL: DIQMTQSPSSLSASVGDRVTITCS ASSSVSYMNWYQQTPGKAPKRW IYDTSKLASGVPSRFSGSGSGTDY TFTISSLQPEDIATYYCQQWSSNPF TFGQGTKLQITR (SEQ ID NO: 81) CDR L1: SSVSY (SEQ ID NO: 82) CDR L2: DTS (SEQ ID NO: 83) CDR L3: QQWSSNPFT (SEQ ID NO: 84) |

DNA sequences encoding ACE-03-VH, ACE-03-VL and ACE-03-LC are as follows:

ACE-03-VH nucleotide sequence:
(SEQ ID NO: 103)
CAGGTTCAATTGCAGCAAAGCGGGGCTGAGTTGGTACGGCCTGGGTCCAG CGTGAAGATATCATGTAAGGCTtctGGATATGCCTTCTCCTCTTACTGGA

TGAACTGGGTCAAGCAACGGCCAGGACAAGGCCTGGAGTGGATTGGGCAA

ATATGGCCCGGGGACGGAGATACTAATTATAATGGCAAGTTTAAGGGGAA

AGCTACACTGACCGCAGACGAAAGCTCCTCTACGGCCTATATGCAGCTCT

CATCTCTTGCGTCCGAAGATAGTGCAGTATATTTTTGTGCGCGCCGCGAG

ACCACCACGGTTGGGAGGTACTATTACGCGATGGATTACTGGGGCCAGGG

GACTACAGTTACGGTTTCATCAGCTAGCACCAAGGGCCCATCGGTCTTCC

CCCTGGCACCCTCCTCCAAGAGCACCTCTGGGGGCACAGCGGCCCTGGGC

TGCCTGGTCAAGGACTACTTCCCCGAACCGGTGACGGTGTCGTGGAACTC

AGGCGCCCTGACCAGCGGCGTGCACACCTTCCCGGCTGTCCTACAGTCCT

CAGGACTCTACTCCCTCAGCAGCGTGGTGACCGTGCCCTCCAGCAGCCTG

GGCACCCAGACCTACATCTGCAACGTGAATCACAAGCCCAGCAACACCAA

GGTGGACAAGAGAGTTGAGCCCAAATCTTGTGACAAAACTCACACATGCC

CACCGTGCCCAGCACCTGAACTCCTGGGGGGAccGGTGCAGCTGGTGCAG

AGCGGCGGCGGCGTGGTGCAGCCCGGCCGCAGCCTGCGCCTGAGCTGCAA

GGCCAGCGGCTACACCTTCACCCGCTACACCATGCACTGGGTGCGCCAGG

CCCCCGGCAAGGGCCTGGAGTGGATCGGCTACATCAACCCCAGCCGCGGC

TACACCAACTACAACCAGAAGGTGAAGGACCGCTTCACCATCAGCACCGA

CAAGAGCAAGAGCACCGCCTTCCTGCAGATGGACAGCCTGCGCCCCGAGG

ACACCGCCGTGTACTACTGCGCCCGCTACTACGACGACCACTACTGCCTG

GACTACTGGGGCCAGGGCACCCCCGTGACCGTGAGCAGCTAA

ACE-03-VL nucleotide sequence:
(SEQ ID NO: 104)
CAGGTTCAATTGCAGCAAAGCGGGGCTGAGTTGGTACGGCCTGGGTCCAG CGTGAAGATATCATGTAAGGCTtctGGATATGCCTTCTCCTCTTACTGGA

TGAACTGGGTCAAGCAACGGCCAGGACAAGGCCTGGAGTGGATTGGGCAA

ATATGGCCCGGGGACGGAGATACTAATTATAATGGCAAGTTTAAGGGGAA

AGCTACACTGACCGCAGACGAAAGCTCCTCTACGGCCTATATGCAGCTCT

CATCTCTTGCGTCCGAAGATAGTGCAGTATATTTTTGTGCGCGCCGCGAG

ACCACCACGGTTGGGAGGTACTATTACGCGATGGATTACTGGGGCCAGGG

GACTACAGTTACGGTTTCATCAGCTAGCACCAAGGGCCCATCGGTCTTCC

CCCTGGCACCCTCCTCCAAGAGCACCTCTGGGGGCACAGCGGCCCTGGGC

TGCCTGGTCAAGGACTACTTCCCCGAACCGGTGACGGTGTCGTGGAACTC

AGGCGCCCTGACCAGCGGCGTGCACACCTTCCCGGCTGTCCTACAGTCCT

CAGGACTCTACTCCCTCAGCAGCGTGGTGACCGTGCCCTCCAGCAGCCTG

GGCACCCAGACCTACATCTGCAACGTGAATCACAAGCCCAGCAACACCAA

GGTGGACAAGAGAGTTGAGCCCAAATCTTGTGACAAAACTCACACATGCC

CACCGTGCCCAGCACCTGAACTCCTGGGGGGAccGGACATCCAGATGACC

CAGAGCCCCAGCAGCCTGAGCGCCAGCGTGGGCGACCGCGTGACCATCAC

CTGCAGCGCCAGCAGCAGCGTGAGCTACATGAACTGGTACCAGCAGACCC

CCGGCAAGGCCCCCAAGCGCTGGATCTACGACACCAGCAAGCTGGCCAGC

GGCGTGCCCAGCCGCTTCAGCGGCAGCGGCAGCGGCACCGACTACACCTT

CACCATCAGCAGCCTGCAGCCCGAGGACATCGCCACCTACTACTGCCAGC

AGTGGAGCAGCAACCCCTTCACCTTCGGCCAGGGCACCAAGCTGCAGATC

ACCCGCTAA

ACE-03-LC nucleotide sequence (anti-CD19 antibody light chain nucleotide sequence):
(SEQ ID NO: 102)
GATATTCAACTCACGCAATCTCCAGCAAGTCTCGCAGTTAGTTTGGGGCA

GCGAGCTACAATAAGTTGCAAGGCGAGCCAATCCGTGGATTATGATGGAG

ACAGCTATCTTAACTGGTATCAGCAAATTCCAGGCCAGCCACCCAAGTTG

CTGATCTACGACGCGTCAAACCTGGTCTCAGGGATCCCTCCAAGATTTAG

CGGCTCAGGTTCAGGTACGGATTTTACGCTCAATATCCATCCTGTAGAGA

AGGTTGATGCAGCTACATACCACTGTCAACAGAGTACCGAGGATCCTTGG

ACCTTCGGAGGCGGTACAAAGCTGGAGATCAAGAGAACCGTGGCTGCACC

ATCTGTCTTCATCTTCCCGCCATCTGATGAGCAGTTGAAATCTGGAACTG

CCTCTGTTGTGTGCCTGCTGAATAACTTCTATCCCAGAGAGGCCAAAGTA

CAGTGGAAGGTGGATAACGCCCTCCAATCGGGTAACTCCCAGGAGAGTGT

CACAGAGCAGGACAGCAAGGACAGCACCTACAGCCTCAGCAGCACCCTGA

CGCTGAGCAAAGCAGACTACGAGAAACACAAAGTCTACGCCTGCGAAGTC

ACCCATCAGGGCCTGAGCTCGCCCGTCACAAAGAGCTTCAACAGGGGAGA

GTGTTAA

In FIG. 3, the SDS-PAGE results show the expression of ACE-02, ACE-03, ACE-00 and ACE-01. It also shows the difference in assembly patterns of ACE-02 and ACE-02-VL2 and the difference in assembly patents of ACE-03 and ACE-03-VL2. These results suggest that ACE-03 was properly expressed and assembled.

1.4. Construction and Expression of ACE-04

A HEK-293 transient expression system (Invitrogen, USA) was used for expressing ALiCE molecule ACE-04 provided herein. ACE-04 is composed of anti-PD-L1 and chimeric OKT3 Fab domains (see FIG. 4A). ACE-04 contains two different heavy chain like chains ACE-04-VH (VL-CL-VH-CH1) and ACE-04-VL (VH-CH1-VL-CL) and two identical light chains (ACE-04-LC). The amino acid sequences of these three type of polypeptides are as follows:

ACE-04-VH amino acid sequence:
(SEQ ID NO: 93)
QMQLVQSGAEVKKPGSSVKVSCKASGGTFSSYAISWVRQAPGQGLEWMGR

IIPILGIANYAQKFQGRVTITADKSTSTAYMELSSLRSEDTAVYYCAKPR

DGYNLVAFDIWGQGTMVTVSS[ASTKGPSVFPLAPSSKSTSGGTAALG

CLVKDYFPEPVTVSWNSGALTSGVHTFPAVLQSSGLYSLSSVVTVPSSSL

GTQTYICNVNHKPSNTKVDKKVEPKSC]DKTHTCPPCPAPELLGGPgg ggsQVQLQQSGAELARPGASVKMSCKASGYTFTRYTMHWVKQRPGQGLEW -continued

IGYINPSRGYTNYNQKFKDKATLTTDKSSSTAYMQLSSLTSEDSAVYYCA

RYYDDHYCLDYWGQGTTVTVSA[ASTKGPSVFPLAPSSKSTSGGTAAL

GCLVKDYFPEPVTVSWNSGALTSGVHTFPAVLQSSGLYSLSSVVTVPSSS

LGTQTYICNVNHKPSNTKVDKRVEPKSC]

ACE-04-VL amino acid sequence:
(SEQ ID NO: 94)
QMQLVQSGAEVKKPGSSVKVSCKASGGTFSSYAISWVRQAPGQGLEWMGR

IIPILGIANYAQKFQGRVTITADKSTSTAYMELSSLRSEDTAVYYCAKPR

DGYNLVAFDIWGQGTMVTVSS[ASTKGPSVFPLAPSSKSTSGGTAALG

CLVKDYFPEPVTVSWNSGALTSGVHTFPAVLQSSGLYSLSSVVTVPSSSL

GTQTYICNVNHKPSNTKVDKKVEPKSC]*DKTHTCPPCPAPELLGGP*gg gg*s*QIVLTQSPAIMSASPGEKVTMTCSASSSVSYMNWYQQKSGTSPKRWI

YDTSKLASGVPAHFRGSGSGTSYSLTISGMEAEDAATYYCQQWSSNPFTF

GSGTKLEIN[RTVAAPSVFIFPPSDEQLKSGTASVVCLLNNFYPREAK

VQWKVDNALQSGNSQESVTEQDSKDSTYSLSSTLTLSKADYEKHKVYACE

VTHQGLSSPVTKSFNRGEC]

ACE-04-LC amino acid sequence (anti-PD-L1 antibody light chain):
(SEQ ID NO: 95)
QLVLTQPPSVGAPGQRVTISCTGSSSNIGAGYDVHWYQQLPGAAPKLLI

YGDINRPSGVPDRFSGSKSGISASLAITGLQAEDEADYYCQSYDSSLSGG

VFGGGTKLTVL[RSVAAPSVFIFPPSDEQLKSGTASVVCLLNNFYPRE

AKVQWKVDNALQSGNSQESVTEQDSKDSTYSLSSTLTLSKADYEKHKVYA

CEVTHQGLSSPVTKSFNRGEC]

The VH and VL amino acid sequences and CDR sequences therein for the first antigen binding domain bivalent Fab region targeting PD-L1 and the second antigen binding domain monovalent Fv region of chimeric OKT3 Fab region are listed in the table below:

DNA sequences encoding ACE-04-VH, ACE-04-VL and ACE-04-LC are as follows:

ACE-04-VH nucleotide sequence:
(SEQ ID NO: 105)
CAGATGCAGCTGGTGCAGTCTGGGGCTGAGGTGAAGAAGCCTGGGTCCTC

GGTGAAGGTCTCCTGCAAGGCTTCTGGAGGCACCTTCAGCAGCTATGCTA

TCAGCTGGGTGCGACAGGCCCCTGGACAAGGGCTTGAGTGGATGGGAAGG

ATCATCCCTATCCTTGGTATAGCAAACTACGCACAGAAGTTCCAGGGCAG

AGTCACGATTACCGCGGACAAATCCACGAGCACAGCCTACATGGAGCTGA

GCAGCCTGAGATCTGAGGACACGGCCGTGTATTACTGTGCGAAACCGAGA

GATGGCTACAATTTGGTTGCTTTTGATATCTGGGGCCAAGGGACGATGGT

CACCGTCTCCTCAGCTAGCACCAAGGGCCCATCGGTCTTCCCCCTGGCAC

CCTCCTCCAAGAGCACCTCTGGGGGCACAGCGGCCCTGGGCTGCCTGGTC

AAGGACTACTTCCCCGAACCGGTGACGGTGTCGTGGAACTCAGGCGCCCT

GACCAGCGGCGTGCACACCTTCCCGGCTGTCCTACAGTCCTCAGGACTCT

ACTCCCTCAGCAGCGTGGTGACCGTGCCCTCCAGCAGCCTGGGCACCCAG

ACCTACATCTGCAACGTGAATCACAAGCCCAGCAACACCAAGGTGGACAA

GAAAGTTGAGCCCAAATCTTGTGACAAAACTCACACATGCCCACCGTGCC

CAGCACCTGAACTCCTGGGGGGACCGGGCGGAGGTGGGAGTCAGGTCCAG

TTGCAACAGTCTGGAGCCGAGCTCGCCAGGCCAGGAGCCTCCGTCAAAAT

GTCATGCAAGGCCTCAGGGTACACATTTACGCGATATACCATGCACTGGG

TGAAACAAAGACCAGGTCAGGGACTTGAATGGATCGGTTACATTAACCCC

TCTAGAGGCTATACGAATTACAACCAGAAATTCAAAGACAAAGCAACACT

TACGACTGACAAATCCAGTAGTACGGCTTACATGCAGCTCTCATCTTTGA

CTTCAGAAGACTCTGCTGTATATTATTGTGCCCGCTATTACGATGACCAT

TABLE 7

VHs, VLs and CDRs of ACE-04

| | | |
|---|---|---|
| Fab region (Anti-PD-L1) | VH:<br>QMQLVQSGAEVKKPGSSVKVSCK<br>ASGGTFSSYAISWVRQAPGQGLE<br>WMGRIIPILGIANYAQKFQGRVTIT<br>ADKSTSTAYMELSSLRSEDTAVYY<br>CAKPRDGYNLVAFDIWGQGTMVT<br>VSS (SEQ ID NO: 4)<br>CDR H1: GGTFSSYA (SEQ ID NO: 5)<br>CDR H2: IIPILGIA (SEQ ID NO: 6)<br>CDR H3: AKPRDGYNLVAFDI (SEQ ID NO: 7) | VL:<br>QLVLTQPPSVGAPGQRVTISCTG<br>SSSNIGAGYDVHWYQQLPGAAPK<br>LLIYGDINRPSGVPDRFSGSKSGIS<br>ASLAITGLQAEDEADYYCQSYDS<br>SLSGGVFGGGTKLTVLR (SEQ ID NO: 8)<br>CDR L1: SSNIGAGYD (SEQ ID NO: 9)<br>CDR L2: GDI (SEQ ID NO: 10)<br>CDR L3: QSYDSSLSGGV (SEQ ID NO: 11) |
| Fv region (Anti-CD3) | VH:<br>QVQLQQSGAELARPGASVKMSCK<br>ASGYTFTRYTMHWVKQRPGQGLE<br>WIGYINPSRGYTNYNQKFKDKATL<br>TTDKSSSTAYMQLSSLTSEDSAVY<br>YCARYYDDHYCLDYWGQGTTVT<br>VSA (SEQ ID NO: 85)<br>CDR H1: GYTFTRYT (SEQ ID NO: 78)<br>CDR H2: INPSRGYT (SEQ ID NO: 79)<br>CDR H3: ARYYDDHYCLDY (SEQ ID NO: 80) | VL:<br>QIVLTQSPAIMSASPGEKVTMTCS<br>ASSSVSYMNWYQQKSGTSPKRWI<br>YDTSKLASGVPAHFRGSGSGTSY<br>SLTISGMEAEDAATYYCQQWSSN<br>PFTFGSGTKLEINR (SEQ ID NO: 86)<br>CDR L1: SSVSY (SEQ ID NO: 82)<br>CDR L2: DTS (SEQ ID NO: 83)<br>CDR L3: QQWSSNPF (SEQ ID NO: 87) |

-continued
TACTGCCTTGATTACTGGGGCCAGGGCACTACTGTTACCGTAAGTGCGGC

TAGCACCAAGGGCCCATCGGTCTTCCCCCTGGCACCCTCCTCCAAGAGCA

CCTCTGGGGGCACAGCGGCCCTGGGCTGCCTGGTCAAGGACTACTTCCCC

GAACCGGTGACGGTGTCGTGGAACTCAGGCGCCCTGACCAGCGGCGTGCA

CACCTTCCCGGCTGTCCTACAGTCCTCAGGACTCTACTCCCTCAGCAGCG

TGGTGACCGTGCCCTCCAGCAGCCTGGGCACCCAGACCTACATCTGCAAC

GTGAATCACAAGCCCAGCAACACCAAGGTGGACAAGAGAGTTGAGCCCAA

ATCTTGTTGA

ACE-04-VL nucleotide sequence:
(SEQ ID NO: 106)
CAGATGCAGCTGGTGCAGTCTGGGGCTGAGGTGAAGAAGCCTGGGTCCTC

GGTGAAGGTCTCCTGCAAGGCTTCTGGAGGCACCTTCAGCAGCTATGCTA

TCAGCTGGGTGCGACAGGCCCCTGGACAAGGGCTTGAGTGGATGGGAAGG

ATCATCCCTATCCTTGGTATAGCAAACTACGCACAGAAGTTCCAGGGCAG

AGTCACGATTACCGCGGACAAATCCACGAGCACAGCCTACATGGAGCTGA

GCAGCCTGAGATCTGAGGACACGGCCGTGTATTACTGTGCGAAACCGAGA

GATGGCTACAATTTGGTTGCTTTTGATATCTGGGGCCAAGGGACGATGGT

CACCGTCTCCTCAGCTAGCACCAAGGGCCCATCGGTCTTCCCCCTGGCAC

CCTCCTCCAAGAGCACCTCTGGGGGCACAGCGGCCCTGGGCTGCCTGGTC

AAGGACTACTTCCCCGAACCGGTGACGGTGTCGTGGAACTCAGGCGCCCT

GACCAGCGGCGTGCACACCTTCCCGGCTGTCCTACAGTCCTCAGGACTCT

ACTCCCTCAGCAGCGTGGTGACCGTGCCCTCCAGCAGCCTGGGCACCCAG

ACCTACATCTGCAACGTGAATCACAAGCCCAGCAACACCAAGGTGGACAA

GAAAGTTGAGCCCAAATCTTGTGACAAAACTCACACATGCCCACCGTGCC

CAGCACCTGAACTCCTGGGGGGACCGGGCGGAGGTGGGAGTCAGATCGTC

CTCACTCAAAGTCCTGCTATTATGTCCGCAAGCCCTGGTGAAAAGGTTAC

CATGACTTGCTCCGCATCTAGTTCTGTCTCTTACATGAACTGGTACCAGC

AAAAGTCTGGAACGTCCCCGAAAAGGTGGATATATGATACGAGCAAATTG

GCAAGCGGAGTACCCGCGCATTTTAGGGGTTCAGGCAGCGGTACGTCATA

TAGCCTGACTATTAGCGGAATGGAGGCGGAGGATGCTGCAACATATTATT

GCCAACAATGGTCATCAAATCCTTTTACTTTCGGCTCAGGCACAAAACTT

GAAATAAATAGAACCGTGGCTGCACCATCTGTCTTCATCTTCCCGCCATC

TGATGAGCAGTTGAAATCTGGAACTGCCTCTGTTGTGTGCCTGCTGAATA

ACTTCTATCCCAGAGAGGCCAAAGTACAGTGGAAGGTGGATAACGCCCTC

CAATCGGGTAACTCCCAGGAGAGTGTCACAGAGCAGGACAGCAAGGACAG

CACCTACAGCCTCAGCAGCACCCTGACGCTGAGCAAAGCAGACTACGAGA

AACACAAAGTCTACGCCTGCGAAGTCACCCATCAGGGCCTGAGCTCGCCC

GTCACAAAGAGcTTCAACAGGGGAGAGTGTTAA

ACE-04-LC (anti-PD-L1 antibody light chain nucleotide sequence):
(SEQ ID NO: 107)
CAGCTCGTGCTGACTCAGCCGCCCTCAGTGTCTGGGGCCCCAGGGCAGAG

GGTCACCATCTCCTGCACTGGGAGCAGCTCCAACATCGGGGCAGGTTATG

-continued
ATGTACACTGGTATCAGCAACTTCCAGGAGCAGCCCCCAAACTCCTCATC

TATGGCGACATCAATCGGCCCTCAGGGGTCCCTGACCGATTCTCTGGCTC

CAAGTCTGGCATCTCAGCCTCCCTGGCTATCACTGGGCTCCAGGCTGAGG

ACGAGGCTGATTATTACTGCCAGTCCTATGACAGCAGCCTGAGTGGGGGG

GTGTTCGGCGGAGGGACCAAGCTGACCGTCCTAAGATCTGTGGCTGCACC

ATCTGTCTTCATCTTCCCGCCATCTGATGAGCAGTTGAAATCTGGAACTG

CCTCTGTTGTGTGCCTGCTGAATAACTTCTATCCCAGAGAGGCCAAAGTA

CAGTGGAAGGTGGATAACGCCCTCCAATCGGGTAACTCCCAGGAGAGTGT

CACAGAGCAGGACAGCAAGGACAGCACCTACAGCCTCAGCAGCACCCTGA

CGCTGAGCAAAGCAGACTACGAGAAACACAAAGTCTACGCCTGCGAAGTC

ACCCATCAGGGCCTGAGCTCGCCCGTCACAAAGAGCTTCAACAGGGGAGA

GTGTTAG

In FIG. 4C, the SDS-PAGE results show the expression of ACE-04 and ACE-05, the difference in the assembly patterns of ACE-04 and ACE-04-VL2 and the difference in the assembly patterns of ACE-05 and ACE-05-VL2. The results suggest that ACE-04 was properly expressed and assembled.

1.5. Construction and Expression of ACE-05

A HEK-293 transient expression system (Invitrogen, USA) was used for expressing another ALiCE molecule provided herein ACE-05 (a binding molecule composed of anti-PD-L1 and anti-CD3 domains; see FIG. 4B). ACE-05 contains two different heavy chain like chains (ACE-05-VH and ACE-05-VL) and two identical light chains (ACE-05-LC). ACE-05 contains a G4S linker (amino acid sequence of GGGGS, SEQ ID NO: 112) in the flexible peptide region. The amino acid sequences of these three type of polypeptides are as follows:

ACE-05-VH amino acid sequence:
(SEQ ID NO: 1)
QMQLVQSGAEVKKPGSSVKVSCKAS<u>GGTFSSYAI</u>SWVRQAPGQGLEWMGR <u>IIPILGIANY</u>AQKFQGRVTITADKSTSTAYMELSSLRSEDTAVYY<u>CAKPR</u>

<u>DGYNLVAFDIWGQGTMVTVSS</u>[ASTKGPSVFPLAPSSKSTSGGTAALG

CLVKDYFPEPVTVSWNSGALTSGVHTFPAVLQSSGLYSLSSVVTVPSSSL

GTQTYICNVNHKPSNTKVDKKVEPKSC]*DKTHTCPPCPAPELLGGP*gg gg*s*EVQLQQSGPELVKPGPSMKISCKAS<u>GYSFTGYTMN</u>WVKQSHGKNLEW

MG<u>LINPYKGVS</u>TYNQKFKDKATLTVDKSSSTAYMELLSLTSEDSAVYY<u>CA</u>

<u>RSGYYGDSDWYFDV</u>WGQGTTLTVFS

ACE-05-VL amino acid sequence:
(SEQ ID NO: 2)
QMQLVQSGAEVKKPGSSVKVSCKAS<u>GGTFSSYAI</u>SWVRQAPGQGLEWMGR <u>IIPILGIANY</u>AQKFQGRVTITADKSTSTAYMELSSLRSEDTAVYY<u>CAKPR</u>

<u>DGYNLVAFDIWGQGTMVTVSS</u>[ASTKGPSVFPLAPSSKSTSGGTAALG

CLVKDYFPEPVTVSWNSGALTSGVHTFPAVLQSSGLYSLSSVVTVPSSSL

GTQTYICNVNHKPSNTKVDKKVEPKSC]*DKTHTCPPCPAPELLGGP*gg gg*s*DIQMTQTTSSLSASLGDRVTISC<u>RASQDIRNYLN</u>WYQQKPDGTVKLL

-continued

IYYTSRLHSGVPSKFSGSGSGTDYSLTISNLEQEDIATYFCQQGNTLPWT

FAGGTKLEIKR

ACE-05-LC amino acid sequence:
(SEQ ID NO: 3)
QLVLTQPPSVSGAPGQRVTISCTGSSSNIGAGYDVHWYQQLPGAAPKLLI

YGDINRPSGVPDRFSGSKSGISASLAITGLQAEDEADYYCQSYDSSLSGG

VFGGGTKLTVL[RTVAAPSVFIFPPSDEQLKSGTASVVCLLNNFYPRE

AKVQWKVDNALQSGNSQESVTEQDSKDSTYSLSSTLTLSKADYEKHKVYA

CEVTHQGLSSPVTKSFNRGEC]

The VH and VL amino acid sequences and CDR sequences therein for the first antigen binding domain bivalent Fab region targeting PD-L1 and the second antigen binding domain monovalent Fv region targeting CD3 are listed in the table below:

TABLE 8

VHs, VLs and CDRs of ACE-05

| Fab region (Anti-PD-L1) | VH: QMQLVQSGAEVKKPGSSVKVSCK ASGGTFSSYAISWVRQAPGQGLE WMGRIIPILGIANYAQKFQGRVTIT ADKSTSTAYMELSSLRSEDTAVYY CAKPRDGYNLVAFDIWGQGTMVT VSS (SEQ ID NO: 4) CDR H1: GGTFSSYA (SEQ ID NO: 5) CDR H2: IIPILGIA (SEQ ID NO: 6) CDR H3: AKPRDGYNLVAFDI (SEQ ID NO: 7) | VL: QLVLTQPPSVSGAPGQRVTISCTG SSSNIGAGYDVHWYQQLPGAAPK LLIYGDINRPSGVPDRFSGSKSGIS ASLAITGLQAEDEADYYCQSYDS SLSGGVFGGGTKLTVLR (SEQ ID NO: 8) CDR L1: SSNIGAGYD (SEQ ID NO: 9) CDR L2: GDI (SEQ ID NO: 10) CDR L3: QSYDSSLSGGV (SEQ ID NO: 11) |
|---|---|---|
| Fv region (Anti-CD3) | VH: EVQLQQSGPELVKPGPSMKISCKA SGYSFTGYTMNWVKQSHGKNLE WMGLINPYKGVSTYNQKFKDKAT LTVDKSSSTAYMELLSLTSEDSAV YYCARSGYYGDSDWYFDVWGQG TTLTVFS (SEQ ID NO: 12) CDR H1: GYSFTGYTMN (SEQ ID NO: 13) CDR H2: LINPYKGVST (SEQ ID NO: 14) CDR H3: SGYYGDSDWYFDV (SEQ ID NO: 15) | VL: DIQMTQTTSSLSASLGDRVTISCR ASQDIRNYLNWYQQKPDGTVKL LIYYTSRLHSGVPSKFSGSGSGTD YSLTISNLEQEDIATYFCQQGNTL PWTFAGGTKLEIKR (SEQ ID NO: 16) CDR L1: RASQDIRNYLN (SEQ ID NO: 17) CDR L2: YTSRLHS (SEQ ID NO: 18) CDR L3: QQGNTLPWT (SEQ ID NO: 19) |

A tri-transfection was performed to transfect the host cells with DNA of ACE-05-VH, ACE-05-VL and ACE-05-LC (at 0.5:0.5:1 w/w ratio). DNA sequences encoding ACE-05-VH, ACE-05-VL and ACE-05-LC are as follows:

ACE-05-VH nucleotide sequence:
(SEQ ID NO: 20)
CAGATGCAGCTGGTGCAGTCTGGGGCTGAGGTGAAGAAGCCTGGGTCCTC

GGTGAAGGTCTCCTGCAAGGCTTCTGGAGGCACCTTCAGCAGCTATGCTA

TCAGCTGGGTGCGACAGGCCCCTGGACAAGGGCTTGAGTGGATGGGAAGG

ATCATCCCTATCCTTGGTATAGCAAACTACGCACAGAAGTTCCAGGGCAG

AGTCACGATTACCGCGGACAAATCCACGAGCACAGCCTACATGGAGCTGA

GCAGCCTGAGATCTGAGGACACGGCCGTGTATTACTGTGCGAAACCGAGA

GATGGCTACAATTTGGTTGCTTTTGATATCTGGGGCCAAGGGACGATGGT

CACCGTCTCCTCAGCTAGCACCAAGGGCCCATCGGTCTTCCCCCTGGCAC

CCTCCTCCAAGAGCACCTCTGGGGGCACAGCGGCCCTGGGCTGCCTGGTC

AAGGACTACTTCCCCGAACCGGTGACGGTGTCGTGGAACTCAGGCGCCCT

GACCAGCGGCGTGCACACCTTCCCGGCTGTCCTACAGTCCTCAGGACTCT

ACTCCCTCAGCAGCGTGGTGACCGTGCCCTCCAGCAGCCTGGGCACCCAG

ACCTACATCTGCAACGTGAATCACAAGCCCAGCAACACCAAGGTGGACAA

GAAAGTTGAGCCCAAATCTTGTGACAAAACTCACACATGCCCACCGTGCC

CAGCACCTGAACTCCTGGGGGGACCGGGCGGAGGTGGGAGTGAGGTGCAG

CTCCAGCAGTCTGGACCTGAGCTGGTGAAGCCTGGACCTTCAATGAAGAT

ATCCTGCAAGGCTTCTGGTTACTCATTCACTGGCTACACCATGAACTGGG

TGAAGCAGAGTCATGGAAAGAACCTTGAGTGGATGGGACTTATTAATCCT

TACAAAGGTGTTAGTACCTACAACCAGAAGTTCAAGGACAAGGCCACACT

GACTGTAGACAAGTCATCCAGCACAGCCTACATGGAACTCCTCAGTCTGA

CATCTGAGGACTCTGCAGTCTATTACTGTGCAAGATCGGGGTACTACGGT

GATAGTGACTGGTACTTCGATGTCTGGGGCCAGGGGACCACGCTGACCGT

CTTCTCATAA

ACE-05-VL nucleotide sequence:
(SEQ ID NO: 21)
CAGATGCAGCTGGTGCAGTCTGGGCTGAGGTGAAGAAGCCTGGGTCCTC

GGTGAAGGTCTCCTGCAAGGCTTCTGGAGGCACCTTCAGCAGCTATGCTA

TCAGCTGGGTGCGACAGGCCCCTGGACAAGGGCTTGAGTGGATGGGAAGG

ATCATCCCTATCCTTGGTATAGCAAACTACGCACAGAAGTTCCAGGGCAG

AGTCACGATTACCGCGGACAAATCCACGAGCACAGCCTACATGGAGCTGA

-continued

```
GCAGCCTGAGATCTGAGGACACGGCCGTGTATTACTGTGCGAAACCGAGA

GATGGCTACAATTTGGTTGCTTTTGATATCTGGGGCCAAGGGACGATGGT

CACCGTCTCCTCAGCTAGCACCAAGGGCCCATCGGTCTTCCCCCTGGCAC

CCTCCTCCAAGAGCACCTCTGGGGGCACAGCGGCCCTGGGCTGCCTGGTC

AAGGACTACTTCCCCGAACCGGTGACGGTGTCGTGGAACTCAGGCGCCCT

GACCAGCGGCGTGCACACCTTCCCGGCTGTCCTACAGTCCTCAGGACTCT

ACTCCCTCAGCAGCGTGGTGACCGTGCCCTCCAGCAGCCTGGGCACCCAG

ACCTACATCTGCAACGTGAATCACAAGCCCAGCAACACCAAGGTGGACAA

GAAAGTTGAGCCCAAATCTTGTGACAAAACTCACACATGCCCACCGTGCC

CAGCACCTGAACTCCTGGGGGGACCGGGCGGAGGTGGGAGTGACATCCAG

ATGACCCAGACCACCTCCTCCCTGTCTGCCTCCCTGGGCGACAGAGTCAC

CATCAGTTGCAGGGCAAGTCAGGACATTAGAAATTATTTAAACTGGTATC

AACAGAAACCAGATGGAACTGTTAAACTCCTGATCTACTACACATCAAGA

TTACACTCAGGAGTCCCATCAAAGTTCAGTGGCAGTGGGTCTGGAACAGA

TTATTCTCTCACCATTAGCAACCTGGAGCAAGAGGATATTGCCACTTACT

TTTGCCAACAGGGTAATACGCTTCCGTGGACGTTCGCTGGAGGCACCAAG

CTGGAAATCAAACGGTAA

ACE-05-LC nucleotide sequence:
                                 (SEQ ID NO: 22)
CAGCTCGTGCTGACTCAGCCGCCCTCAGTGTCTGGGGCCCCAGGGCAGAG

GGTCACCATCTCCTGCACTGGGAGCAGCTCCAACATCGGGGCAGGTTATG

ATGTACACTGGTATCAGCAACTTCCAGGAGCAGCCCCCAAACTCCTCATC

TATGGCGACATCAATCGGCCCTCAGGGGTCCCTGACCGATTCTCTGGCTC

CAAGTCTGGCATCTCAGCCTCCCTGGCTATCACTGGGCTCCAGGCTGAGG

ACGAGGCTGATTATTACTGCCAGTCCTATGACAGCAGCCTGAGTGGGGGG

GTGTTCGGCGGAGGGACCAAGCTGACCGTCCTAAGAaccGTGGCTGCACC

ATCTGTCTTCATCTTCCCGCCATCTGATGAGCAGTTGAAATCTGGAACTG

CCTCTGTTGTGTGCCTGCTGAATAACTTCTATCCCAGAGAGGCCAAAGTA

CAGTGGAAGGTGGATAACGCCCTCCAATCGGGTAACTCCCAGGAGAGTGT

CACAGAGCAGGACAGCAAGGACAGCACCTACAGCCTCAGCAGCACCCTGA

CGCTGAGCAAAGCAGACTACGAGAAACACAAAGTCTACGCCTGCGAAGTC

ACCCATCAGGGCCTGAGCTCGCCCGTCACAAAGAGCTTCAACAGGGGAGA

GTGTTAA
```

Transfection was performed as described above in Section 1.1. More specifically, polyethylenimine (PEI) was used as a transfection reagent (used at a ratio of DNA:PEI=1:4 (w/w)). Six to seven days after the transfection when the cell survival rate was measured to be about 60% to 70%, the batch culture was discontinued, and the expression medium was collected and centrifuged (4,800 rpm, 30 min, 4° C.) to remove the debris. The supernatant was then filtered by using a 0.22 μm TOP-filter (Millipore, USA). Subsequently, the filtered supernatant including ACE-05 molecules underwent an affinity chromatography purification process using Hitrap™ KappaSelect (GE healthcare, USA), followed by dialysis with pH 7.4 PBS using Slide-A Lyzer Dialysis Cassette (Thermo, USA) for elution buffer change. Purified proteins were analyzed by SDS-PAGE, capillary electrophoresis, and size exclusion chromatography (SEC). The level of expression using HEK-293F transient expression system was determined to be around 50 mg/L in this experiment. The purification assay using Hitrap™ KappaSelect showed that most of the molecules expressed in the medium were recovered. The purified ACE-05 molecules were also analyzed for their purity using Agilent 2100 Bioanalyzer (Agilent Technologies, Germany) and SEC-HPLC (Thermo-Fisher, USA). The purity analysis was performed using the protocols provided by the manufactures.

Figure 4D:
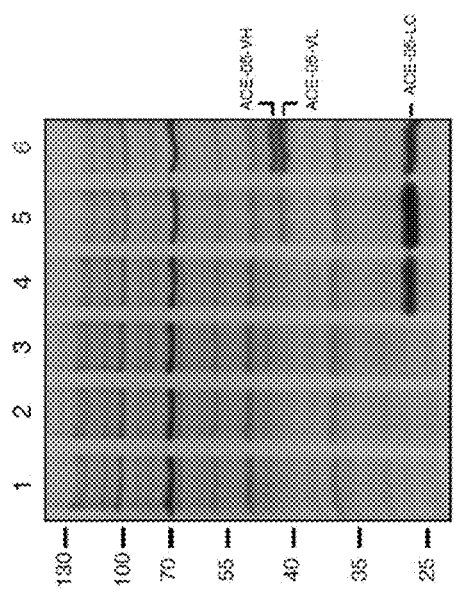
FIG. 4D shows the results of the SDS-PAGE performed to identify the assembly pattern of ACE-05 (top) and illustrates the potential regulatory mechanisms in ACE-05 assembly (bottom).
Figure 4D:
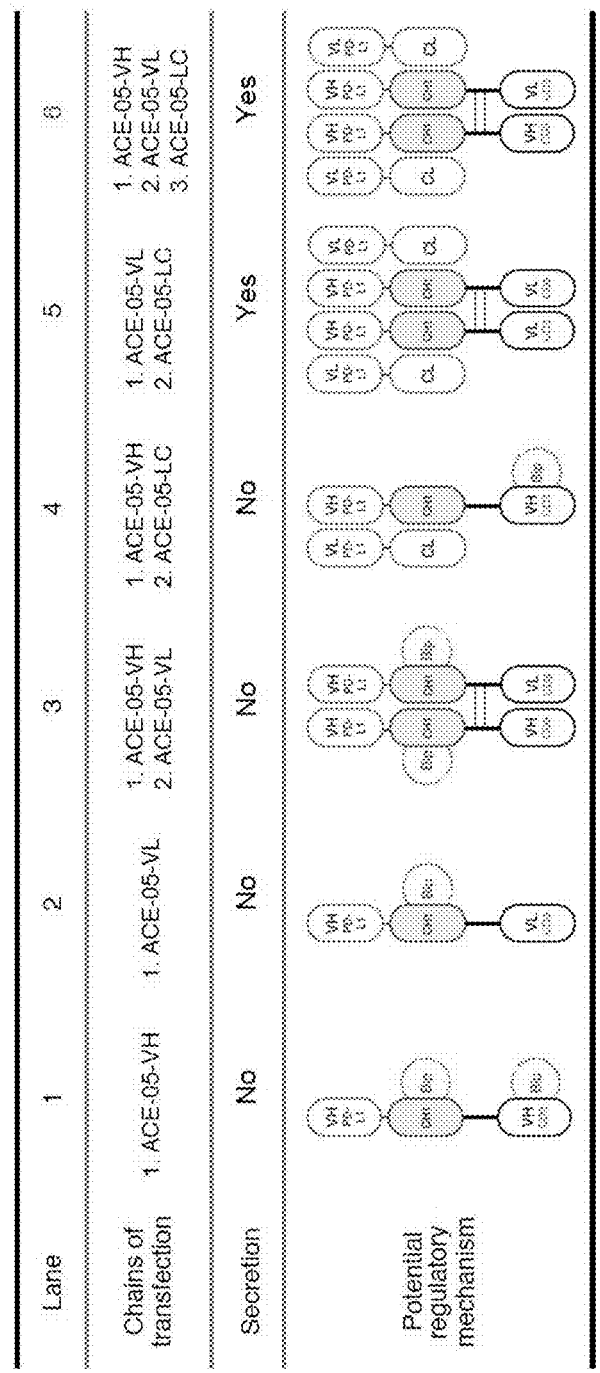

In FIG. 4C, the SDS-PAGE results show the expression of ACE-05 and ACE-04, the difference in the assembly patterns of ACE-05 and ACE-05-VL2, and the difference in the assembly patterns of ACE-04 and ACE-04-VL2. FIG. 4D shows the results of the SDS-PAGE performed to identify the assembly pattern of ACE-05 (top) and illustrates the potential regulatory mechanism in ACE-05 assembly.

Figure 4E:
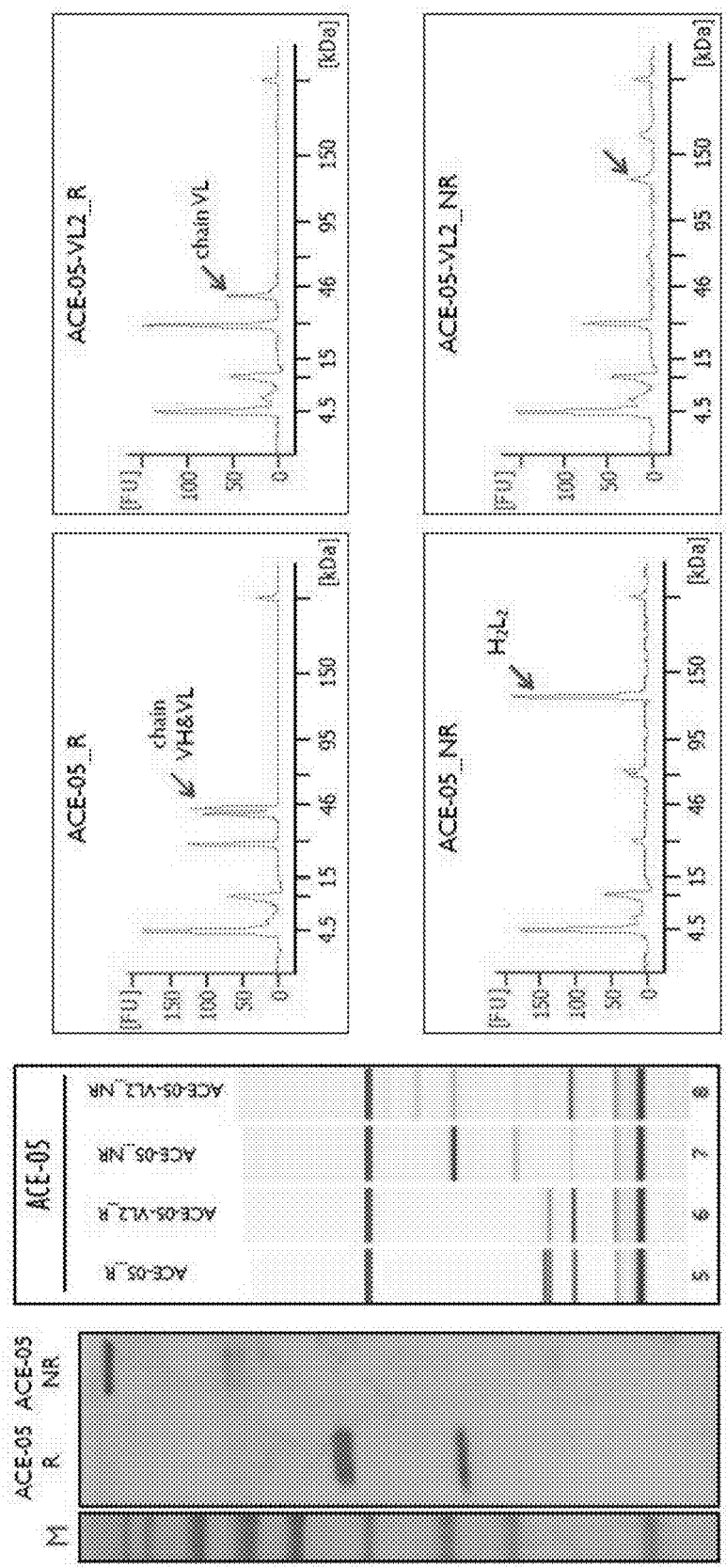
FIGS. 4E-4F show the results of SDS-PAGE and capillary electrophoresis performed to identify the conformations of ACE-05 as well as the heterodimerization efficiency between ACE-05-VH and ACE-05-VL chains. "M" represents marker; "R" represents reducing; "NR" represents non reducing; "IN" represents input; "FT" represents flow through; "W" represents washing; "Elu." represents elution.
Figure 4F:
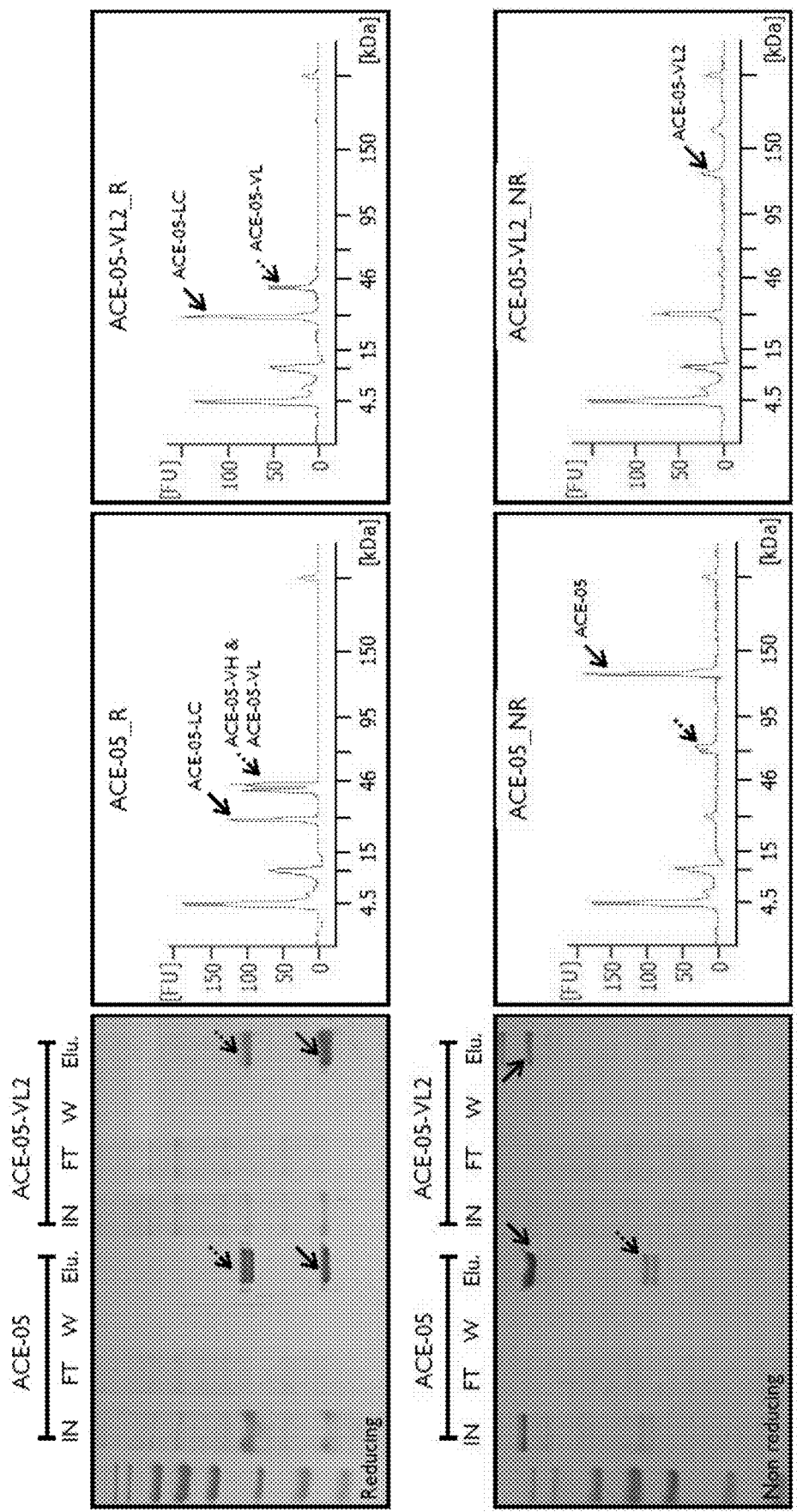
Figure 4G:
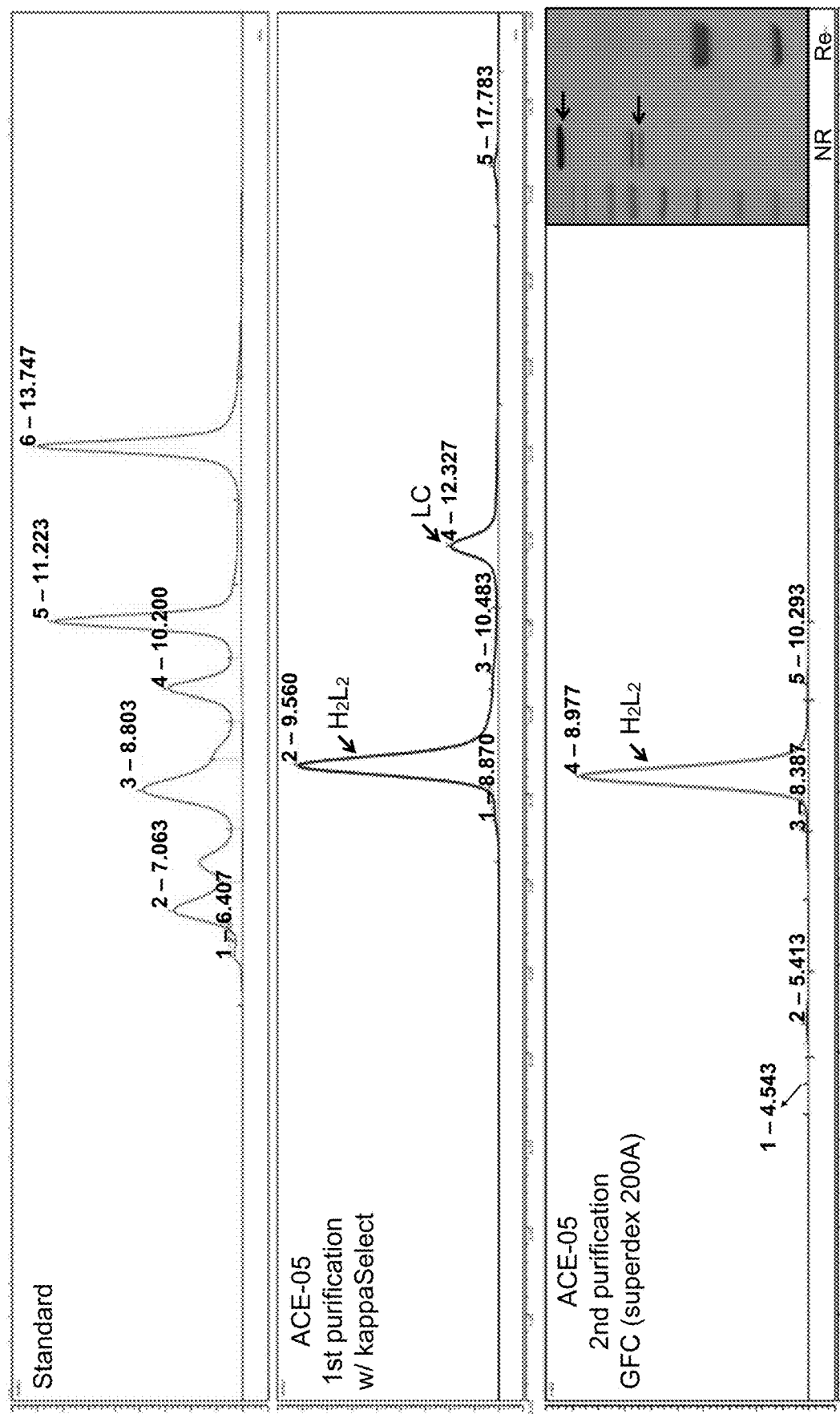
FIG. 4G shows the size exclusion chromatography performed to identify the purity of ACE-05.

FIGS. 4E-4F show the SDS-PAGE and capillary electrophoresis performed to identify the conformations of ACE-05 as well as heterodimerization efficiency between ACE-05-VH and ACE-05-VL chains. The left panels in FIGS. 4E-4F show SDS-PAGE results of purified ACE-05. The left panel in FIG. 4E also shows the results of affinity chromatography for ACE-05 and ACE-05-VL2 proteins using KappaSelect. The right four panels in FIGS. 4E-4F show almost the same amount of ACE-05-VH and ACE-05-VL chains, the amount of the ACE-05-LC, and high efficiency of heterodimerization between ACE-05-VH and ACE-05-VL chains. The capillary electrophoresis result also suggests that ACE-05 was properly expressed and assembled. FIG. 4G shows the size exclusion chromatography performed to identify purity of ACE-05. As shown, KappaSelect purified sample contains free light chains. A second gel filtration chromatography (GFC) step was then applied to remove free light chains, which generated pure and properly assembled ACE-05 molecules. As expected, ACE-05-VH and ACE-05-LC dimer and ACE-05-VL and ACE-05-LC dimer were observed in NR lane of the SDS-PAGE image. Hydrophobic interaction between ACE-05-VH and ACE-05-VL was broken by SDS detergent.

Figure 4H:
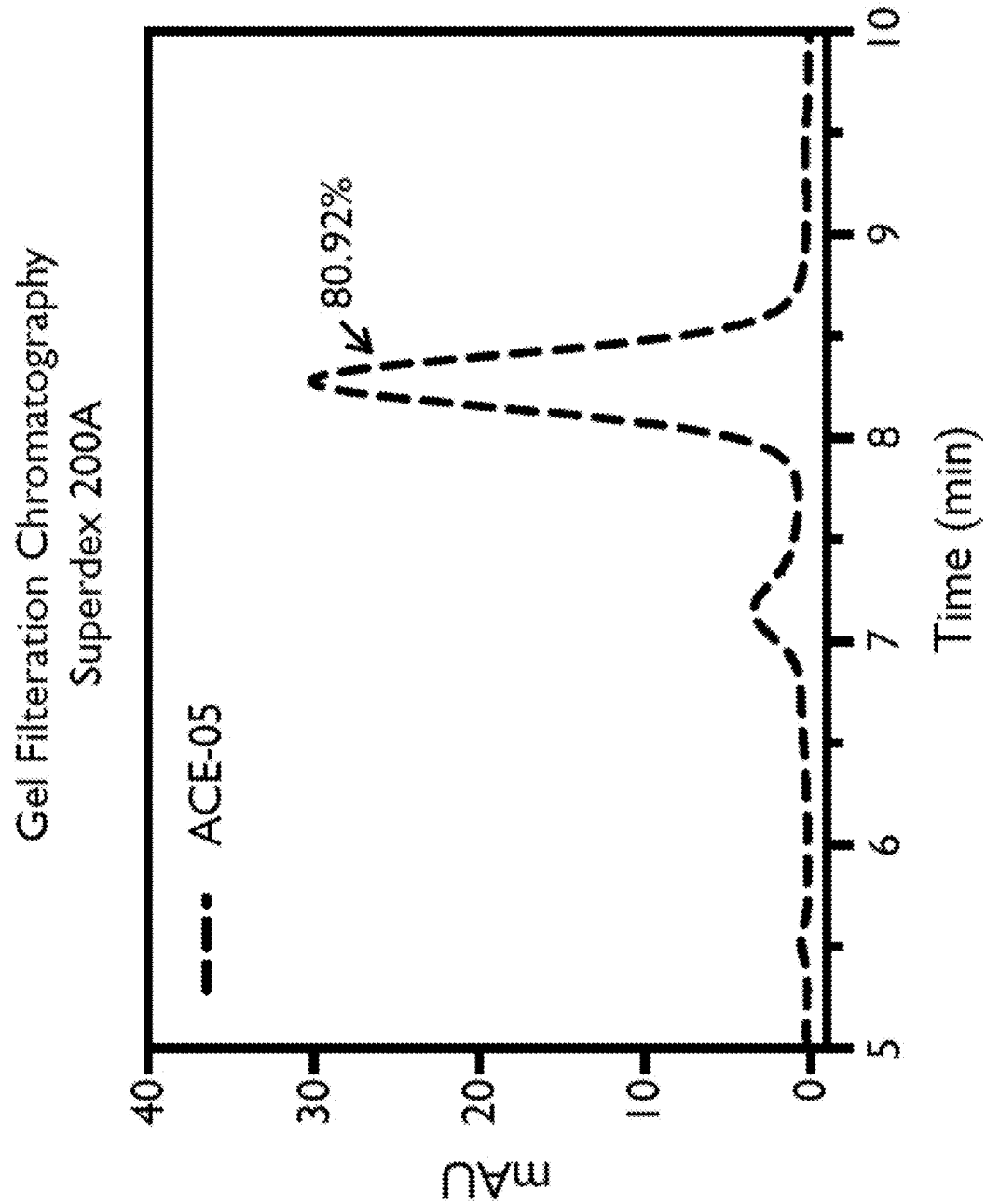
FIG. 4H shows the results of size exclusion chromatography for gel filtration analysis of ACE-05.
Figure 4I:
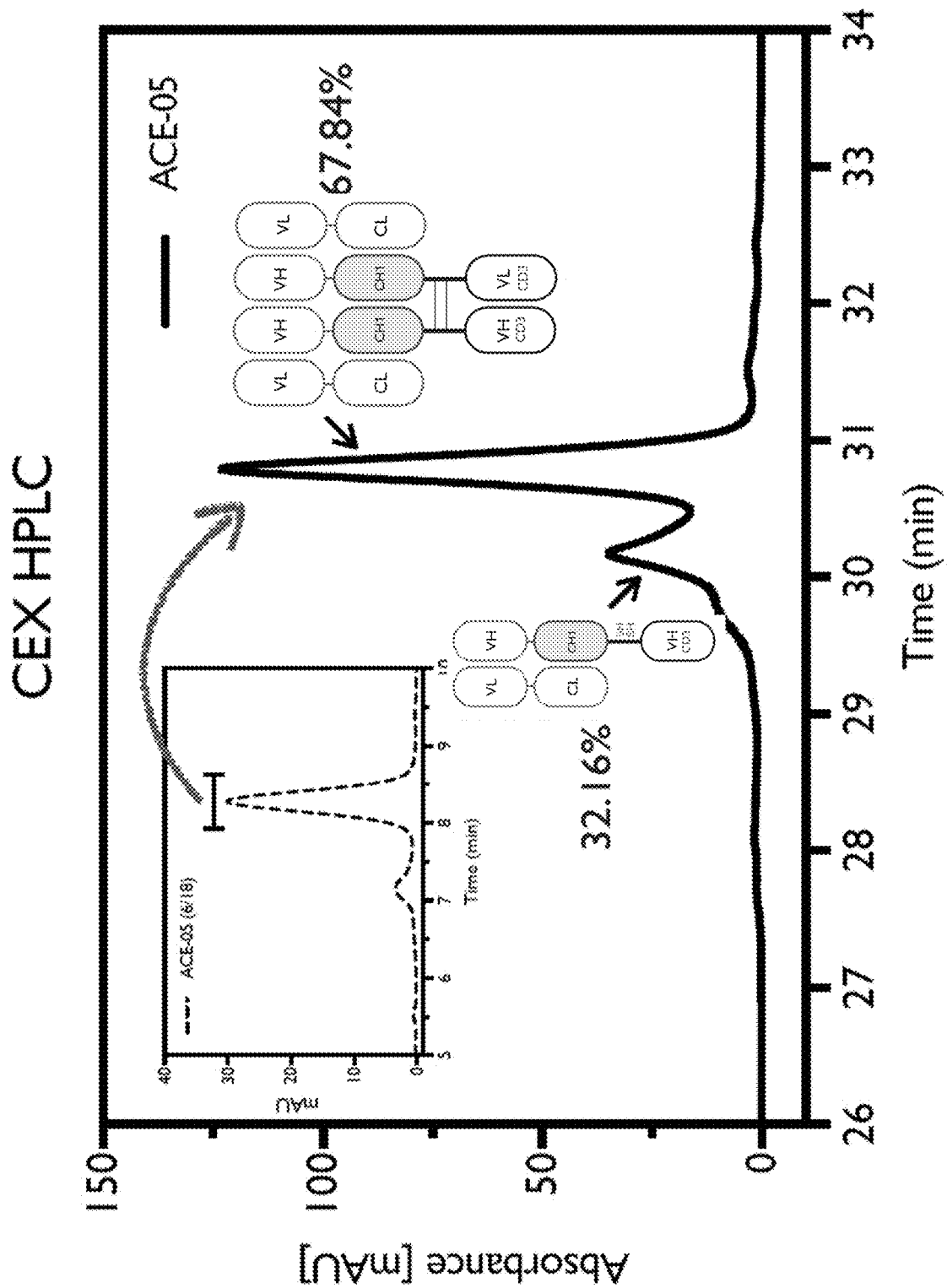
FIG. 4I shows the results of cationic exchange chromatography (CEX) performed to identify the structure conformations of ACE-05.

FIG. 4H shows the results of size exclusion chromatography for gel filtration analysis of ACE-05. The gel filtration analysis was performed to examine ACE-05 conformations after kappa-select affinity purification. About 19% aggregation of ACE-05 was detected by Superdex 200A column chromatography. FIG. 4I shows the results of cationic exchange chromatography (CEX) performed to identify the structural conformations of ACE-05. The major peak isolated from gel filtration was analyzed and separated into 2 peaks through CEX column. The higher peak (67.87%) is the assembled ACE-05, and the lower peak (32%) is the ACE-05-VH chain that has free thiol groups in the hinge region.

1.6. Construction and Expression of ACE-09

Figure 5:
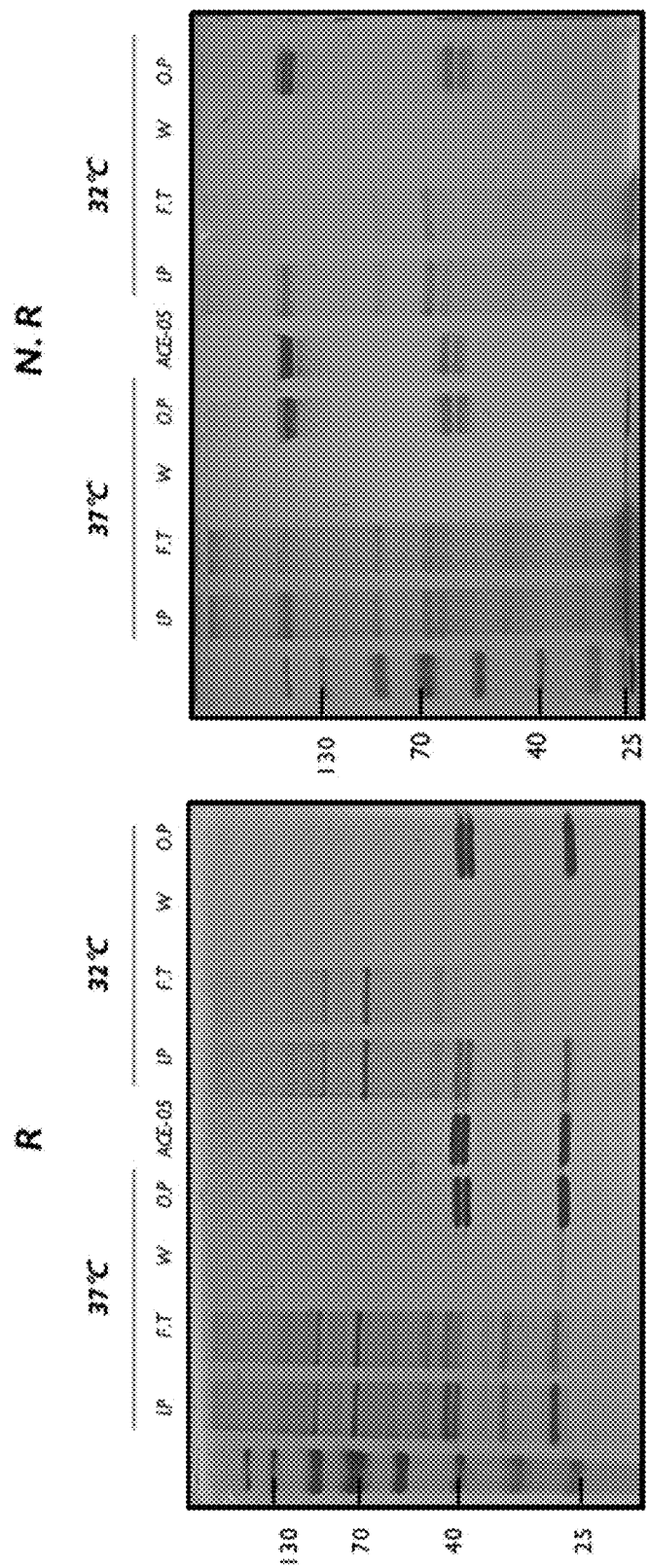
FIG. 5 shows the results of SDS-PAGE performed to identify the assembly pattern of ACE-09 and ACE-05 at 37° C. and 32° C. (top) and summarizes features of ACE-09 and ACE-05 (bottom). In the figures on top, lanes that are labeled with "ACE-05" show results of ACE-05; the rest of the lanes show the results of ACE-09; "R" represents reducing; "N.R" represents "non reducing"; "IP" represents input; "F.T" represents flow through; "W" represents washing; "OP" represents output.

A HEK-293 transient expression system (Invitrogen, USA) was also used for corroborating the proper expression and assembly of ACE-09 (a binding molecule composed of anti-PD-L1 and UCHT1 domains) using a similar method described in Sections above. ACE-09 contains two different heavy chain like chains (ACE-09-VH and ACE-09-VL) and two identical light chains (ACE-09-LC) (FIG. 5 bottom). In comparison to ACE-05, ACE-09 does not contain the G4S linker (amino acid sequence of GGGGS (SEQ ID NO: 130)) that ACE-05 contains in the flexible peptide region (FIG. 5 bottom). The amino acid sequences of these three type of polypeptides are as follows:

ACE-09-VH amino acid sequence (without the G4S linker (SEQ ID NO: 130)):

(SEQ ID NO: 96)
QMQLVQSGAEVKKPGSSVKVSCKAS<u>GGTFSSYAI</u>SWVRQAPGQGLEWMGR

<u>IIPILGIANYAQKFQ</u>GRVTITADKSTSTAYMELSSLRSEDTAVYYC<u>AKPR</u>

<u>DGYNLVAFDI</u>WGQGTMVTVSS[ASTKGPSVFPLAPSSKSTSGGTAALG

CLVKDYFPEPVTVSWNSGALTSGVHTFPAVLQSSGLYSLSSVVTVPSSSL

GTQTYICNVNHKPSNTKVDKKVEPKSC]*DKTHTCPPCPAPELLGGP*EV

QLQQSGPLVKPGPSMKISCKAS<u>GYSFTGYTMN</u>WVKQSHGKNLEWMGL<u>IN</u>

<u>PYKGVST</u>YNQKFKDKATLTVDKSSSTAYMELLSLTSEDSAVYYCAR<u>SGYY</u>

<u>GDSDWYFDV</u>WGQGTTLTVFS

ACE-09-VL amino acid sequence (without the G4S linker (SEQ ID NO: 130)):

(SEQ ID NO: 97)
QMQLVQSGAEVKKPGSSVKVSCKAS<u>GGTFSSYAI</u>SWVRQAPGQGLEWMGR

<u>IIPILGIANYAQKFQ</u>GRVTITADKSTSTAYMELSSLRSEDTAVYYC<u>AKPR</u>

<u>DGYNLVAFDI</u>WGQGTMVTVSS[ASTKGPSVFPLAPSSKSTSGGTAALG

CLVKDYFPEPVTVSWNSGALTSGVHTFPAVLQSSGLYSLSSVVTVPSSSL

GTQTYICNVNHKPSNTKVDKKVEPKSC]*DKTHTCPPCPAPELLGGP*DI

QMTQTTSSLSASLGDRVTISC<u>RASQDIRNYLN</u>WYQQKPDGTVKLLIY<u>YTS</u>

<u>RLHS</u>GVPSKFSGSGSGTDYSLTISNLEQEDIATYFC<u>QQGNTLPWT</u>FAGGT

KLEIKR

ACE-09-LC amino acid sequence (anti-PD-L1 antibody light chain):

(SEQ ID NO: 95)
QLVLTQPPSVSGAPGQRVTISCTGS<u>SSNIGAGYD</u>VHWYQQLPGAAPKLLI

Y<u>GDI</u>NRPSGVPDRFSGSKSGISASLAITGLQAEDEADYYC<u>QSYDSSLSGG</u>

VFGGGTKLTVL[RSVAAPSVFIFPPSDEQLKSGTASVVCLLNNFYPRE

AKVQWKVDNALQSGNSQESVTEQDSKDSTYSLSSTLTLSKADYEKHKVYA

CEVTHQGLSSPVTKSFNRGEC]

The VH and VL amino acid sequences and CDR sequences therein for the bivalent Fab region targeting PD-L1 and the UCHT1 are listed in the table below:

TABLE 9

VHs, VLs and CDRs of ACE-09

| | | VH: | VL: |
|---|---|---|---|
| Fab region (Anti-PD-L1) | | QMQLVQSGAEVKKPGSSVKVSCK ASGGTFSSYAISWVRQAPGQGLE WMGRIIPILGIANYAQKFQGRVTIT ADKSTSTAYMELSSLRSEDTAVYY CAKPRDGYNLVAFDIWGQGTMVT VSS (SEQ ID NO: 4) CDR H1: GGTFSSYA (SEQ ID NO: 5) CDR H2: IIPILGIA (SEQ ID NO: 6) CDR H3: AKPRDGYNLVAFDI (SEQ ID NO: 7) | QLVLTQPPSVSGAPGQRVTISCTG SSSNIGAGYDVHWYQQLPGAAPK LLIYGDINRPSGVPDRFSGSKSGIS ASLAITGLQAEDEADYYCQSYDS SLSGGVFGGGTKLTVLR (SEQ ID NO: 8) CDR L1: SSNIGAGYD (SEQ ID NO: 9) CDR L2: GDI (SEQ ID NO: 10) CDR L3: QSYDSSLSGGV (SEQ ID NO: 11) |
| Fv region (Anti-CD3) | | EVQLQQSGPELVKPGPSMKISCKA SGYSFTGYTMNWVKQSHGKNLE WMGLINPYKGVSTYNQKFKDKAT LTVDKSSSTAYMELLSLTSEDSAV YYCARSGYYGDSDWYFDVWGQG TTLTVFS (SEQ ID NO: 12) CDR H1: GYSFTGYTMN (SEQ ID NO: 13) CDR H2: LINPYKGVST (SEQ ID NO: 14) CDR H3: SGYYGDSDWYFDV (SEQ ID NO: 15) | DIQMTQTTSSLSASLGDRVTISCR ASQDIRNYLNWYQQKPDGTVKL LIYYTSRLHSGVPSKFSGSGSGTD YSLTISNLEQEDIATYFCQQGNTL PWTFAGGTKLEIKR (SEQ ID NO: 16) CDR L1: RASQDIRNYLN (SEQ ID NO: 17) CDR L2: YTSRLHS (SEQ ID NO: 18) CDR L3: QQGNTLPWT (SEQ ID NO: 19) |

DNA sequences encoding ACE-09-VH, ACE-09-VL and ACE-09-LC are as follows:

ACE-09-VH nucleotide sequence (without G4S linker (SEQ ID NO: 130)):
(SEQ ID NO: 108)
CAGATGCAGCTGGTGCAGTCTGGGGCTGAGGTGAAGAAGCCTGGGTCCTC

GGTGAAGGTCTCCTGCAAGGCTTCTGGAGGCACCTTCAGCAGCTATGCTA

TCAGCTGGGTGCGACAGGCCCCTGGACAAGGGCTTGAGTGGATGGGAAGG

ATCATCCCTATCCTTGGTATAGCAAACTACGCACAGAAGTTCCAGGGCAG

AGTCACGATTACCGCGGACAAATCCACGAGCACAGCCTACATGGAGCTGA

GCAGCCTGAGATCTGAGGACACGGCCGTGTATTACTGTGCGAAACCGAGA

GATGGCTACAATTTGGTTGCTTTTGATATCTGGGGCCAAGGGACGATGGT

CACCGTCTCCTCAGCTAGCACCAAGGGCCCATCGGTCTTCCCCCTGGCAC

CCTCCTCCAAGAGCACCTCTGGGGGCACAGCGGCCCTGGGCTGCCTGGTC

AAGGACTACTTCCCCGAACCGGTGACGGTGTCGTGGAACTCAGGCGCCCT

GACCAGCGGCGTGCACACCTTCCCGGCTGTCCTACAGTCCTCAGGACTCT

ACTCCCTCAGCAGCGTGGTGACCGTGCCCTCCAGCAGCCTGGGCACCCAG

ACCTACATCTGCAACGTGAATCACAAGCCCAGCAACACCAAGGTGGACAA

GAAAGTTGAGCCCAAATCTTGTGACAAAACTCACACATGCCCACCGTGCC

CAGCACCTGAACTCCTGGGGGGACcGGAGGTGCAGCTCCAGCAGTCTGGA

CCTGAGCTGGTGAAGCCTGGACCTTCAATGAAGATATCCTGCAAGGCTTC

TGGTTACTCATTCACTGGCTACACCATGAACTGGGTGAAGCAGAGTCATG

GAAAGAACCTTGAGTGGATGGGACTTATTAATCCTTACAAAGGTGTTAGT

ACCTACAACCAGAAGTTCAAGGACAAGGCCACACTGACTGTAGACAAGTC

ATCCAGCACAGCCTACATGGAACTCCTCAGTCTGACATCTGAGGACTCTG

CAGTCTATTACTGTGCAAGATCGGGGTACTACGGTGATAGTGACTGGTAC

TTCGATGTCTGGGGCCAGGGGACCACGCTGACCGTCTTCTCATAA

ACE-09-VL nucleotide sequence (without G4S linker (SEQ ID NO: 130)):
(SEQ ID NO: 109)
CAGATGCAGCTGGTGCAGTCTGGGGCTGAGGTGAAGAAGCCTGGGTCCTC

GGTGAAGGTCTCCTGCAAGGCTTCTGGAGGCACCTTCAGCAGCTATGCTA

TCAGCTGGGTGCGACAGGCCCCTGGACAAGGGCTTGAGTGGATGGGAAGG

ATCATCCCTATCCTTGGTATAGCAAACTACGCACAGAAGTTCCAGGGCAG

AGTCACGATTACCGCGGACAAATCCACGAGCACAGCCTACATGGAGCTGA

GCAGCCTGAGATCTGAGGACACGGCCGTGTATTACTGTGCGAAACCGAGA

GATGGCTACAATTTGGTTGCTTTTGATATCTGGGGCCAAGGGACGATGGT

CACCGTCTCCTCAGCTAGCACCAAGGGCCCATCGGTCTTCCCCCTGGCAC

CCTCCTCCAAGAGCACCTCTGGGGGCACAGCGGCCCTGGGCTGCCTGGTC

AAGGACTACTTCCCCGAACCGGTGACGGTGTCGTGGAACTCAGGCGCCCT

GACCAGCGGCGTGCACACCTTCCCGGCTGTCCTACAGTCCTCAGGACTCT

ACTCCCTCAGCAGCGTGGTGACCGTGCCCTCCAGCAGCCTGGGCACCCAG

ACCTACATCTGCAACGTGAATCACAAGCCCAGCAACACCAAGGTGGACAA

GAAAGTTGAGCCCAAATCTTGTGACAAAACTCACACATGCCCACCGTGCC

CAGCACCTGAACTCCTGGGGGGAccgGACATCCAGATGACCCAGACCACC

TCCTCCCTGTCTGCCTCCCTGGGCGACAGAGTCACCATCAGTTGCAGGGC

AAGTCAGGACATTAGAAATTATTTAAACTGGTATCAACAGAAACCAGATG

GAACTGTTAAACTCCTGATCTACTACACATCAAGATTACACTCAGGAGTC

CCATCAAAGTTCAGTGGCAGTGGGTCTGGAACAGATTATTCTCTCACCAT

TAGCAACCTGGAGCAAGAGGATATTGCCACTTACTTTTGCCAACAGGGTA

ATACGCTTCCGTGGACGTTCGCTGGAGGCACCAAGCTGGAAATCAAACGG

TAA

ACE-09-LC nucleotide sequence (anti-PD-L1 antibody light chain nucleotide sequence):
(SEQ ID NO: 107)
CAGCTCGTGCTGACTCAGCCGCCCTCAGTGTCTGGGGCCCCAGGGCAGAG

GGTCACCATCTCCTGCACTGGGAGCAGCTCCAACATCGGGGCAGGTTATG

ATGTACACTGGTATCAGCAACTTCCAGGAGCAGCCCCCAAACTCCTCATC

TATGGCGACATCAATCGGCCCTCAGGGGTCCCTGACCGATTCTCTGGCTC

CAAGTCTGGCATCTCAGCCTCCCTGGCTATCACTGGGCTCCAGGCTGAGG

ACGAGGCTGATTATTACTGCCAGTCCTATGACAGCAGCCTGAGTGGGGGG

GTGTTCGGCGGAGGGACCAAGCTGACCGTCCTAAGATCTGTGGCTGCACC

ATCTGTCTTCATCTTCCCGCCATCTGATGAGCAGTTGAAATCTGGAACTG

CCTCTGTTGTGTGCCTGCTGAATAACTTCTATCCCAGAGAGGCCAAAGTA

CAGTGGAAGGTGGATAACGCCCTCCAATCGGGTAACTCCCAGGAGAGTGT

CACAGAGCAGGACAGCAAGGACAGCACCTACAGCCTCAGCAGCACCCTGA

CGCTGAGCAAAGCAGACTACGAGAAACACAAAGTCTACGCCTGCGAAGTC

ACCCATCAGGGCCTGAGCTCGCCCGTCACAAAGAGCTTCAACAGGGGAGA

GTGTTAG

FIG. 5 shows the SDS-PAGE results of affinity chromatography for ACE-09 using KappaSelect and the SDS-PAGE result of ACE-09 and ACE-05 at 37° C. and 32° C. The results indicate that ACE-09 was properly expressed and assembled. Furthermore, ACE-09 has the same VHs and VLs in the Fab and Fv regions as ACE-05 (shown in Tables 8 and 9), but ACE-09 does not contain the G4S linker (amino acid sequence of GGGGS (SEQ ID NO: 130)) in ACE-05 between the antibody hinge region and the second Fv domain (FIG. 5 bottom). G4S flexible linkers may reduce steric hindrance and optimize the binding of the second Fv domain to immune cells (e.g., effector cells including T cells), and thus lead to increased redirecting efficiency of immune cells to target cells (e.g., cancer cells). Unexpectedly, ACE-05 and ACE-09 showed similar level of expression, suggesting that the G4S linker (SEQ ID NO: 130) may offer flexibility that benefits the ALiCE molecules' activities without affecting their expression and assembly.

1.7. Construction and Expression of ACE-10

Figure 6B:
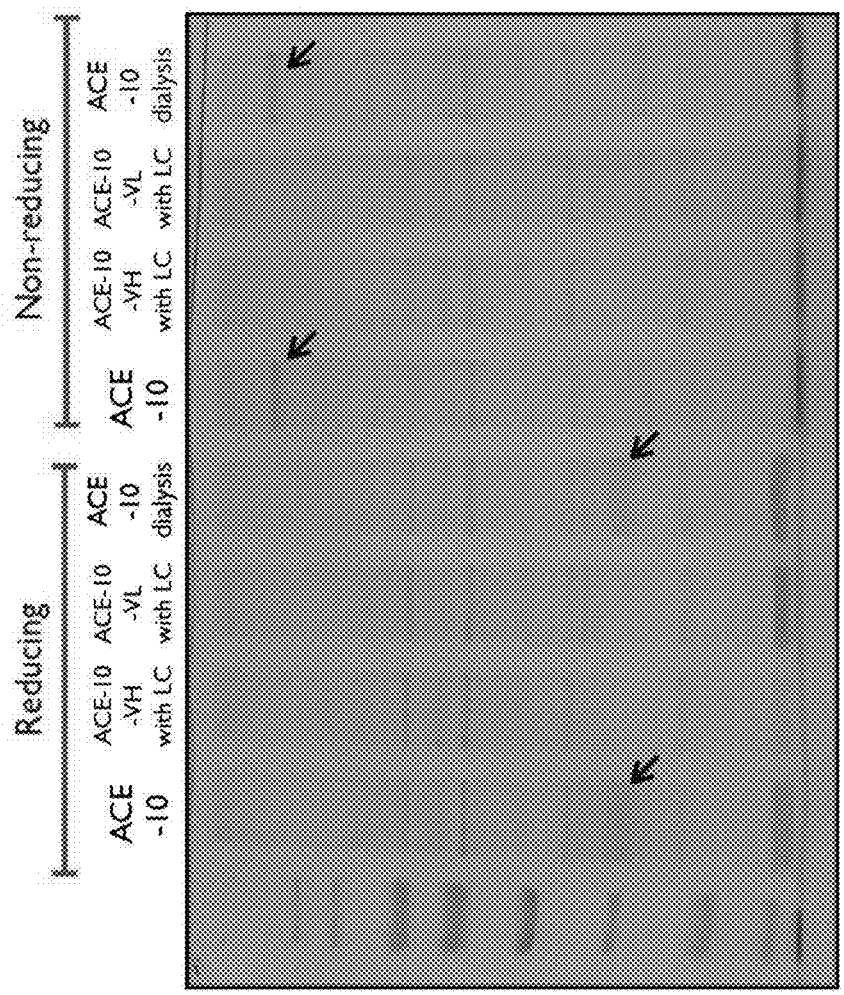
FIGS. 6B-6C show the expression and assembly analysis of the ACE-10 molecule (under reducing (left) and non-reducing (right) conditions).
Figure 6A:
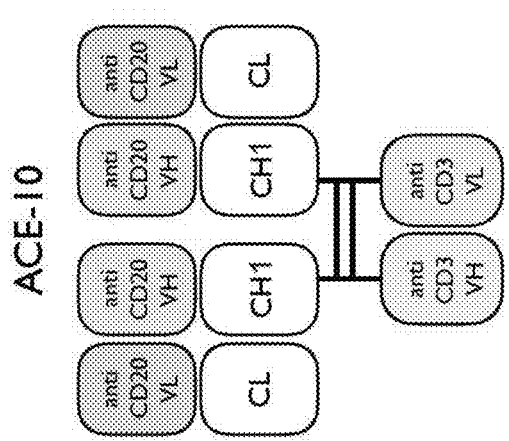
FIG. 6A illustrates the structure of ACE-10.

A HEK-293 transient expression system (Invitrogen, USA) was also used for corroborating the proper expression and assembly of ACE-10 (a binding molecule composed of anti-CD20 and anti-CD3 domains; see FIG. 6A) using a similar method described in Section 1.1 and Section 1.2 above. ACE-10 contains two different heavy chain like chains (ACE-10-VH and ACE-10-VL) and two identical light chains (ACE-10-LC). The amino acid sequences of these three type of polypeptides are as follows:

ACE-10-VH amino acid sequence:
(SEQ ID NO: 23)
QVQLQQPGAELVKPGASVKMSCKASGYTFTSYNMHWVKQTPGRGLEWIGAIYPGNGDTSYNQKFKGKATLTADKSSSTAYMQLSSLTSEDSAVYYCARSTYYGGDWYFNVWGAGTTVTVSA[ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC]*DKTHTCPPCPAPELLGGP*gggsEVQLQQSGPELVKPGPSMKISCKASGYSFTGYTMNWVKQSHGKNLEWMGLINPYKGVSTYNQKFKDKATLTVDKSSSTAYMELLSLTSEDSAVYYCARSGYYGDSDWYFDVWGQGTTLTVFS ACE-10-VL amino acid sequence:
(SEQ ID NO: 24)
QVQLQQPGAELVKPGASVKMSCKASGYTFTSYNMHWVKQTPGRGLEWIGAIYPGNGDTSYNQKFKGKATLTADKSSSTAYMQLSSLTSEDSAVYYCARSTYYGGDWYFNVWGAGTTVTVSA[ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC]*DKTHTCPPCPAPELLGGP*ggggsDIQMTQTTSSLSASLGDRVTISCRASQDIRNYLNWYQQKPDGTVKLLIYYTSRLHSGVPSKFSGSGSGTDYSLTISNLEQEDIATYFCQQGNTLPWTFAGGTKLEIKR ACE-10-LC amino acid sequence:
(SEQ ID NO: 25)
QIVLSQSPAILSASPGEKVTMTCRASSSVSYIHWFQQKPGSSPKPWIYATSNLASGVPVRFSGSGSGTSYSLTISRVEAEDAATYYCQQWTSNPPTFGGGTKLEIK[RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC]

The VH and VL amino acid sequences and CDR sequences therein for the bivalent Fab region targeting CD20 and the monovalent Fv region targeting CD3 are listed in the table below:

TABLE 10

| VHs, VLs and CDRs of ACE-10 | | |
|---|---|---|
| Fab region (Anti-CD20) | VH: QVQLQQPGAELVKPGASVKMSCKASGYTFTSYMHWVKQTPGRGLEWIGAIYPGNGDTSYNQKFKGKATLTADKSSSTAYMQLSSLTSEDSAVYCARSTYYGGDWYFNVWGAGTTVTVSA (SEQ ID NO: 26) CDR H1: GYTFTSYN (SEQ ID NO: 27) CDR H2: IYPGNGDT (SEQ ID NO: 28) CDR H3: ARSTYYGGDWYFNV (SEQ ID NO: 29) | VL: QIVLSQSPAILSASPGEKVTMTCRASSSVSYIHWFQQKPGSSPKPWIYATSNLASGVPVRFSGSGSGTSYSLTISRVEAEDAATYYCQQWTSNPPTFGGGTKLEIKR (SEQ ID NO: 30) CDR L1: SSVSY (SEQ ID NO: 31) CDR L2: ATS (SEQ ID NO: 32) CDR L3: QQWTSNPPT (SEQ ID NO: 33) |
| Fv region (Anti-CD3) | VH: EVQLQQSGPELVKPGPSMKISCKASGYSFTGYTMNWVKQSHGKNLEWMGLINPYKGVSTYNQKFKDKATLTVDKSSSTAYMELLSLTSEDSAVYYCARSGYYGDSDWYFDVWGQGTTLTVFS (SEQ ID NO: 12) CDR H1: GYSFTGYTMN (SEQ ID NO: 13) CDR H2: LINPYKGVST (SEQ ID NO: 14) CDR H3: SGYYGDSDWYFDV (SEQ ID NO: 15) | VL: DIQMTQTTSSLSASLGDRVTISCRASQDIRNYLNWYQQKPDGTVKLLIYYTSRLHSGVPSKFSGSGSGTDYSLTISNLEQEDIATYFCQQGNTLPWTFAGGTKLEIKR (SEQ ID NO: 16) CDR L1: RASQDIRNYLN (SEQ ID NO: 17) CDR L2: YTSRLHS (SEQ ID NO: 18) CDR L3: QQGNTLPWT (SEQ ID NO: 19) |

DNA sequences encoding ACE-10-VH, ACE-10-VL and ACE-10-LC are as follows:

ACE-10-VH nucleotide sequence:
(SEQ ID NO: 34)
CAGGTGCAGCTGCAGCAGCCTGGAGCCGAGCTGGTGAAGCCCGGCGCCAG

CGTGAAGATGAGCTGCAAGGCCAGCGGCTACACCTTCACCAGCTACAACA

TGCACTGGGTGAAGCAGACCCCTGGAAGAGGACTGGAGTGGATCGGCGCC

ATCTACCCCGGCAACGGCGACACCAGCTACAACCAGAAGTTCAAGGGCAA

GGCCACCCTGACCGCCGACAAGAGCAGCAGCACCGCCTACATGCAGCTGA

GCAGCCTGACCAGCGAGGACAGCGCCGTGTACTACTGCGCCCGCAGCACC

TACTACGGCGGCGACTGGTACTTCAACGTGTGGGGAGCTGGAACCACCGT

GACCGTGAGCGCCGCTAGCACCAAGGGCCCATCGGTCTTCCCCCTGGCAC

CCTCCTCCAAGAGCACCTCTGGGGGCACAGCGGCCCTGGGCTGCCTGGTC

AAGGACTACTTCCCCGAACCGGTGACGGTGTCGTGGAACTCAGGCGCCCT

GACCAGCGGCGTGCACACCTTCCCGGCTGTCCTACAGTCCTCAGGACTCT

ACTCCCTCAGCAGCGTGGTGACCGTGCCCTCCAGCAGCCTGGGCACCCAG

ACCTACATCTGCAACGTGAATCACAAGCCCAGCAACACCAAGGTGGACAA

GAAGGTTGAGCCCAAATCTTGTGACAAAACTCACACATGCCCACCGTGCC

CAGCACCTGAACTCCTGGGGGGACCGGGCGGAGGTGGGAGTGAGGTGCAG

CTCCAGCAGTCTGGACCTGAGCTGGTGAAGCCTGGACCTTCAATGAAGAT

ATCCTGCAAGGCTTCTGGTTACTCATTCACTGGCTACACCATGAACTGGG

TGAAGCAGAGTCATGGAAAGAACCTTGAGTGGATGGGACTTATTAATCCT

TACAAAGGTGTTAGTACCTACAACCAGAAGTTCAAGGACAAGGCCACACT

GACTGTAGACAAGTCATCCAGCACAGCCTACATGGAACTCCTCAGTCTGA

CATCTGAGGACTCTGCAGTCTATTACTGTGCAAGATCGGGGTACTACGGT

GATAGTGACTGGTACTTCGATGTCTGGGGCCAGGGGACCACGCTGACCGT

CTTCTCATAA

ACE-10-VL nucleotide sequence:
(SEQ ID NO: 35)
CAGGTGCAGCTGCAGCAGCCTGGAGCCGAGCTGGTGAAGCCCGGCGCCAG

CGTGAAGATGAGCTGCAAGGCCAGCGGCTACACCTTCACCAGCTACAACA

TGCACTGGGTGAAGCAGACCCCTGGAAGAGGACTGGAGTGGATCGGCGCC

ATCTACCCCGGCAACGGCGACACCAGCTACAACCAGAAGTTCAAGGGCAA

GGCCACCCTGACCGCCGACAAGAGCAGCAGCACCGCCTACATGCAGCTGA

GCAGCCTGACCAGCGAGGACAGCGCCGTGTACTACTGCGCCCGCAGCACC

TACTACGGCGGCGACTGGTACTTCAACGTGTGGGGAGCTGGAACCACCGT

GACCGTGAGCGCCGCTAGCACCAAGGGCCCATCGGTCTTCCCCCTGGCAC

CCTCCTCCAAGAGCACCTCTGGGGGCACAGCGGCCCTGGGCTGCCTGGTC

AAGGACTACTTCCCCGAACCGGTGACGGTGTCGTGGAACTCAGGCGCCCT

GACCAGCGGCGTGCACACCTTCCCGGCTGTCCTACAGTCCTCAGGACTCT

ACTCCCTCAGCAGCGTGGTGACCGTGCCCTCCAGCAGCCTGGGCACCCAG

ACCTACATCTGCAACGTGAATCACAAGCCCAGCAACACCAAGGTGGACAA

GAAGGTTGAGCCCAAATCTTGTGACAAAACTCACACATGCCCACCGTGCC

CAGCACCTGAACTCCTGGGGGGACCGGGCGGAGGTGGGAGTGACATCCAG

ATGACCCAGACCACCTCCTCCCTGTCTGCCTCCCTGGGCGACAGAGTCAC

CATCAGTTGCAGGGCAAGTCAGGACATTAGAAATTATTTAAACTGGTATC

AACAGAAACCAGATGGAACTGTTAAACTCCTGATCTACTACACATCAAGA

TTACACTCAGGAGTCCCATCAAAGTTCAGTGGCAGTGGGTCTGGAACAGA

TTATTCTCTCACCATTAGCAACCTGGAGCAAGAGGATATTGCCACTTACT

TTTGCCAACAGGGTAATACGCTTCCGTGGACGTTCGCTGGAGGCACCAAG

CTGGAAATCAAACGGTAA

ACE-10-LC nucleotide sequence:
(SEQ ID NO: 36)
CAGATCGTGCTGAGCCAGAGCCCtGCtATCCTGAGCGCCAGCCCtGGCGA

GAAGGTGACCATGACCTGCCGCGCCAGCAGCAGCGTGAGCTACATCCACT

GGTTCCAGCAGAAGCCCGGCAGCAGCCCCAAGCCCTGGATCTACGCCACC

AGCAACCTGGCCAGCGGAGTGCCTGTGCGCTTCAGCGGCAGCGGCAGCGG

CACCAGCTACAGCCTGACCATCAGCAGAGTGGAGGCTGAGGACGCCGCTA

CCTACTACTGCCAGCAGTGGACCAGCAACCCCCCCACCTTCGGCGGCGGC

ACCAAGCTGGAGATCAAGAGAACCGTGGCTGCACCATCTGTCTTCATCTT

CCCGCCATCTGATGAGCAGTTGAAATCTGGAACTGCCTCTGTTGTGTGCC

TGCTGAATAACTTCTATCCCAGAGAGGCCAAAGTACAGTGGAAGGTGGAT

AACGCCCTCCAATCGGGTAACTCCCAGGAGAGTGTCACAGAGCAGGACAG

CAAGGACAGCACCTACAGCCTCAGCAGCACCCTGACGCTGAGCAAAGCAG

ACTACGAGAAACACAAAGTCTACGCCTGCGAAGTCACCCATCAGGGCCTG

AGCTCGCCCGTCACAAAGAGCTTCAACAGGGGAGAGTGTTAG

Figure 6C:
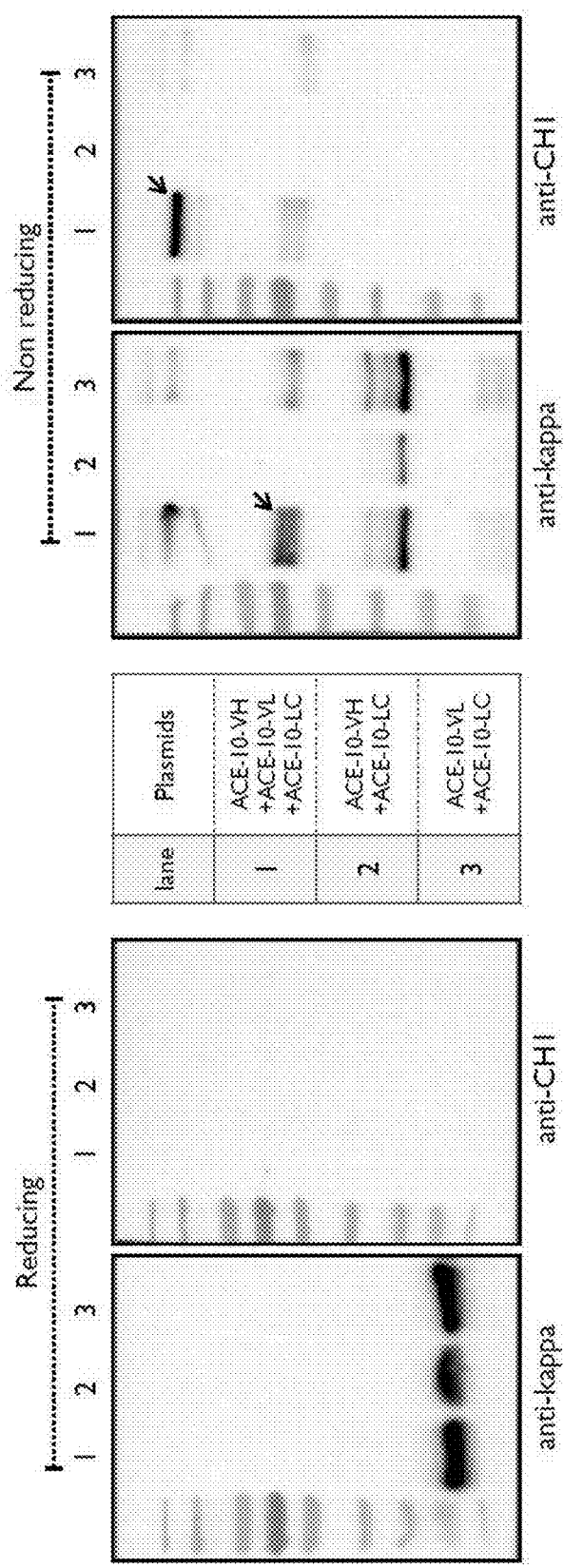

FIGS. 6B-6C show the expression analysis of the ACE-10 molecule. As shown, ACE-10 was properly expressed and assembled. In addition, the results indicate that assembly of ACE-10 is regulated in a VH-BiP dependent manner.

1.8. Construction and Expression of ACE-11

Figure 7B:
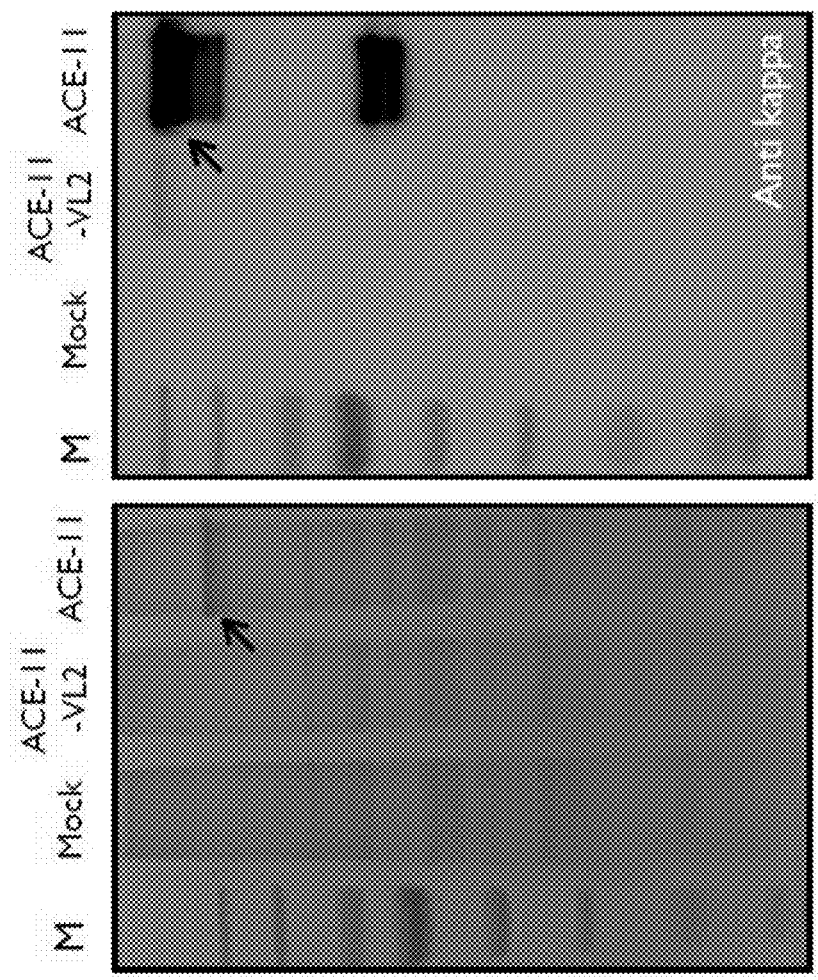
FIG. 7B shows the results of SDS-PAGE performed to identify the expression and assembly pattern of ACE-11 and ACE-11-VL2 (analyzed by Coomassie Blue staining (left) and Western blot (right)). "M" represents marker. The arrows indicate the bands of assembled ACE-11 under non reducing condition.
Figure 7A:
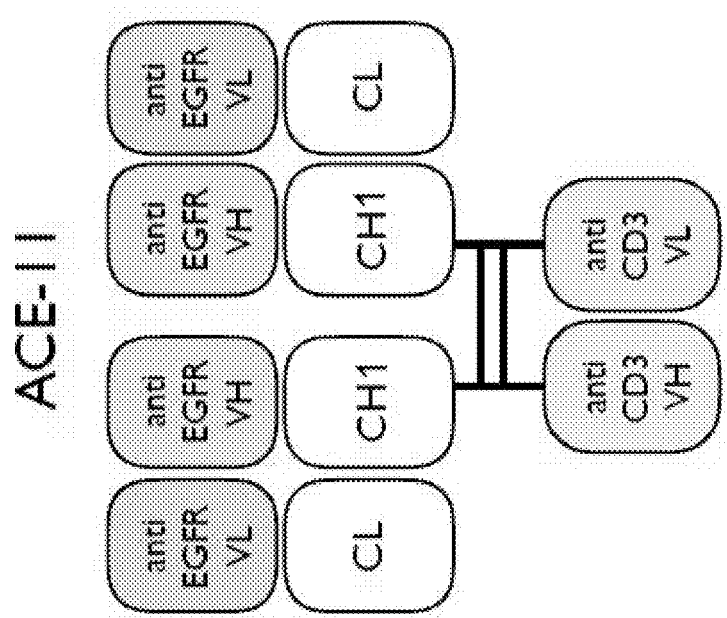
FIG. 7A illustrates the structure of ACE-11.

A HEK-293 transient expression system (Invitrogen, USA) was also used for corroborating the proper expression and assembly of ACE-11 (a binding molecule composed of anti-EGFR and anti-CD3 domains; see FIG. 7A) using a similar method described in Section 1.1 and Section 1.2 above. ACE-11 has the same overall structure as ACE-05 and ACE-10, and contains two different heavy chain like chains (ACE-11-VH and ACE-11-VL) and two identical light chains (ACE-11-LC). The amino acid sequences of these three type of polypeptides are as follows:

ACE-11-VH amino acid sequence:
(SEQ ID NO: 37)
QVQLKQSGPGLVQPSQSLSITCTVS<u>GFSLTNYG</u>VHWVRQSPGKGLEWLGV <u>IWSGGNTDYNTPFFTS</u>RLSINKDNSKSQVFFKMNSLQSNDTAIYYC<u>ARALT</u>

<u>YYDYEFAY</u>WGQGTLVTVSA[ASTKGPSVFPLAPSSKSTSGGTAALGCL

VKDYFPEPVTVSWNSGALTSGVHTFPAVLQSSGLYSLSSVVTVPSSSLGT

QTYICNVNHKPSNTKVDKKVEPKSC]*DKTHTCPPCPAPELLGGP*gggg sEVQLQQSGPELVKPGPSMKISCKASG<u>YSFTGYTMN</u>WVKQSHGKNLEWMG

-continued

LINPYKGVSTYNQKFKDKATLTVDKSSSTAYMELLSLTSEDSAVYYC<u>ARS</u>
<u>GYYGDSDWYFDV</u>WGQGTTLTVFS

ACE-11-VL amino acid sequence:
(SEQ ID NO: 38)
QVQLKQSGPGLVQPSQSLSITCTVS<u>GFSLTNYG</u>VHWVRQSPGKGLEWLGV
<u>IWSGGNT</u>DYNTPFTSRLSINKDNSKSQVFFKMNSLQSNDTAIYYC<u>ARALT</u>
<u>YYDYEFAY</u>WGQGTLVTVSA[ASTKGPSVFPLAPSSKSTSGGTAALGCL
VKDYFPEPVTVSWNSGALTSGVHTFPAVLQSSGLYSLSSVVTVPSSSLGT
QTYICNVNHKPSNTKVDKKVEPKSC]*DKTHTCPPCPAPELLGGP*ggggg
sDIQMTQTTSSLSASLGDRVTISC<u>RASQDIRNYLN</u>WYQQKPDGTVKLLIY
<u>YTSRLHS</u>GVPSKFSGSGSGTDYSLTISNLEQEDIATYFC<u>QQGNTLPWT</u>FA
GGTKLEIKR ACE-11-LC amino acid sequence:
(SEQ ID NO: 39)
DILLTQSPVILSVSPGERVSFSCRAS<u>QSIGTN</u>IHWYQQRTNGSPRLLIK<u>Y</u>
<u>ASESIS</u>GIPSRFSGSGSGTDFTLSINSVESEDIADYYC<u>QQNNNWPTT</u>FGA
GTKLELK[RTVAAPSVFIFPPSDEQLKSGTASVVCLLNNFYPREAKVQ
WKVDNALQSGNSQESVTEQDSKDSTYSLSSTLTLSKADYEKHKVYACEVT
HQGLSSPVTKSFNRGEC]

The VH and VL amino acid sequences and CDR sequences therein for the first antigen binding domain bivalent Fab region targeting EGFR and the second antigen binding domain monovalent Fv region targeting CD3 are listed in the table below:

TABLE 11

VHs, VLs and CDRs of ACE-11

| Fab region (Anti-CD20) | VH: QVQLKQSGPGLVQPSQSLSITCTVS GFSLTNYGVHWVRQSPGKGLEWL GVIWSGGNTDYNTPFTSRLSINKD NSKSQVFFKMNSLQSNDTAIYYCA RALTYYDYEFAYWGQGTLVTVSA (SEQ ID NO: 40) CDR H1: GFSLTNYG (SEQ ID NO: 41) CDR H2: IWSGGNT (SEQ ID NO: 42) CDR H3: ARALTYYDYEFAY (SEQ ID NO: 43) | VL: DILLTQSPVILSVSPGERVSFSCRA SQSIGTNIHWYQQRTNGSPRLLIK YASESISGIPSRFSGSGSGTDFTLSI NSVESEDIADYYCQQNNNWPTTF GAGTKLELKR (SEQ ID NO: 44) CDR L1: QSIGTN (SEQ ID NO: 45) CDR L2: YAS (SEQ ID NO: 46) CDR L3: QQNNNWPTT (SEQ ID NO: 47) |
|---|---|---|
| Fv region (Anti-CD3) | VH: EVQLQQSGPELVKPGPSMKISCKA SGYSFTGYTMNWVKQSHGKNLE WMGLINPYKGVSTYNQKFKDKAT LTVDKSSSTAYMELLSLTSEDSAV YYCARSGYYGDSDWYFDVWGQG TTLTVFS (SEQ ID NO: 12) CDR H1: GYSFTGYTMN (SEQ ID NO: 13) CDR H2: LINPYKGVST (SEQ ID NO: 14) CDR H3: SGYYGDSDWYFDV (SEQ ID NO: 15) | VL: DIQMTQTTSSLSASLGDRVTISCR ASQDIRNYLNWYQQKPDGTVKL LIYYTSRLHSGVPSKFSGSGSGTD YSLTISNLEQEDIATYFCQQGNTL PWTFAGGTKLEIKR (SEQ ID NO: 16) CDR L1: RASQDIRNYLN (SEQ ID NO: 17) CDR L2: YTSRLHS (SEQ ID NO: 18) CDR L3: QQGNTLPWT (SEQ ID NO: 19) |

DNA sequences encoding ACE-11-VH, ACE-11-VL and ACE-11-LC are as follows:

ACE-11-VH nucleotide sequence:
(SEQ ID NO: 48)
CAAGTCCAACTGAAACAATCGGGTCCGGGTCTGGTCCAACCGTCCCAATC

ACTGAGCATCACCTGTACCGTGTCGGGCTTCTCGCTGACCAATTATGGTG

TGCATTGGGTTCGTCAGAGTCCGGGCAAAGGTCTGGAATGGCTGGGCGTT

ATTTGGTCCGGCGGTAATACCGATTACAACACCCCGTTTACGAGTCGCCT

GTCCATCAATAAAGACAACTCGAAAAGCCAGGTGTTTTTCAAAATGAATT

CACTGCAATCGAACGATACCGCGATTTATTACTGCGCACGTGCTCTGACG

TATTACGACTATGAATTTGCCTACTGGGGCCAGGGTACCCTGGTGACGGT

TAGCGCGGCTAGCACCAAGGGCCCATCGGTCTTCCCCCTGGCACCCTCCT

CCAAGAGCACCTCTGGGGGCACAGCGGCCCTGGGCTGCCTGGTCAAGGAC

TACTTCCCCGAACCGGTGACGGTGTCGTGGAACTCAGGCGCCCTGACCAG

CGGCGTGCACACCTTCCCGGCTGTCCTACAGTCCTCAGGACTCTACTCCC

TCAGCAGCGTGGTGACCGTGCCCTCCAGCAGCCTGGGCACCCAGACCTAC

ATCTGCAACGTGAATCACAAGCCCAGCAACACCAAGGTGGACAAGAAGGT

TGAGCCCAAATCTTGTGACAAAACTCACACATGCCCACCGTGCCCAGCAC

CTGAACTCCTGGGGGACCGGGCGGAGGTGGGAGTGAGGTGCAGCTCCAG

CAGTCTGGACCTGAGCTGGTGAAGCCTGGACCTTCAATGAAGATATCCTG

CAAGGCTTCTGGTTACTCATTCACTGGCTACACCATGAACTGGGTGAAGC

AGAGTCATGGAAAGAACCTTGAGTGGATGGGACTTATTAATCCTTACAAA

GGTGTTAGTACCTACAACCAGAAGTTCAAGGACAAGGCCACACTGACTGT

AGACAAGTCATCCAGCACAGCCTACATGGAACTCCTCAGTCTGACATCTG

AGGACTCTGCAGTCTATTACTGTGCAAGATCGGGGTACTACGGTGATAGT

GACTGGTACTTCGATGTCTGGGGCCAGGGGACCACGCTGACCGTCTTCTC

ATAA

ACE-11-VL nucleotide sequence:
(SEQ ID NO: 49)
CAAGTCCAACTGAAACAATCGGGTCCGGGTCTGGTCCAACCGTCCCAATC

ACTGAGCATCACCTGTACCGTGTCGGGCTTCTCGCTGACCAATTATGGTG

TGCATTGGGTTCGTCAGAGTCCGGGCAAAGGTCTGGAATGGCTGGGCGTT

ATTTGGTCCGGCGGTAATACCGATTACAACACCCCGTTTACGAGTCGCCT

GTCCATCAATAAAGACAACTCGAAAAGCCAGGTGTTTTTCAAAATGAATT

CACTGCAATCGAACGATACCGCGATTTATTACTGCGCACGTGCTCTGACG

TATTACGACTATGAATTTGCCTACTGGGGCCAGGGTACCCTGGTGACGGT

TAGCGCGGCTAGCACCAAGGGCCCATCGGTCTTCCCCCTGGCACCCTCCT

CCAAGAGCACCTCTGGGGGCACAGCGGCCCTGGGCTGCCTGGTCAAGGAC

TACTTCCCCGAACCGGTGACGGTGTCGTGGAACTCAGGCGCCCTGACCAG

CGGCGTGCACACCTTCCCGGCTGTCCTACAGTCCTCAGGACTCTACTCCC

TCAGCAGCGTGGTGACCGTGCCCTCCAGCAGCCTGGGCACCCAGACCTAC

ATCTGCAACGTGAATCACAAGCCCAGCAACACCAAGGTGGACAAGAAGGT

TGAGCCCAAATCTTGTGACAAAACTCACACATGCCCACCGTGCCCAGCAC

CTGAACTCCTGGGGGACCGGGCGGAGGTGGGAGTGACATCCAGATGACC

CAGACCACCTCCTCCCTGTCTGCCTCCCTGGGCGACAGAGTCACCATCAG

TTGCAGGGCAAGTCAGGACATTAGAAATTATTTAAACTGGTATCAACAGA

AACCAGATGGAACTGTTAAACTCCTGATCTACTACACATCAAGATTACAC

TCAGGAGTCCCATCAAAGTTCAGTGGCAGTGGGTCTGGAACAGATTATTC

TCTCACCATTAGCAACCTGGAGCAAGAGGATATTGCCACTTACTTTTGCC

AACAGGGTAATACGCTTCCGTGGACGTTCGCTGGAGGCACCAAGCTGGAA

ATCAAACGGTAA

ACE-11-LC nucleotide sequence:
(SEQ ID NO: 50)
GATATTCTGCTGACCCAGAGCCCGGTGATCCTGAGTGTTTCCCGGGCGA

ACGTGTGTCATTTTCGTGTCGCGCGAGCCAGTCTATTGGTACCAATATCC

ACTGGTATCAGCAACGTACGAACGGCTCTCCGCGCCTGCTGATTAAATAC

GCCAGTGAATCCATTTCAGGCATCCCGAGCCGCTTTTCGGGCAGCGGTTC

TGGCACCGATTTCACGCTGAGTATTAACTCCGTGGAATCAGAAGATATCG

CAGACTATTACTGCCAGCAAAACAATAACTGGCCGACCACGTTTGGTGCT

GGCACCAAACTGGAACTGAAAAGAACCGTGGCTGCACCATCTGTCTTCAT

CTTCCCGCCATCTGATGAGCAGTTGAAATCTGGAACTGCCTCTGTTGTGT

GCCTGCTGAATAACTTCTATCCCAGAGAGGCCAAAGTACAGTGGAAGGTG

GATAACGCCCTCCAATCGGGTAACTCCCAGGAGAGTGTCACAGAGCAGGA

CAGCAAGGACAGCACCTACAGCCTCAGCAGCACCCTGACGCTGAGCAAAG

CAGACTACGAGAAACACAAAGTCTACGCCTGCGAAGTCACCCATCAGGGC

CTGAGCTCGCCCGTCACAAAGAGCTTCAACAGGGGAGAGTGTTAA.

FIG. 7B shows the expression and assembly of ACE-11 and ACE-11-VL2. The arrows indicate the bands of assembled ACE-11. The results suggest that ACE-11 was properly expressed and assembled.

1.9. Construction and Expression of ACE-12

A HEK-293 transient expression system (Invitrogen, USA) was also used for corroborating the proper expression and assembly of ACE-12 (a binding molecule composed of anti-PD-L1 and UCHT1 domains) using a similar method described in the Sections above. ACE-12 contains two different heavy chain like chains (ACE-12-VH and ACE-12-VL) and two identical light chains (ACE-12-LC). ACE-12 contains the G4S linker having amino acid sequences of GGGGSGGGGS (SEQ ID NO: 113) and GGSGGGGSG (SEQ ID NO: 114), whereas ACE-05 contains the G4S linker having amino acid sequence of GGGGS (SEQ ID NO: 112) in the flexible peptide region. The amino acid sequences of these three type of polypeptides are as follows:

ACE-12-VH amino acid sequence (with 10 residues GGGGSGGGGS (SEQ ID NO: 131)):

(SEQ ID NO: 98)

QMQLVQSGAEVKKPGSSVKVSCKAS<u>GGTFSSYA</u>ISWVRQAPGQGLEWMGR

<u>IIPILGIA</u>NYAQKFQGRVTITADKSTSTAYMELSSLRSEDTAVYYC<u>AKPR</u>

<u>DGYNLVAFDI</u>WGQGTMVTVSS[ASTKGPSVFPLAPSSKSTSGGTAALG

CLVKDYFPEPVTVSWNSGALTSGVHTFPAVLQSSGLYSLSSVVTVPSSSL

GTQTYICNVNHKPSNTKVDKKVEPKSC]*DKTHTCPPCPAPELLGGP*gg ggsggggsEVQLQQSGPELVKPGPSMKISCKAS<u>GYSFTGYTMN</u>WVKQSHG

KNLEWMG<u>LINPYKGVST</u>YNQKFKDKATLTVDKSSSTAYMELLSLTSEDSA

VYYCAR<u>SGYYGDSDWYFDV</u>WGQGTTLTVFS

ACE-12-VL amino acid sequence (with 9 residues GGSGGGGSG (SEQ ID NO: 132)):

(SEQ ID NO: 99)

QMQLVQSGAEVKKPGSSVKVSCKAS<u>GGTFSSYA</u>ISWVRQAPGQGLEWMGR

<u>IIPILGIA</u>NYAQKFQGRVTITADKSTSTAYMELSSLRSEDTAVYYC<u>AKPR</u>

<u>DGYNLVAFDI</u>WGQGTMVTVSS[ASTKGPSVFPLAPSSKSTSGGTAALG

CLVKDYFPEPVTVSWNSGALTSGVHTFPAVLQSSGLYSLSSVVTVPSSSL

GTQTYICNVNHKPSNTKVDKKVEPKSC]*DKTHTCPPCPAPELLGGP*gg sggggsgDIQMTQTTSSLSASLGDRVTISC<u>RASQDIRNYLN</u>WYQQKPDGT

VKLLIY<u>YTSRLHS</u>GVPSKFSGSGSGTDYSLTISNLEQEDIATYFC<u>QQGNT</u>

<u>LPWT</u>FAGGTKLEIKR

ACE-12-LC amino acid sequence (anti-PD-L1 antibody light chain):

(SEQ ID NO: 95)

QLVLTQPPSVSGAPGQRVTISCTGS<u>SSNIGAGYD</u>VHWYQQLPGAAPKLLI

Y<u>GDI</u>NRPSGVPDRFSGSKSGISASLAITGLQAEDEADYYC<u>QSYDSSLSGG</u>

<u>V</u>FGGGTKLTVL[RSVAAPSVFIFPPSDEQLKSGTASVVCLLNNFYPRE

AKVQWKVDNALQSGNSQESVTEQDSKDSTYSLSSTLTLSKADYEKHKVYA

CEVTHQGLSSPVTKSFNRGEC]

The VH and VL amino acid sequences and CDR sequences therein for the first antigen binding domain bivalent Fab region targeting PD-L1 and the second antigen binding domain monovalent Fv region of UCHT1 are listed in the table below:

TABLE 12

VHs, VLs and CDRs of ACE-12

| | | VH: | VL: |
|---|---|---|---|
| Fab region (Anti-PD-L1) | | QMQLVQSGAEVKKPGSSVKVSCK ASGGTFSSYAISWVRQAPGQGLE WMGRIIPILGIANYAQKFQGRVTIT ADKSTSTAYMELSSLRSEDTAVYY CAKPRDGYNLVAFDIWGQGTMVT VSS (SEQ ID NO: 4) CDR H1: GGTFSSYA (SEQ ID NO: 5) CDR H2: IIPILGIA (SEQ ID NO: 6) CDR H3: AKPRDGYNLVAFDI (SEQ ID NO: 7) | QLVLTQPPSVSGAPGQRVTISCTG SSSNIGAGYDVHWYQQLPGAAPK LLIYGDINRPSGVPDRFSGSKSGIS ASLAITGLQAEDEADYYCQSYDS SLSGGVFGGGTKLTVLR (SEQ ID NO: 8) CDR L1: SSNIGAGYD (SEQ ID NO: 9) CDR L2: GDI (SEQ ID NO: 10) CDR L3: QSYDSSLSGGV (SEQ ID NO: 11) |
| Fv region (Anti-CD3) | | EVQLQQSGPELVKPGPSMKISCKA SGYSFTGYTMNWVKQSHGKNLE WMGLINPYKGVSTYNQKFKDKAT LTVDKSSSTAYMELLSLTSEDSAV YYCARSGYYGDSDWYFDVWGQG TTLTVFS (SEQ ID NO: 12) CDR H1: GYSFTGYTMN (SEQ ID NO: 13) CDR H2: LINPYKGVST (SEQ ID NO: 14) CDR H3: SGYYGDSDWYFDV (SEQ ID NO: 15) | DIQMTQTTSSLSASLGDRVTISCR ASQDIRNYLNWYQQKPDGTVKL LIYYTSRLHSGVPSKFSGSGSGTD YSLTISNLEQEDIATYFCQQGNTL PWTFAGGTKLEIKR (SEQ ID NO: 16) CDR L1: RASQDIRNYLN (SEQ ID NO: 17) CDR L2: YTSRLHS (SEQ ID NO: 18) CDR L3: QQGNTLPWT (SEQ ID NO: 19) |

DNA sequences encoding ACE-12-VH, ACE-12-VL and ACE-12-LC are as follows:

ACE-12-VH nucleotide sequence (with 10 residues
GGGGSGGGGS (SEQ ID NO: 131)):
(SEQ ID NO: 110)
CAGATGCAGCTGGTGCAGTCTGGGGCTGAGGTGAAGAAGCCTGGGTCCTC

GGTGAAGGTCTCCTGCAAGGCTTCTGGAGGCACCTTCAGCAGCTATGCTA

TCAGCTGGGTGCGACAGGCCCCTGGACAAGGGCTTGAGTGGATGGGAAGG

ATCATCCCTATCCTTGGTATAGCAAACTACGCACAGAAGTTCCAGGGCAG

AGTCACGATTACCGCGGACAAATCCACGAGCACAGCCTACATGGAGCTGA

GCAGCCTGAGATCTGAGGACACGGCCGTGTATTACTGTGCGAAACCGAGA

GATGGCTACAATTTGGTTGCTTTTGATATCTGGGGCCAAGGGACGATGGT

CACCGTCTCCTCAGCTAGCACCAAGGGCCCATCGGTCTTCCCCCTGGCAC

CCTCCTCCAAGAGCACCTCTGGGGGCACAGCGGCCCTGGGCTGCCTGGTC

AAGGACTACTTCCCCGAACCGGTGACGGTGTCGTGGAACTCAGGCGCCCT

GACCAGCGGCGTGCACACCTTCCCGGCTGTCCTACAGTCCTCAGGACTCT

ACTCCCTCAGCAGCGTGGTGACCGTGCCCTCCAGCAGCCTGGGCACCCAG

ACCTACATCTGCAACGTGAATCACAAGCCCAGCAACACCAAGGTGGACAA

GAAAGTTGAGCCCAAATCTTGTGACAAAACTCACACATGCCCACCGTGCC

CAGCACCTGAACTCCTGGGGGGACCGGGCGGAGGTGGGAGTGGAGGCGGA

GGATCTGAGGTGCAGCTCCAGCAGTCTGGACCTGAGCTGGTGAAGCCTGG

ACCTTCAATGAAGATATCCTGCAAGGCTTCTGGTTACTCATTCACTGGCT

ACACCATGAACTGGGTGAAGCAGAGTCATGGAAAGAACCTTGAGTGGATG

GGACTTATTAATCCTTACAAAGGTGTTAGTACCTACAACCAGAAGTTCAA

GGACAAGGCCACACTGACTGTAGACAAGTCATCCAGCACAGCCTACATGG

AACTCCTCAGTCTGACATCTGAGGACTCTGCAGTCTATTACTGTGCAAGA

TCGGGGTACTACGGTGATAGTGACTGGTACTTCGATGTCTGGGGCCAGGG

GACCACGCTGACCGTCTTCTCATAA

ACE-12-VL nucleotide sequence (with 9 residues
GGSGGGGSG (SEQ ID NO: 132)):
(SEQ ID NO: 111)
CAGATGCAGCTGGTGCAGTCTGGGGCTGAGGTGAAGAAGCCTGGGTCCTC

GGTGAAGGTCTCCTGCAAGGCTTCTGGAGGCACCTTCAGCAGCTATGCTA

TCAGCTGGGTGCGACAGGCCCCTGGACAAGGGCTTGAGTGGATGGGAAGG

ATCATCCCTATCCTTGGTATAGCAAACTACGCACAGAAGTTCCAGGGCAG

AGTCACGATTACCGCGGACAAATCCACGAGCACAGCCTACATGGAGCTGA

GCAGCCTGAGATCTGAGGACACGGCCGTGTATTACTGTGCGAAACCGAGA

GATGGCTACAATTTGGTTGCTTTTGATATCTGGGGCCAAGGGACGATGGT

CACCGTCTCCTCAGCTAGCACCAAGGGCCCATCGGTCTTCCCCCTGGCAC

CCTCCTCCAAGAGCACCTCTGGGGGCACAGCGGCCCTGGGCTGCCTGGTC

AAGGACTACTTCCCCGAACCGGTGACGGTGTCGTGGAACTCAGGCGCCCT

GACCAGCGGCGTGCACACCTTCCCGGCTGTCCTACAGTCCTCAGGACTCT

ACTCCCTCAGCAGCGTGGTGACCGTGCCCTCCAGCAGCCTGGGCACCCAG

ACCTACATCTGCAACGTGAATCACAAGCCCAGCAACACCAAGGTGGACAA

GAAAGTTGAGCCCAAATCTTGTGACAAAACTCACACATGCCCACCGTGCC

CAGCACCTGAACTCCTGGGGGGACCGGGCGGATCCGGCGGAGGCGGCAGC

GGAGACATCCAGATGACCCAGACCACCTCCTCCCTGTCTGCCTCCCTGGG

CGACAGAGTCACCATCAGTTGCAGGGCAAGTCAGGACATTAGAAATTATT

TAAACTGGTATCAACAGAAACCAGATGGAACTGTTAAACTCCTGATCTAC

TACACATCAAGATTACACTCAGGAGTCCCATCAAAGTTCAGTGGCAGTGG

GTCTGGAACAGATTATTCTCTCACCATTAGCAACCTGGAGCAAGAGGATA

TTGCCACTTACTTTTGCCAACAGGGTAATACGCTTCCGTGGACGTTCGCT

GGAGGCACCAAGCTGGAAATCA

AACGGTAA

ACE-12-LC nucleotide sequence (anti-PD-L1 antibody
light chain nucleotide sequence):
(SEQ ID NO: 107)
CAGCTCGTGCTGACTCAGCCGCCCTCAGTGTCTGGGGCCCCAGGGCAGAG

GGTCACCATCTCCTGCACTGGGAGCAGCTCCAACATCGGGGCAGGTTATG

ATGTACACTGGTATCAGCAACTTCCAGGAGCAGCCCCCAAACTCCTCATC

TATGGCGACATCAATCGGCCCTCAGGGGTCCCTGACCGATTCTCTGGCTC

CAAGTCTGGCATCTCAGCCTCCCTGGCTATCACTGGGCTCCAGGCTGAGG

ACGAGGCTGATTATTACTGCCAGTCCTATGACAGCAGCCTGAGTGGGGGG

GTGTTCGGCGGAGGGACCAAGCTGACCGTCCTAAGATCTGTGGCTGCACC

ATCTGTCTTCATCTTCCCGCCATCTGATGAGCAGTTGAAATCTGGAACTG

CCTCTGTTGTGTGCCTGCTGAATAACTTCTATCCCAGAGAGGCCAAAGTA

CAGTGGAAGGTGGATAACGCCCTCCAATCGGGTAACTCCCAGGAGAGTGT

CACAGAGCAGGACAGCAAGGACAGCACCTACAGCCTCAGCAGCACCCTGA

CGCTGAGCAAAGCAGACTACGAGAAACACAAAGTCTACGCCTGCGAAGTC

ACCCATCAGGGCCTGAGCTCGCCCGTCACAAAGAGCTTCAACAGGGGAGA

GTGTTAG

Figure 8:
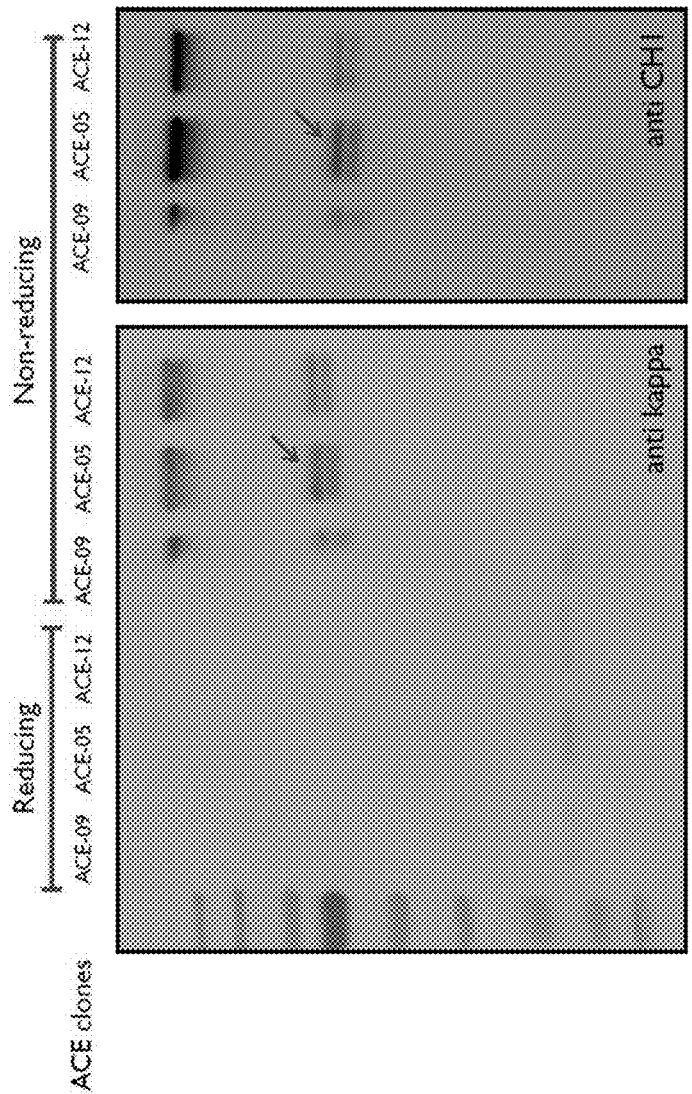
FIG. 8 shows the results of SDS-PAGE performed to identify the assembly pattern of ACE-12, ACE-05 and ACE-09. The arrows indicate the bands of ACE-05-VH+LC dimer and ACE-05-VL+LC dimer under non-reducing condition using anti-kappa (left) and anti-CH1 (right) antibodies in Western blot.

FIG. 8 shows the results of SDS-PAGE performed to identify the assembly of ACE-12, ACE-05 and ACE-09. The results indicate that ACE-12 was properly expressed and assembled. Furthermore, ACE-12, ACE-05, and ACE-09 have the same VHs and VLs in the Fab and Fv regions (shown in Tables 8, 9 and 12), and their structures differ in the lengths of the G4S linkers between the antibody hinge region and the second Fv domain (FIG. 8 bottom). G4S flexible linkers may reduce steric hindrance and optimize the binding of the second Fv domain to immune cells (e.g., effector cells including T cells), and thus lead to increased redirecting efficiency of immune cells to target cells (e.g., cancer cells). Unexpectedly, ACE-12, ACE-05 and ACE-09 showed similar level of expression. Linkers in different lengths may offer different level of flexibility that benefits the ALiCE molecules' activities without affecting their expression and assembly.

In sum, the above experiments illustrate the successful construction and expression of exemplary binding molecules provided herein and show that these ALiCE molecules can be properly expressed and assembled.

Example 2

Analysis of Binding Affinity of Exemplary Binding Molecules Using Enzyme-Linked Immunosorbent Assay (ELISA)

Figure 9:
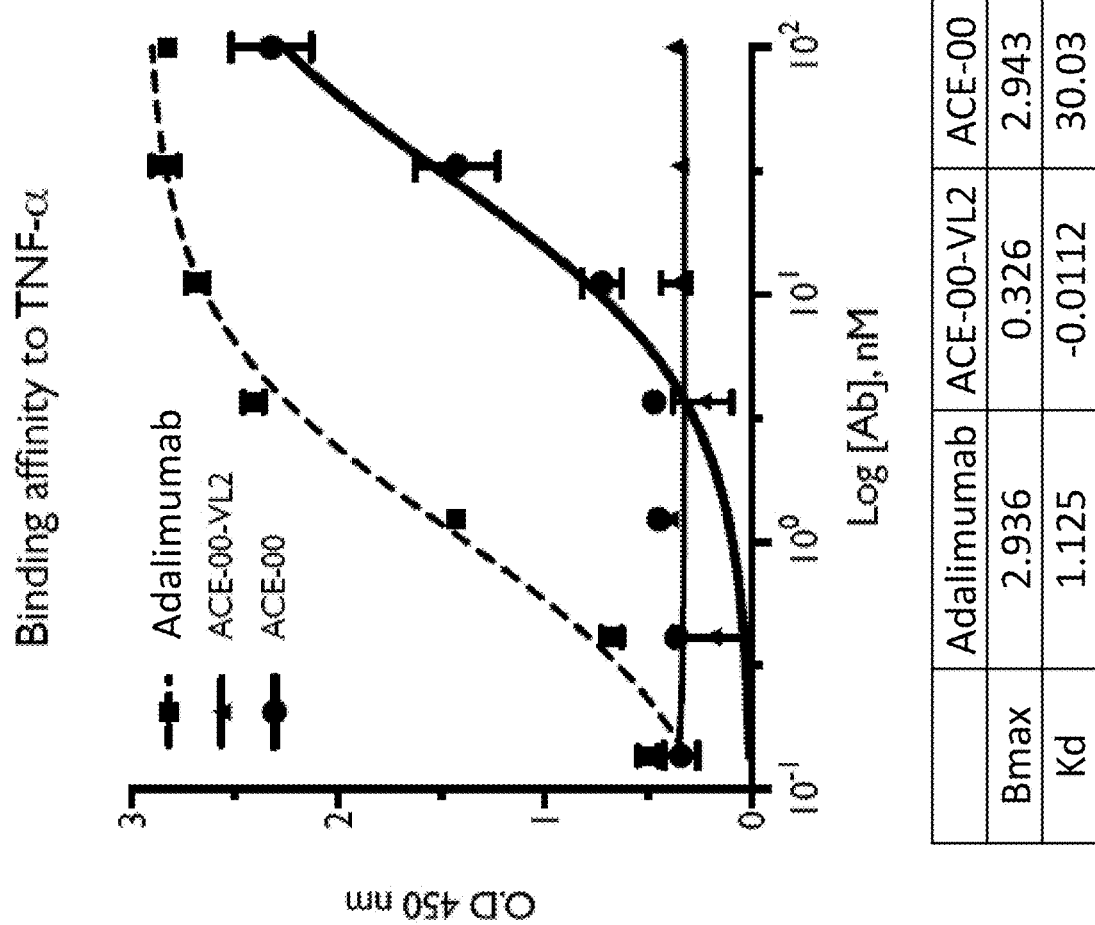
FIG. 9 shows the results of the Enzyme-Linked Immunosorbent Assay (ELISA) for determining the affinity of ACE-00 and ACE-00-VL2 to TNF alpha.

Affinity of ACE-00 and ACE-00-VL2 to TNF alpha was measured by Enzyme-Linked Immunosorbent Assay (ELISA). Bmax is the maximum binding affinity extrapolated from experimental results (calculated using curve fitting methods provided in GraphPad Prism software 7). As shown in FIG. 9, $K_D$ of the parent antibody adalimumab to TNF alpha was determined to be 1.125 nM; $K_D$ of ACE-00, which has only a monovalent binding domain to TNF alpha, was determined to be 30.03 nM; and ACE-00-VL2, which is composed of a ACE-00-VL homodimer, was determined to have no affinity to TNF alpha.

Figure 10B:
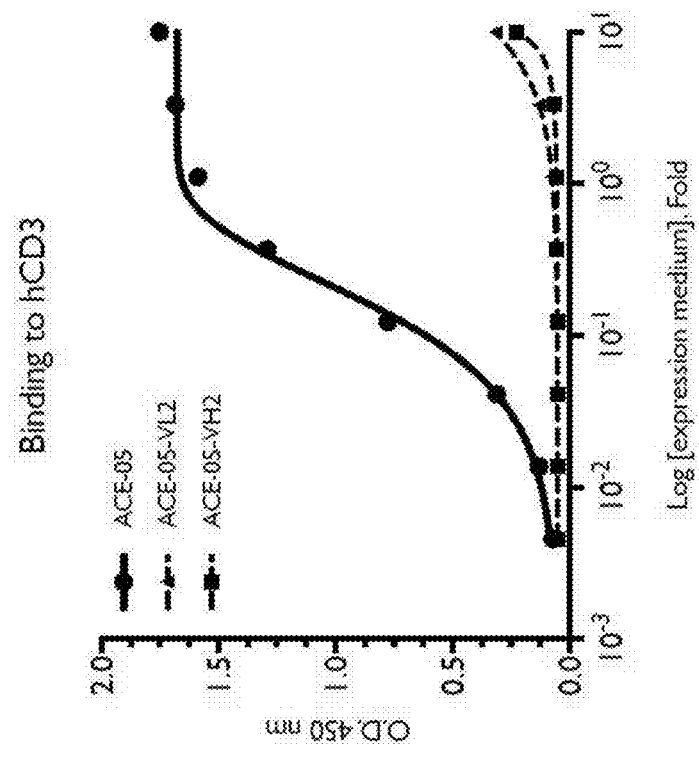
FIGS. 10A-10C show the analysis of binding affinity of ACE-05 to PD-L1 (10A) and CD3 (10B-10C) using ELISA.
Figure 10A:
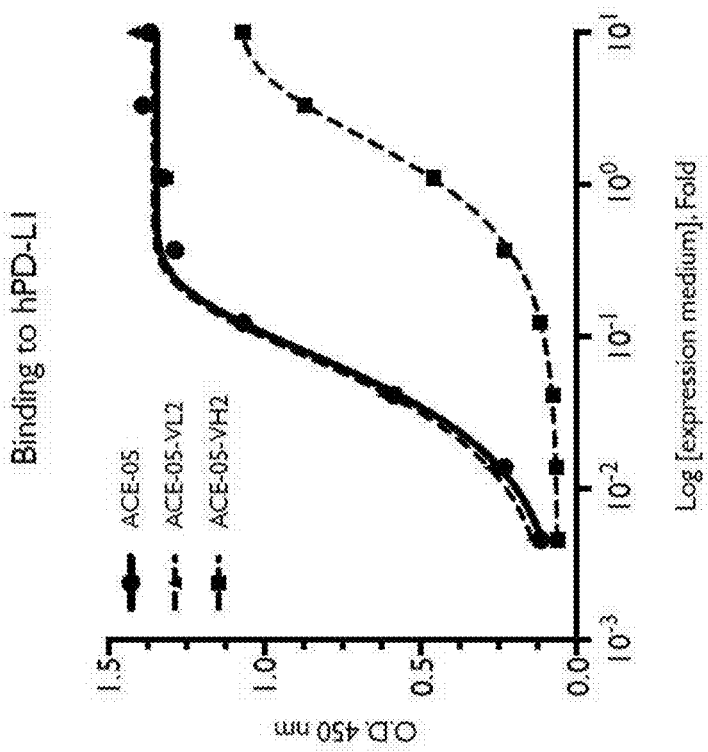
Figure 10C:
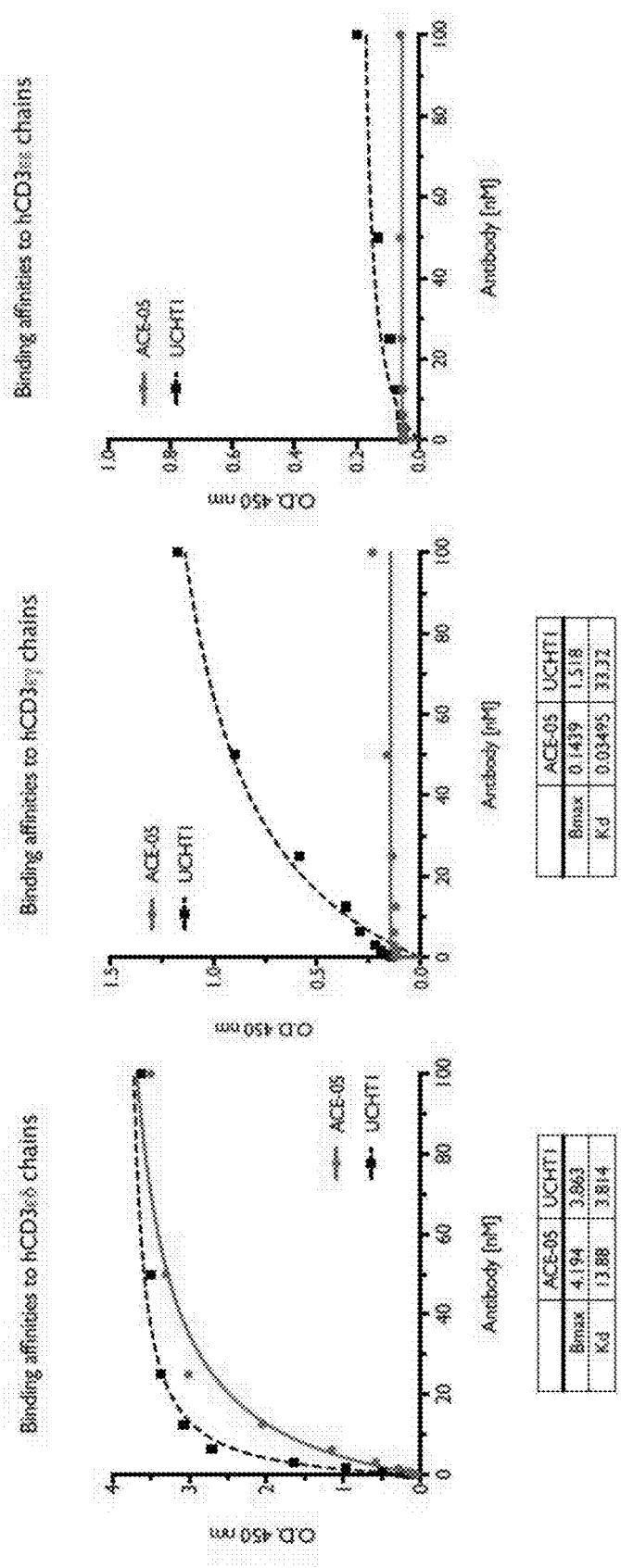

The affinity of ACE-05 and control antibodies to each antigen (e.g., PD-L1 and CD3 for ACE-05) was measured using ELISA. More specifically, antigens such as human PD-L1 (YBL-007 made by Y-Biologics, Inc.) and CD3 (Sino Biological) were immobilized on an immune-plate (Thermo scientific, USA) at a concentration of 1 to 10 µg/ml (100 to 1000 ng/well) using pH 7.4 PBS as a coating buffer at 4° C. overnight. Next day, plate was washed once with 200 µl of PBST, and then a surface blocking was performed at room temperature with 5% skim milk for 1-2 hours. Subsequently, after washing each well twice with 200 µl of PBST, ACE-05 and control antibodies were diluted at a ratio of 1/2 to 1/5 and allowed to react at room temperature for 1-2 hours. Each well was then washed three times with 200 µl of PB ST to remove unbound samples. Horseradish peroxidase (HRP)-conjugated anti-human IgG (Fab specific) antibodies (Sigma, USA) were added to wells at a ratio of 1:1000 for a reaction at room temperature. After three times of washing with 200 ul of PBST, a color reaction of HRP was induced using TMB solution (GEhealthcare, USA) in a volume of 100 µl/well. The reaction was terminated by using a stop solution (2.5 M $H_2SO_4$, 100 µl/well). A spectrophotometer was used to measure the absorbance at a wavelength of A450 to calculate the binding affinity. The GraphPad Prism software 7 was used to analyze the affinity of ACE-05 and other control antibodies to their respective targets. The results are shown in FIGS. 10A, 10B and 10C.

Figure 11:
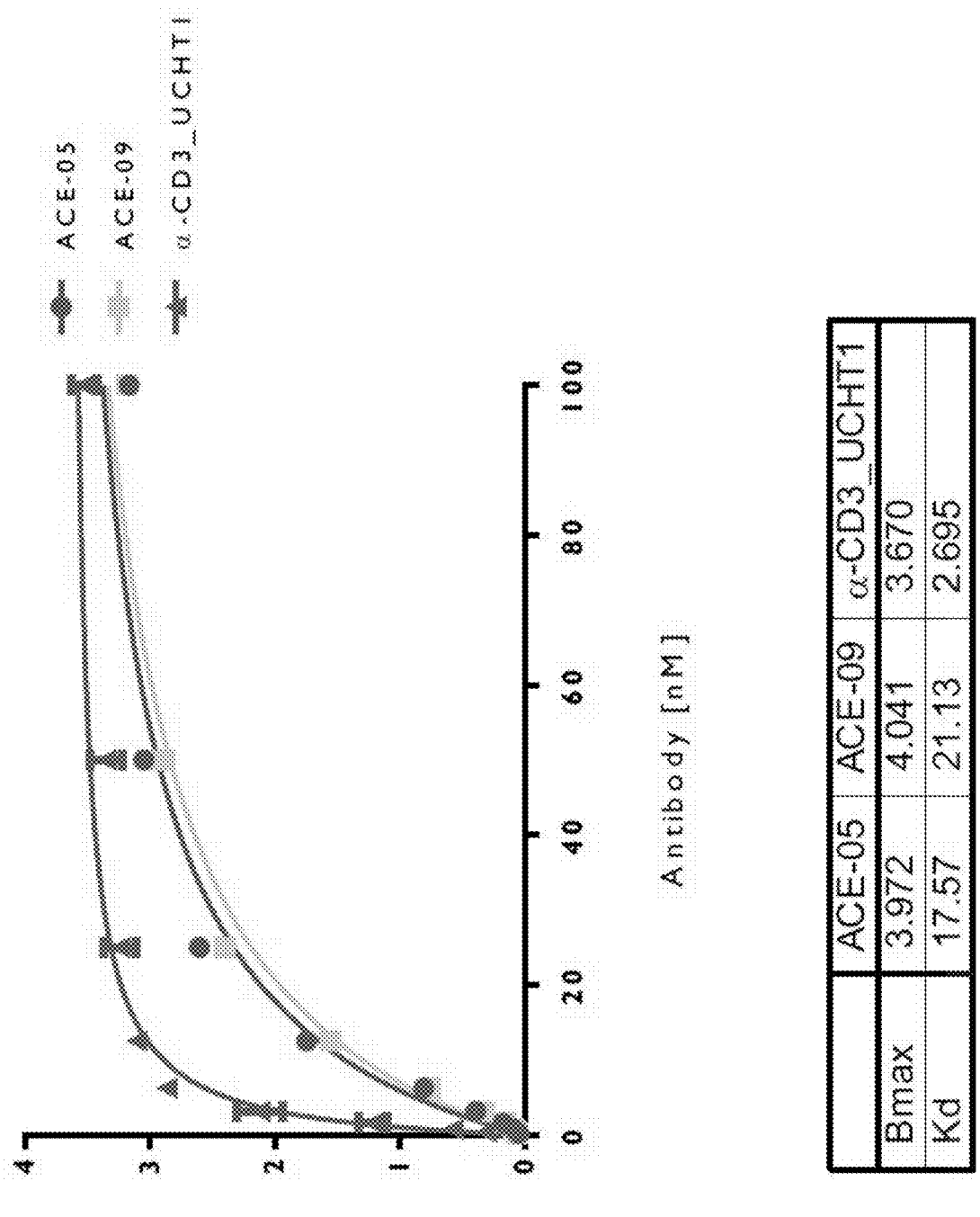
FIG. 11 shows the analysis of binding affinity of ACE-05 and ACE-09 to CD3 using ELISA.

The affinity of ACE-09, ACE-05 and a control antibody to CD3 was measured using similar methods described above. As shown in FIG. 11, ACE-09 showed a similar level of binding affinity as ACE-05.

Example 3

Analysis of Binding Kinetics of ACE-05 Using Surface Plasmon Resonance (SPR)

Figure 12A:
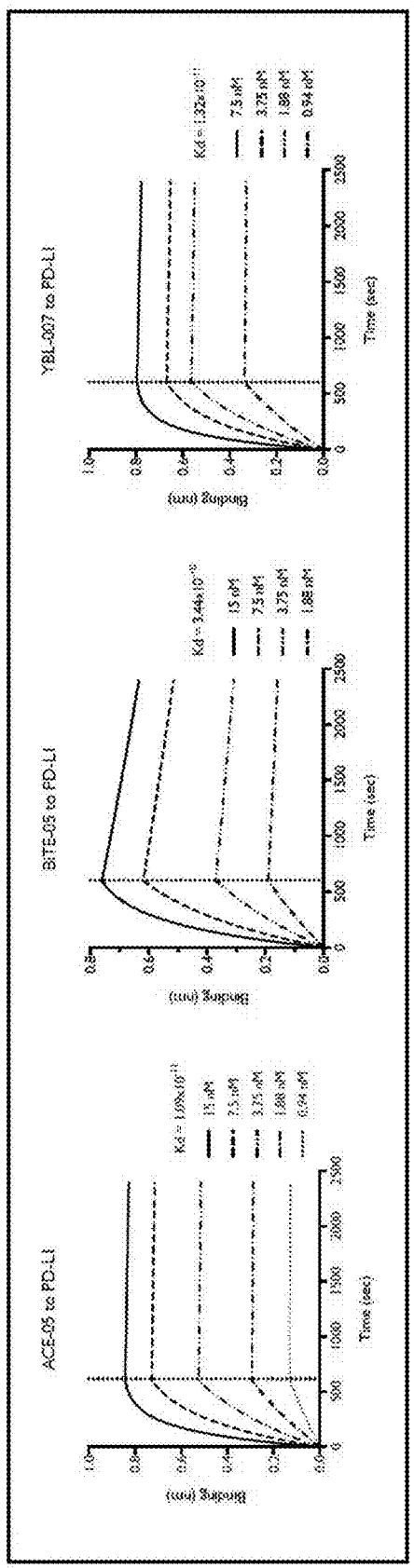
Figure 12B:
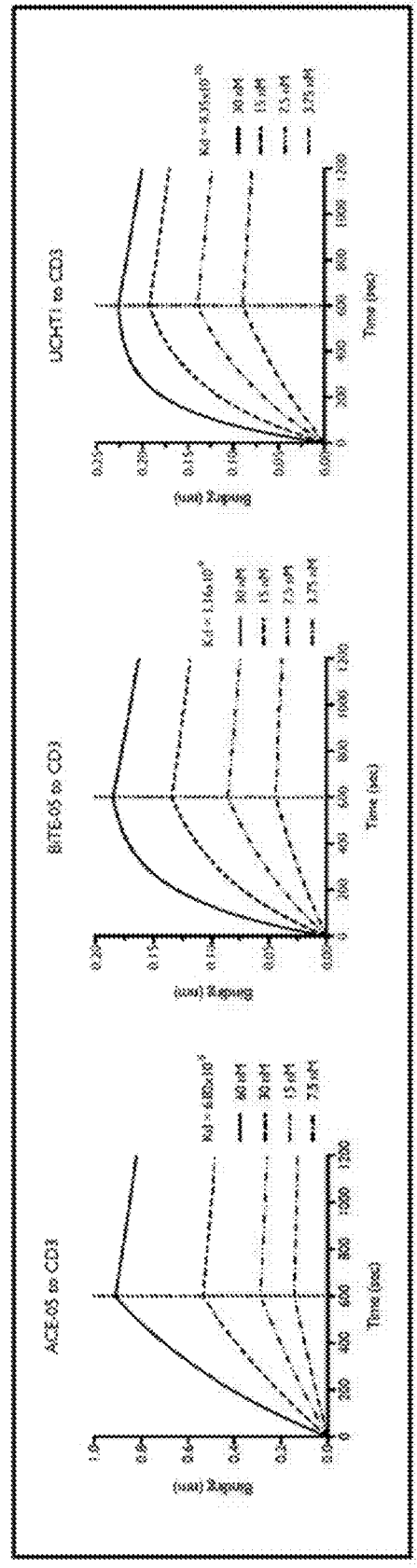

Binding kinetics of ACE-05 to human PD-L1 and CD3 were measured using Surface Plasmon Resonance (SPR) analysis. Measurement of label-free kinetics (protein-protein interaction) using OCTET® QKe system (ForteBio, USA) was performed by using an anti-human IgG capture (AHC) biosensor (ForteBio, USA) for human PD-L1 and amine reactive (ARG2) biosensor for CD3εδ chains. PD-L1 and CD3εδ were fixed on their respective biosensor surfaces and sequentially reacted with ACE-05 that had been diluted with kinetic buffers of different concentrations. Sensorgrams were collected over time. Parental antibodies which were used for making ACE-05 (i.e., anti-hPD-L1 antibody (YBL-007, produced in house using conventional methods known in the art) and anti-CD3 antibody (UCHT1 from BioLegend, USA)) were also tested and compared to ACE-05 in this experiment. As shown in FIGS. 12A-12C, the binding kinetics of ACE-05 to human PD-L1 were comparable to the parental anti-PD-L1 antibody (i.e., YBL-007 from Y-Biologics, Inc.) and the $K_D$ was less than $1.09 \times 10^{-11}$ (see FIGS. 12A-12C). In contrast and as expected, the binding affinity of ACE-05 to CD3 was much lower than the parental anti-CD3 antibody (UCHT1 from BioLegend, USA) and the $K_D$ was determined to be $6.82 \times 10^{-9}$ (see FIG. 5C). As shown in FIGS. 12A-12C, the binding kinetics of ACE-05 was also compared to a bispecific T cell engager (BiTE), i.e., BiTE-05. BiTE is an existing bispecific antibody technology, which generates fusion proteins consisting of two single-chain variable fragments (scFvs) of different antibodies, or amino acid sequences from four different genes, on a single peptide chain of about 55 kilodaltons. More detailed description of BiTE technology can be found, e.g., in Huehls et al., *Immunol Cell Biol.*, 2015, 93(3): 290-296; Baeuerle et al., *Drug Discovery Today*, 2005, 10: 1237-1244; and Kufer et al., *Trends in Biotechnology*, 2004, 22(5): 238-244. ACE-05 was demonstrated to have higher affinity to human PD-L1 than BiTE-05. On the other hand, ACE-05 was demonstrated to have lower affinity to CD3 than BiTE-05, and thus expected to have less cytotoxicity than BiTE-05.

Figure 12D:
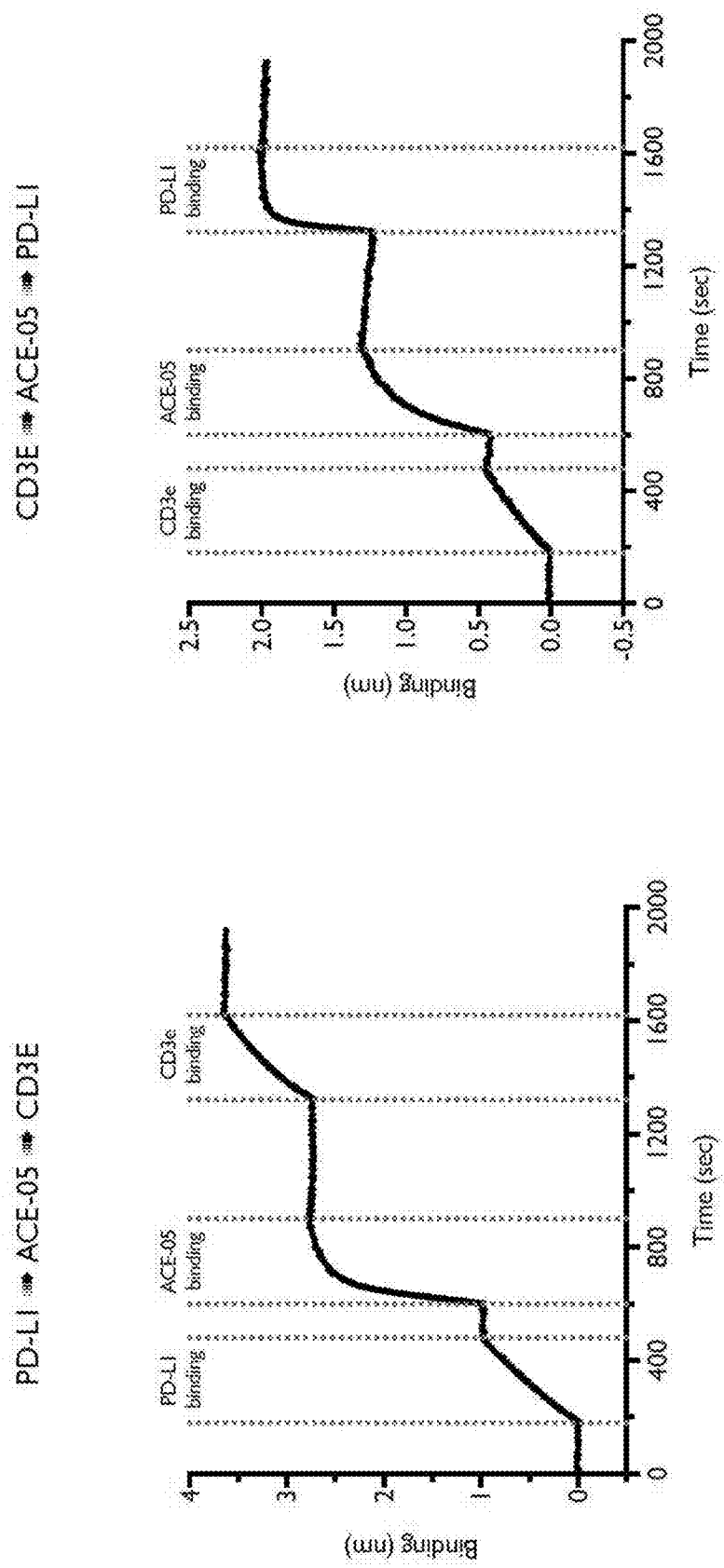
FIG. 12D shows the kinetics analysis of ACE-05 binding simultaneously to PD-L1 and CD3 using Surface Plasmon Resonance (SPR).

In FIG. 12D, label-free kinetics OCTET® system (ForteBio, USA) was used to examine simultaneous binding of ACE-05 to hPD-L1 and hCD3. As ligands, histidine labeled recombinant ligand proteins (e.g., hPD-L1-his, hCD3εδ-his) and Fc-labeled recombinant ligand proteins (e.g., hPD-L1-Fc, hCD3εδ-Fc) were prepared. To capture (immobilize) first antigen on the biosensor chip, a histidine capturing NTA chip (ForteBio, USA) was used. After the first ligand was fully captured on the NTA chip, ACE-05 diluted with kinetic buffer was analyzed. Subsequently, second ligand also diluted in kinetic buffer was analyzed to assess simultaneous binding of ACE-05 to the second ligand.

Example 4

T Cell Redirecting (Activity) and T Cell Cytotoxicity

ACE-05 was tested for its activity for redirecting and activating T cells. In the T cell redirecting (activity) assay, a HEK293E-PD-L1 cell line stably expressing PD-L1 was generated and used as an antigen donor. CD3 positive Jurkat cell line engineered to contain NFAT luciferase reporter system was used as an effector cell (Jurkat luciferase reporter cell, produced in house using conventional methods known in the art).

Figure 13A:
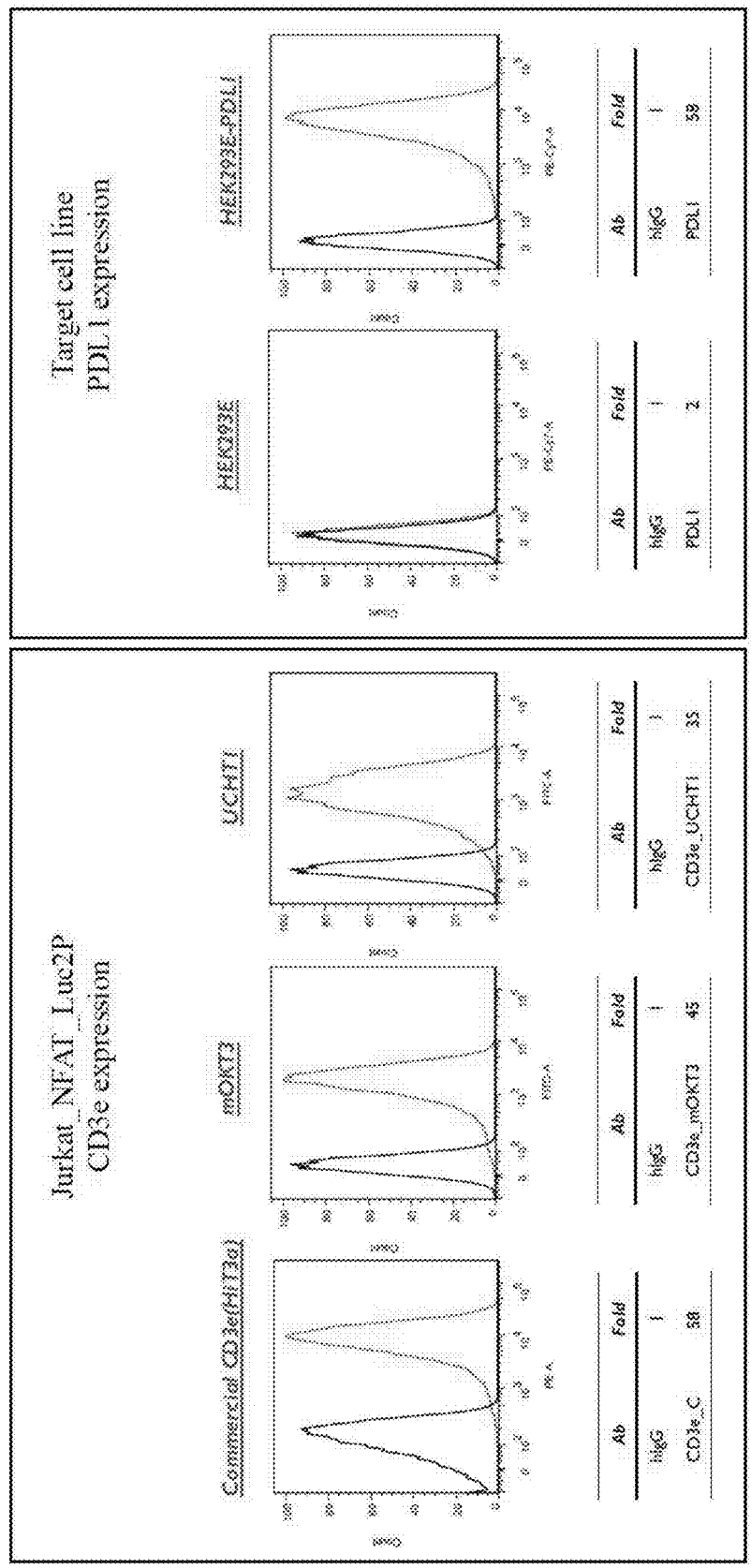
FIG. 13A shows PD-L1 expression levels in HEK293E-PD-L1 cells and the parental HEK293E cells (right panel) and CD3 expression levels in Jurkat luciferase reporter cells as measured by various CD3 antibodies (left panel).

FACS analysis was then used to determine PD-L1 and CD3 expression levels in the above mentioned cell lines. PD-L1 expression levels in HEK293E-PD-L1 cell and the parental HEK293E cell are shown in FIG. 13A (right panel). CD3 expression level in the Jurkat luciferase reporter cell as measured by various CD3 antibodies is also shown in FIG. 13A (left panel).

The T cell redirecting (activity) assay was performed as follows: HEK293E cells and HEK293E-PD-L1 cells ($7 \times 10^4$ cells/well) were seeded on Poly-L-Lysine (Sigma) coated white bottom plates and incubated for 24 hrs. The next day, Jurkat luciferase reporter cells ($1.4 \times 10^5$ cells/well) were treated with serial dilutions of ACE-05, UCHT1 (parental anti-CD3 antibody from BioLegend, USA) and control molecules, and then incubated at 37° C. for 7 hrs. Bio-Glo Luciferase assay (Promega, USA) was performed to detect degrees of Jurkat activation. In the case of ACE-05, to identify synergistic effect of both PD-1/PD-L1 interaction blocking and PD-L1 targeted T cell redirecting, PD-1/PD-L1 blockade assay was performed using PD-1/PD-L1 Blockade Bioassay kit (Promega, USA). Data were processed and analyzed using GraphPad Prism 7 software.

Figure 13B:
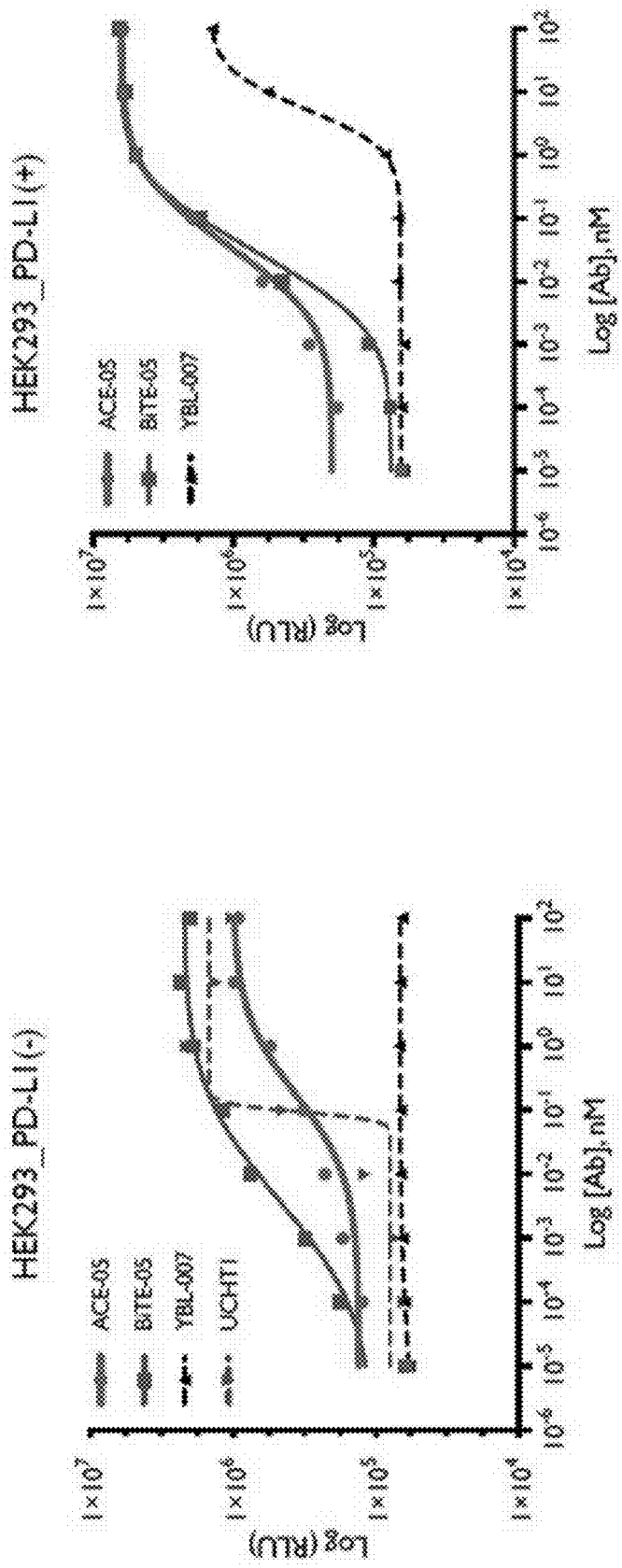
FIGS. 13B-13E show the results of the T cell redirecting (activity) assay for ACE-05 and BiTE-05.

As shown in FIG. 13B, when the target cells expressing PD-L1 (HEK293E-PD-L1 cell) were used, ACE-05 was able to activate the effector T cells (Jurkat luciferase reporter cells); whereas when the target cells not expressing PD-L1 (HEK293E) were used, the effector T cells could not be effectively activated by ACE-05. These results indicate that ACE-05 demonstrates target cell-dependent activation of T cells. ACE-05 was also compared with BiTE-05 in this study. As shown in FIG. 13B, ACE-05 demonstrated more efficient T cell activation than BiTE-05 in the presence of PD-L1. However, in the absence of PD-L1, T cell activation in the presence of BiTE-05 was higher than ACE-05. Therefore, BiTE-05 shows higher cell-independent T cell activation than ACE-05.

Figure 13C:
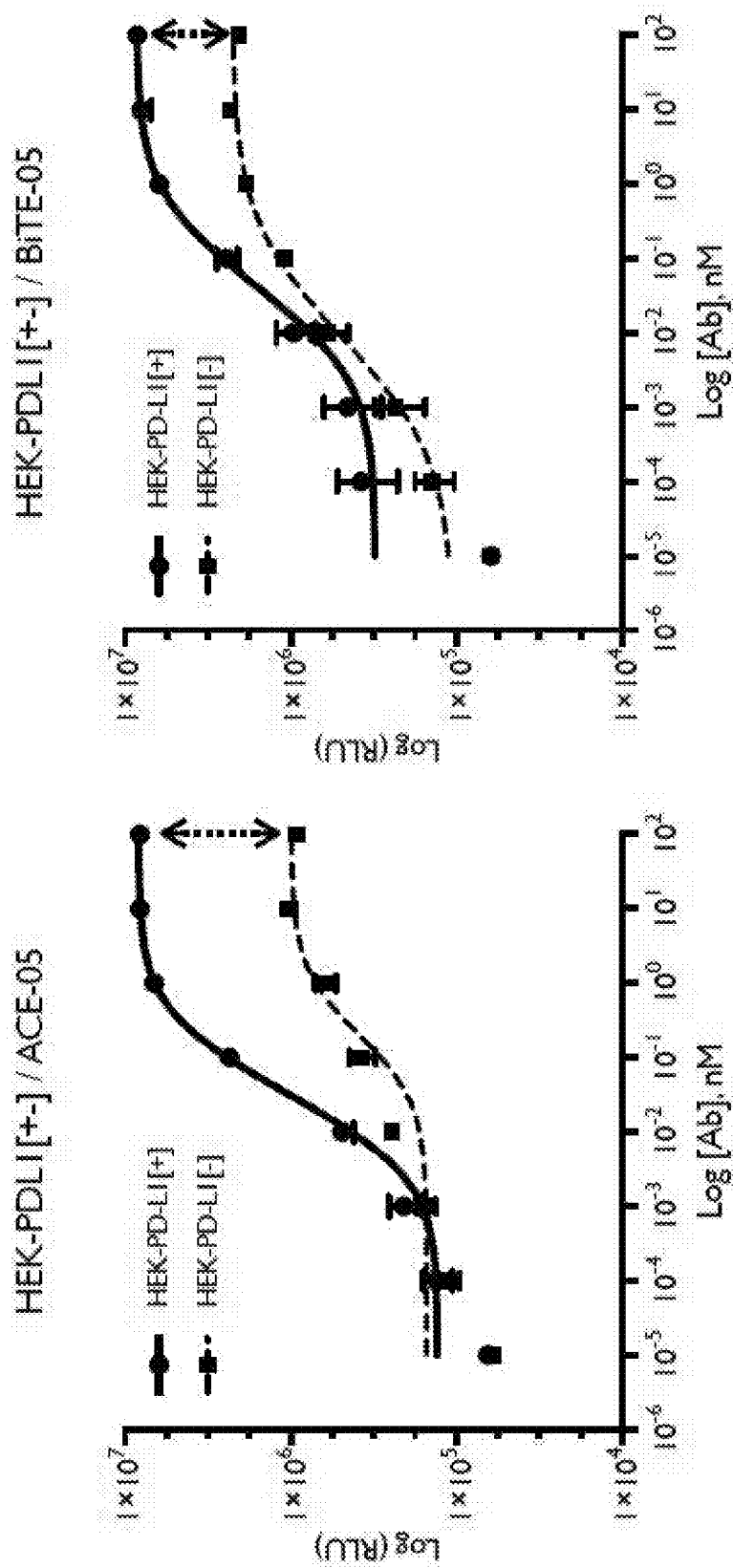
Figure 13E:
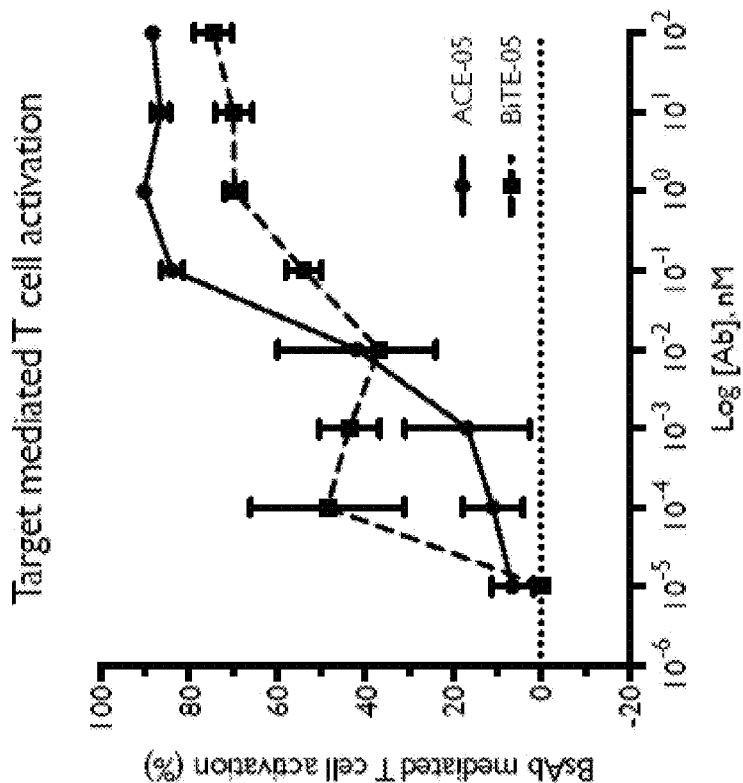
Figure 13D:
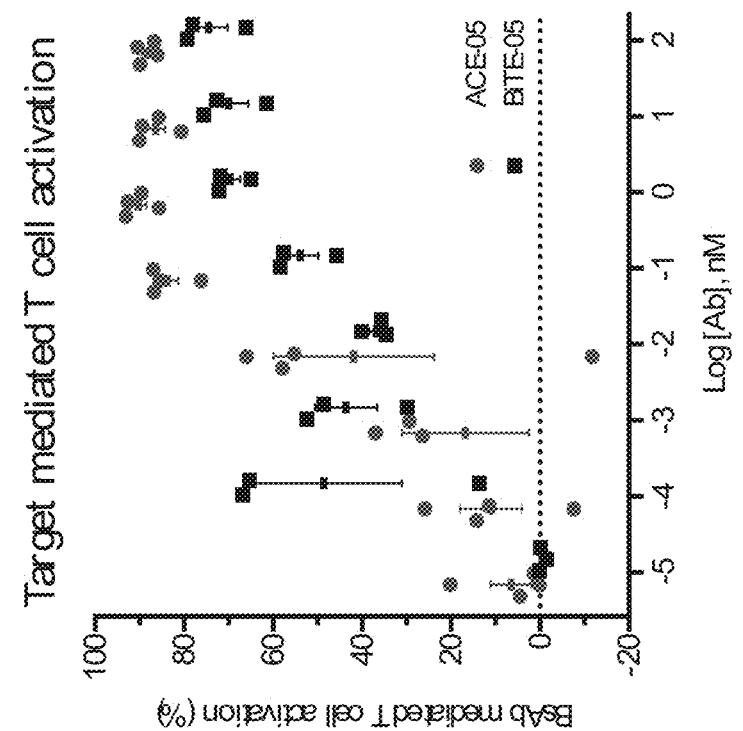

FIG. 13C is the same data from FIG. 13B plotted separately for ACE-05 (left panel) and BiTE-05 (right panel) each with or without PD-L1, showing that the dynamic range of ACE-05 mediated T cell activation was much higher than BiTE-05 mediated T cell activation (indicated by vertical dotted arrows), consistent with observations from FIG. 13B. FIGS. 13D-13E show only target mediated (HEK expressing PD-L1) T cell activation of ACE-05 and BiTE-05, using the same data presented in FIG. 13C.

Figure 13F:
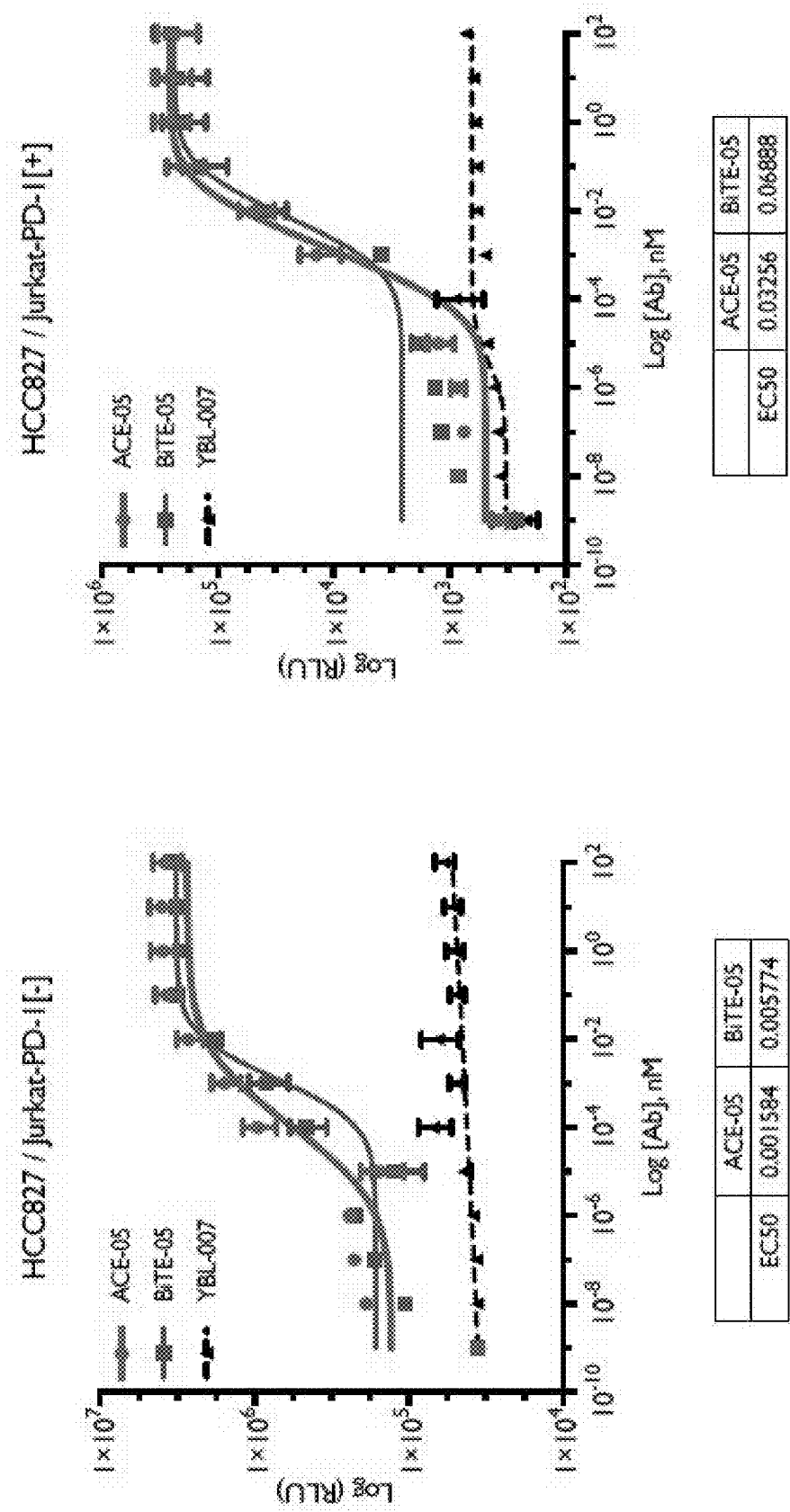
FIG. 13F shows T cell activation in the presence of ACE-05, BiTE-05, or YBL-007 in different T cell stages.

T cell response against cancer varies in cancer immune cycle. HCC827 PD-L1 positive Non Small Cell Lung Carcinoma (NSCLC) and Jurkat luciferase reporter cells with or without PD-1 expression were used to measure T cell response against cancer. Priming and activation stage of T cell was represented as Jurkat-PD-1 [−], and resting and tolerance stage of T cell was represented as Jurkat-PD-1 [+] in FIG. 13F. As shown, the results indicate that the anti-cancer efficacy of ACE-05 is expected to be much higher than BiTE-05 in both developmental stages of T cell.

Figure 13G:
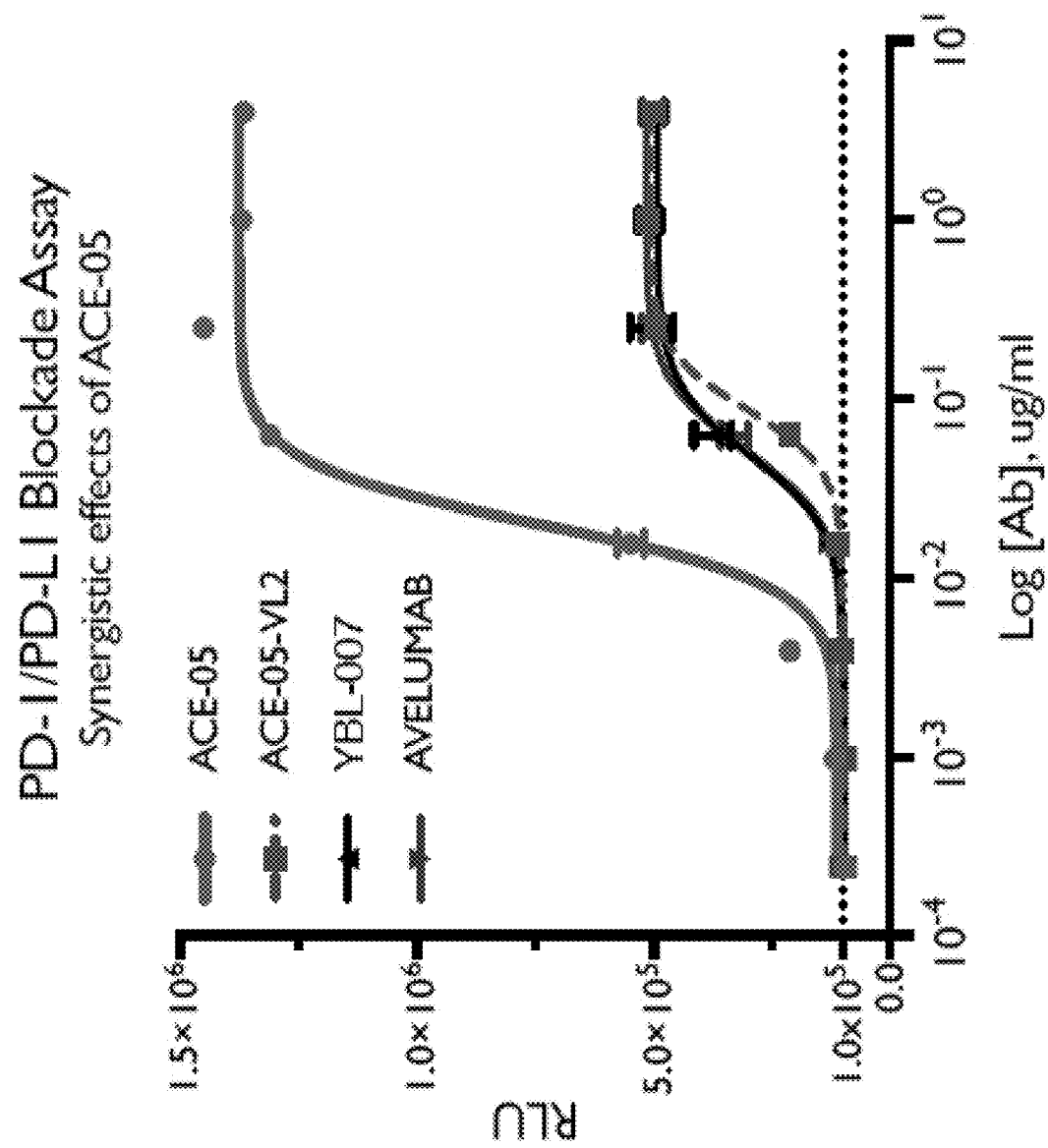
FIGS. 13G-13H show the results of the PD-1/PD-L1 blockage assay for ACE-05.
Figure 13H:
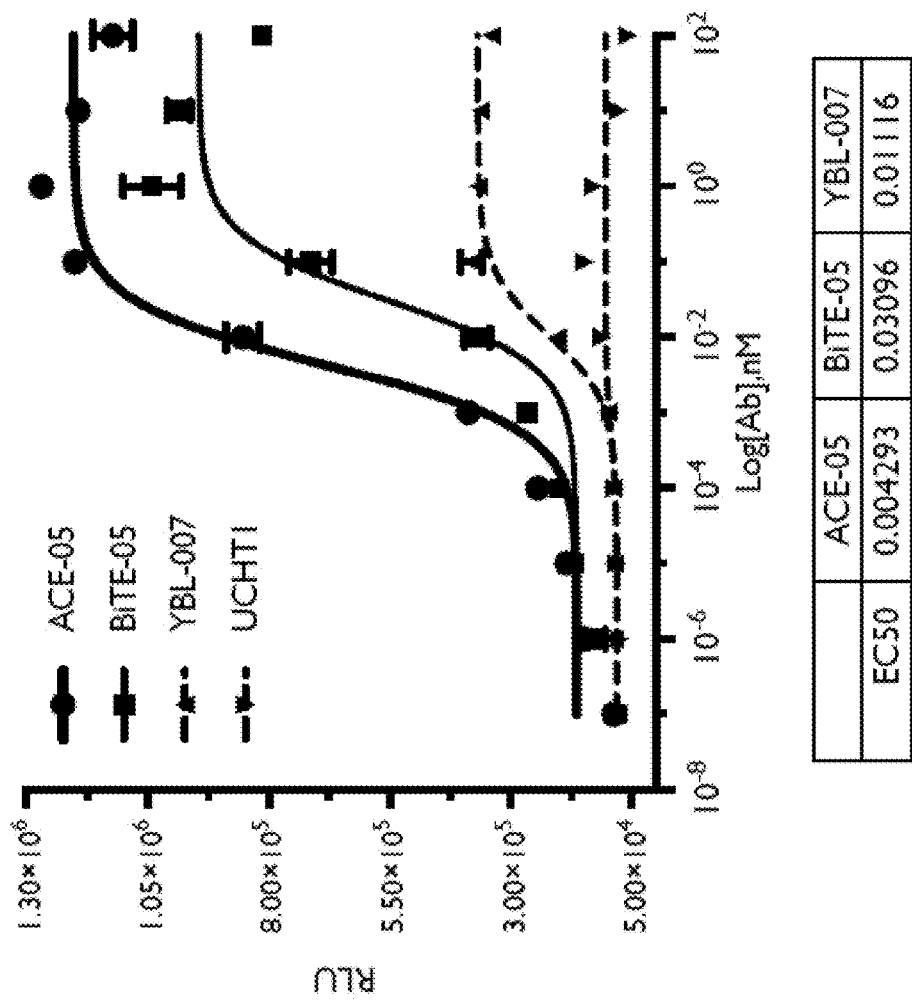

To identify synergistic effect from both blocking PD-1/PD-L1 interaction and PD-L1 targeted T cell redirecting, PD-1/PD-L1 Blockade Bioassay kit (Promega, USA) was used for measuring the biological ability of ACE-05. PD-1/PD-L1 blockade assay was performed by following the protocols provided by the manufacture. The result of the PD-1/PD-L1 blockage assay is shown in FIG. 13G, which demonstrates that ACE-05 could block PD-1/PD-L1 interaction as well as T cell redirecting. FIG. 13H further indicates that, when compared side by side with BiTE-05, ACE-05 shows the highest T cell activation signal because of the synergistic effects from simultaneous PD-L1 blockade and T cell redirecting. YBL-007 is anti-PD-L1 antibody and UCHT1 is anti-CD3 antibody.

Figure 13I:
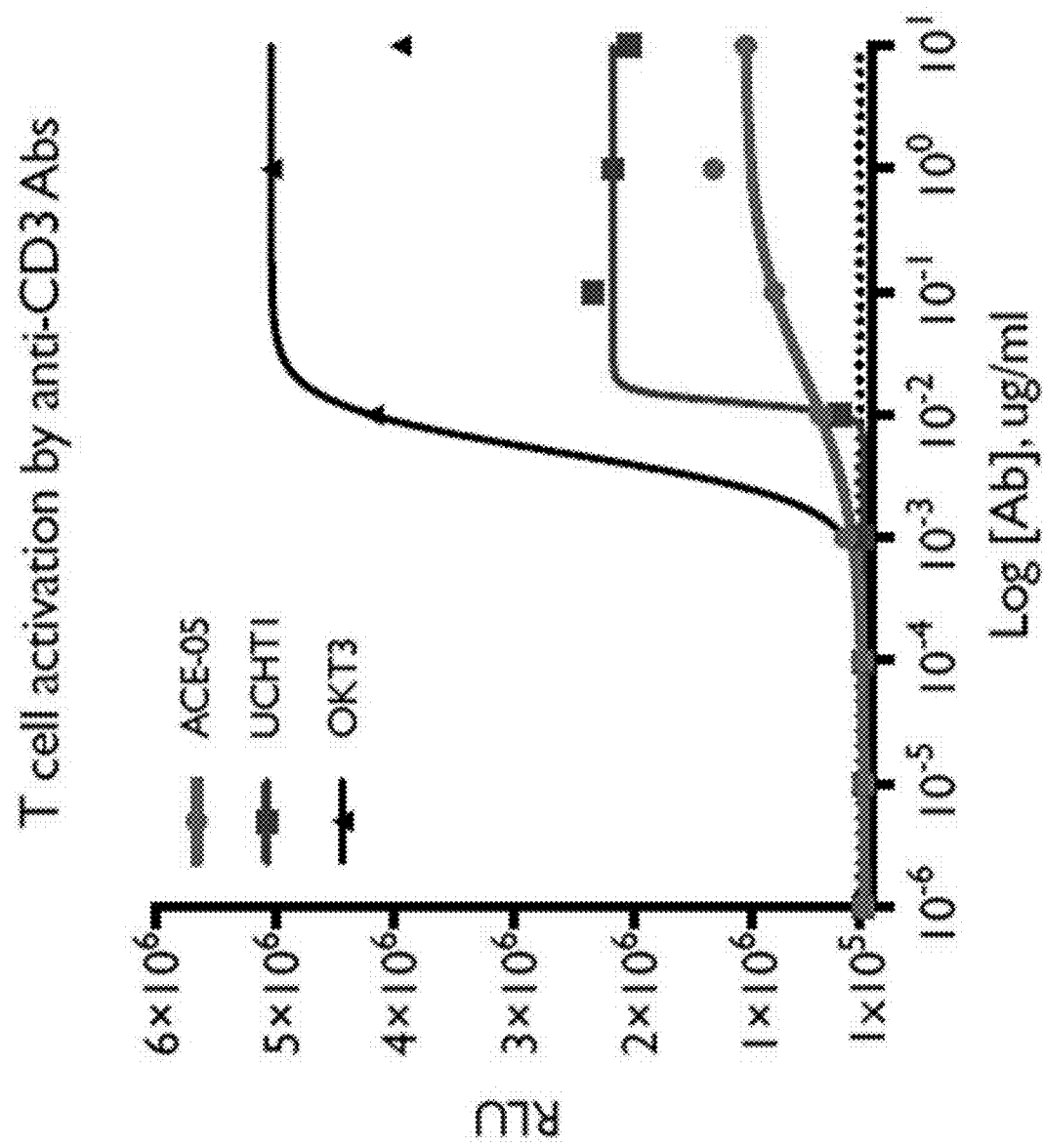
FIGS. 13I-13J show T cell activation by ACE-05, BiTE-05, UCHT1 (an anti-CD3 antibody from BioLegend, USA), or OKT3 (an anti-CD3 antibody from BioLegend, USA).
Figure 13J:
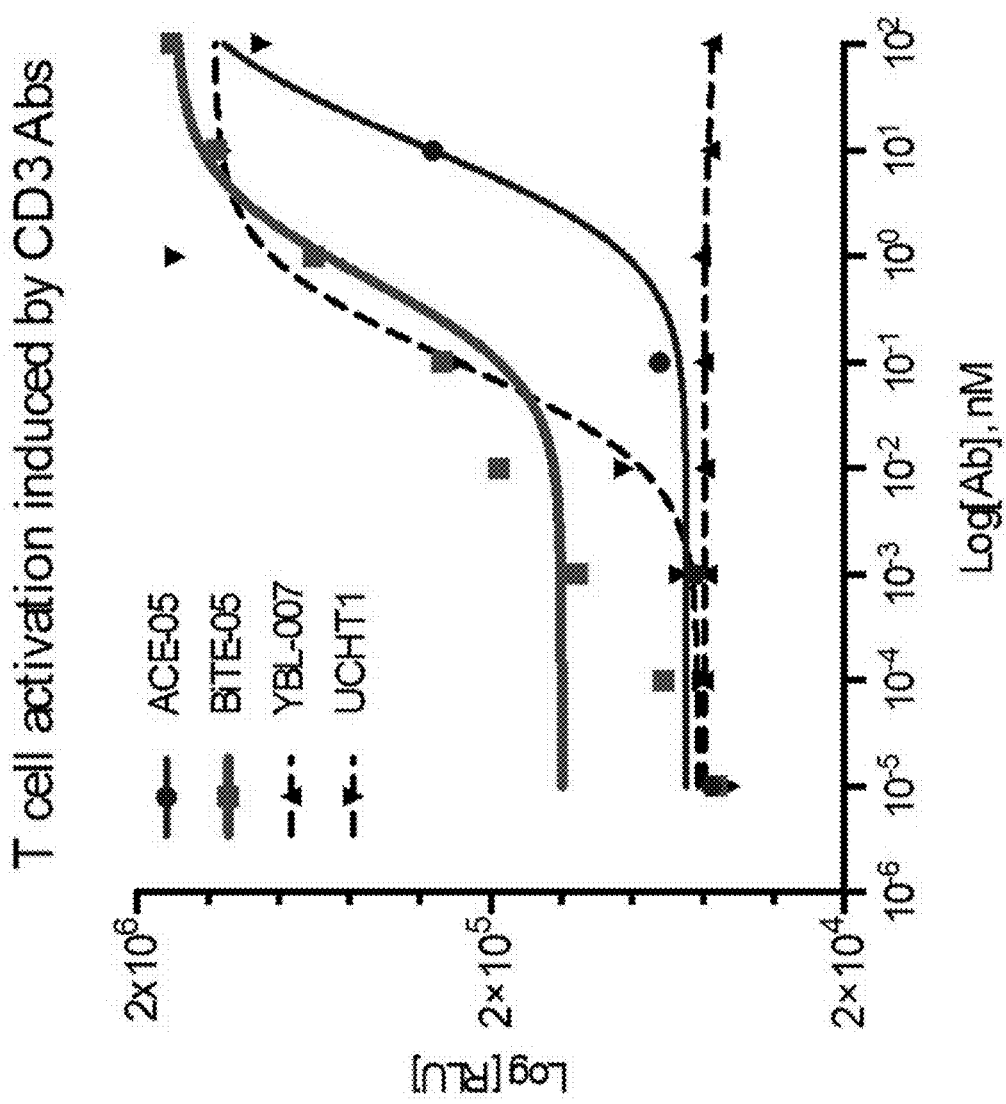

In addition, as shown in FIG. 13I, ACE-05 shows less target independent T cell activation than the anti-CD3 antibody. This result is consistent with the observed lower affinity of ACE-05 to CD3 as compared with the parental anti-CD3 antibody. Thus, these results indicate that ACE-05 will exhibit less cytotoxicity than anti-CD3 antibody because monovalent anti-CD3 domain alone is inefficient to activate T cells. FIG. 13J shows data from the same assay comparing ACE-05 and BiTE-05 side by side, indicating that BiTE-05 shows highest T cell activation signal in the absence of PD-L1 target because the affinity of BiTE-05 towards CD3 is much higher than that of ACE-05, implicating a higher level of cytotoxicity.

Figure 13K:
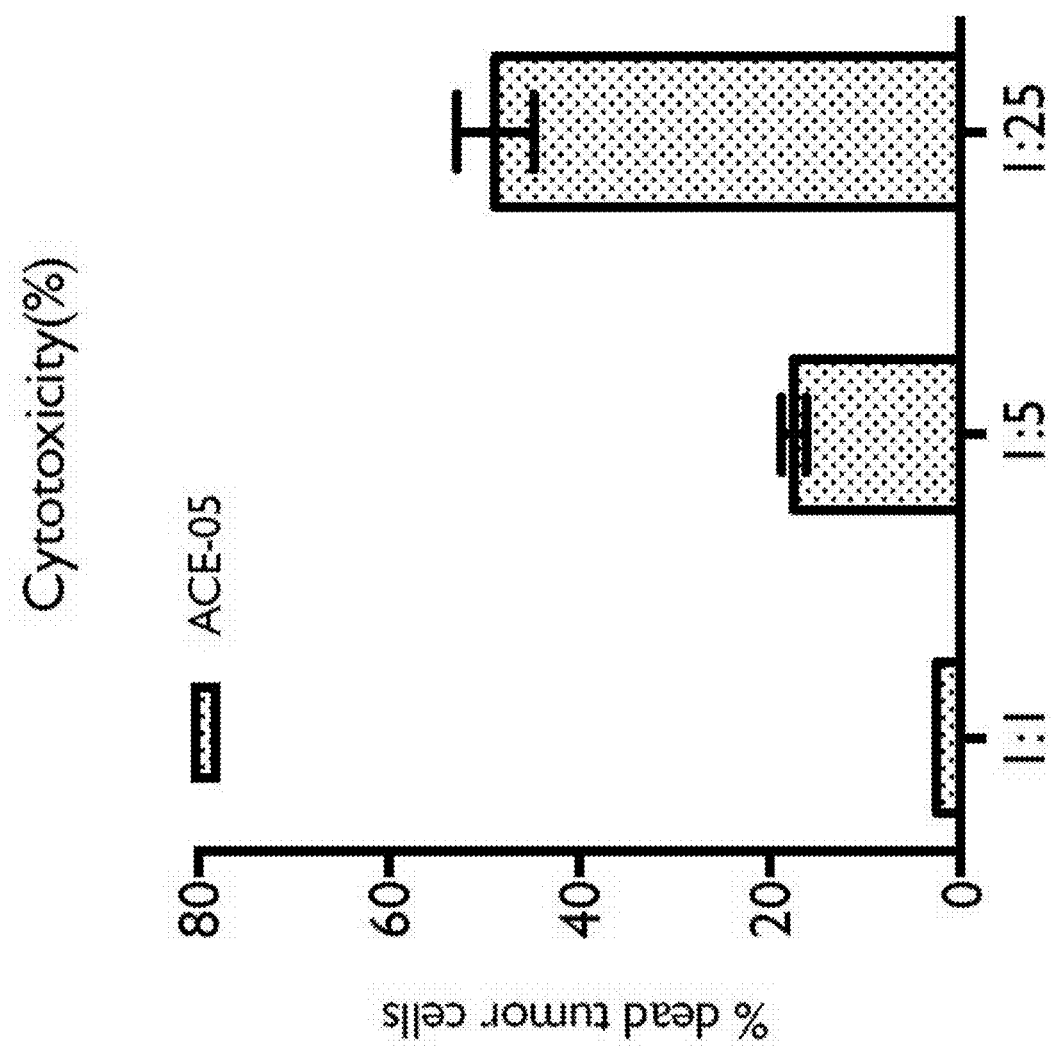
FIG. 13K shows the results of T cell cytotoxicity assay for determining ACE-05 mediated T cell cytotoxicity.
Figure 13L:
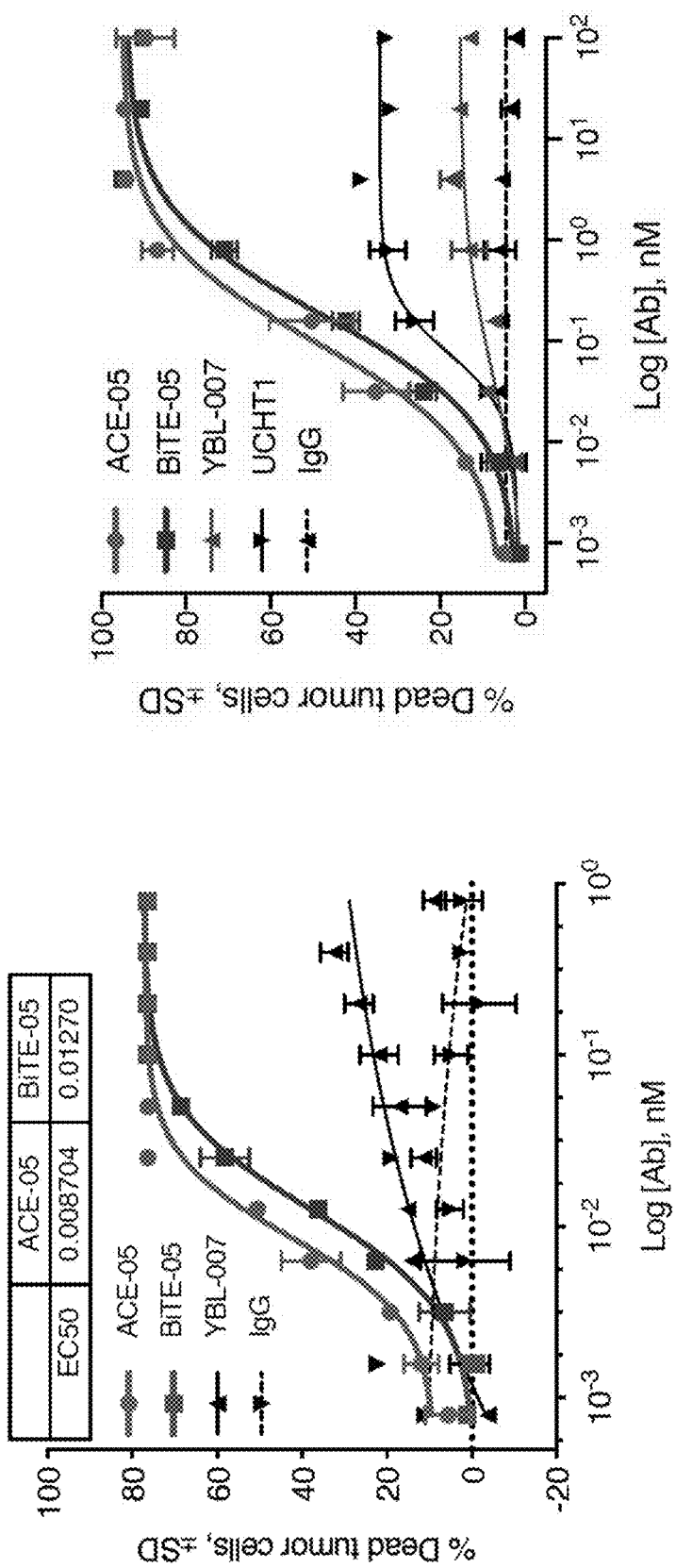
FIG. 13L shows the results of T cell cytotoxicity mediated by ACE-05, BiTE-05, YBL-007, or UCHT1. "IgG" represents normal human IgG used as a negative control.
Figure 13M:
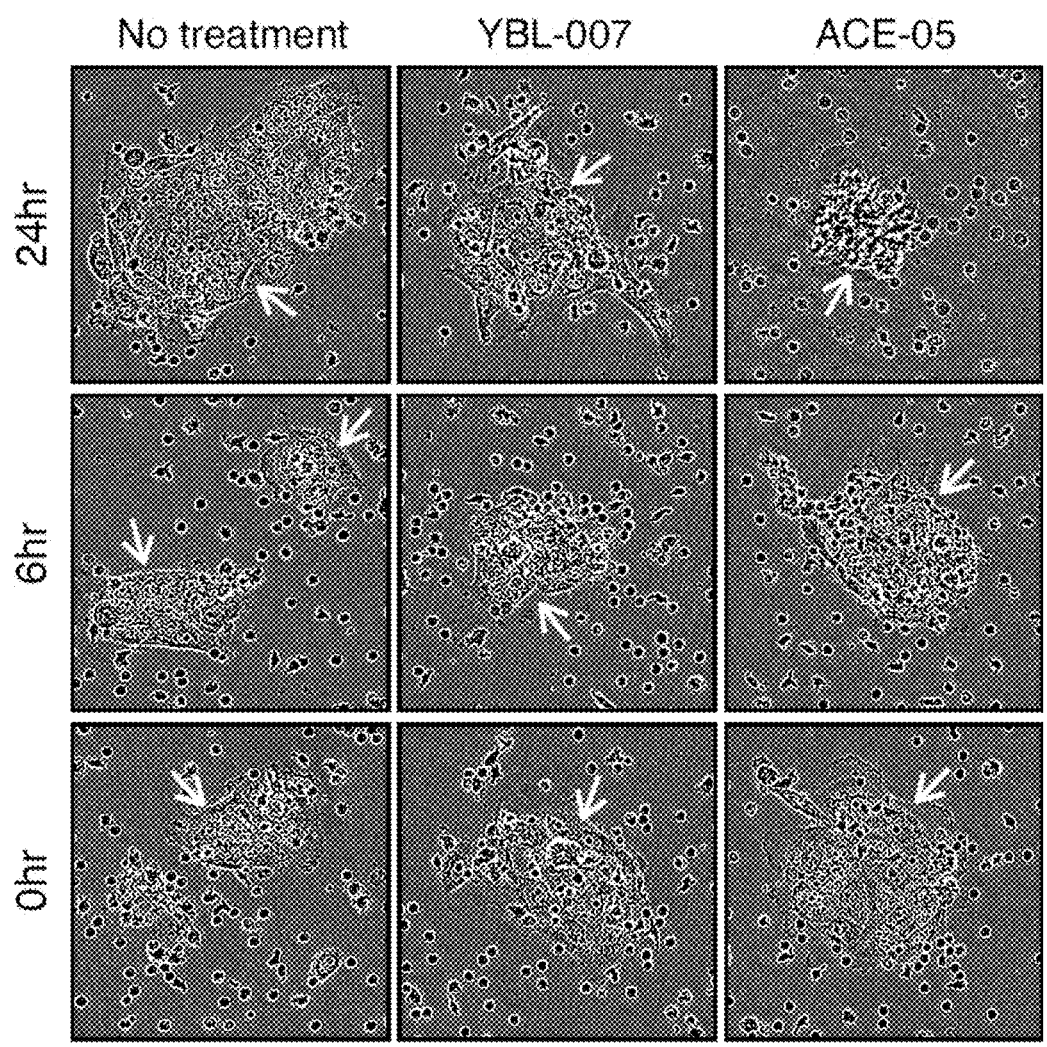
FIG. 13M shows the T cell cytotoxicity on tumor cells when in direct contact with PBMC cells in the presence of ACE-05 or YBL-007. Arrows indicate target HCC827 cancer cells.

ACE-05 mediated T cell cytotoxicity was determined using a LDH (lactate dehydrogenase) assay. PBMC from healthy donors were used as effector cells and HCC827 non-small cell lung cancer cells (ATCC) having over-expressed PD-L1 were used as target cells. LDH released from dead tumor cells was measured by LDH assay system and different ratios of T:E (target:effector) were tested in the presence of ACE-05 (FIG. 13K). Furthermore, ACE-05 showed dose-dependent tumor killing ability against HCC827 cells (PD-L1 positive) that were co-incubated with PBMC isolated from healthy donor (FIG. 13L). FIG. 13M shows the T cell cytotoxicity on tumor cells when in direct contact with PBMC in the presence of ACE-05 or YBL-007. Over a period of 24 hours, the target HCC827 cancer cells were killed in the presence of ACE-05, whereas the target HCC827 cells grew with no treatment or in the presence of YBL-007.

Figure 13N:
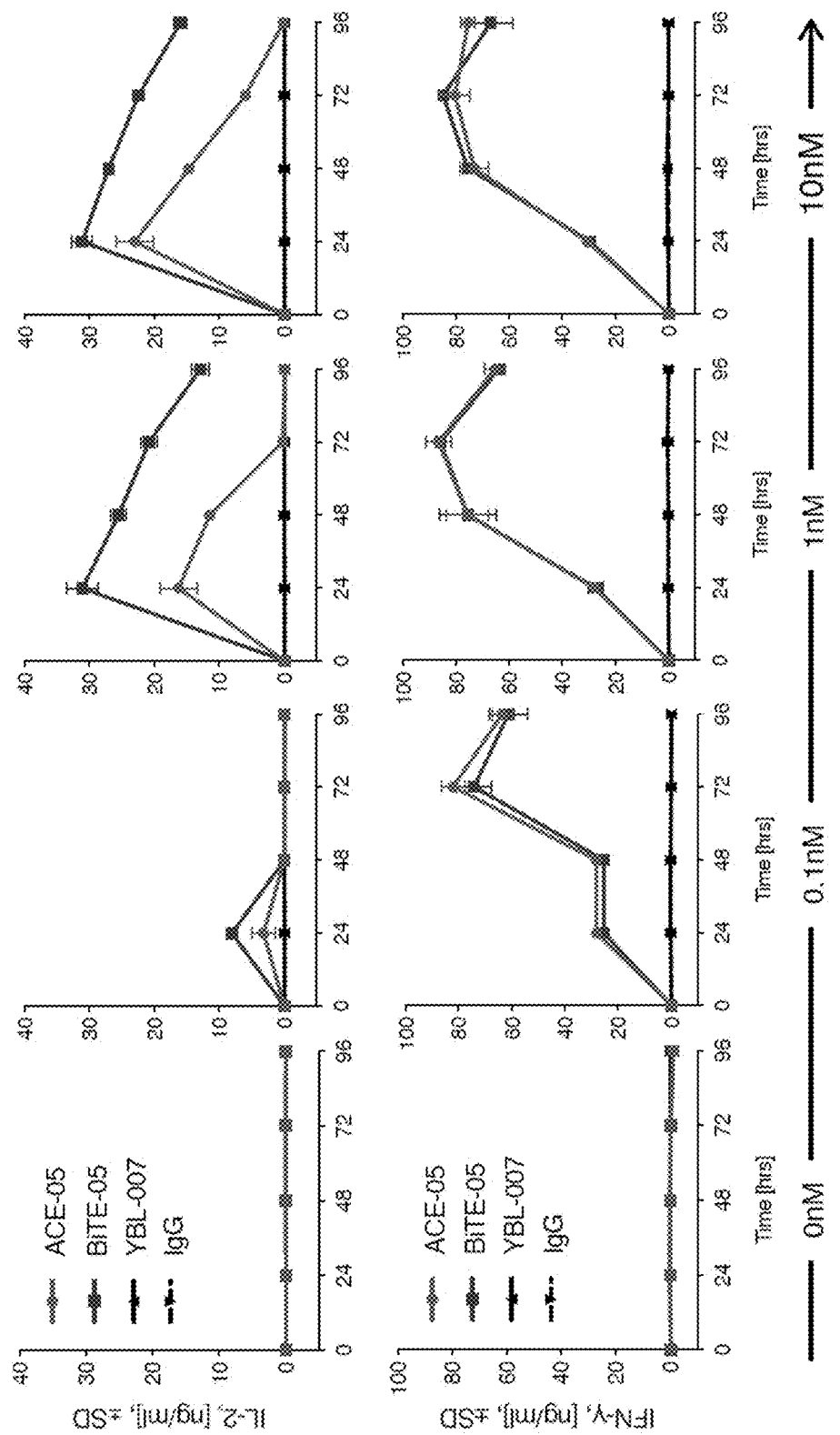
FIG. 13N shows IL-2 and INF-γ levels in the presence of ACE-05, BiTE-05 or YBL-007 in co-cultivated PBMC and HCC827 cells. "IgG" represents normal human IgG used as a negative control.

The levels of immune cytokines released by activated leukocytes may reflect adverse events related to off-target T cell activation. Thus, IL-2 and INF-γ levels in the presence of ACE-05 or BiTE-05 were monitored in co-cultivated PBMC from healthy donors and HCC827 cells using IL-2 or IFN-γ assay kit (BioLegend, USA). Lower level of IL-2 was observed in the presence of ACE-05 than that of BiTE-5, suggesting that it is less likely for ACE-05 to active CD3+ T cells, which are major sources of IL-2 secretion. Thus, ACE-05 may induce less off-target activation of T cells than BiTE-05. In addition, the presence of ACE-05 and BiTE-05 led to similar levels of INF-γ that is released by NKT or NK cells (FIG. 13N).

Figure 13O:
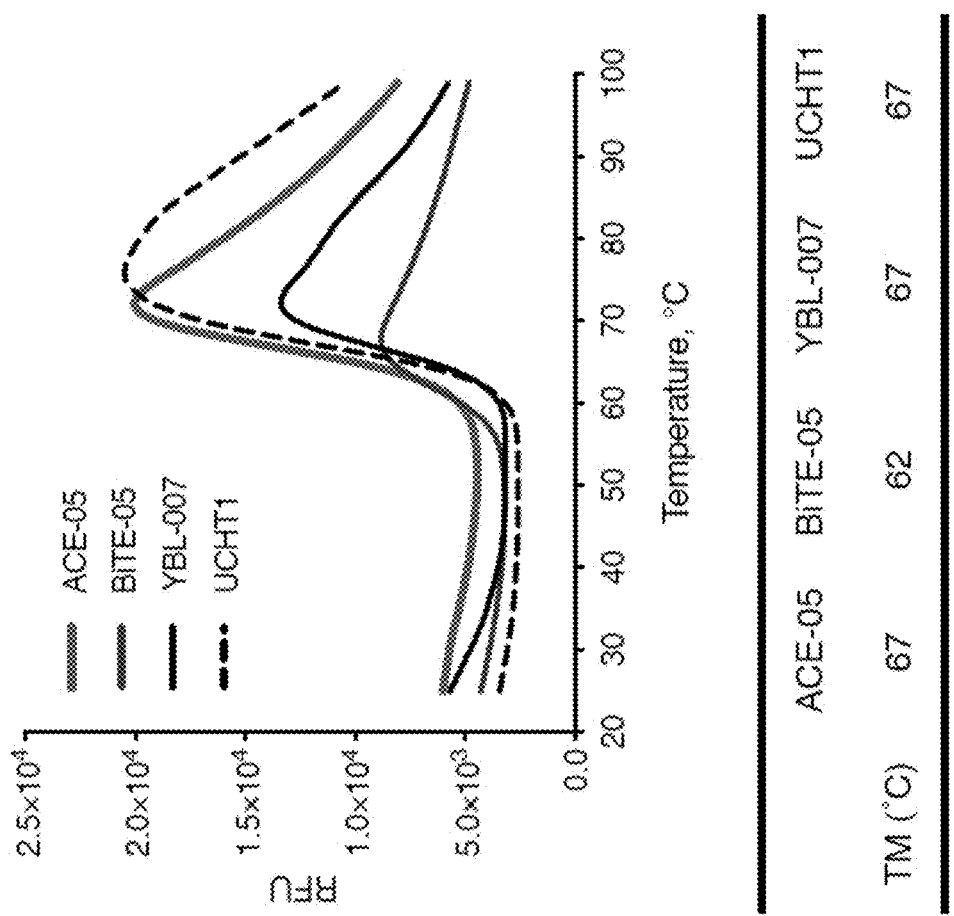
FIG. 13O shows the thermodynamic stability results of ACE-05, BiTE-05, YBL-007, and UCHT1.

The thermodynamic stability of ACE-05 was evaluated using C1000 Thermal Cycler with CFX 96TM ORM system (BioRad, USA). 3 μM binding molecules were mixed with 10 μl of 1/25 diluted CYPRO orange protein stain (Invitrogen, USA), and 50 μl of the mixtures were allowed to incubate for 30 min at 25° C. Samples were denatured by heating at 1° C./min from room temperature to 99° C. The amount of CYPRO-stained denatured proteins were recorded and the melting Temperature™ was calculated by CFX manager software. As shown in FIG. 13O, ACE-05 had higher thermodynamic stability than BiTE-05.

Figure 14B:
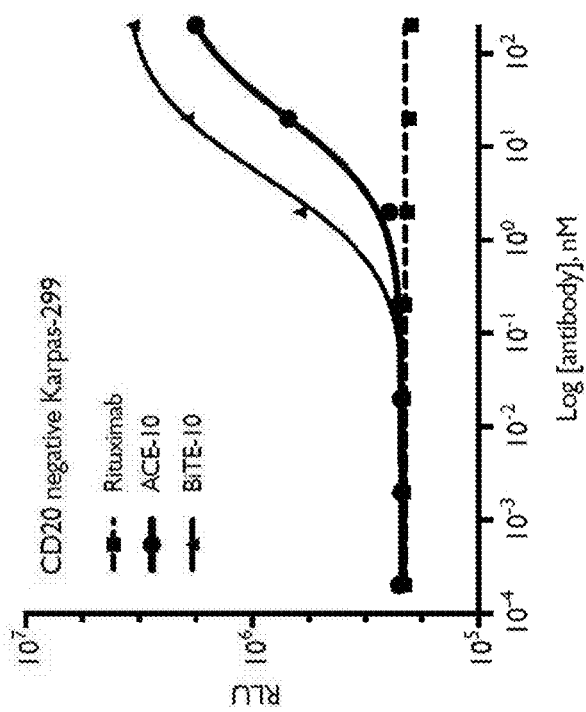
FIGS. 14A-14B show the results of T cell redirecting assay performed for determining ACE-10 mediated T cell activation. "hIgG" represents normal human IgG used as a control.
Figure 14A:
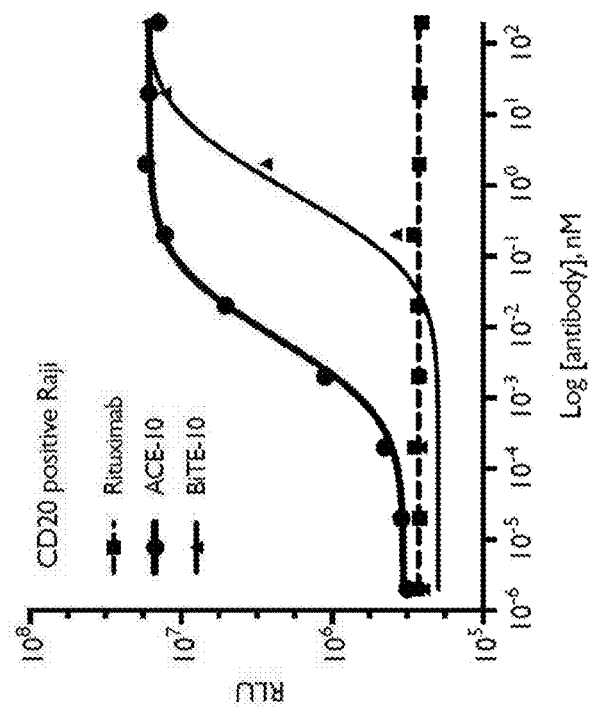

T cell redirecting assay was performed to determine ACE-10 mediated T cell activation via targeting CD20. CD20 positive Raji cells were used as antigen donor target cells and Karpas-299 cells were used as a CD20 negative control. ACE-10 shows more effective T cell activation than that of BiTE-10. Comparison of the results in the CD20 positive Raji cells and the results in the CD20 negative Karpas-299 cells suggests that the T cell activation depends on CD20 expression in the target cells (see FIGS. 14A-14B).

Figure 15:
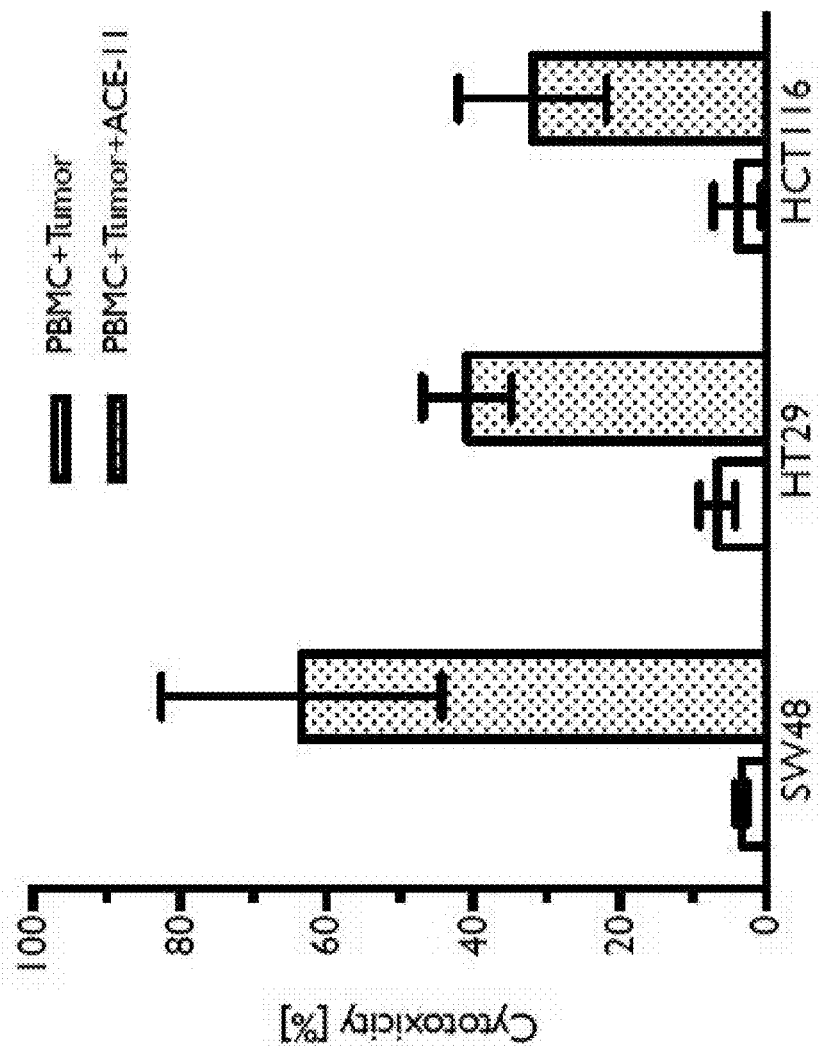
FIG. 15 shows the results of T cell cytotoxicity assay for determining ACE-11 mediated T cell cytotoxicity.

ACE-11 mediated T cell cytotoxicity was also determined using the LDH assay. PBMC from healthy donors were used as effector cells and EGFR-positive SW48, HT29 and HCT116 colon cancer cells were used as target cells. LDH released from dead tumor cells was measured by the LDH assay system. HT29 and HCT116 cancer cells have Ras and Raf mutations that can lead to continuous activation of growth signal. ACE-11 showed cytotoxicity in all three cancer cell lines. Results are shown in FIG. 15.

Example 5

Pharmacokinetic Study in Sprague-Dawley (SD) Rats

A pharmacokinetic study of ACE-05 and control antibodies was performed in SD rats. The study was approved by the institutional animal care and use committee (Approval number: QBSIACUC-A17099).

Figure 16A:
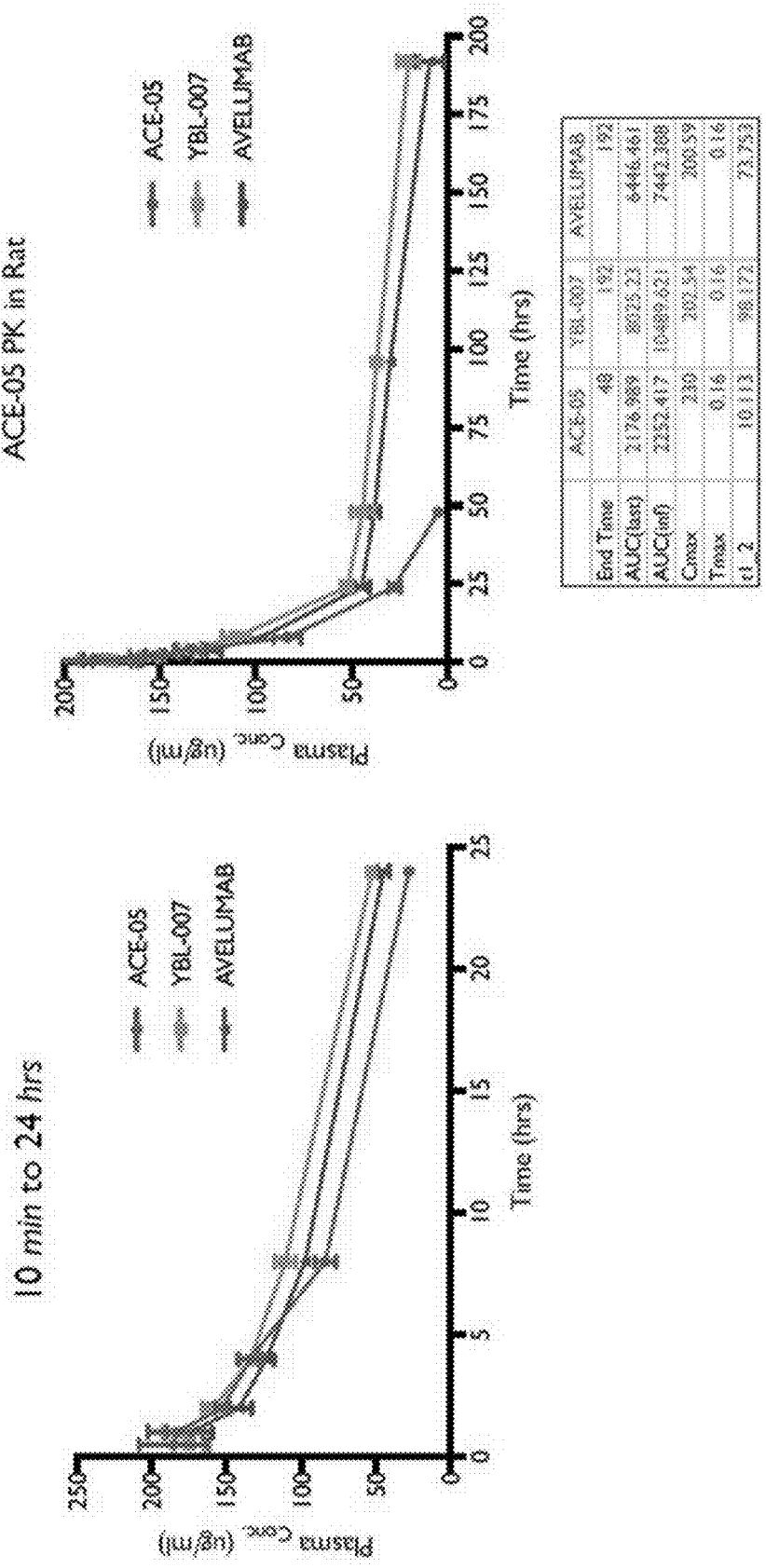
FIG. 16A-16B show the results of ACE-05 pharmacokinetic study in Sprague-Dawley (SD) rat.
Figure 16B:
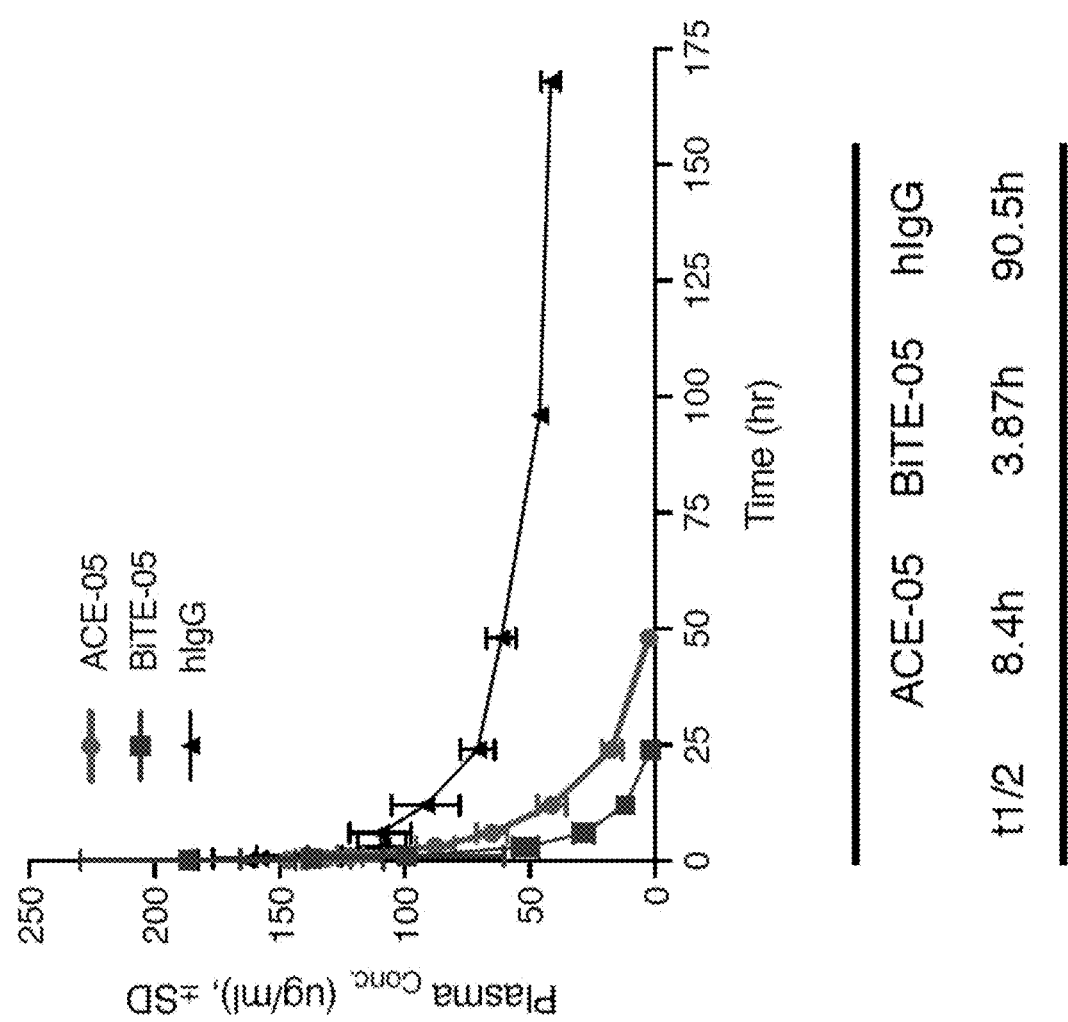
Figure 17A:
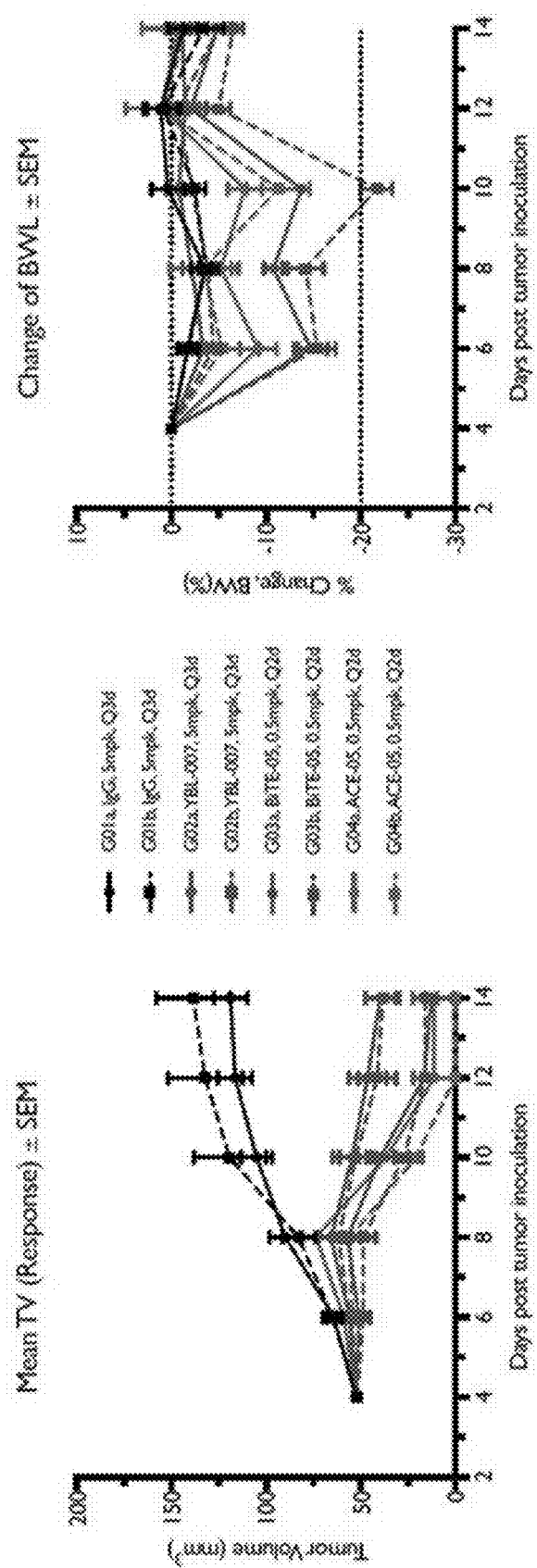
FIG. 17A shows the results of the HCC827 (PD-L1 positive tumor) xenograft study in a humanized mouse model.
Figure 17B:
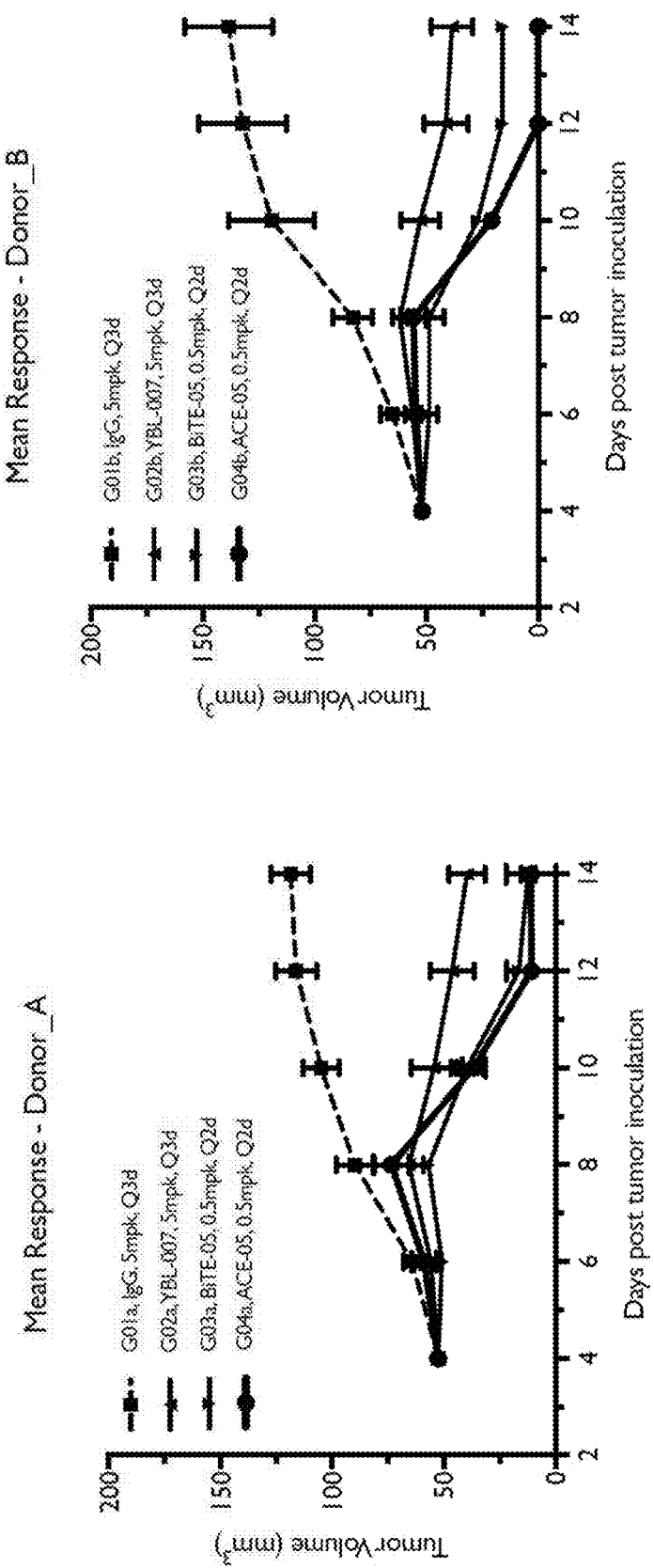
FIG. 17B shows the anti-tumor effects of ACE-05 and other test articles in PBMC donor A and donor B.
Figure 17C:
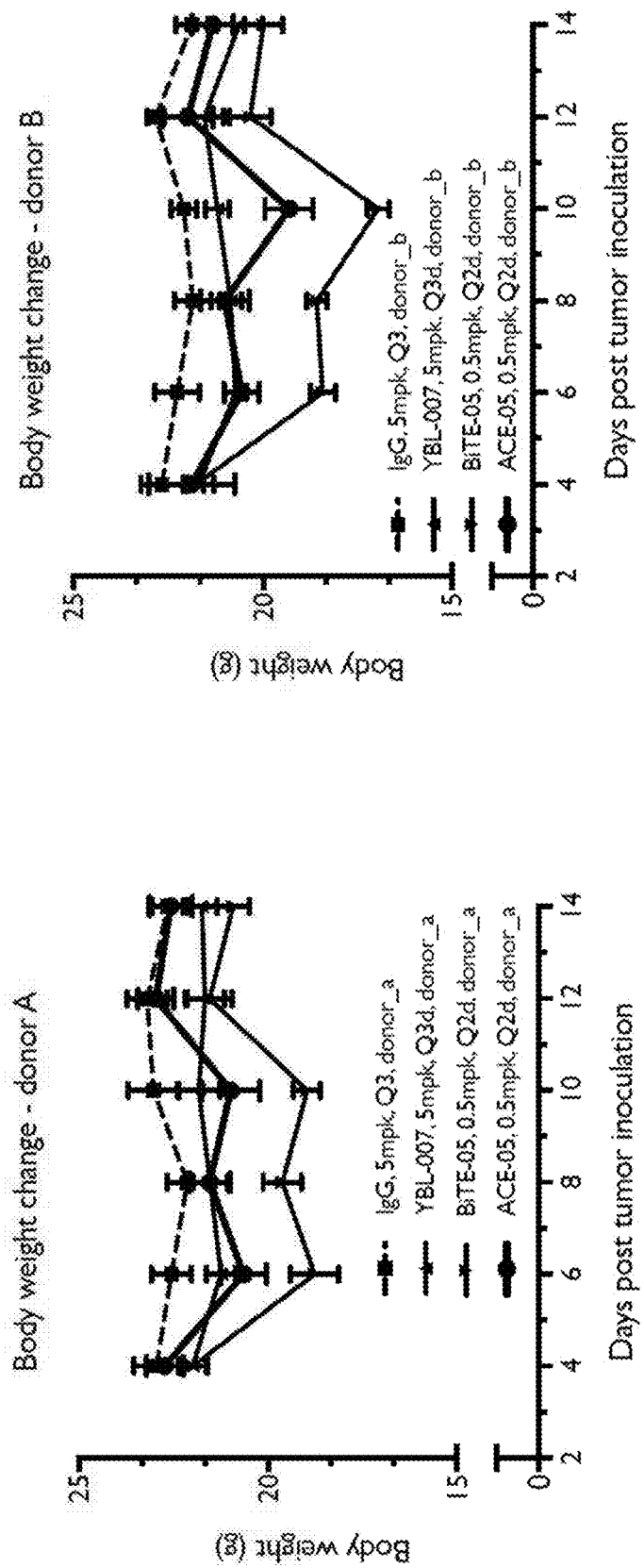
FIG. 17C shows body weight changes of donor A and donor B.
Figure 17D:
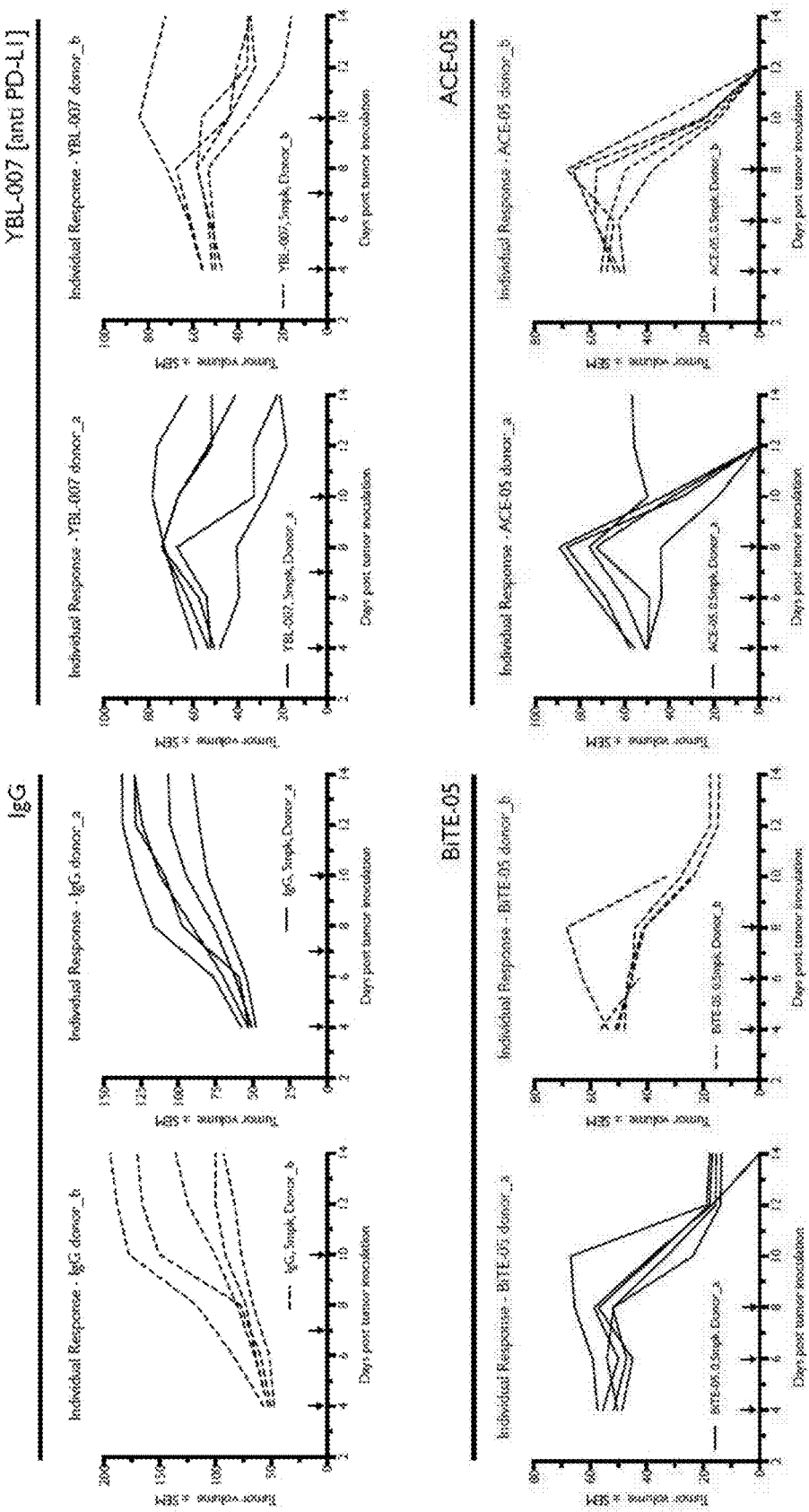
FIG. 17D shows individual anti-tumor efficacy responses.
Figure 17E:
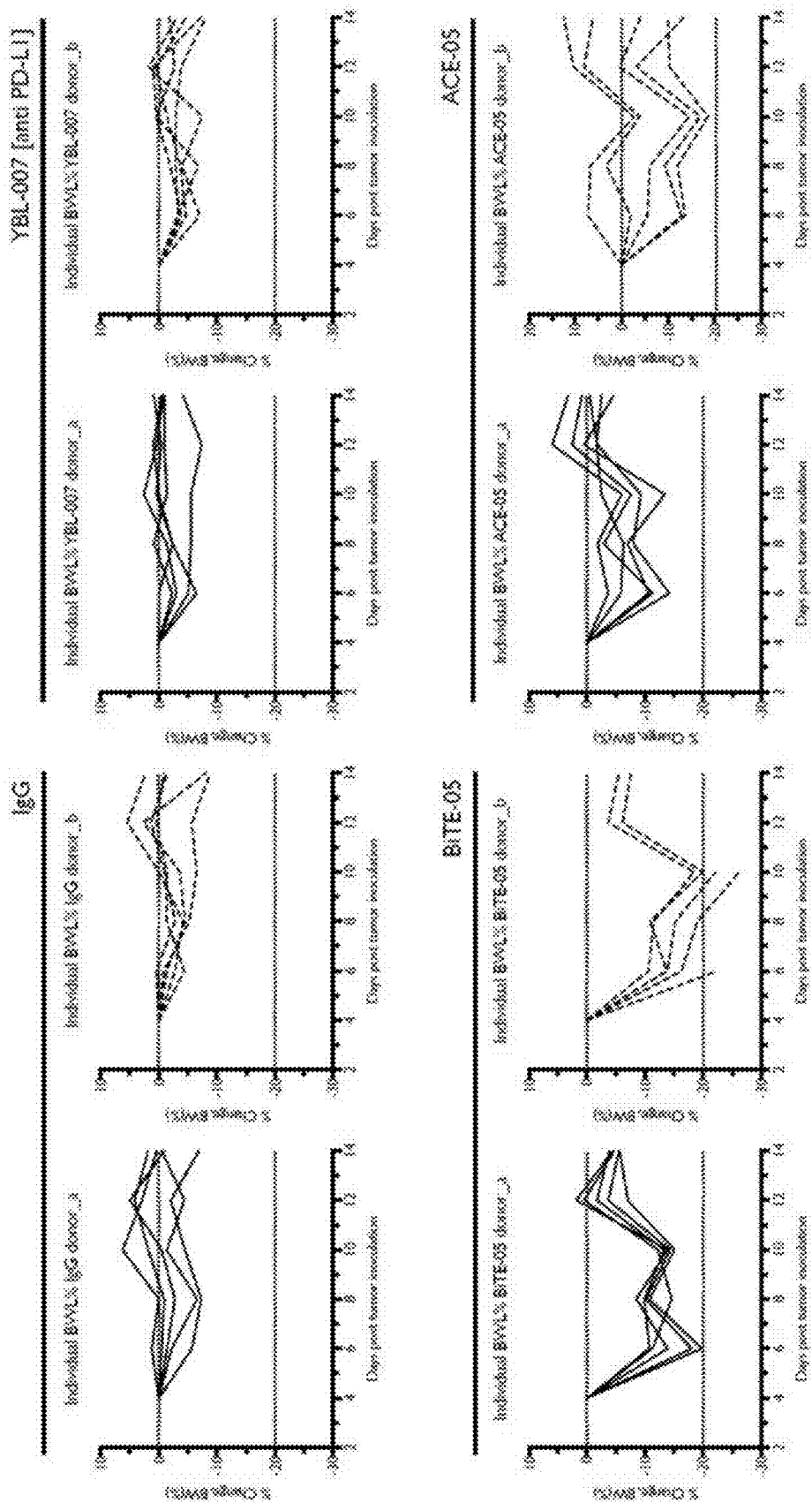
FIG. 17E shows individual body weight loss (%) (side-effect).
Figure 17F:
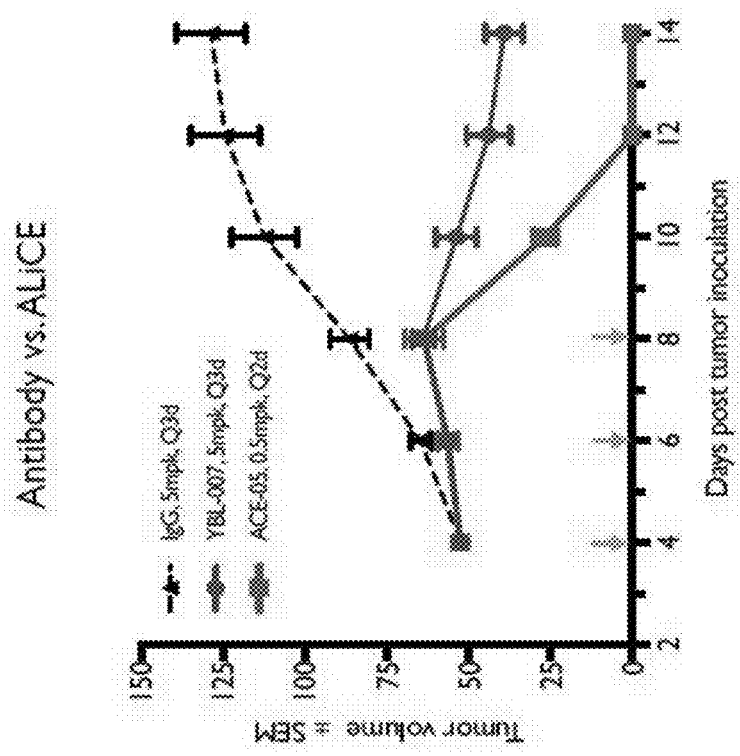
FIG. 17F shows the comparison of anti-tumor efficacy of BiTE and ACE-05 and the comparison of the parental PD-L1 antibody and ACE-05.
Figure 17F:
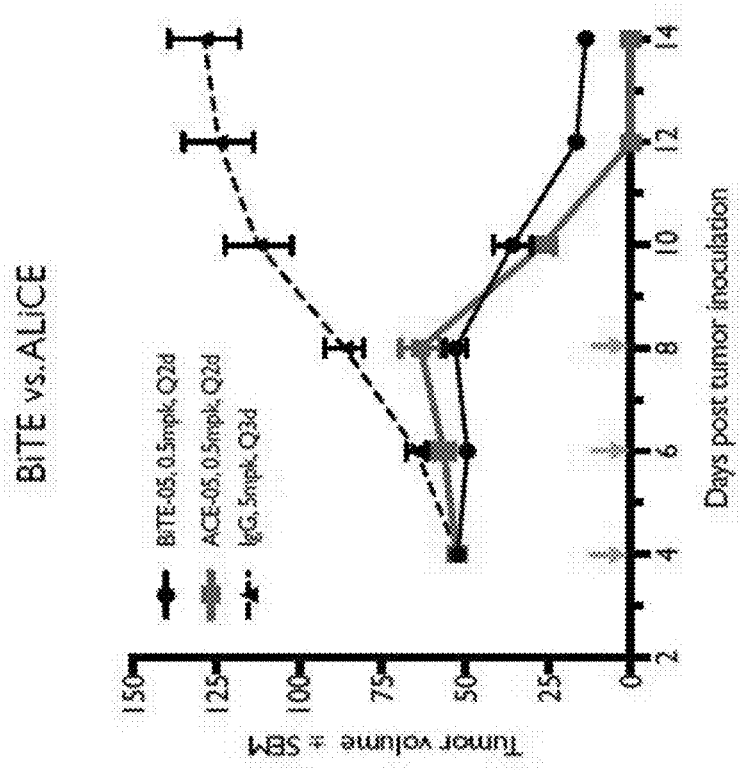

SD rats received a single intravenous dose of 10 mg/kg of ACE-05 or control antibodies (YBL-007 or avelumab) via the tail vein (n=3 male rats/group). A total 500 μl of serum was collected from each animal at the flowing time points: 10 minutes, 30 minutes, 1 hour, 2 hours, 4 hours, 8 hours, 24 hours, 3 days, 5 days, and 9 days after administration of ACE-05 or control antibodies. Samples were centrifuged at 10,000~13,000 rpm for 2 min and 70 μl of plasma from each sample was separated and stored at −80° C. until further analysis. The concentration of each sample was determined by ELISA. 96-well immune-plate (Thermo Scientific, USA) was coated with PD-L1 (generated by Y-Biologics, Inc.). Rat plasma samples diluted at 1:1000, 1:4000, or 1:8000 were added to the wells. Bounded samples were detected with HRP conjugated anti-human IgG (Fab specific) (Sigma, USA). The wells were developed by TMB substrate (Sigma, USA) according to the manufacture's protocol at a ratio of 1:500. A450 was then measured. The concentration of ACE-05 and control antibodies were determined by comparing with standard curves using the sample proteins of known concentrations. The observance data was analyzed by BA Calc 2007 software. The pharmacokinetic study results are shown in FIG. 16A. As shown, the half-life of ACE-05 was measured to be 10.113 hrs. However, it is most likely that the actual half-life of ACE-05 is much longer than 10 hrs, because the half-life of the parental antibodies were determined to be 98 and 73 hrs in this experiment, which were much shorter than typical half-life for such antibodies (7 or 10 days). As shown in FIG. 16B, ACE-05 exhibited longer half-life than BiTE-05, suggesting the ACE-05 has higher plasma stability than BiTE.

Example 6

Evaluation of Efficacy of ACE-05 in Treating Human Non-Small Cell Lung Cancer

The efficacy of ACE-05 in treating human non-small cell lung cancer was evaluated and compared with other antibodies using HCC827 cell line in NCG mice (CrownBio, USA). The study was designed as shown in the table below:

Example 7

Dose Limit Study on Anti-Cancer Efficacy of ACE-05 and BiTE-05

To find an effective dose of ACE-05, a dose limits study was performed in an HCC827 humanized xenograft model (FIGS. 18A-18D). NCG female mice (CrownBio, USA) 6-8 weeks old were chosen for PBMC reconstituted humanization and divided into 14 study groups (6 mice/group). Before grouping and treatment, all animals were weighed and the tumor volumes were measured using a caliper. Since the tumor volume can affect the effectiveness of any given treatment, tumor volume was used as numeric parameter to randomize selected animals into specified groups. The grouping was performed by using StudyDirector™ software (Studylog Systems, USA). "Matched distribution" randomization method was selected for group allocation, which showed minimal group to group variation in tumor volume.

Human PBMCs from 2 donors were implanted via i.v. 3 days before tumor cell inoculation. Each mouse was inoculated subcutaneously at the right flank region with HCC827 tumor cells ($5 \times 10^6$) in 0.1 ml of PBS for tumor development. Five different concentration of ACE-05 and BiTE-05 from 0.5 mpk (mg/kg) to 0.0005 mpk (0.5, 0.1, 0.05, 0.005, and 0.0005 mpk) were treated day 4 post HCC827 inoculation. Test articles administration was scheduled on every 3 days, i.e., on day 4, day 7, day 10, and day 13 (Q3d, 4 doses total), as shown with 4 vertical arrows above the x-axis in FIG. 18A.

Tumor dimension (FIGS. 18A-18C) and body weight (FIG. 18D) were scored on every 2 or 3 days after the initial

TABLE 13

Study design

| Group | N* | HCC827 (day 0) | PBMC (day −3) | Treatment | Dose (mg/kg) | Dosing Route | Schedule |
|---|---|---|---|---|---|---|---|
| 1 | 10 | Day 0, s.c., HCC827 | Day −3, i.v., PBMC | IgG | 5 mpk | i.v. | Q3d (day 4, 7, 10) |
| 2 | 10 | ($5 \times 10^6$/100 μL/ | ($5 \times 10^6$/100 μL/ | YBL-007 | 5 mpk | i.v. | Q3d (day 4, 7, 10) |
| 3 | 10 | mouse) | mouse) | Bite-05 | 0.5 mpk | i.v. | Q2d (day 4, 6, 8) |
| 4 | 10 | | | ACE-05 | 0.5 mpk | i.v. | Q2d (day 4, 6, 8) |

Figure 18A:
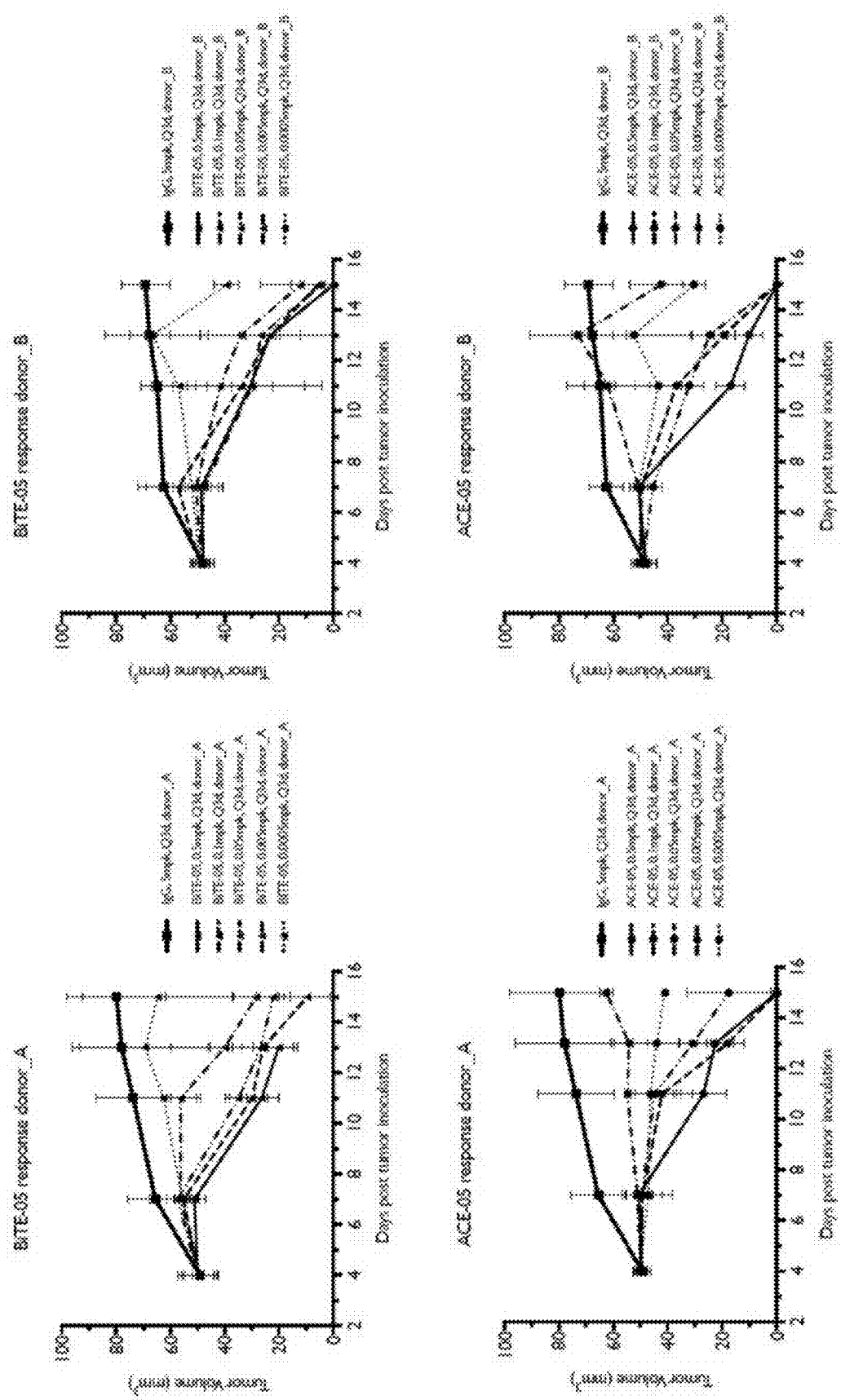
FIGS. 18A-18D show the results of the dose limit study showing the anti-tumor effects of ACE-05 and other test articles in PBMC donor A and donor B in a humanized mouse model inoculated with HCC827 (PD-L1 positive tumor) xenograft.
Figure 18B:
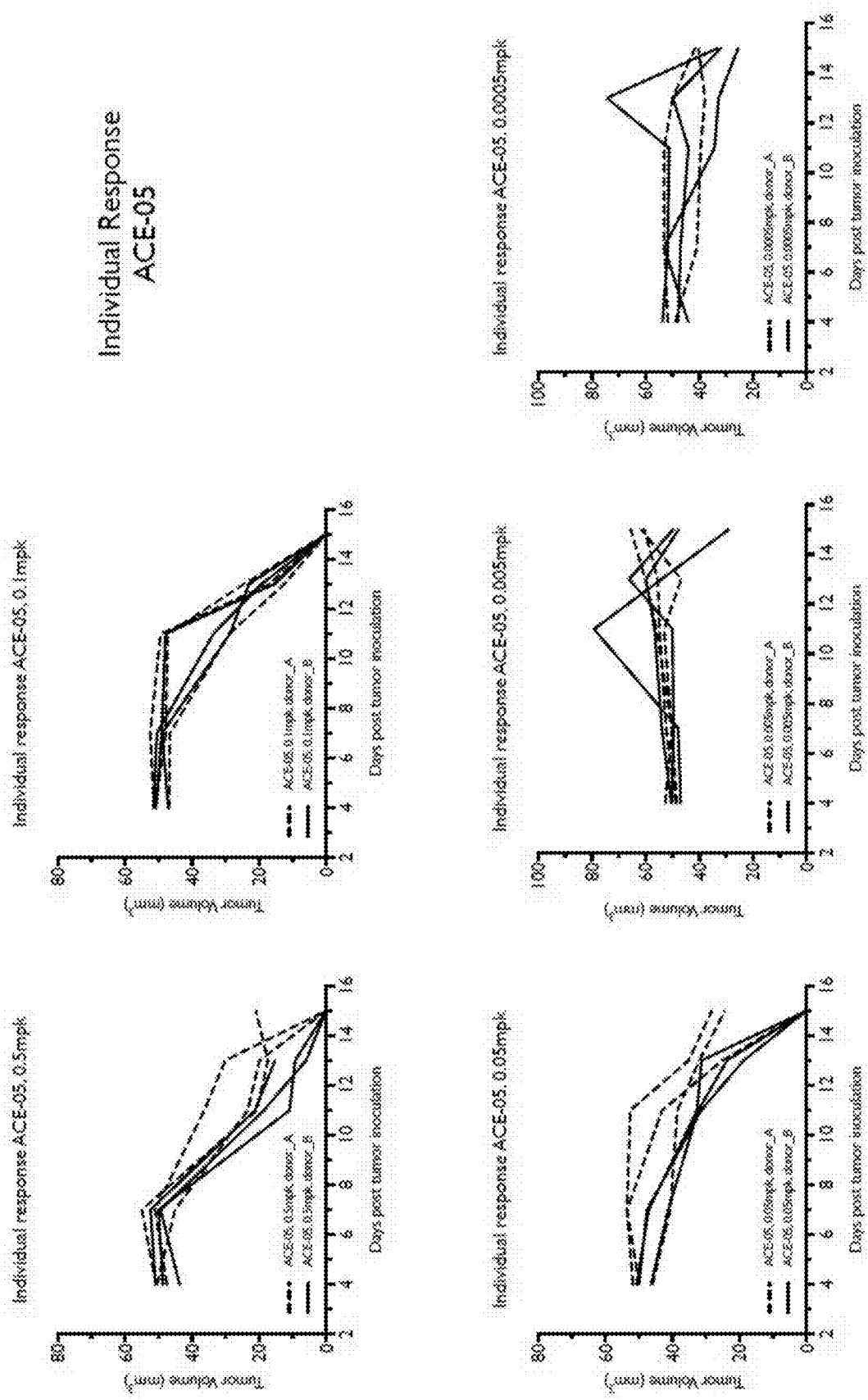
Figure 18C:
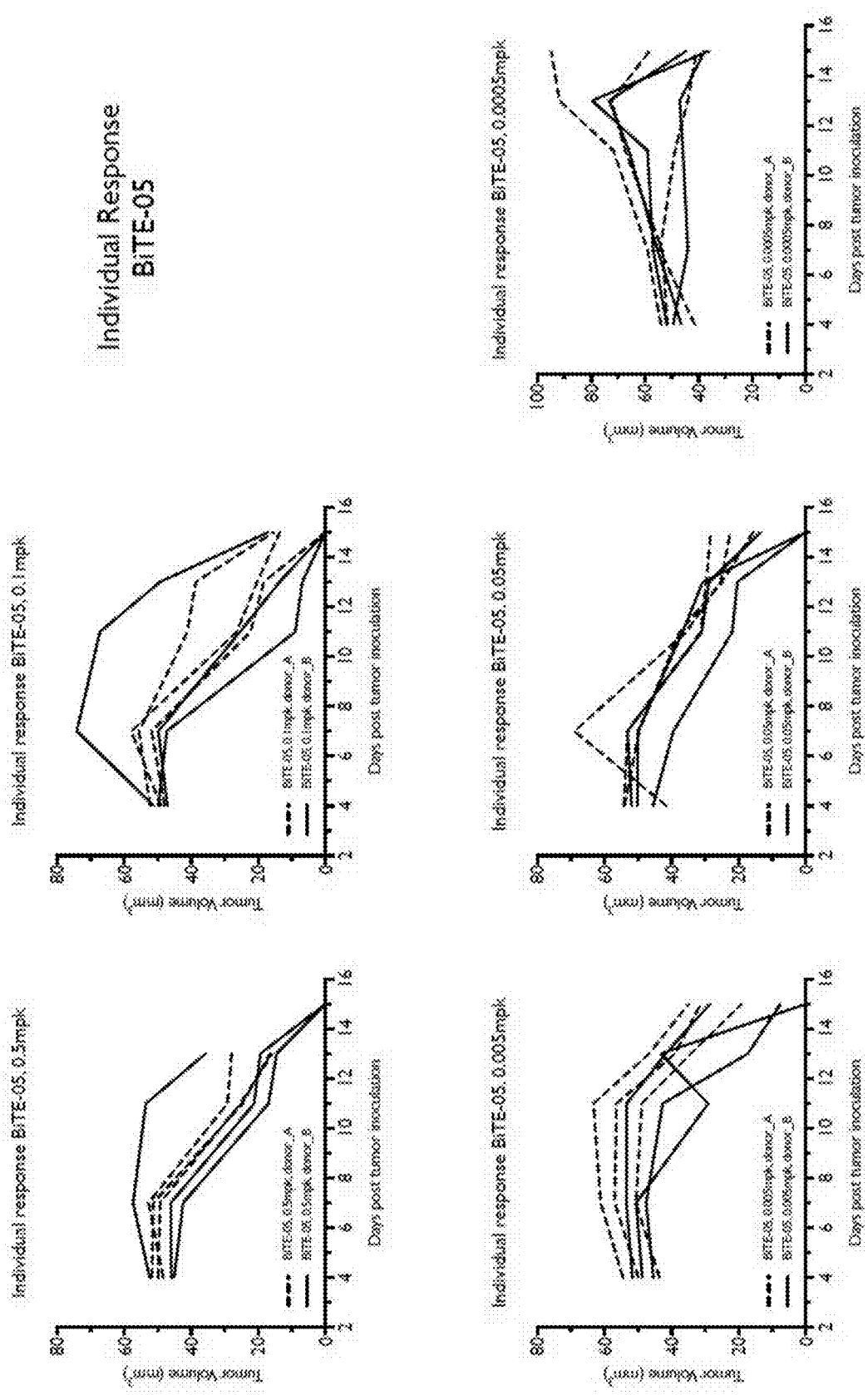
Figure 18D:
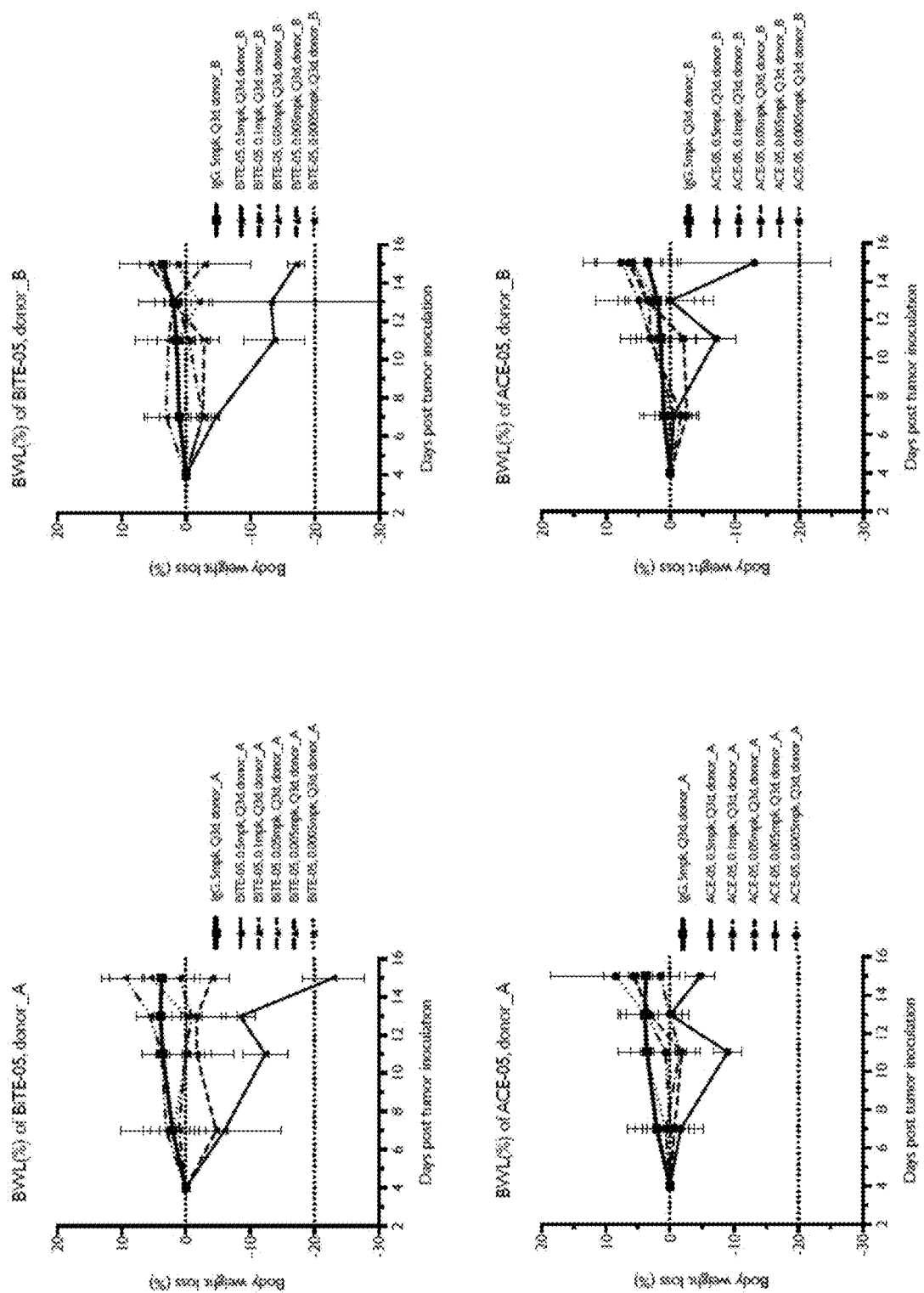

Note:
N: animal number;
*2 donors will be used,
n = 5/group
Dosing volume: adjust dosing volume based on body weight (5 uL/g)
Treatment regimen may be changed per BW loss or other adverse effect according to rules set forth and/or client requests FIGS. 17A-17F show the results of the HCC827 (PD-L1 positive tumor) xenograft study in a humanized mice model. 6-8 weeks old female NCG mice were chosen for PBMC reconstitution. As shown in Table 13, there were 4 study groups (10 mice/group) and 2 PBMC donors (5 mice/donor). Test articles were treated with ACE-05, BiTE-05, IgG, and YBL-007 4 days after tumor inoculation (size of TV=50 mm³) and PBMC isolated from each donors were reconstituted days before tumor inoculation. ACE-05 and BiTE-05 were injected on day 4, day 6, day 8 (total 3 times). IgG and YBL-007 were injected on day 4, day 7 and day 10 (total 3 times). On day 12 of this study, tumors of 9 out of 10 mice were completely gone after ACE-05 treatment. Body weight loss (BWL) (%) of BiTE treated group was much higher than ACE-05 treated group. Three mice out of 10 from the BiTE treated group were terminated because of over 20% of BWL during this study. The results show that ACE-05 is effective in treating the observed lung cancer and also indicates that ACE-05 exhibits greater safety than the BiTE-05, the bispecific antibody generated using BiTE technology.

administration of test molecules. The standard error of the mean (SEM) of tumor volume and changes of body weight from each group were plotted against time in FIG. 18A, respectively. FIGS. 18B-18C show anti-tumor efficacy of individual mouse in each dose group treated with ACE-05 and BiTE-05, respectively. Four mice were terminated on day 15 in the BiTE-05 treated group, but only 1 mouse was terminated in ACE-05 treated group. In most animals treated with 0.5 mpk, 0.1 mpk, and 0.05 mpk of ACE-05, tumors were completely disappeared (FIG. 18B), in contrast with the group treated with BiTE-05 (FIG. 18C).

Table 14 summarizes the anti-tumor activity of ACE-05 and BiTe-05. The mean tumor volume (TV) on day 15 is shown with the standard error of the mean. Percentage tumor growth inhibition (TGI %) is the difference between the mean tumor volume of a test group and control group, calculated using the following formula: TGI (%)=(Mean TV of control−Mean TV of treated)/Mean TV of control×100. T/C (%) was calculated using the following formula: T/C (%)=mean TV of treated/mean TV of control×100. The results show that ACE-05 is more effective than BiTE-05 in treating the observed lung cancer over a range of concentrations.

TABLE 14

Anti-tumor activity of ACE-05 and BiTE-05

| Group | Test article | Dose/schedule | TV (mm³) on Day 15, mean | TGI (%) | T/C (%) | Mortality on Day 15 |
|---|---|---|---|---|---|---|
| 1a | IgG | 5 mpk/Q3d | 79.99 ± 10.56 | — | — | — |
| 1b | | | 69.21 ± 5.15 | — | — | — |
| 5a | BiTE-05 | 0.5 mpk/Q3d | 0.00 ± 0 | 100.00% | 0.00% | Dead(I), TS(2) |
| 5b | | | 0.00 ± 0 | 100.00% | 0.00% | Dead(I) |
| 6a | | 0.1 mpk/Q3d | 9.70 ± 4.88 | 87.87% | 12.13% | — |
| 6b | | | 5.71 ± 5.71 | 91.75% | 8.25% | — |
| 7a | | 0.05 mpk/Q3d | 22.22 ± 3.66 | 72.23% | 27.77% | — |
| 7b | | | 4.51 ± 4.51 | 93.48% | 6.52% | — |
| 8a | | 0.005 mpk/Q3d | 28.52 ± 4.81 | 64.34% | 35.66% | — |
| 8b | | | 12.08 ± 8.55 | 82.55% | 17.45% | — |
| 9a | | 0.0005 mpk/Q3d | 64.69 ± 15.97 | 19.12% | 80.88% | — |
| 9b | | | 39.42 ± 2.62 | 43.04% | 56.96% | — |
| 10a | ACE-05 | 0.5 mpk/Q3d | 7.00 ± 7.00 | 91.24% | 8.76% | — |
| 10b | | | 0.00 ± 0 | 100.00% | 0.00% | TS(1) |
| 11a | | 0.1 mpk/Q3d | 0.00 ± 0 | 100.00% | 0.00% | — |
| 11b | | | 0.00 ± 0 | 100.00% | 0.00% | — |
| 12a | | 0.05 mpk/Q3d | 17.56 ± 8.85 | 78.04% | 21.96% | — |
| 12b | | | 0.00 ± 0 | 100.00% | 0.00% | — |
| 13a | | 0.005 mpk/Q3d | 62.60 ± 1.55 | 21.74% | 78.26% | — |
| 13b | | | 42.17 ± 6.57 | 39.07% | 60.93% | — |
| 14a | | 0.0005 mpk/Q3d | 40.96 ± 0.92 | 20.86% | 79.14% | — |
| 14b | | | 30.27 ± 2.41 | 56.27% | 43.73% | — |

From the foregoing, it will be appreciated that, although specific embodiments have been described herein for the purpose of illustration, various modifications may be made without deviating from the spirit and scope of what is provided herein. All of the references referred to above are incorporated herein by reference in their entireties.

What is claimed:

1. A binding molecule, comprising:
   (a) a first polypeptide and a second polypeptide, each comprising an antibody light chain,
   (b) a third polypeptide comprising, in the order from N-terminus to C-terminus, a first variable heavy (VH) region and a first constant heavy 1 (CH1) region, and a second VH region; and
   (c) a fourth polypeptide comprising, in the order from N-terminus to C-terminus, a third VH region and a second CH1 region, and a variable light (VL) region,
   wherein the first polypeptide and the first VH region and the first CH1 region of the third polypeptide form a first antigen binding Fab region;
   wherein the second polypeptide and the third VH region and the second CH1 region of the fourth polypeptide form a second antigen binding Fab region;
   wherein the second VH region of the third polypeptide and the VL region of the fourth polypeptide form an antigen binding Fv region;
   wherein the first Fab region and the second Fab region bind to epidermal growth factor receptor (EGFR), and the Fv region binds to Cluster of Differentiation 3 (CD3);
   wherein the antibody light chains of the first and the second polypeptide each comprise three Complementarity Determining Regions (CDRs) having amino acid sequences of SEQ ID NO.: 45, SEQ ID NO.: 46, and SEQ ID NO.: 47;
   wherein in the third polypeptide, the first VH region comprises three CDRs having amino acid sequences of SEQ ID NO.: 41, SEQ ID NO.: 42, and SEQ ID NO.: 43, and the second VH region comprises three CDRs having amino acid sequences of SEQ ID NO.: 13, SEQ ID NO.: 14, and SEQ ID NO.: 15; and
   wherein in the fourth polypeptide, the third VH region comprises three CDRs having amino acid sequences of SEQ ID NO.: 41, SEQ ID NO.: 42, and SEQ ID NO.: 43, and the VL region comprises three CDRs having amino acid sequences of SEQ ID NO.: 17, SEQ ID NO.: 18, and SEQ ID NO.: 19.

2. The binding molecule of claim 1, wherein the first Fab region and the second Fab region are linked to the Fv region via a flexible peptide region.

3. The binding molecule of claim 2, wherein the flexible peptide region comprises an antibody hinge region.

4. The binding molecule of claim 3, wherein the antibody hinge region comprises an interchain disulfide bond between the third polypeptide and the fourth polypeptide.

5. The binding molecule of claim 3, wherein the flexible peptide region further comprises a linker.

6. The binding molecule of claim 1, wherein:
(a) the antibody light chains of the first and the second polypeptide each comprise a VL region that comprises the amino acid sequence of SEQ ID NO.: 44;
(b) in the third polypeptide, the first VH region comprises the amino acid sequence of SEQ ID NO.: 40, and the second VH region comprises the amino acid sequence of SEQ ID NO.: 12; and
(c) in the fourth polypeptide, the third VH region comprises the amino acid sequence of SEQ ID NO.: 40, and the VL region comprises the amino acid sequence of SEQ ID NO.: 16.

7. The binding molecule of claim 1, wherein the first polypeptide and the second polypeptide each has the amino acid sequence of SEQ ID NO.: 39; the third polypeptide has the amino acid sequence of SEQ ID NO.: 37; and the fourth polypeptide has the amino acid sequence of SEQ ID NO.: 38.

8. A method of making a binding molecule comprising:
(i) expressing the binding molecule from one or more vectors in a host cell, wherein the one or more vectors comprise
  (a) a first nucleic acid encoding a first polypeptide and a second nucleic acid encoding a second polypeptide, wherein each of the first polypeptide and the second polypeptide is an antibody light chain,
  (b) a third nucleic acid encoding a third polypeptide comprising, in the order from N-terminus to C-terminus, a first VH region and a first CH1 region, and a second VH region; and
  (c) a fourth nucleic acid encoding a fourth polypeptide comprising, in the order from N-terminus to C-terminus, a third VH region and a second CH1 region, and a VL region,
  wherein the first polypeptide and the first VH region and the first CH1 region of the third polypeptide form a first antigen binding Fab region;
  wherein the second polypeptide and the third VH region and the second CH1 region of the fourth polypeptide form a second antigen binding Fab region;
  wherein the second VH region of the third polypeptide and the VL region of the fourth polypeptide form an antigen binding Fv region;
  wherein the first Fab region and the second Fab region bind to EGFR, and the Fv region binds to CD3,
  wherein the antibody light chains of the first and the second polypeptide each comprise three Complementarity Determining Regions (CDRs) having amino acid sequences of SEQ ID NO.: 45, SEQ ID NO.: 46, and SEQ ID NO.: 47,
  wherein in the third polypeptide, the first VH region comprises three CDRs having amino acid sequences of SEQ ID NO.: 41, SEQ ID NO.: 42, and SEQ ID NO.: 43, and the second VH region comprises three CDRs having amino acid sequences of SEQ ID NO.: 13, SEQ ID NO.: 14, and SEQ ID NO.: 15, and
  wherein in the fourth polypeptide, the third VH region comprises three CDRs having amino acid sequences of SEQ ID NO.: 41, SEQ ID NO.: 42, and SEQ ID NO.: 43, and the VL region comprises three CDRs having amino acid sequences of SEQ ID NO.: 17, SEQ ID NO.: 18, and SEQ ID NO.: 19, and
(ii) purifying the binding molecule.

9. The method of claim 8, wherein the first Fab region and the second Fab region are linked to the Fv region via a flexible peptide region.

10. The method of claim 9, wherein the flexible peptide region comprises an antibody hinge region.

11. The method of claim 10, wherein the flexible peptide region further comprises a linker.

12. The method of claim 8, wherein:
(a) the antibody light chains of the first and the second polypeptide each comprise a VL region that comprises the amino acid sequence of SEQ ID NO.: 44;
(b) in the third polypeptide, the first VH region comprises the amino acid sequence of SEQ ID NO.: 40, and the second VH region comprises the amino acid sequence of SEQ ID NO.: 12; and
(c) in the fourth polypeptide, the third VH region comprises the amino acid sequence of SEQ ID NO.: 40, and the VL region comprises the amino acid sequence of SEQ ID NO.: 16.

13. The method of claim 8, wherein the first polypeptide and the second polypeptide each has the amino acid sequence of SEQ ID NO.: 39; the third polypeptide has the amino acid sequence of SEQ ID NO.: 37; and the fourth polypeptide has the amino acid sequence of SEQ ID NO.: 38.

14. A pharmaceutical composition comprising a therapeutically effective amount of a binding molecule and a pharmaceutically acceptable carrier, wherein the binding molecule comprises:
(a) a first polypeptide and a second polypeptide, each comprising an antibody light chain,
(b) a third polypeptide comprising, in the order from N-terminus to C-terminus, a first variable heavy (VH) region and a first constant heavy 1 (CH1) region, and a second VH region; and
(c) a fourth polypeptide comprising, in the order from N-terminus to C-terminus, a third VH region and a second CH1 region, and a variable light (VL) region,
wherein the first polypeptide and the first VH region and the first CH1 region of the third polypeptide form a first antigen binding Fab region;
wherein the second polypeptide and the third VH region and the second CH1 region of the fourth polypeptide form a second antigen binding Fab region;
wherein the second VH region of the third polypeptide and the VL region of the fourth polypeptide form an antigen binding Fv region;
wherein the first Fab region and the second Fab region bind to Epidermal Growth Factor Receptor (EGFR), and the Fv region binds to CD3;
wherein the antibody light chains of the first and the second polypeptide each comprise three Complimentary Determining Regions (CDRs) having amino acid sequences of SEQ ID NO.: 45, SEQ ID NO.: 46, and SEQ ID NO.: 47,
wherein in the third polypeptide, the first VH region comprises three CDRs having amino acid sequences of SEQ ID NO.: 41, SEQ ID NO.: 42, and SEQ ID NO.: 43, and the second VH region comprises three CDRs having amino acid sequences of SEQ ID NO.: 13, SEQ ID NO.: 14, and SEQ ID NO.: 15, and
wherein in the fourth polypeptide, the third VH region comprises three CDRs having amino acid sequences of SEQ ID NO.: 41, SEQ ID NO.: 42, and SEQ ID NO.: 43, and the VL region comprises three CDRs having amino acid sequences of SEQ ID NO.: 17, SEQ ID NO.: 18, and SEQ ID NO.: 19.

* * * * *

UNITED STATES PATENT AND TRADEMARK OFFICE
CERTIFICATE OF CORRECTION

PATENT NO. : 10,654,944 B2  
APPLICATION NO. : 16/372196  
DATED : May 19, 2020  
INVENTOR(S) : Seil Jang, Bum-Chan Park and Young Woo Park Page 1 of 1

It is certified that error appears in the above-identified patent and that said Letters Patent is hereby corrected as shown below:

In the Specification

In Column 121, Table 11, replace "Anti-CD20" with --anti-EGFR--;

In the Claims

In Column 245, Claim 1, Line 67, replace "polypeptide" with --polypeptides--;
In Column 247, Claim 6, Line 3, replace "polypeptide" with --polypeptides--;
In Column 247, Claim 8, Line 48, replace "polypeptide" with --polypeptides--;
In Column 248, Claim 12, Line 7, replace "polypeptide" with --polypeptides--; and
In Column 248, Claim 14, Line 51, replace "polypeptide" with --polypeptides--.

Signed and Sealed this  
Twenty-sixth Day of January, 2021

Drew Hirshfeld  
*Performing the Functions and Duties of the*  
*Under Secretary of Commerce for Intellectual Property and*  
*Director of the United States Patent and Trademark Office*